(12) United States Patent
Zhang et al.

(10) Patent No.: US 9,174,974 B2
(45) Date of Patent: Nov. 3, 2015

(54) MACROCYCLIC FACTOR VIIA INHIBITORS

(71) Applicant: BRISTOL-MYERS SQUIBB COMPANY, Princeton, NJ (US)

(72) Inventors: Xiaojun Zhang, Furlong, PA (US); Peter Glunz, Yardley, PA (US); Eldon Scott Priestley, Yardley, PA (US); James A. Johnson, Pennington, NJ (US); Nicholas Ronald Wurtz, Pennington, NJ (US); Vladimir Ladziata, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/405,507

(22) PCT Filed: Jun. 5, 2013

(86) PCT No.: PCT/US2013/044196
§ 371 (c)(1),
(2) Date: Dec. 4, 2014

(87) PCT Pub. No.: WO2013/184734
PCT Pub. Date: Dec. 12, 2013

(65) Prior Publication Data
US 2015/0148313 A1 May 28, 2015

Related U.S. Application Data

(60) Provisional application No. 61/657,194, filed on Jun. 8, 2012.

(51) Int. Cl.
*C07D 401/12* (2006.01)
*C07D 401/14* (2006.01)
*C07D 413/12* (2006.01)
*C07D 273/02* (2006.01)
*C07D 413/14* (2006.01)
*C07D 417/14* (2006.01)
*C07F 9/6558* (2006.01)

(52) U.S. Cl.
CPC ............ *C07D 413/12* (2013.01); *C07D 273/02* (2013.01); *C07D 401/12* (2013.01); *C07D 413/14* (2013.01); *C07D 417/14* (2013.01); *C07F 9/65583* (2013.01)

(58) Field of Classification Search
CPC ............................. C07D 401/12; C07D 401/14
See application file for complete search history.

(56) References Cited

U.S. PATENT DOCUMENTS 7,592,331 B2 * 9/2009 Priestley et al. ............... 514/183
8,420,830 B2 * 4/2013 Wurtz et al. .................. 548/454

FOREIGN PATENT DOCUMENTS

WO   WO 2007/002313   1/2007
WO   WO 2008/079759   7/2008
WO   WO 2008/079836   7/2008

OTHER PUBLICATIONS

Arnold, C.S. et al., "The antithrombotic and anti-inflammatory effects of BCX-3607, a small molecule tissue factor/factor VIIa inhibitor", Thrombosis Research, vol. 117, pp. 343-349 (2006).
Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).
Bundgaard, H., "Prodrugs as a means to improve the delivery of peptide drugs", Advanced Drug Delivery Reviews, vol. 8, pp. 1-38 (1992).
Bundgaard, H., ed., Design of Prodrugs, Elsevier Science Publishers B.V., publ. (1985) (table of contents).
Carson, S.D. et al., "The role of tissue factor in the production of thrombin", Blood Coagulation and Fibrinolysis, vol. 4, pp. 281-292 (1993).
Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).
Frédérick, R. et al., "Modulators of the Coagulation Cascade: Focus and Recent Advances in Inhibitors of Tissue Factor, Factor VIIa and their Complex", Current Medicinal Chemistry, vol. 12, No. 4, pp. 397-417 (2005).
Giesen, P.L.A. et al., "Blood-borne tissue factor: Another view of thrombosis", Proc. Natl. Acad. Sci. USA, vol. 96, pp. 2311-2315 (1999).
Girard, T.J. et al., "The role of tissue factor/factor VIIa in the pathophysiology of acute thrombotic formation", Current Opinion in Pharmacology, vol. 1, pp. 159-163 (2001).

(Continued)

*Primary Examiner* — Bruck Kifle
(74) *Attorney, Agent, or Firm* — Barry H. Jacobsen

(57) ABSTRACT

The present invention provides compounds of Formula (I): as defined in the specification and compositions comprising any of such novel compounds. These compounds are Factor VIIa inhibitors which may be used as medicaments.

9 Claims, No Drawings

(56) References Cited

OTHER PUBLICATIONS

Himber, J. et al., "Inhibition of tissue factor limits the growth of venous thrombus in the rabbit", Journal of Thrombosis and Haemostasis, vol. 1, pp. 889-895 (2003).
Hirsh, J. et al., "New anticoagulants", Blood, vol. 105, No. 2, pp. 453-463 (2005).
Hoffman, M., "A cell-based model of coagulation and the role of factor VIIa", Blood Reviews, vol. 17, pp. S1-S5 (2003).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).
Lazarus, R.A. et al., "Inhibitors of Tissue Factor•Factor VIIa for Anticoagulant Therapy", Current Medicinal Chemistry, vol. 11, No. 17, pp. 2275-2290 (2004).
Lee, A. et al., "Dose-Response Study of Recombinant Factor VIIa/Tissue Factor Inhibitor Recombinant Nematode Anticoagulant Protein c2 in Prevention of Postoperative Venous Thromboembolism in Patients Undergoing Total Knee Replacement", Circulation, vol. 104, pp. 74-78 (2001).
Meneton, P. et al., "Cardiovascular abnormalities with normal blood pressure in tissue kallikrein-deficient mice", Proc. Natl. Acad. Sci., vol. 98, No. 5, pp. 2634-2639 (2001).
Miyaura, N. et al., "Palladium-Catalyzed Cross-Coupling Reactions of Organoboron Compound", Chem. Rev., vol. 95, No. 7, pp. 2457-2483 (1995).
Montalbetti, C.A.G.N. et al., "Amide bond formation and peptide coupling", Tetrahedron, vol. 61, pp. 10827-10852 (2005).
Moons, A.H.M. et al., "Recombinant Nematode Anticoagulant Protein c2, an Inhibitor of the Tissue Factor/Factor VIIa Complex, in Patients Undergoing Elective Coronary Angioplasty" Journal of the American College of Cardiology, vol. 41, No. 12, pp. 2147-2153i (2003).
Morrissey, J.H., "Tissue factor: in at the start . . . and the finish?" Journal of Thrombosis and Haemostasis, vol. 1, pp. 878-880 (2003).
Morrissey, J.H. et al., "Quantitation of Activated Factor VII Levels in Plasma Using a Tissue Factor Mutant Selectively Deficient in Promoting Factor VII Activation", Blood, vol. 81, No. 3, pp. 734-744 (1993).
Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).
Olivero, A.G. et al., "A Selective, Slow Binding Inhibitor of Factor VIIa Binds to a Nonstandard Active Site Conformation and Attenuates Thrombus Formation in Vivo", The Journal of Biological Chemistry, vol. 280, No. 10, pp. 9160-9169 (2005).
Petasis, N.A. et al., "A New and Practical Synthesis of α-Amino Acids from Alkenyl Boronic Acids", J. Am. Chem. Soc., vol. 119, No. 2, pp. 445-446 (1997).
Petasis, N.A. et al., "A New Synthesis of α-Arylglycines from Aryl Boronic Acids", Tetrahedron, vol. 53, No. 48, pp. 16463-16470 (1997).
Suleymanov, O.D. et al., "Pharmacological Interruption of Acute Thrombus Formation with Minimal Hemorrhagic Complications by a Small Molecule Tissue Factor/Factor VIIa Inhibitor: Comparison to Factor Xa and Thrombin Inhibition in a Nonhuman Primate Thrombosis Model", The Journal of Pharmacology and Experimental Therapeutics, vol. 306, No. 3, pp. 1115-1121 (2003).
Szalony, J.A. et al., Administration of a small molecule tissue factor/Factor VIIa inhibitor in a non-human primate thrombosis model of venous thrombosis: effects on thrombus formation and bleeding time, Thrombosis Research, vol. 112, pp. 167-174 (2003).
Szalony, J.A. et al., "Pharmacological Intervention at Disparate Sites in the Coagulation Cascade: Comparison of Anti-thrombotic Efficacy vs. Bleeding Propensity in a Rat Model of Acute Arterial Thrombosis", Journal of Thrombosis and Thrombolysis, vol. 14, No. 2, pp. 113-121 (2002).
Widder, K.J. et al., eds., Section III: "Prodrugs", Methods in Enzymology, vol. 112, pp. 309-396, Academic Press, Inc., publ. (1985).
Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).
Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).
Young, W.B. et al., "Factor VIIa inhibitors: Chemical optimization, preclinical pharmacokinetics, pharmacodynamics, and efficacy in an arterial baboon thrombosis model", Bioorganic & Medicinal Chemistry Letters, vol. 16, pp. 2037-2041 (2006).
Zbinden, K.G. et al., "Dose-dependent antithrombotic activity of an orally active tissue factor/factor VIIa inhibitor without concomitant enhancement of bleeding propensity", Bioorganic & Medicinal Chemistry, vol. 14, pp. 5357-5369 (2006).

* cited by examiner

MACROCYCLIC FACTOR VIIA INHIBITORS

CROSS-REFERENCE TO RELATED APPLICATIONS

The present application is a 371 application of International Application No. PCT/US2013/044196 filed on Jun. 5, 2013, which claims priority benefit of U.S. provisional application Ser. No. 61/657,194, filed Jun. 8, 2014 each of which is fully incorporated by reference herein.

FIELD OF THE INVENTION

The present invention relates to novel macrocyclic factor VIIa inhibitors and pharmaceutical compositions thereof.

BACKGROUND OF THE INVENTION

Factor VII is a plasma serine protease involved in the initiation of the coagulation cascade. It is present in human blood at a concentration of approximately 500 ng/mL, with about 1% of the total amount in the proteolytically active form factor VIIa (Morrissey, J. H. et al., Blood, 81:734-744 (1993)). Factor VIIa binds with high affinity to its cofactor, tissue factor, in the presence of calcium ions to form a complex with enhanced proteolytic activity (Carson, S. D. et al., Blood Coag. Fibrinol., 4:281-292 (1993)). Tissue factor is normally expressed in cells surrounding the vasculature, and is exposed to factor VIIa in blood by vessel injury or atherosclerotic plaque rupture. Once formed, the tissue factor/factor VIIa complex initiates blood coagulation by proteolytic cleavage of factor X to factor Xa, factor IX to factor IXa and autoactivation of additional factor VII to VIIa. Factor Xa, generated either directly by tissue factor/factor VIIa or indirectly through action of factor IXa, catalyzes the conversion of prothrombin to thrombin. Thrombin converts fibrinogen to fibrin, which polymerizes to form the structural framework of a blood clot, and activates platelets, which are a key cellular component of coagulation (Hoffman, M., Blood Reviews, 17:S1-S5 (2003)). In addition, there is evidence that tissue factor is present in blood, likely in an encrypted form that is de-encrypted during clot formation. (Giesen, P. L. A. et al., Proc. Natl. Acad. Sci., 96:2311-2315 (1999); Himber, J. et al., J. Thromb. Haemost., 1:889-895 (2003)). The tissue factor/factor VIIa complex derived from blood borne tissue factor may play an important role in propagation of the coagulation cascade (clot growth) and in thrombus formation in the absence of vessel wall injury (i.e., stasis induced deep vein thrombosis or sepsis). The source of blood borne tissue factor is an area of active research (Morrissey, J. H., J. Thromb. Haemost., 1:878-880 (2003)).

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al., Blood, 105:453-463 (2005)).

Because of its key role in the coagulation cascade, researchers have postulated that inhibition of factor VIIa could be used to treat or prevent thrombotic or thromboembolic disease. (Girard, T. J. et al., Curr. Opin. Pharmacol., 1:159-163 (2001); Lazarus, R. A. et al., Curr. Med. Chem., 11:2275-2290 (2004); Frederick, R. et al., Curr. Med. Chem., 12:397-417 (2005).) Several studies have confirmed that various biological and small molecule inhibitors of factor VIIa have in vivo antithrombotic efficacy with a low bleeding liability. For instance, it has been demonstrated that a biological factor VIIa inhibitor XK1, comprising a hybrid of Factor X light chain and tissue factor pathway inhibitor first kunitz domain, prevents thrombus formation in a rat model of arterial thrombosis, with no change in bleeding time or total blood loss (Szalony, J. A. et al., J. Thrombosis and Thrombolysis, 14:113-121 (2002)). In addition, small molecule active site directed factor VIIa inhibitors have demonstrated antithrombotic efficacy in animal models of arterial thrombosis (Suleymanov, O. et al., J. Pharmacology and Experimental Therapeutics, 306:1115-1121 (2003); Olivero, A. G. et al., J. Biol. Chem., 280:9160-9169 (2005); Young, W. B. et al., Bioorg. Med. Chem. Lett., 16:2037-2041 (2006); Zbinden, K. G. et al., Bioorg. Med. Chem., 14:5357-5369 (2006)) and venous thrombosis (Szalony, J. A. et al., Thrombosis Research, 112:167-174 (2003); Arnold, C. S. et al., Thrombosis Research, 117:343-349 (2006)), with little impact on bleeding time or blood loss. Moreover, the biological factor VIIa inhibitor recombinant nematode anticoagulant protein c2 (rNAPc2) is currently under clinical investigation for treatment of acute coronary syndromes. Results of initial clinical trials demonstrate that rNAPc2 prevents deep vein thrombosis in patients undergoing total knee replacement (Lee, A. et al., Circulation, 104:74-78 (2001)), reduces systemic thrombin generation in patients undergoing coronary angioplasty (Moons, A. H. M., J. Am. Coll. Cardiol., 41:2147-2153 (2003)), and reduces magnitude and duration of ischemic events in patients with acute coronary syndromes (Giugliano, R. P. et al., World Congress of Cardiology, Barcelona, Poster #3897 (2006)).

U.S. Patent Publication No. 2007/0208054 A1, published Sep. 7, 2007, discloses a series of macrocyclic factor VIIa inhibitors of the following formula:

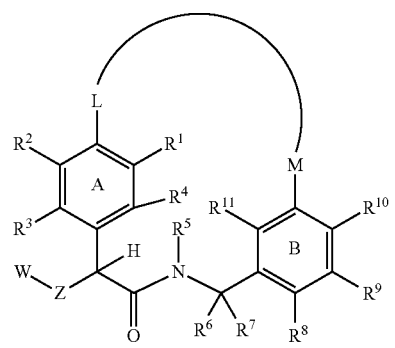

wherein ring A is phenyl or a pyridyl isomer defined by replacing one of $CR^1$, $CR^2$, $CR^3$, or $CR^4$ in ring A of the above formula with N;

ring B is phenyl or a pyridyl isomer defined by replacing one of $CR^8$, $CR^9$, $CR^{10}$, or $CR^{11}$ in ring B of the above formula with N;

M is —CONH—, —SO$_2$NH—, —NHCO—, or —NHSO$_2$—;
X is O, S(O)$_p$, or NR$^{16}$;
Y is O or NR$^{16a}$;
Z is NH, O or S;
W is substituted with 0-2 R$^{14}$ and is selected from:

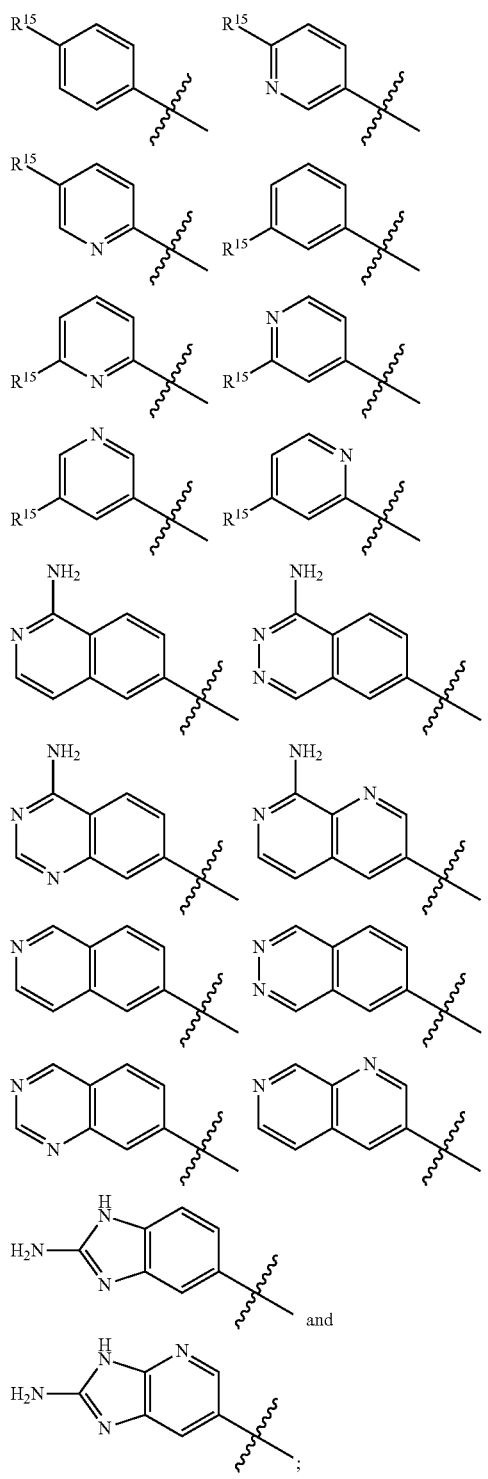

and
L and other variables are defined therein.

It is desirable to find new compounds with improved pharmacological characteristics compared with known factor VIIa inhibitors. For example, it is desirable to find new compounds with improved factor VIIa inhibitory activity and selectivity for factor VIIa versus other serine proteases, i.e., factor Xa, XIa, FXIIa, thrombin, tissue kallikrein (HK1) and activated protein C (APC), etc. It is also advantageous for the new compounds to exhibit improved inhibition of clot formation and better membrane permeability to facilitate oral bioavailability. It is also desirable to find compounds with advantageous and improved characteristics in one or more of the following categories:

(a) advantageous dosage regimes (e.g., lower dosages and/or once-daily dosing);

(b) improved pharmaceutical properties (i.e., solubility, permeability, amenability to sustained release formulations);

(c) factors which decrease blood concentration peak-to-trough characteristics (i.e., clearance and/or volume of distribution);

(d) factors that increase the concentration of active drug in plasma (i.e., reduced protein binding; reduced volume of distribution; avoidance of P-glycoprotein substrates);

(e) factors that decrease the liability for clinical drug-drug interactions (cytochrome P450 enzyme inhibition or induction, such as CYP 2D6 inhibition, see Dresser, G. K. et al., Clin. Pharmacokinet., 38:41-57 (2000));

(f) factors that decrease the potential for adverse side-effects (e.g., pharmacological selectivity beyond factor VIIa); and (g) factors that improve manufacturing feasibility (e.g., difficulty of synthesis, number of chiral centers, chemical stability, and ease of handling).

It is especially important to find compounds having a desirable combination of the aforementioned pharmacological characteristics.

SUMMARY OF THE INVENTION

The present disclosure provides novel macrocyclic compounds and their analogues, including stereoisomers, tautomers, pharmaceutically acceptable salts, or solvates thereof, which are useful as selective inhibitors of the factor VIIa.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in therapy.

The compounds of the invention may be used for the manufacture of a medicament for the treatment and/or prophylaxis of thromboembolic disorders.

The compounds of the invention can be used alone, in combination with other compounds of the present invention, or in combination with one or more, preferably one to two, and other agent.

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

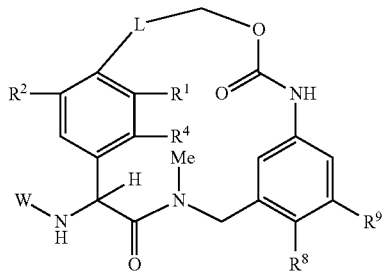

or a stereoisomer, a tautomer, a pharmaceutically acceptable salt, a solvate, or a prodrug thereof, wherein:

W is

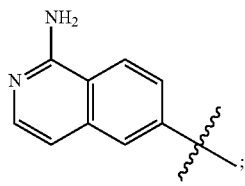 [SMILES: *c1ccc2c(N)nccc2c1]

wherein the ring moiety is substituted with 0-2 F atoms;

L is independently selected from: $CH(C_{1-2}$ alkyl), $CF_2$, $CH(CH_2F)$, $CH(CHF_2)$, and $CH_2CH(OH)$;

$R^1$ and $R^2$ are independently selected from: H, $C_{1-2}$ alkyl and $C_{1-2}$ alkoxy;

$R^4$ and $R^9$ are independently selected from: H, F and Cl; and $R^8$ is independently selected from: $—O(CH_2)_{1-4}O(C_{1-4}$ alkyl), $—CON(C_{1-4}$ alkyl)$_2$, $—SO_2(C_{1-6}$ alkyl), $—SO_2$(cyclopropyl), $—P(=O)(OC_{1-4}$ alkyl)$_2$,

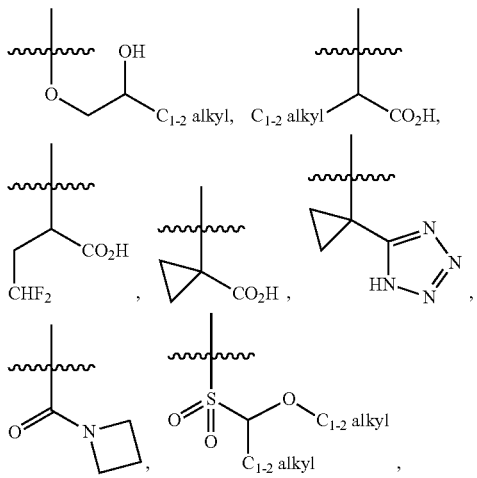

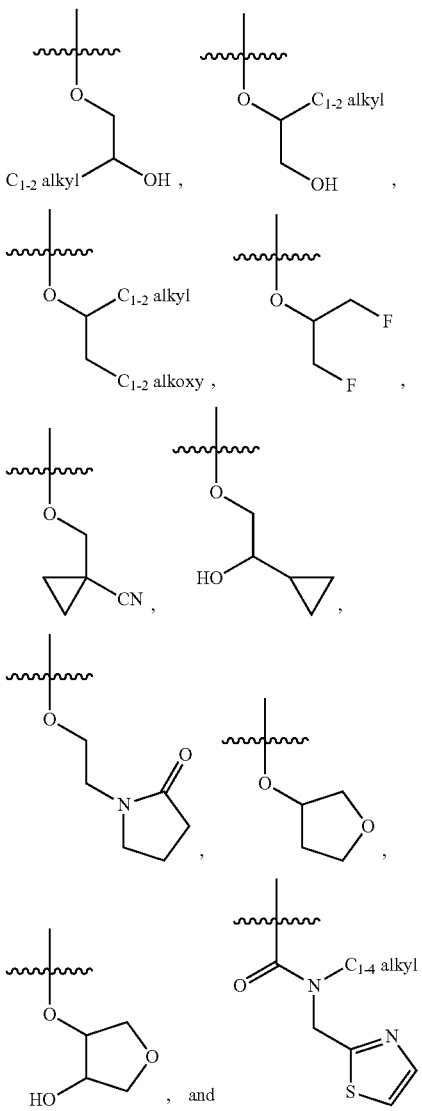

, and

In a second aspect, the present invention includes a compound of Formula (I), or a stereoisomer, a tautomer, a pharmaceutically acceptable salt, or a solvate thereof, within the scope of the first aspect, wherein:

W is independently selected from:

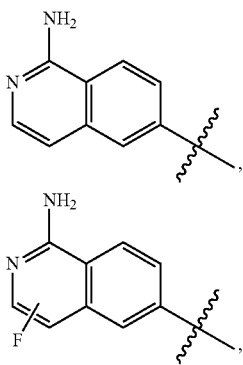

, and

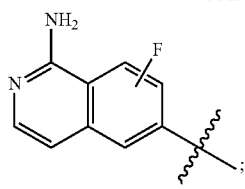

L is independently selected from: CH(Me), CF$_2$, CH(CH$_2$F), CH(CHF$_2$), and CH$_2$CH(OH);

R$^1$ and R$^2$ are independently selected from: H, Me and OMe; and

R$^4$ and R$^9$ are independently selected from: H and F.

In a third aspect, the present invention includes a compound of Formula (I), or a stereoisomer, a tautomer, a pharmaceutically acceptable salt, or a solvate thereof, within the scope of the first or second aspect, wherein:

W is independently selected from:

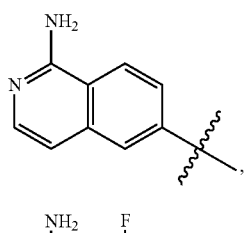

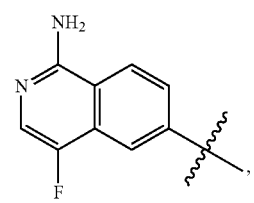

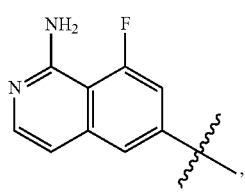, and

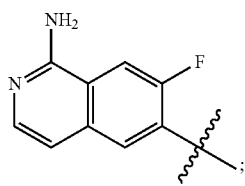;

and

R$^8$ is independently selected from: —O(CH$_2$)$_3$OMe, —CON(Me)$_2$, —CON(Et)$_2$, —SO$_2$Et, —SO$_2$(i-Pr), —SO$_2$(t-Bu), —SO$_2$(cyclopropyl), —P(=O)(OC$_{1-4}$ alkyl)$_2$,

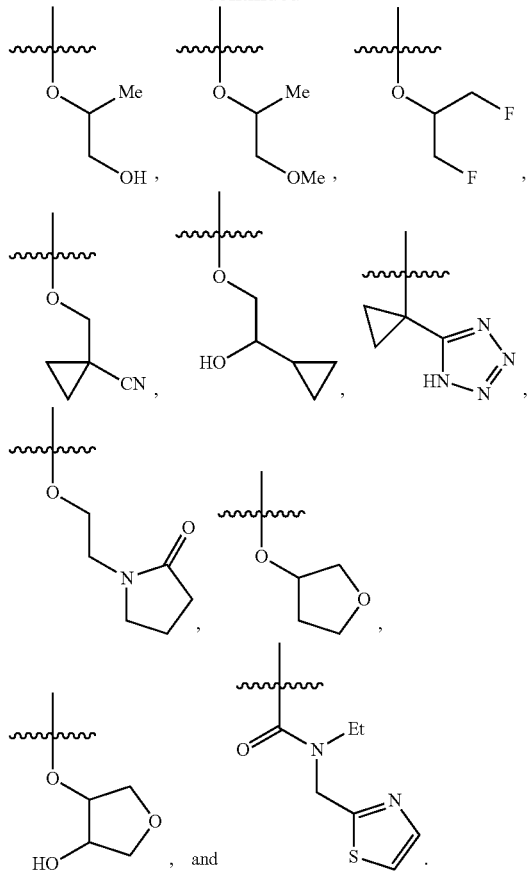

In a fourth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the fourth aspect.

In another embodiment, L is CH(Me).
In another embodiment, L is CF$_2$.
In another embodiment, L is CH(CH$_2$F) or CH(CHF$_2$).
In another embodiment, L is CH$_2$CH(OH).
In another embodiment, W is

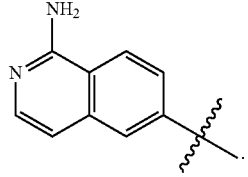 [SMILES: *c1ccc2c(N)nccc2c1]

In another embodiment, W is

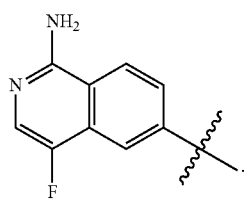 [SMILES: *c1ccc2c(N)ncc(F)c2c1]

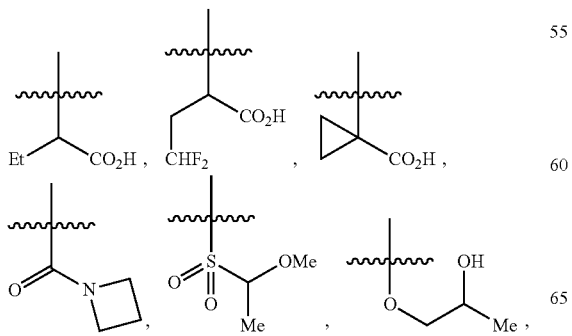

In another embodiment, W is

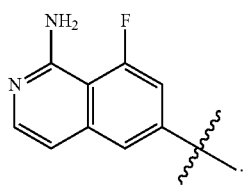

In another embodiment, W is

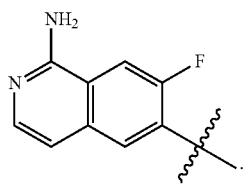

In another embodiment, R⁸ is independently —O(CH₂)₁₋₄O(C₁₋₄ alkyl),

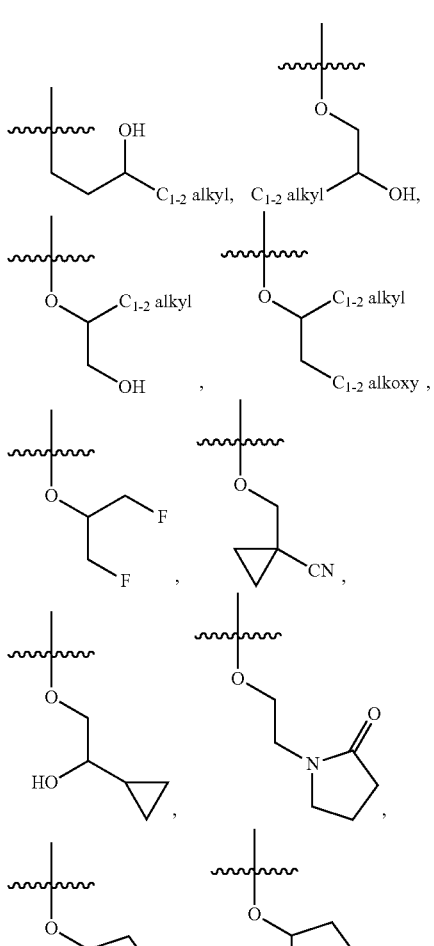

In another embodiment, R⁸ is independently —CON(C₁₋₄ alkyl)₂, —SO₂(C₁₋₆ alkyl), —SO₂(cyclopropyl), —P(=O)(OC₁₋₄ alkyl)₂,

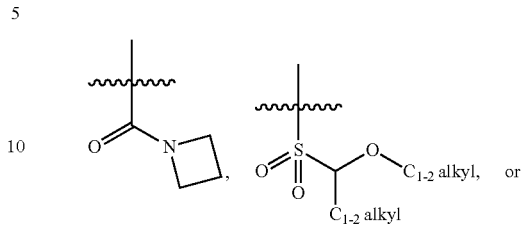

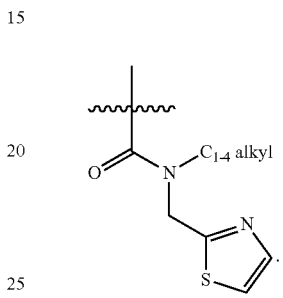

In another embodiment, R⁸ is independently —CON(C₁₋₄ alkyl)₂,

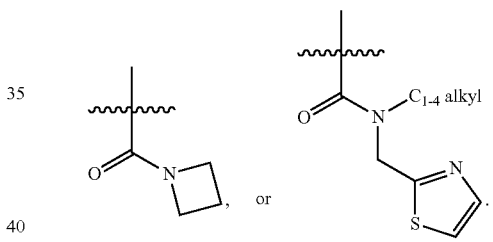

In another embodiment, R⁸ is independently —SO₂(C₁₋₆ alkyl), —SO₂(cyclopropyl), or

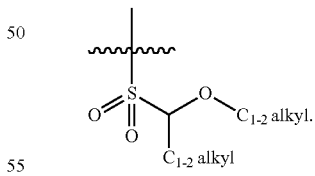

In another embodiment, R⁸ is independently

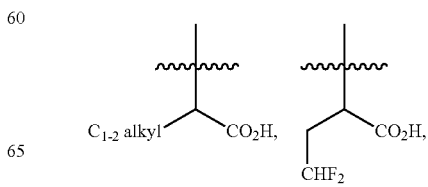

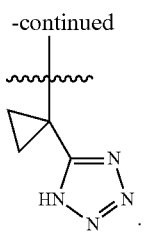

Additionally, the present invention describes compounds that have a beneficial improvement in factor VIIa inhibitory activity and in selectivity vs. tissue kallikrein, in comparison to compounds previously disclosed in the art, such as those disclosed in U.S. Patent Publication No. 2007/0208054 A1. The compounds of the present invention are expected to be efficacious at lower doses, due to the improved FVIIa inhibitory potency, and, with the improved selectivity, have decreased potential for adverse side-effects associated with inhibition of tissue kallikrein. Tissue kallikrein knockout mice have been shown to lack the ability to generate kinins in most tissues, and develop cardiac abnormalities in early adulthood (Meneton, P. et al., *Proc. Nat. Acad. Sci.*, 98:2634-2639 (2001)), raising serious concerns about the potential negative impact of inhibition of tissue kallikrein in humans.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the modulation of platelet reactivity comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In one embodiment, the present invention provides a method for the treatment and/or prophylaxis of thromboembolic disorders, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a compound of the present invention for use in therapy.

In another embodiment, the present invention provides a compound of the present invention for use in therapy for the treatment and/or prophylaxis of thromboembolic disorders.

In another embodiment, the present invention also provides the use of a compound of the present invention for the manufacture of a medicament for the treatment and/or prophylaxis of thromboembolic disorders.

In another embodiment, the present invention provides a method for the treatment and/or prophylaxis of thromboembolic disorders, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of thromboembolic disorders.

The compounds of the present invention may be employed in combination with additional therapeutic agent(s) selected from one or more, preferably one to three, of the following therapeutic agents: potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In another embodiment, additional therapeutic agent(s) used in combined pharmaceutical compositions or combined methods or combined uses, are selected from one or more, preferably one to three, of the following therapeutic agents in treating a thromboembolic disorder: an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent.

In another embodiment, additional therapeutic agent(s) used in combined pharmaceutical compositions or combined methods or combined uses, are selected from one or more, preferably one to three, of the following therapeutic agents in treating a thromboembolic disorder: warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, antistreplase, urokinase, and streptokinase.

In another embodiment, additional therapeutic agent(s) used in combined pharmaceutical compositions or combined methods or combined uses, are selected from one or more, preferably one to three, of the following therapeutic agents in treating a thromboembolic disorder: an antihypertensive agent selected from ACE inhibitors, AT-1 receptor antagonists, ET receptor antagonists, dual ET/AII receptor antagonists, and vasopeptidase inhibitors, or an antithrombotic agent selected from an antiplatelet agent selected from GPIIb/IIIa blockers, $P2Y_1$ and $P2Y_{12}$ antagonists, thromboxane receptor antagonists, and aspirin.

In another embodiment, the additional therapeutic agent(s) are an anti-platelet agent or a combination thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" (or alkylene), is intended to include $C_1$, $C_2$, $C_3$, $C_4$, $C_5$, and $C_6$ alkyl groups. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo.

The term "counter ion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of Formula (I) may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112: 309-396, Academic Press (1985);

b) Bundgaard, H., Chapter 5, "Design and Application of Prodrugs", Krosgaard-Larsen, P. et al., eds., *A Textbook of Drug Design and Development, pp.* 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
MeOH methanol
EtOH ethanol
i-PrOH or IPA isopropanol
AcOH or HOAc acetic acid
DCM dichloromethane
DIEA or DIPEA diethylpropyl amine
DMF dimethyl formamide
DMSO dimethyl sulfoxide
EtOAc ethyl acetate
Et$_2$O diethyl ether
BINAP 2,2'-bis(diphenylphosphino)-1,1'-binaphthyl
Boc tert-butyloxycarbonyl
CH$_2$Cl$_2$ dichloromethane
CH$_3$CN or ACN acetonitrile
Cs$_2$CO$_3$ cesium carbonate
Cu(OAc)$_2$ copper (II) acetate
DCM dichloromethane
DEAD diethyl azodicarboxylate
DIAD diisopropyl azodicarboxylate
DIBAL diisobutylaluminum hydride
HCl hydrochloric acid
H$_2$SO$_4$ sulfuric acid
HEPES 4-(2-hydroxyethyl)piperaxine-1-ethanesulfonic acid
Hex hexane
Hunig's base N, N-diisopropylethyl amine
K$_2$CO$_3$ potassium carbonate
K—O-t-Bu/t-BuOK potassium tert-butoxide
LAH/LiAlH$_4$ lithium aluminum hydride
LiBH$_4$ lithium borohydride
mCPBA or m-CPBA meta-chloroperbenzoic acid
NBS N-bromosuccinimide
NCS N-chlorosuccinimide
Pd/C palladium on carbon
Pd$_2$(dba)$_3$ tris(dibenzylideneacetone)dipalladium(0)
Pd(OAc)$_2$ palladium acetate
PCy$_3$ tricyclohexylphosphine
P(t-Bu)$_3$ tri-tert-butylphosphine
SiO$_2$ silica oxide
SnCl$_2$ tin(II) chloride
TBAI tetra-n-butylammonium iodide
TMSCN trimethylsilyl cyanide
TEA triethylamine
TFA trifluoroacetic acid
THF tetrahydrofuran
TRIS tris(hydroxymethyl)aminomethane
KOAc potassium acetate
K$_3$PO$_4$ potassium phosphate
MgSO$_4$ magnesium sulfate
MsOH or MSA methylsulfonic acid
NaCl sodium chloride
NaHCO$_3$ sodium bicarbonate
NaOH sodium hydroxide
Na$_2$SO$_4$ sodium sulfate
Na$_2$S$_2$O$_4$ sodium dithionite
NaBH$_4$ sodium borohydride
NaO-t-Bu/t-BuONa sodium tert-butoxide
NH$_4$Cl ammonium chloride
OTs tosylate, para-toluenesulfonate
Xantphos 4,5-bis(diphenylphosphino)-9,9-dimethylxanthene
Zn zinc
ZnCl$_2$ zinc chloride Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (Wuts, P. G. M. and Greene, T. W. *Protecting Groups in Organic Synthesis*, 4th Edition, Wiley (2007)).

Compounds having the general Formula (I) can be prepared according to the general methods shown in the Schemes below. Compounds of formula (I) can be prepared using the general method shown in Scheme 1. Using the Petasis boronic acid Mannich reaction (Petasis, N. A. et al., *J. Am. Chem. Soc.*, 119:445-446 (1997); Petasis, N. A. et al., *Tetrahedron*, 53:16463-16470 (1997)), amines 1 are reacted with glyoxylic acid and phenyl boronic acids 2 to afford arylglycines 3. Arylglycines 3 in turn are coupled with amines 4 to afford amino alcohol amides 5. Treatment of amides 5 with phosgene (or a phosgene equivalent such as triphosgene) to generate the carbamic chloride intermediate in situ, followed by slow addition of this intermediate into a basic reaction mixture, such as triethylamine or Hunig's base in DCM or acetonitrile, effects macrocyclization to yield compounds 6 of formula (I) after protecting group manipulation if necessary.

Petasis boronic acid Mannich reaction is typically conducted in a solvent such as, but not limited to, toluene, dichloromethane, 1,2-dichloroethane, methanol, ethanol, dimethylformamide, or acetonitrile, or appropriate mixtures thereof. In some cases, mixtures of acetonitrile and dimethylformamide are preferred. Fluorinated alcohols such as hexafluoroisopropanol are useful additives that may improve the rate and or yield of the reaction. If necessary, the reaction is heated conventionally or in a microwave reactor to achieve a practical reaction rate.

The preparation of amines 1 is described in the experimental procedures for Intermediates 1-4. Preparation of phenylboronic acids 2 is described in the synthesis of Intermediate 5 and in examples. Additionally, preparation of phenylboronic acids 2 can be achieved through methods known to one skilled in the art of organic synthesis. The preparation of amines 4 is described in the experimental procedures for Intermediates 6, 8 and in the examples. Additionally, preparation of N-methylated benzylamines 4 can be achieved through methods known to one skilled in the art of organic synthesis.

Coupling reagents and conditions can be found in Bodanszky, *Principles of Peptide Synthesis*, Second Edition, Springer Verlag Ed, Berlin (1993) and in a recent review (Montalbetti, C. A. G. N. et al., *Tetrahedron*, 61:10819-11046 (2005)). Coupling reagents include, but not limited to, CDI, DIC, and EDCI. Optionally, an intermediate activated ester can be prepared by adding one equivalent of 1-hydroxybenzotriazole or 1-hydroxy-7-azabenzotriazole. Other coupling reagents include, but not limited to, BOP or HATU, which are usually reacted in the presence of a tertiary base such as DIEA or TEA. BOP is a preferred reagent for preparation of compounds of Formula (I). Addition of catalytic or stoichiometric DMAP may improve the reaction rate or yield. The reaction may be conducted in solvents such as, but not limited to, DCE, DCM, DMF, or mixtures thereof. Finally, it may be necessary to run the macrocyclization reaction under dilute conditions (initial concentration of 4<0.1 M) to favor macrocyclization over dimerization. Depending on the particular substituent groups present in the final compounds, deprotection steps may be required before or after the macrocyclization step to afford compounds of Formula (I).

Scheme 1

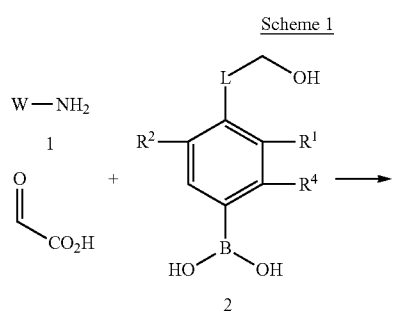

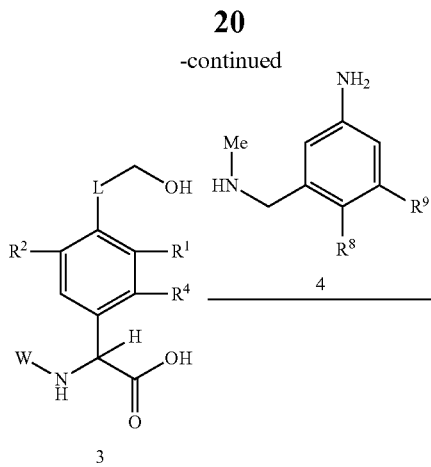

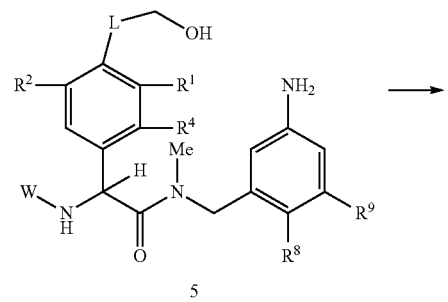

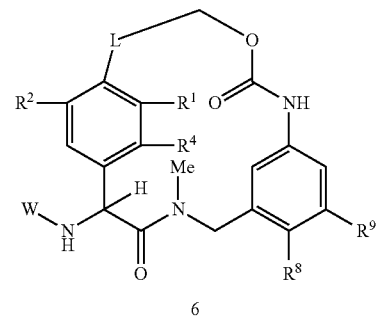

Compounds of formula (I) can also be prepared using the general method shown in Scheme 2. Using the Petasis boronic acid Mannich reaction, amines 1 are reacted with glyoxylic acid and elaborated phenyl boronic acids 7 to afford arylglycines 8. The protecting group PG in 8, for instance, a carbamate such as Cbz, may be deprotected by catalytic hydrogenation to an N-methylated benzylamine 9 Amino acids 9 can be cyclized to macrocycles 6 by slow addition of this intermediate into a mixture of base such as triethylamine or Hunig's base and coupling reagent such as BOP in DCM or acetonitrile. After a final protecting group manipulation, compounds of formula (I) are obtained.

Scheme 2

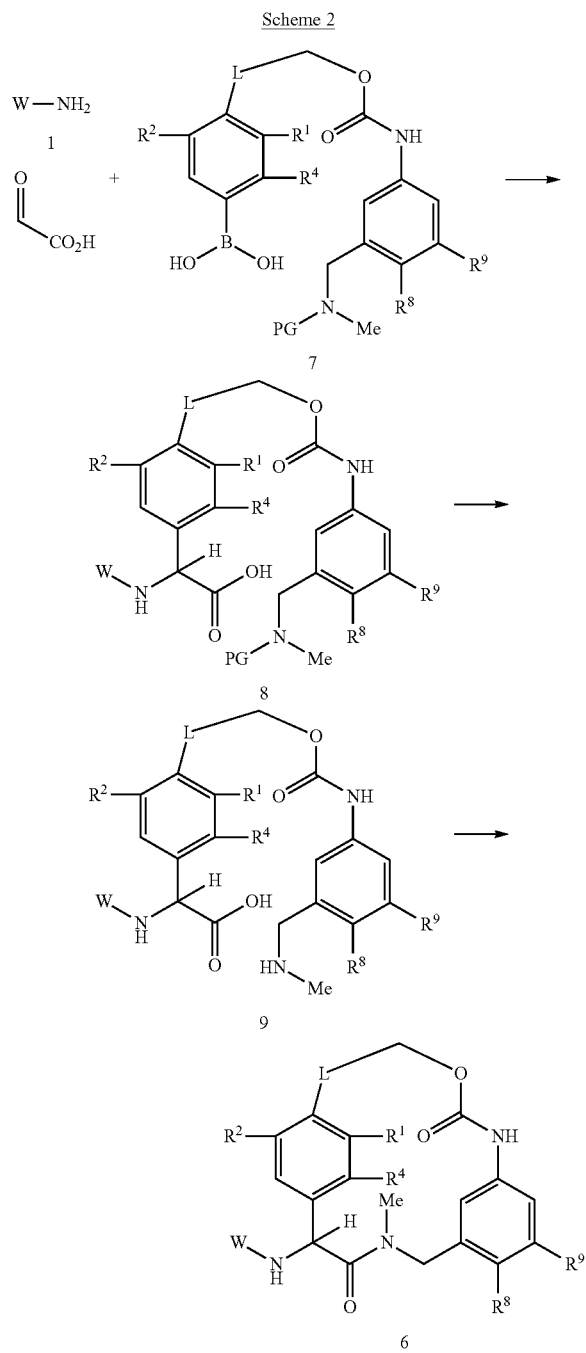

Preparation of the elaborated phenyl boronic acids 7 is described in Scheme 3. Treatment of amines 11 with phosgene (or a phosgene equivalent such as triphosgene) to generate the carbamic chloride intermediate in situ, followed by addition of this intermediate into a reaction mixture of aryl bromides 10 and base, such as triethylamine or Hunig's base in DCM or acetonitrile, affords carbamates 12. The bromide in carbamates 12 is converted to the boronic acids 7 by the Suzuki-Miyara coupling (Miyaura, N. et al., *Chem. Rev.*, 95:2457 (1995)).

Scheme 3

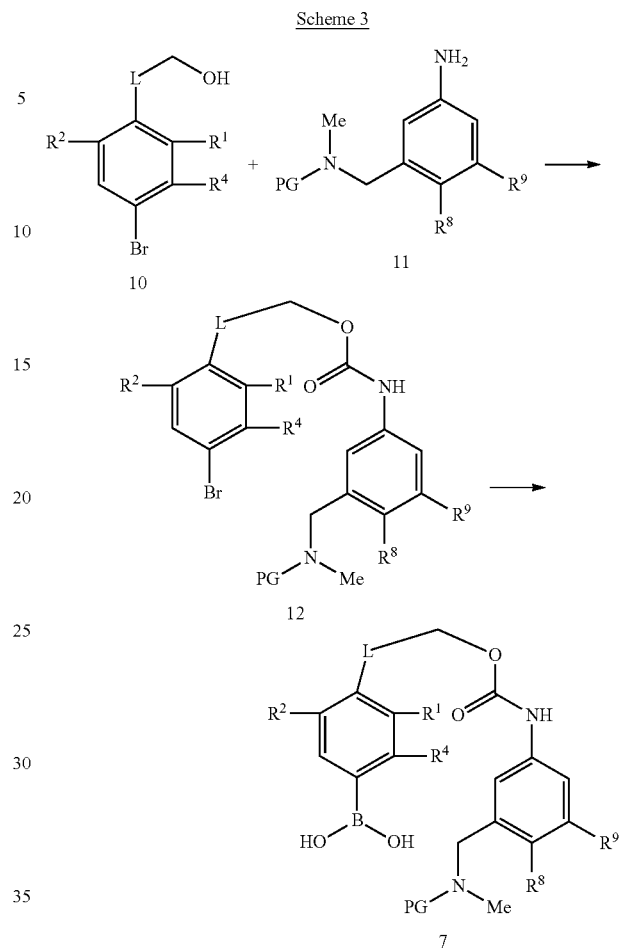

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm). Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). LCMS chromatograms were obtained on a Shimadzu HPLC system running Discovery VP software, coupled with a Waters ZQ mass spectrometer running MassLynx version 3.5 software using:

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 u C18 (4.5×30 mm). Flow rate was 4 ml/min. and UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3 u C18(2) (2.0×30 mm). Flow rate was 1 ml/min. and UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3 u C18(2) (4.5×30 mm). Flow rate was 5 ml/min. and UV detection was set to 220 nm. The LC column was maintained at room temperature.

Method D: 30-95% acetonitrile in H$_2$O with 0.1% TFA in 8 min run, Waters Xbridge 4.6×50 mm 5 um C18, flow rate 1.2 mL/min and UV detection was set to 220 nm. The LC column was maintained at room temperature.

Method E: 10-95% methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method F: 5-95% acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. and UV detection was set to 220 nm. The LC column was maintained at room temperature.

III. Biology

The compounds of the present invention are inhibitors of factor VIIa and are useful as anticoagulants for the prevention or treatment of thromboembolic disorders in mammals. In general, a thromboembolic disorder is a circulatory disease caused by blood clots (i.e., diseases involving fibrin formation, platelet activation, and/or platelet aggregation). The term "thromboembolic disorders (or conditions)" as used herein includes arterial or venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary and cerebral arterial thrombosis, cerebral embolism, kidney embolisms, pulmonary embolisms, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, and vessel grafts. The procedures include, but are not limited to: cardiopulmonary bypass, percutaneous coronary intervention, and hemodialysis.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant or antithrombotic effect of compounds of the present invention is believed to be due to inhibition of coagulation factor VIIa.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

A. In Vitro Assays

The effectiveness of compounds of the present invention as inhibitors of the coagulation Factors, VIIa, IXa, Xa, XIa, XIIa, plasma kallikrein or thrombin, tissue kallikrein and activated protein C, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

a. FVIIa Ki (25° C.): FVIIa Peptide Substrate Assay

S2288 (range of concentrations) and FVIIa inhibitor were incubated for 15 minutes (min) at 25° C. Reactions were initiated by addition of a solution of full-length human TF (6 nM), FVIIa (0.75 nM), and PCPS (25 µM). FVIIa hydrolyses S2288, which was monitored for up to 60 min at 405 nm. Steady-state reaction velocity data (vs) was globally fit to Equation 1 for competitive inhibition.

$$vs = V\max[S]/([S]+Km(1+[I]/Ki)) \quad \text{(Eq. 1)}$$

where Vmax is maximum velocity, [S] is substrate concentration, Km is the Michaelis-Menten constant, [I] is the inhibitor concentration, and Ki is the inhibitor dissociation constant (GraFit, version 5, Erithacus Software Ltd, West Sussex, UK).

FVIIa-Xase Ki (37° C.): S2765 (0.5 mM), PCPS (25 µM), calcium chloride (5 mM), full-length human TF (3 nM), human FVIIa (5 pM), and FVIIa inhibitor were incubated for 15 min at 37° C. Reactions were initiated by the addition of human FX (range of concentrations). Preliminary experiments revealed that the plasma purified FX contains a residual amount of human FVIIa which could not be removed by affinity chromatography. The residual FVIIa is sufficient, when combined with PCPS, calcium and TF to catalyze the conversion of FX to Xa, and was increased by the addition of 5 pM human FVIIa. FXa in turn hydrolyses S2765, which was monitored for 60 min at 405 nm. FXase activity was derived from the parabolic change in absorbance over time according to Equation 2:

$$\text{Absorbance} = \frac{1}{2}\text{a}t^2 + bt + c \quad \text{(Eq. 2)}$$

where a is proportional to the rate of FX activation=product=vs; b is proportional to the hydrolysis of S2765 in the absence of FXa; c is the absorbance at t=0. Steady-state reaction velocity data (vs) was globally fit to Equation 3 for non-competitive inhibition modified for contaminating enzyme (FVIIa) in the substrate (FX) as $$vs = (k\text{cat}(E + f[S])/((Km + [S])(1 + [I]/Ki)) \quad \text{(Eq. 3)}$$

where kcat is the enzyme turnover rate, E is the concentration of enzyme added, f is the molar fraction of enzyme contained in the substrate, and the rest as defined above.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; CHROMOGENIX®) at a concentration of 0.0002-0.00035 M.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; CHROMOGENIX® or AnaSpec) at a concentration of 0.0002-0.001 M.

Factor XIIa determinations were made in 50 mM HEPES buffer at pH 7.4 containing 145 mM NaCl, 5 mM KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; CHROMOGENIX®) at a concentration of 0.00008-0.0004 M. The $K_m$ value used for calculation of $K_i$ was 0.00005 to 0.00007 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; CHROMOGENIX® or AnaSpec) at a concentration of 0.0002-0.0004 M.

Tissue kallikrein-1 activity was determined in reactions containing 0.05 nM enzyme and 90 µM substrate (H-D-Val-Leu-Arg-AFC) in buffer (0.1M sodium phosphate pH 7.4, 0.2 M NaCl, 0.5% PEG 8000, and 1% DMSO). Assays were performed using 96-well microtiter plates (COSTAR® 3600, CORNING®, NY, USA) and a thermostatic temperature controlled plate reader (SPECTRAMAX® Gemini, Molecular Devices, Sunnyvale, Calif., USA). Fluorescence was monitored using 400 nm excitation and 505 nm emission wavelengths.

APC activity was determined in reactions containing 0.05 nM enzyme and 90 µM substrate (pyroGlu-Pro-Arg-pNA) in buffer (0.1M sodium phosphate pH 7.4, 0.2 M NaCl, 0.5% PEG 8000, and 1% DMSO). Assays were performed using 96-well microtiter plates (COSTAR® 3600, CORNING®, NY, USA) and a thermostatic temperature controlled plate reader (SPECTRAMAX® Gemini, Molecular Devices, Sunnyvale, Calif., USA). Fluorescence was monitored using 400 nm excitation and 505 nm emission wavelengths.

The Michaelis constant, $K_m$, for substrate hydrolysis by each protease, was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o-v_s)/v_s = I/(K_i(1+S/K_m)) \text{ for a competitive inhibitor with one binding site; or}$$

$$v_s/v_o = A+((B-A)/1+((IC_{50}/(I)_n))); \text{ and}$$

$$K_i = IC_{50}/(1+S/K_m) \text{ for a competitive inhibitor}$$

where:

$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme:inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FVIIa versus protease P=$K_i$ for protease P/$K_i$ for FVIIa). Compounds with selectivity ratios >20 are considered selective. Compounds with selectivity ratios >100 are preferred, and compounds with selectivity ratios >500 are more preferred.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 50 or 100 percent, respectively. The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat, or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Illinois). Similarly, clotting times can be determined from laboratory animal species or humans dosed with compounds of the invention.

Prothrombin Time (PT) is determined using thromboplastin (Thromboplastin C Plus, Dade-Behring, Illinois) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Deficient FVII-PT (FVII-def PT) was performed by mixing human FVII immunodepleted plasma with normal pooled plasma from different species to produce a clotting time of about 40 seconds (s). For PT and FVII-def PT, plasma (50 µl) was warmed to 37° C. for 3 min before adding PT reagent (100 µl). Determinations were performed in duplicate and expressed as a mean ratio of treated vs. baseline control. The concentrations required to prolong clotting time by two-fold (EC2×) were calculated by linear interpolation (Microsoft Excel, Redmond, Wash., USA) and are expressed as total plasma concentrations, not final assay concentrations after addition of clotting assay reagents.

Activated Partial Thromboplastin Time (aPTT) is determined using ALEXIN® (Trinity Biotech, Ireland) or ACTIN® (Dade-Behring, Illinois) following the directions in the package insert. Plasma (0.05 mL) is warmed to 37° C. for 1 minute. ALEXIN® or ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

b. Parallel Artificial Membrane Permeability Assay (PAMPA)

The PAMPA gastrointestinal tract (GIT) lipid, donor and solution concentrates and PAMPA 96-well sandwich plates were obtained from pION Inc. (Woburn, Ma). The 96-well high-sensitivity UV plates were obtained from Greiner Bio-One (Monroe, N.C.). The 96-well, 2-mL, 0.45-μm hydrophilic PVDF filter block was purchased from Whatman (Freiburg, Germany). The 96-well, 2-mL, deep-well mix plates were obtained from CORNING® (Lowell, Mass.). The 96-well V-bottom storage plates used to store compounds in DMSO were obtained from BD Biosciences (Bedford, Mass.).

Test compounds and the control compounds were mixed 1:100 in 600 μL of donor solution to create a final concentration of 100 μM and filtered. Following filtration, 150 μL was transferred to a UV plate and 200 μL of donor solution was transferred to the bottom portion of the sandwich plate. This UV plate was used as a $T_0$ or "reference" plate and was read by UV plate reader at 250 to 498 nm. The top portion of the sandwich plate was painted with 4 μL of lipid and 200 μL of acceptor buffer was added. The top and bottom plates were then combined and the sandwich plate was incubated for 4 hours. Following incubation, the sandwich plate was separated, 150 μL of acceptor buffer was transferred to a UV plate and read by the UV plate reader, and 150 μL of donor buffer from the sandwich plate was transferred to a UV plate and also read by the UV plate reader.

Results for test compounds were reported as permeability coefficient (Pc) in nm/s at both pH 7.4 and at pH 5.5 for donor solution. The formula used to calculate Pc for test compounds is as follows:

$$Pc=(C_A(t) \cdot V_A)/(S \cdot C_0 \cdot t)$$

where:
$C_A(t)$=concentration of acceptor well after time t
$V_A$=volume of acceptor well
S=surface area of the membrane
$C_0$=initial concentration of donor
t=Time
Validation of the assay was made by comparing control criteria with historical references and human absorption values.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arterio-Venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, Factor XII, Factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

Comparator Compounds

The following comparator compounds and their preparations are disclosed in US 2007/0208054A1:

| Comparator No. (Example No. in US 2007/0208054 A1) | Structure |
|---|---|
| Comparator 1 (Example 20 in US 2007/0208054 A1) | |
| Comparator 2 (Example 27 in US 2007/0208054 A1) | 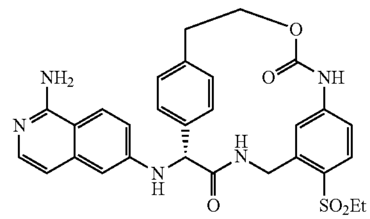 |
| Comparator 3 (Example 33 in US 2007/0208054 A1) | 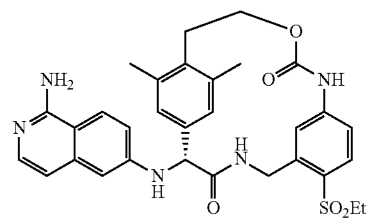 |
| Comparator 4 (Example 76 in US 2007/0208054 A1) | 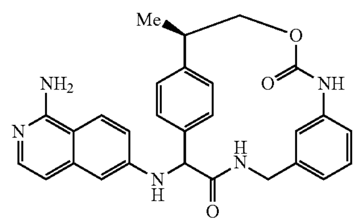 [SMILES: C[C@H]1COC(=O)Nc2cccc(c2)CNC(=O)C(Nc2ccc3c(N)nccc3c2)c2ccc1cc2] |

The following representative in vitro biological data was measured in a binding assay for the Comparator Compounds and the exemplified examples herein:

TABLE 1

| Representative In Vitro Biological Data for Comparator Compounds | | | | |
|---|---|---|---|---|
| Comparator No. | Structure | FVIIa Ki, nM 37° C. | HK1 Ki, nM 37° C. | Ki(HK1)/ Ki(FVIIa) |
| Comparator 1 | | 38 | 3330 | 87 |

TABLE 1-continued

Representative In Vitro Biological Data for Comparator Compounds

| Comparator No. | Structure | FVIIa Ki, nM 37° C. | HK1 Ki, nM 37° C. | Ki(HK1)/ Ki(FVIIa) |
|---|---|---|---|---|
| Comparator 2 | *structure* | 11 | 110 | 10 |
| Comparator 3 | *structure* | 1.1 | 70 | 64 |
| Comparator 4 | *structure* | >140 | ND | |

TABLE 2

Representative In Vitro Biological Data for Exemplified Compounds

| Example No. in this application | Structure | FVIIa Ki, nM 37° C. | HK1 Ki, nM 37° C. | Ki(HK1)/ Ki(FVIIa) |
|---|---|---|---|---|
| Example 1 | *structure* | 2.5 | 650 | 260 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 2 | 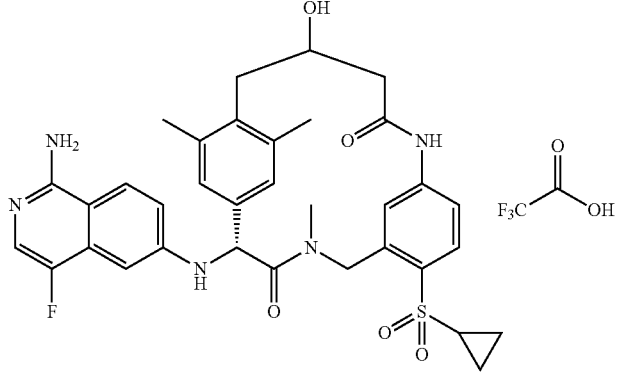 [SMILES: Cc1cc2cc(C)c1CC(O)CC(=O)Nc1ccc(S(=O)(=O)C3CC3)c(c1)CN(C)C(=O)[C@@H]2Nc1ccc2c(N)ncc(F)c2c1 ; O=C(O)C(F)(F)F] | 2.3 | 1620 | 704 |
| Example 3 | 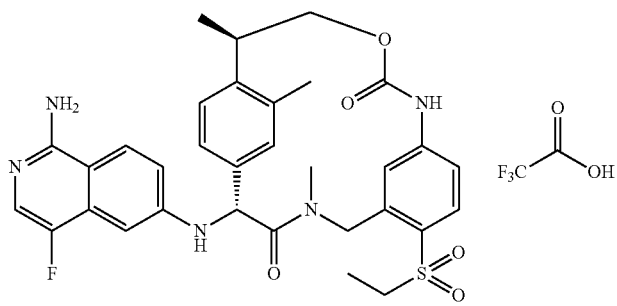 [SMILES: CCS(=O)(=O)c1ccc2cc1CN(C)C(=O)[C@H](Nc1ccc3c(N)ncc(F)c3c1)c1ccc(c(C)c1)[C@@H](C)COC(=O)N2 ; O=C(O)C(F)(F)F] | 2.3 | 270 | 117 |
| Example 4 | 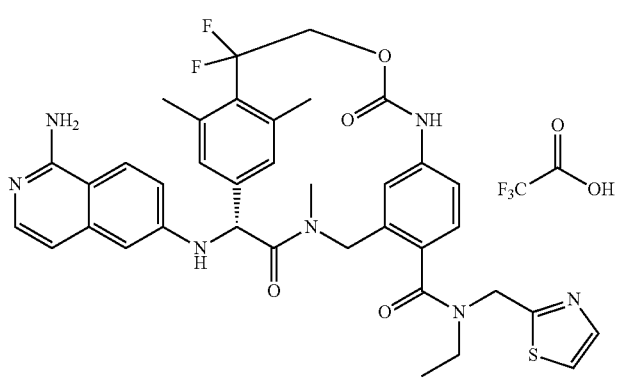 [SMILES: CCN(Cc1nccs1)C(=O)c1ccc2cc1CN(C)C(=O)[C@H](Nc1ccc3c(N)nccc3c1)c1cc(C)c(c(C)c1)C(F)(F)COC(=O)N2 ; O=C(O)C(F)(F)F] | 2.2 | 300 | 136 |
| Example 5 | 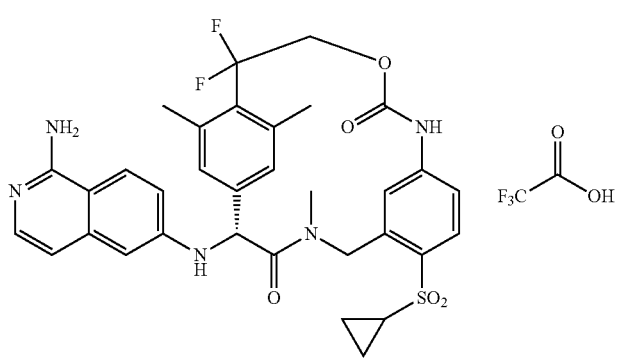 [SMILES: Cc1cc2cc(C)c1C(F)(F)COC(=O)Nc1ccc(S(=O)(=O)C3CC3)c(c1)CN(C)C(=O)[C@@H]2Nc1ccc2c(N)nccc2c1 ; O=C(O)C(F)(F)F] | 2.0 | 290 | 145 |

TABLE 2-continued

Representative In Vitro Biological Data for Exemplified Compounds

| Example No. in this application | Structure | FVIIa Ki, nM 37° C. | HK1 Ki, nM 37° C. | Ki(HK1)/ Ki(FVIIa) |
|---|---|---|---|---|
| Example 6 | 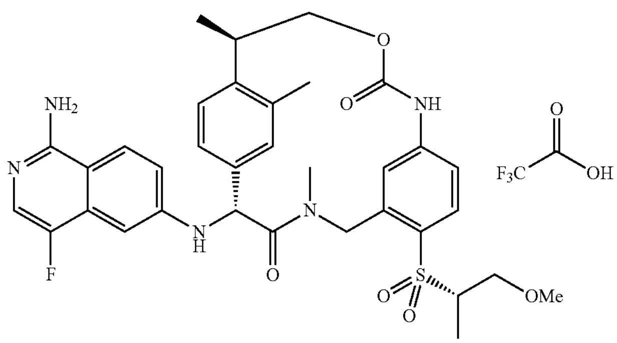 [SMILES: COC[C@H](C)S(=O)(=O)c1ccc2cc1CN(C)C(=O)[C@H](Nc1ccc3c(N)ncc(F)c3c1)c1ccc(c(C)c1)[C@@H](C)COC(=O)N2 ; O=C(O)C(F)(F)F] | 1.8 | 550 | 306 |
| Example 7 | 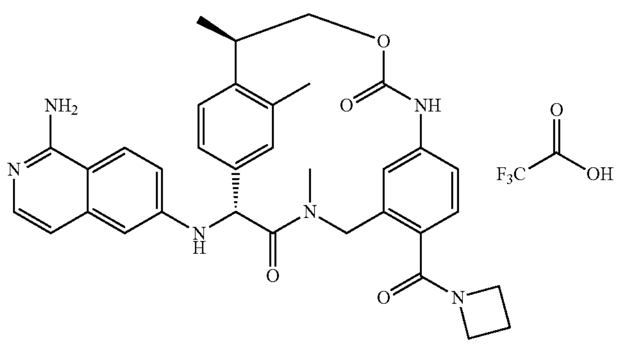 [SMILES: Cc1cc2ccc1[C@@H](C)COC(=O)Nc1ccc(C(=O)N3CCC3)c(c1)CN(C)C(=O)[C@@H]2Nc1ccc2c(N)nccc2c1 ; O=C(O)C(F)(F)F] | 1.2 | 630 | 525 |
| Example 8 | 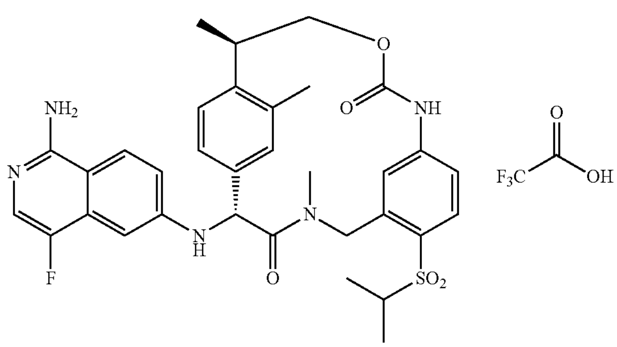 [SMILES: Cc1cc2ccc1[C@@H](C)COC(=O)Nc1ccc(S(=O)(=O)C(C)C)c(c1)CN(C)C(=O)[C@@H]2Nc1ccc2c(N)ncc(F)c2c1 ; O=C(O)C(F)(F)F] | 1.2 | 700 | 583 |
| Example 9 | 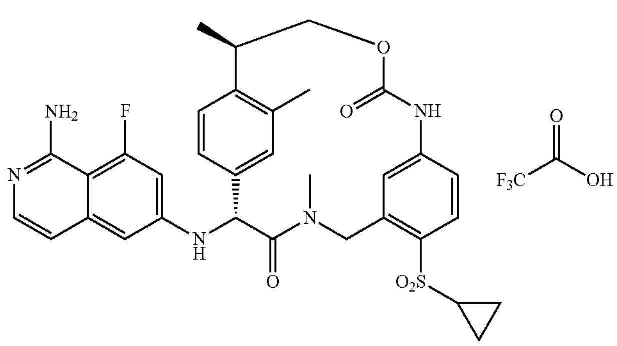 [SMILES: Cc1cc2ccc1[C@@H](C)COC(=O)Nc1ccc(S(=O)(=O)C3CC3)c(c1)CN(C)C(=O)[C@@H]2Nc1cc(F)c2c(N)nccc2c1 ; O=C(O)C(F)(F)F] | 1.0 | 100 | 100 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 10 | 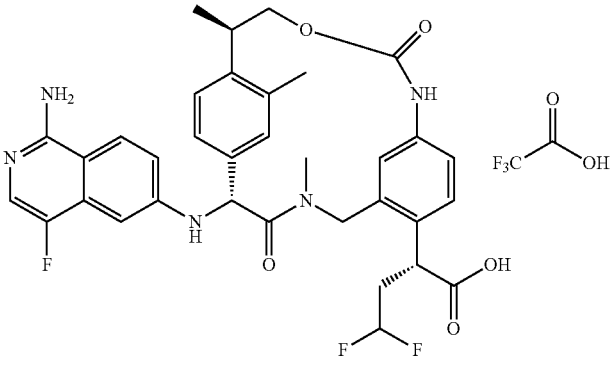 [SMILES: Cc1cc2ccc1[C@@H](C)COC(=O)Nc1ccc([C@@H](CC(F)F)C(=O)O)c(c1)CN(C)C(=O)[C@@H]2Nc1ccc2c(N)ncc(F)c2c1 ; O=C(O)C(F)(F)F] | 0.9 | 320 | 356 |
| Example 11 | 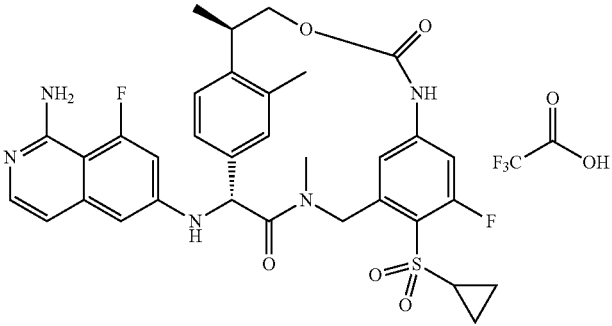 [SMILES: Cc1cc2ccc1[C@@H](C)COC(=O)Nc1cc(F)c(S(=O)(=O)C3CC3)c(c1)CN(C)C(=O)[C@@H]2Nc1cc(F)c2c(N)nccc2c1 ; O=C(O)C(F)(F)F] | 0.66 | 96 | 145 |
| Example 12 | 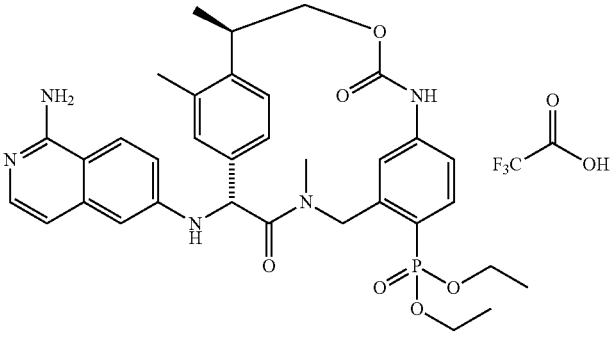 [SMILES: CCOP(=O)(OCC)c1ccc2cc1CN(C)C(=O)[C@H](Nc1ccc3c(N)nccc3c1)c1ccc(c(C)c1)[C@@H](C)COC(=O)N2 ; O=C(O)C(F)(F)F] | 0.62 | 390 | 629 |
| Example 13 | 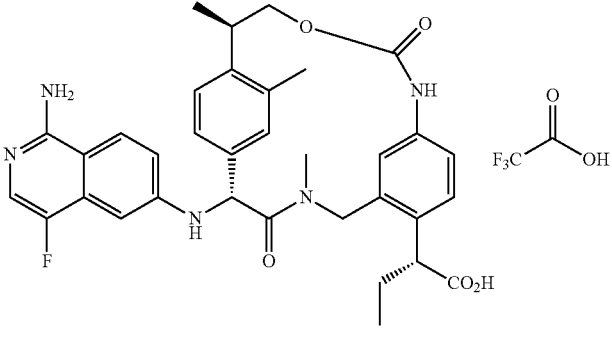 [SMILES: CC[C@@H](C(=O)O)c1ccc2cc1CN(C)C(=O)[C@H](Nc1ccc3c(N)ncc(F)c3c1)c1ccc(c(C)c1)[C@@H](C)COC(=O)N2 ; O=C(O)C(F)(F)F] | 0.61 | 380 | 623 |

TABLE 2-continued

Representative In Vitro Biological Data for Exemplified Compounds

| Example No. in this application | Structure | FVIIa Ki, nM 37° C. | HK1 Ki, nM 37° C. | Ki(HK1)/ Ki(FVIIa) |
|---|---|---|---|---|
| Example 14 | 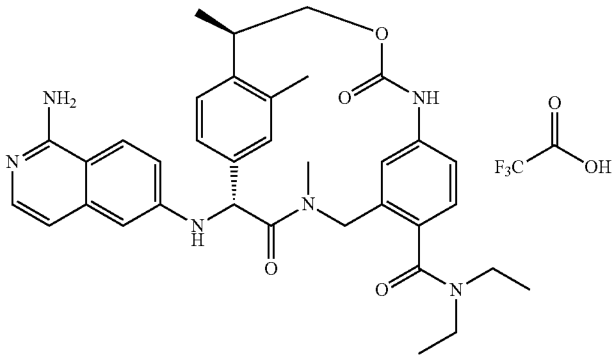 [SMILES: CCN(CC)C(=O)c1ccc2cc1CN(C)C(=O)[C@H](Nc1ccc3c(N)nccc3c1)c1ccc(c(C)c1)[C@@H](C)COC(=O)N2 ; O=C(O)C(F)(F)F] | 0.57 | 600 | 1053 |
| Example 15 | 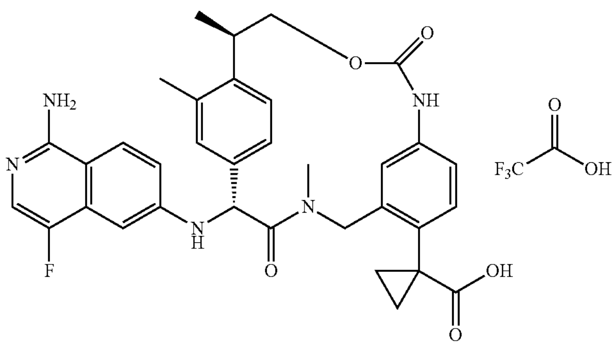 [SMILES: Cc1cc2ccc1[C@@H](C)COC(=O)Nc1ccc(C3(C(=O)O)CC3)c(c1)CN(C)C(=O)[C@@H]2Nc1ccc2c(N)ncc(F)c2c1 ; O=C(O)C(F)(F)F] | 0.55 | 1100 | 2000 |
| Example 16 | 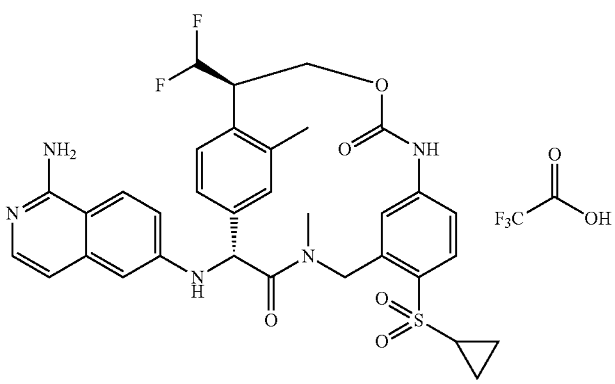 [SMILES: Cc1cc2ccc1[C@@H](C(F)F)COC(=O)Nc1ccc(S(=O)(=O)C3CC3)c(c1)CN(C)C(=O)[C@@H]2Nc1ccc2c(N)nccc2c1 ; O=C(O)C(F)(F)F] | 0.50 | 180 | 360 |
| Example 17 | 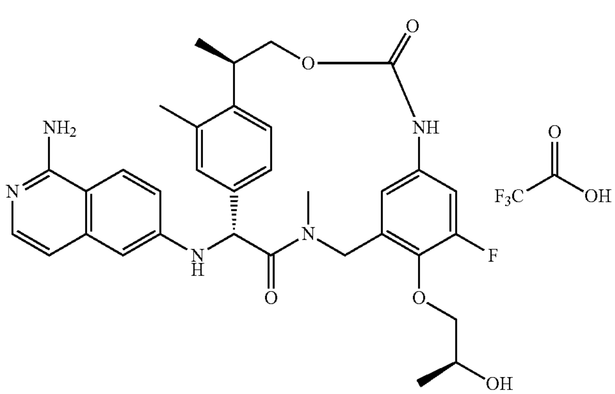 [SMILES: Cc1cc2ccc1[C@@H](C)COC(=O)Nc1cc(F)c(OC[C@H](C)O)c(c1)CN(C)C(=O)[C@@H]2Nc1ccc2c(N)nccc2c1 ; O=C(O)C(F)(F)F] | 0.46 | 400 | 870 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 18 | 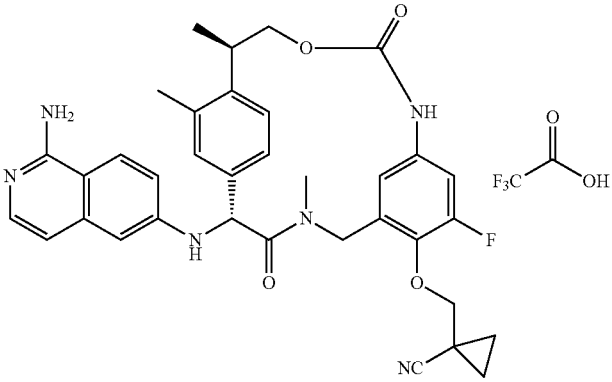 [SMILES: Cc1cc2ccc1[C@@H](C)COC(=O)Nc1cc(F)c(OCC3(C#N)CC3)c(c1)CN(C)C(=O)[C@@H]2Nc1ccc2c(N)nccc2c1 ; O=C(O)C(F)(F)F] | 0.44 | 490 | 1114 |
| Example 19 | 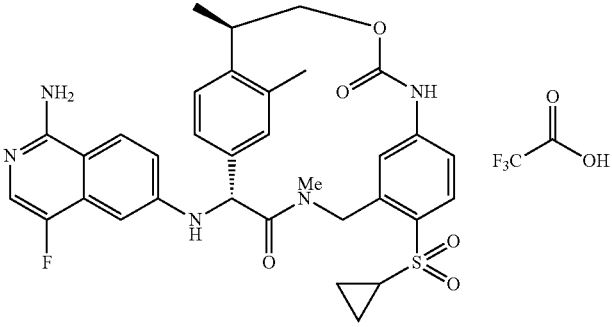 [SMILES: Cc1cc2ccc1[C@@H](C)COC(=O)Nc1ccc(S(=O)(=O)C3CC3)c(c1)CN(C)C(=O)[C@@H]2Nc1ccc2c(N)ncc(F)c2c1 ; O=C(O)C(F)(F)F] | 0.43 | 650 | 1511 |
| Example 20 | 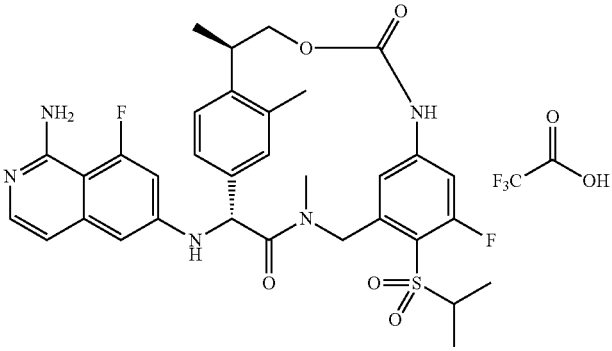 [SMILES: Cc1cc2ccc1[C@@H](C)COC(=O)Nc1cc(F)c(S(=O)(=O)C(C)C)c(c1)CN(C)C(=O)[C@@H]2Nc1cc(F)c2c(N)nccc2c1 ; O=C(O)C(F)(F)F] | 0.36 | 120 | 333 |
| Example 21 | 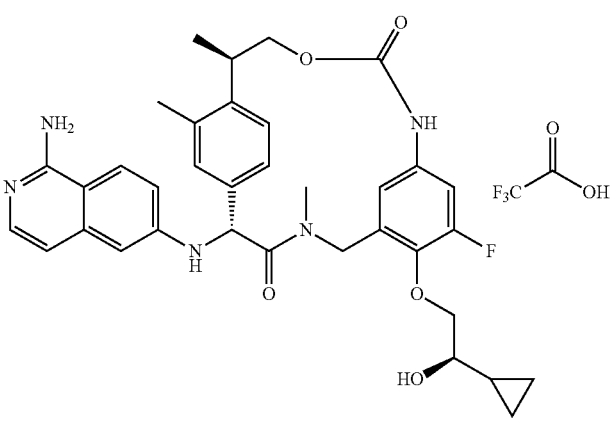 [SMILES: Cc1cc2ccc1[C@@H](C)COC(=O)Nc1cc(F)c(OC[C@H](O)C3CC3)c(c1)CN(C)C(=O)[C@@H]2Nc1ccc2c(N)nccc2c1 ; O=C(O)C(F)(F)F] | 0.34 | 550 | 1618 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 22 | 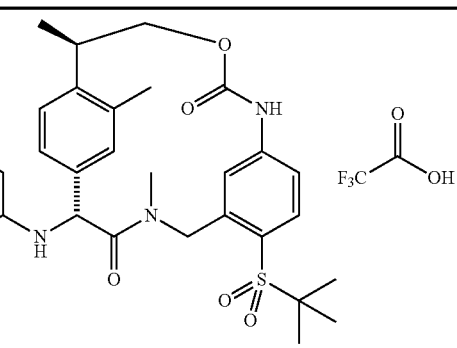 | 0.31 | 780 | 2516 |
| Example 23 | 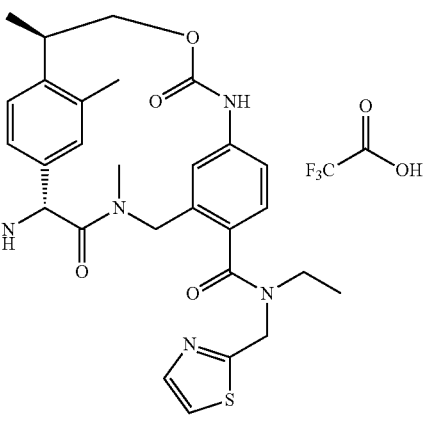 | 0.30 | 330 | 1100 |
| Example 24 | 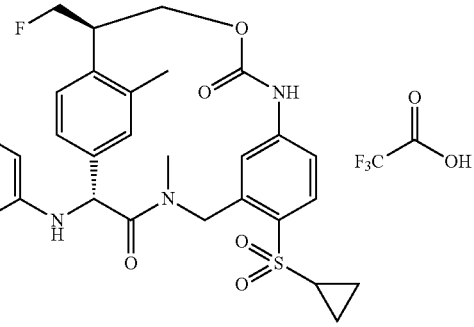 | 0.28 | 200 | 714 |
| Example 25 | 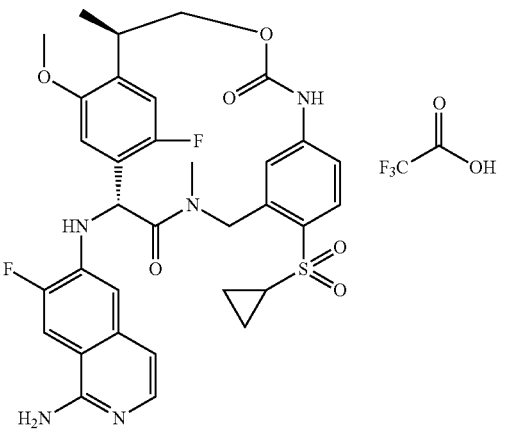 [SMILES: COc1cc2c(F)cc1[C@@H](C)COC(=O)Nc1ccc(S(=O)(=O)C3CC3)c(c1)CN(C)C(=O)[C@@H]2Nc1cc2ccnc(N)c2cc1F ; O=C(O)C(F)(F)F] | 0.25 | 270 | 1080 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 26 | 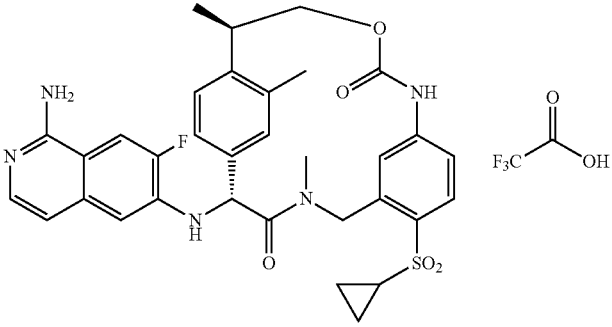 [SMILES: Cc1cc2ccc1[C@@H](C)COC(=O)Nc1ccc(S(=O)(=O)C3CC3)c(c1)CN(C)C(=O)[C@@H]2Nc1cc2ccnc(N)c2cc1F ; O=C(O)C(F)(F)F] | 0.23 | 790 | 3434 |
| Example 27 | 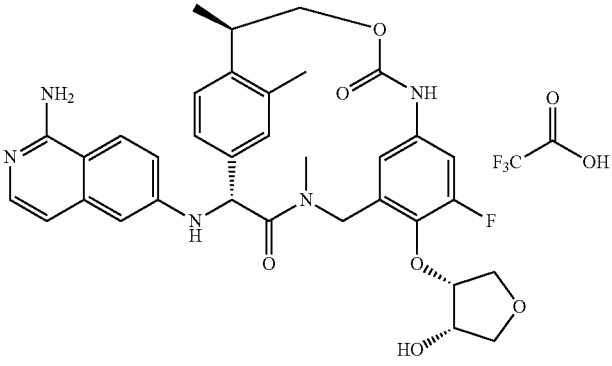 [SMILES: Cc1cc2ccc1[C@@H](C)COC(=O)Nc1cc(F)c(O[C@@H]3COC[C@@H]3O)c(c1)CN(C)C(=O)[C@@H]2Nc1ccc2c(N)nccc2c1 ; O=C(O)C(F)(F)F] | 0.23 | 320 | 1391 |
| Example 28 | 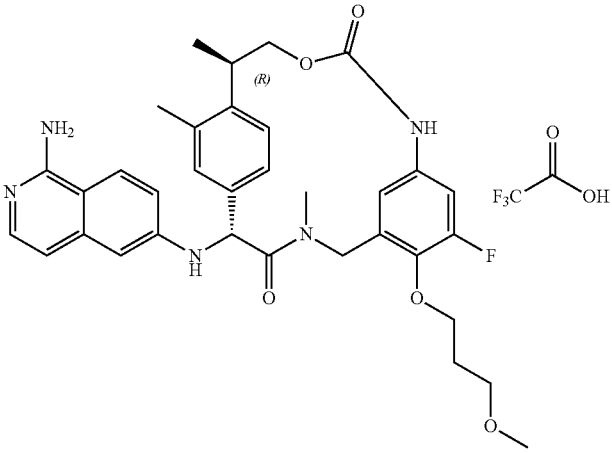 | 0.2 | 290 | 1450 |
| Example 29 | 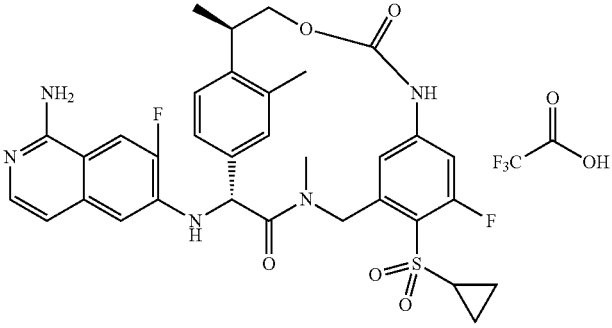 [SMILES: Cc1cc2ccc1[C@@H](C)COC(=O)Nc1cc(F)c(S(=O)(=O)C3CC3)c(c1)CN(C)C(=O)[C@@H]2Nc1cc2ccnc(N)c2cc1F ; O=C(O)C(F)(F)F] | 0.17 | 750 | 4412 |

TABLE 2-continued
Representative In Vitro Biological Data for Exemplified Compounds
| Example No. in this application | Structure | FVIIa Ki, nM 37° C. | HK1 Ki, nM 37° C. | Ki(HK1)/ Ki(FVIIa) |
|---|---|---|---|---|
| Example 30 | 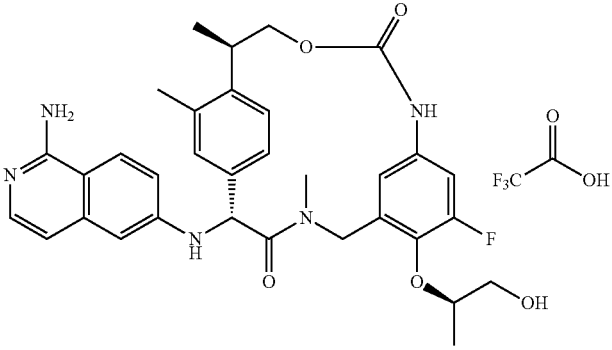 [SMILES: Cc1cc2ccc1[C@@H](C)COC(=O)Nc1cc(F)c(O[C@H](C)CO)c(c1)CN(C)C(=O)[C@@H]2Nc1ccc2c(N)nccc2c1 ; O=C(O)C(F)(F)F] | 0.17 | 70 | 412 |
| Example 31 | 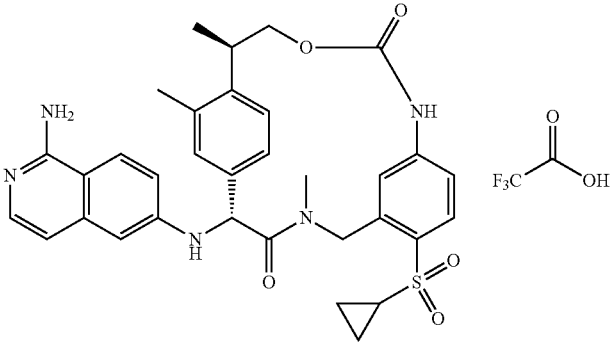 [SMILES: Cc1cc2ccc1[C@@H](C)COC(=O)Nc1ccc(S(=O)(=O)C3CC3)c(c1)CN(C)C(=O)[C@@H]2Nc1ccc2c(N)nccc2c1 ; O=C(O)C(F)(F)F] | 0.17 | 270 | 1588 |
| Example 32 | 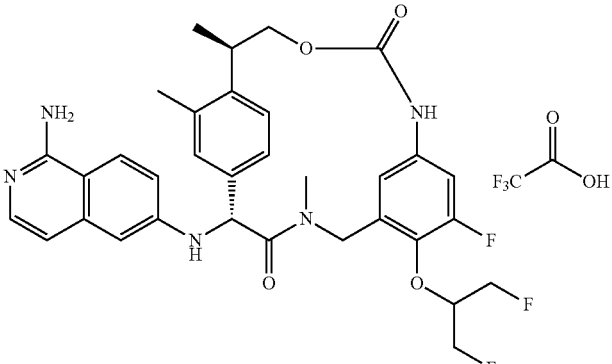 | 0.15 | 41 | 273 |
| Example 33 | 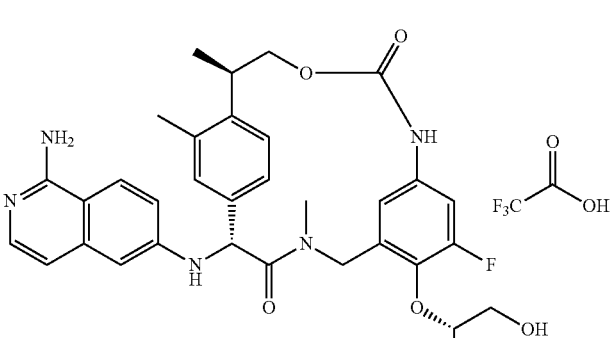 | 0.14 | 50 | 357 |

TABLE 2-continued

Representative In Vitro Biological Data for Exemplified Compounds

| Example No. in this application | Structure | FVIIa Ki, nM 37° C. | HK1 Ki, nM 37° C. | Ki(HK1)/ Ki(FVIIa) |
|---|---|---|---|---|
| Example 34 | 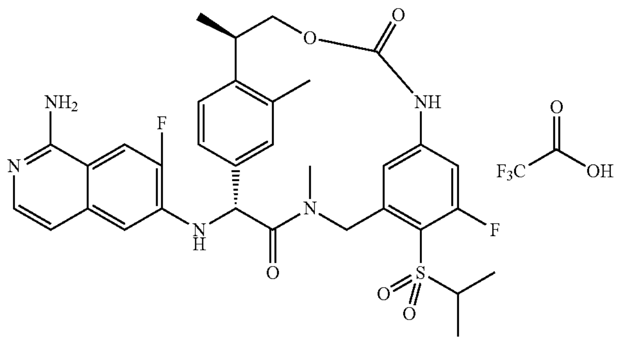 [SMILES: Cc1cc2ccc1[C@@H](C)COC(=O)Nc1cc(F)c(S(=O)(=O)C(C)C)c(c1)CN(C)C(=O)[C@@H]2Nc1cc2ccnc(N)c2cc1F ; O=C(O)C(F)(F)F] | 0.14 | 2100 | 15000 |
| Example 35 | 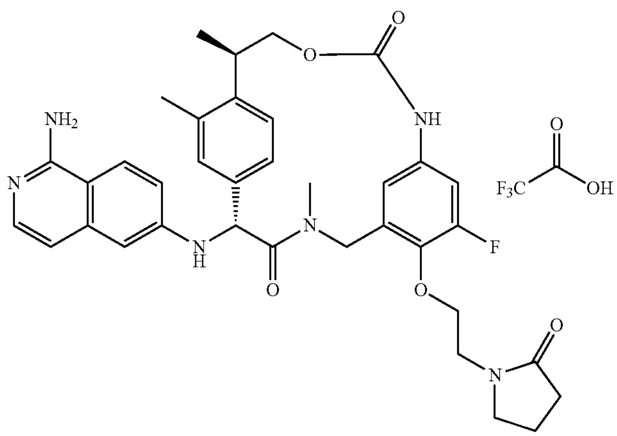 [SMILES: Cc1cc2ccc1[C@@H](C)COC(=O)Nc1cc(F)c(OCCN3CCCC3=O)c(c1)CN(C)C(=O)[C@@H]2Nc1ccc2c(N)nccc2c1 ; O=C(O)C(F)(F)F] | 0.14 | 210 | 1500 |
| Example 36 | 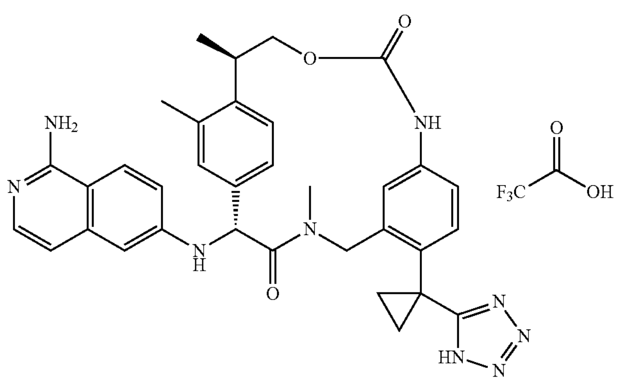 [SMILES: Cc1cc2ccc1[C@@H](C)COC(=O)Nc1ccc(C3(c4nnn[nH]4)CC3)c(c1)CN(C)C(=O)[C@@H]2Nc1ccc2c(N)nccc2c1 ; O=C(O)C(F)(F)F] | 0.12 | 230 | 1917 |
| Example 37 | 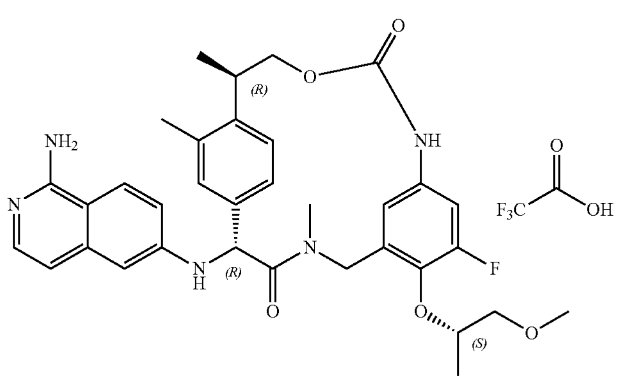 | 0.14 | 190 | 1357 |

TABLE 2-continued

Representative In Vitro Biological Data for Exemplified Compounds

| Example No. in this application | Structure | FVIIa Ki, nM 37° C. | HK1 Ki, nM 37° C. | Ki(HK1)/ Ki(FVIIa) |
|---|---|---|---|---|
| Example 38 | [structure] | 0.05 | 290 | 5800 |
| Example 39 | [structure] | 0.02 | 100 | 5000 |

Surprisingly, it was discovered that the compounds of the present invention possess beneficial pharmacological characteristics which were superior to those of compounds disclosed in US 2007/0208054 A1. The compounds of the present invention showed significantly improved inhibitory potency against FVIIa and a higher level of selectivity against tissue kallikrein, which may reduce the efficacious dose and reduce adverse side effects.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., other anti-platelet agents or other pharmaceutically active material. Additionally, the present compounds may be used in combination with one or more of various other therapeutic agents, including: anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phosphodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving $P2Y_1$ or anti-platelet activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1: 6-Amino-1-(di-tert-butoxycarbonylamino)isoquinoline

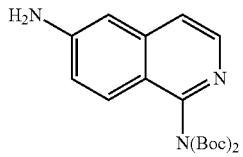

Intermediate 1 was prepared according to the procedure reported in WO 07/076431.

Intermediate 2: 6-Amino-1-(di-tert-butoxycarbonylamino)-8-fluoro isoquinoline

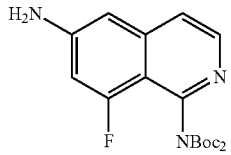

Intermediate 2 was prepared according to the procedure reported in WO 07/076431.

Intermediate 3: 6-Amino-1-(di-tert-butoxycarbonylamino)-4-fluoroisoquinoline

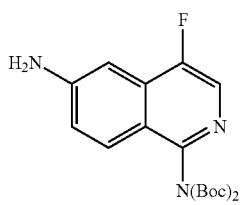

Intermediate 3A: Methyl 2-methyl-4-nitrobenzoate

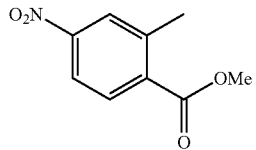

To 2-methyl-4-nitrobenzoic acid (10.5 g, 58.0 mmol) in $CH_2Cl_2$ (80 ml) was added 2.0 M oxalyl chloride in methylene chloride (39.9 ml, 80 mmol), followed by DMF (0.224 ml, 2.90 mmol). The mixture was stirred at 40° C. for 1.5 h and then at rt for 0.5 h. Solvent was removed and the residue was put on high vacuum for 0.5 h. The acyl chloride prepared was then dissolved in methylene chloride (40 mL) and cooled at 0° C., MeOH (40 mL) was added and the mixture was stirred at 0° C. for 0.5 h. Solvent was removed, the crude was diluted with EtOAc, washed with sat. sodium bicarbonate, brine. The organic layer was dried over sodium sulfate and concentrated to give Intermediate 3A (11.35 g, 58.2 mmol, 100% yield) as a white solid. $^1$H NMR (400 MHz, chloroform-d) δ ppm 7.98-8.11 (m, 3H) 3.93 (s, 3H) 2.67 (s, 3H).

Intermediate 3B: (E)-Methyl 2-(2-(dimethylamino)vinyl)-4-nitrobenzoate

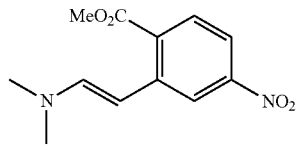 [SMILES: COC(=O)c1ccc([N+](=O)[O-])cc1/C=C/N(C)C]

To Intermediate 3A (11.35 g, 58.2 mmol) in DMF (15 ml) was added 1-tert-butoxy-N,N,N',N'-tetramethylmethanediamine (39.6 ml, 192 mmol). The mixture was heated at 143° C. for 3.0 h. DMF was removed by vacuum distillation at 70° C. to leave a semi solid. The semi-solid was triturated with EtOAc/hexanes (1:4) and stored at 4° C. overnight. The precipitate was collected by filtration to give Intermediate 3B (10.2 g, 40.8 mmol, 70.1% yield) as a dark solid. $^1$H NMR (400 MHz, chloroform-d) δ ppm 8.21 (d, J=2.20 Hz, 1H) 7.87 (d, J=8.79 Hz, 1H) 7.66 (dd, J=8.79, 2.20 Hz, 1H) 7.02 (d, J=13.19 Hz, 1H) 6.12 (d, J=13.74 Hz, 1H) 3.91 (s, 3H) 2.94 (s, 6H).

Intermediate 3C: 6-Nitroisoquinolin-1(2H)-one

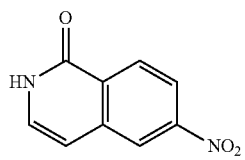 [SMILES: O=c1[nH]ccc2cc([N+](=O)[O-])ccc12]

To Intermediate 3B (1.54 g, 6.15 mmol) in a microwave tube was added 8.0 N ammonia in ethylene glycol (7.69 mL, 61.5 mmol). The tube was placed in microwave and heated at 140° C. for 30 min. The reaction mixture was triturated with EtOAc, stored at 0° C. over night. The precipitate was collected to give Intermediate 3C (0.995 g, 5.23 mmol, 85% yield) as a brown solid. The filtrate was washed with water. The organic layer was dried over sodium sulfate. After evaporation of solvent, the crude was triturated with EtOAc to give additional product. $^1$H NMR (400 MHz, DMSO-$d_6$) δ ppm 11.35 (br. s., 1H) 8.63 (d, J=2.20 Hz, 1H) 8.39 (d, J=8.79 Hz, 1H) 8.19 (dd, J=8.79, 2.20 Hz, 1H) 7.36 (d, J=7.03 Hz, 1H) 6.82 (d, 1H); MS (ESI) m/z: 191.1 (M+H)$^+$.

Intermediate 3D: 4-Fluoro-3-methoxy-6-nitro-3,4-dihydroisoquinolin-1(2H)-one

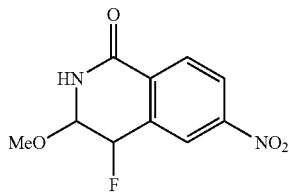 [SMILES: COC1NC(=O)c2ccc([N+](=O)[O-])cc2C1F]

To Intermediate 3C (6.5 g, 34.2 mmol) in acetonitrile (180 mL) and MeOH (180 mL) was added Selectfluor (15.44 g, 43.6 mmol). The mixture was heated at 82° C. for 1.5 h. Solvent was removed under vacuum. The crude was suspended in EtOAc, stirred with 160 mL of 0.5N HCl, and the organic layer was collected. The aqueous layer was further extracted with EtOAc, the combined organic layers were washed with brine, dried over sodium sulfate. After evaporation of solvent, Intermediate 3D (8.1 g, 33.7 mmol, 99% yield) was obtained as a brownish solid. $^1$H NMR (400 MHz, chloroform-d) δ ppm 8.56 (br, 1H) 8.11-8.38 (m, 3H) 5.83-5.99 (dd, J=47.8, 3.85 Hz) and 5.38-5.54 (dd, J=48.37, 2.2 Hz, 1H) 4.89-4.97 (m, 2H) 3.39 and 3.38 (s, 3H).

Intermediate 3E: 4-Fluoro-6-nitroisoquinolin-1(2H)-one

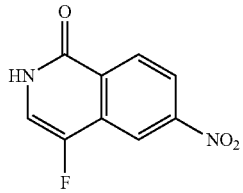 [SMILES: O=c1[nH]cc(F)c2cc([N+](=O)[O-])ccc12]

To a solution of Intermediate 3D (8.1 g, 33.7 mmol) in acetonitrile (100 mL) was added 4.0N HCl in dioxane (25.3 mL, 101 mmol). The mixture was stirred at 65° C. for 1.5 h. HPLC and LCMS indicated complete conversion of starting material. Solvent was removed to give Intermediate 3E (8.1 g, 33.1 mmol, 98% yield) as a yellow solid. $^1$H NMR (400 MHz, DMSO-$d_6$) δ ppm 8.38-8.46 (m, 2H) 8.31 (dd, J=8.79, 2.20 Hz, 1H) 7.61 (d, 1H); $^{19}$F NMR (376 MHz, DMSO-$d_6$) δ ppm −160.17 (s., 1F); MS (ESI) m/z: 209.2 (M+H)$^+$.

Intermediate 3F: 1-Chloro-4-fluoro-6-nitroisoquinoline

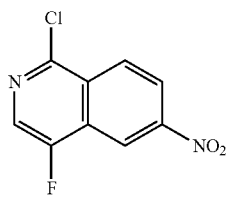 [SMILES: O=[N+]([O-])c1ccc2c(Cl)ncc(F)c2c1]

To Intermediate 3E (8.8 g, 36.0 mmol) was added phosphoryl trichloride (59.3 mL, 648 mmol). The suspension was heated at 115° C. for 1.0 h. Solvent was removed under high vacuum. The residue was diluted with EtOAc, washed with sat. sodium bicarbonate, brine and dried over sodium sulfate. After evaporation of solvent, the crude product was dissolved in a small amount of chloroform and charged to a 120 g silica gel cartridge which was eluted with 2% EtOAc in hexanes for 6 min, then a 15 min gradient from 2% to 25% EtOAc in hexanes. The desired fractions were combined and concentrated to give Intermediate 3F (8.5 g, 37.5 mmol, 104% yield) as a slightly yellow solid. $^1$H NMR (400 MHz, chloroform-d) δ ppm 9.01 (s, 1H) 8.46-8.56 (m, 2H) 8.34 (s, 1H); $^{19}$F NMR (376 MHz, chloroform-d) δ ppm −136.54 (s, 1F); MS (ESI) m/z: (M+H)$^+$ 227.1.

Intermediate 3G: 4-Fluoro-6-nitroisoquinolin-1-amine

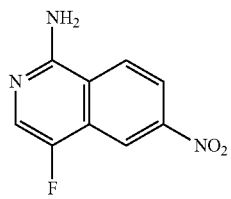 [SMILES: Nc1ncc(F)c2cc([N+](=O)[O-])ccc12]

A mixture of Intermediate 3F (580 mg, 2.56 mmol), BINAP (159 mg, 0.256 mmol) and tris(dibenzylideneacetone)dipalladium (0) (117 mg, 0.128 mmol) in toluene (12 mL) was degassed with Ar for 10 min. To this mixture was added diphenylmethanamine (0.471 mL, 2.82 mmol) and sodium tert-butoxide (312 mg, 3.25 mmol). The mixture was heated at 90° C. for 4.0 h. After it cooled to rt, it was diluted with EtOAc/water/brine, filtered though a pad of wet CELITE®. The organic layer was collected and washed with brine, dried over sodium sulfate and concentrated to give the crude imine.

The crude imine was dissolved in THF (15 mL) and treated with 4.0N HCl (9.60 mL, 38.4 mmol) for 30 min. HPLC and LCMS indicated complete hydrolysis of imine to amine. The mixture was diluted with EtOAc, the aqueous was collected, and the organic was further extracted with 4.0 N HCl (2×10 mL). The aqueous layers were combined and treated at 0° C. with 5.0 N NaOH to adjust the pH to 12-13. The precipitate formed was then collected by filtration, dried under a vacuum oven. It was then redissolved in MeOH/methylene chloride and evaporated to dryness to give Intermediate 3G (300 mg, 1.448 mmol, 56.6% yield, >95% purity by $^1$H NMR) as a brown solid. $^1$H NMR (400 MHz, DMSO-$d_6$) δ ppm 8.59 (d, J=2.20 Hz, 1H) 8.51 (dd, J=9.34, 2.20 Hz, 1H) 8.29 (dd, J=9.34, 2.20 Hz, 1H) 7.99 (d, J=2.20 Hz, 1H) 7.16 (s, 2H).

Intermediate 3H: tert-Butyl N-[(tert-butoxy)carbonyl]-N-(4-fluoro-6-nitroisoquinolin-1-yl)carbamate

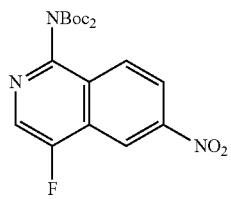

To Intermediate 3G (205 mg, 0.990 mmol) suspended in acetonitrile (8.0 mL) was added TEA (0.552 mL, 3.96 mmol) and DMAP (30.2 mg, 0.247 mmol). The cloudy reaction mixture turned clear in 20 min. The reaction was continued at rt for 6 h. It was then diluted with EtOAc, washed with 0.5 N HCl, sat. sodium carbonate and brine, dried over sodium sulfate. After evaporation of solvent, the crude product was dissolved in a small amount of chloroform and charged to a 24 g silica gel cartridge which was eluted with hexanes for 5 min, then a 18 min gradient from 0% to 30% EtOAc in hexanes. The desired fractions were combined and concentrated to give compound Intermediate 3H (266 mg, 0.653 mmol, 66% yield) as a yellow solid. $^1$H NMR (400 MHz, methanol-d$_3$) δ ppm 9.06 (d, J=2.20 Hz, 1H) 8.58 (dd, J=9.23, 2.20 Hz, 1H) 8.51 (s, 1H) 8.27 (d, J=9.23 Hz, 1H) 1.30 (s, 18H); $^{19}$F NMR (376 MHz, methanol-d$_3$) δ ppm −136.64 (s, 1F).

Intermediate 3

To Intermediate 3H (380 mg, 0.933 mmol) in MeOH (8 mL) was added 10% Pd/C (150 mg, 0.933 mmol) and 1.0 N HCl (0.075 mL, 0.075 mmol). The mixture was hydrogenated with a hydrogen balloon for 30 min. Pd/C was removed by filtration and the filtrate was concentrated to give Intermediate 3 (350 mg, 0.927 mmol, 99% yield) as a yellow solid. $^1$H NMR (400 MHz, acetonitrile-d$_3$) δ ppm 7.96 (d, J=3.08 Hz, 1H) 7.65 (dd, J=9.23, 2.20 Hz, 1H) 7.13 (dd, J=9.23, 2.20 Hz, 1H) 6.95 (d, J=2.20 Hz, 1H) 1.27 (s, 18H); $^{19}$F NMR (376 MHz, acetonitrile-d$_3$) δ ppm −142.33 (s., 41F); MS (ESI) m/z: 378.3 (M+H)$^+$.

Intermediate 4: 6-Amino-1-(di-tert-butoxycarbonylamino)-4-fluoroisoquinoline

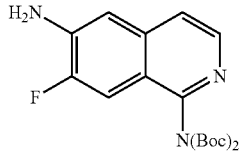

Intermediate 4A: N$^6$,N$^6$-Dibenzyl-7-fluoroisoquinoline-1,6-diamine

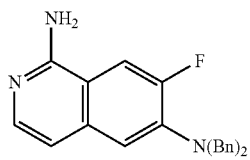

To a steel bomb charged with N,N-dibenzyl-1-chloro-7-fluoroisoquinolin-6-amine (3.953 g, 10.49 mmol, see WO 2007/002313 for preparation) was added 15 mL of 7N NH$_3$ in ethylene glycol (prepared by condensing ammonia in ethylene glycol) and the reaction sealed and heated at 165° C. overnight (20 h). The reaction mixture was poured into sat. NaHCO$_3$ (200 mL) and extracted with DCM (3×200 mL). The combined organics were washed with brine (150 mL) and dried (Na$_2$SO$_4$), filtered and concentrated to leave Intermediate 4A (3.71 g, 99% yield) as a yellow solid. MS (ESI) m/z: 358.1 [M+1]$^+$.

Intermediate 4B: tert-Butyl N-[(tert-butoxy)carbonyl]-N-[6-(dibenzylamino)-7-fluoroisoquinolin-1-yl]carbamate

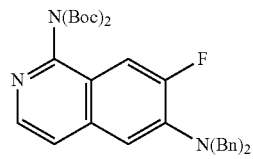

To a solution of Intermediate 4A (1.73 g, 3.78 mmol) in acetonitrile (20 mL) was added BOC$_2$O (1.229 mL, 5.29 mmol) followed by TEA (0.527 mL, 3.78 mmol) and DMAP (0.092 g, 0.756 mmol), then the suspension was stirred at rt for 1 h. Solvent was removed under vacuum and the residue purified on Isco (120 g) eluting with 0 to 75% EtOAc/hexanes to give Intermediate 4B (2.185 g, 3.92 mmol, 104% yield) as a white solid. $^1$H NMR (400 MHz, chloroform-d) δ ppm 1.38 (s, 18H) 4.54 (s, 4H) 7.04 (d, J=8.53 Hz, 1H) 7.28-7.40 (m, 11H) 7.53 (d, J=14.05 Hz, 1H) 8.25 (d, J=5.77 Hz, 1H); MS (ESI) m/z: 558.2 [M+1]$^+$.

Intermediate 4

To a solution of Intermediate 4B (385 mg, 0.690 mmol) in ethanol (15 mL) was added 20% palladium hydroxide on carbon, Degussa E101 (97 mg, 0.138 mmol) followed by 1,4-cyclohexadiene (5 mL) and the reaction heated in the microwave at 100° C. for 1.5 h. The reaction appears ~4/5 complete. Additional catalyst and 1,4-cyclohexadiene were added and the reaction heated at 100° C. for 0.5 h. The mixture was filtered and volatiles removed. The residue was purified on Isco, eluting with 10 to 100% EtOAc/hexanes to give Intermediate 4 (247 mg, 0.654 mmol, 95% yield) as a white solid. MS (ESI) m/z: 378.1 [M+1]$^+$. $^1$H NMR (400 MHz, chloroform-d) δ ppm 8.25 (1H, d, J=5.77 Hz), 7.49 (1H, d, J=11.80 Hz), 7.37 (1H, d, J=5.77 Hz), 7.01 (1H, d, J=8.53 Hz), 4.34 (2H, s), 1.35 (18H, s).

Intermediate 5: (R)-(4-(1-Hydroxypropan-2-yl)-3-methylphenyl)boronic acid

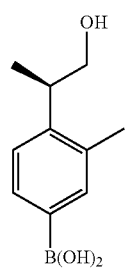

Intermediate 5A: (R)-2-(4-Bromo-2-methylphenyl)propan-1-ol

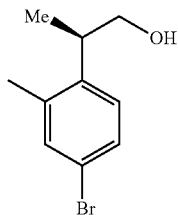

Intermediate 5A was prepared according to the procedure reported in WO 2008/079836.

Intermediate 5B: (R)-(4-(1-((tert-Butyldimethylsilyl)oxy)propan-2-yl)-3-methylphenyl)boronic acid

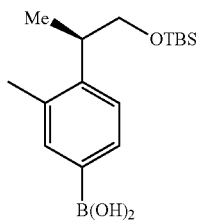 [SMILES: Cc1cc(B(O)O)ccc1[C@@H](C)CO[Si](C)(C)C(C)(C)C]

Intermediate 5B was prepared according to the procedure reported in WO 2008/079836.

Intermediate 5

Intermediate 5B (4.00 g, 12.97 mmol) was dissolved in MeOH:H$_2$O (90:10) with 0.1% TFA (100 mL) and stirred at rt for 5 h and then concentrated. The resultant oil was coevaporated with acetonitrile (3×) to give Intermediate 5 (2.33 g, 12.01 mmol, 93% yield) as a white solid. MS (ESI) m/z: 177.1 (M-OH)$^+$.

Intermediate 6: 4-(Cyclopropylthio)-3-((methylamino)methyl)aniline hydrochloride

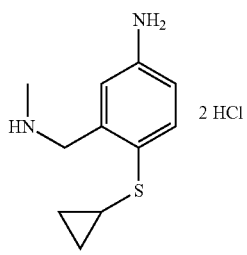

Intermediate 6A: 1-(2-(Cyclopropylthio)-5-nitrophenyl)-N-methylmethanamine

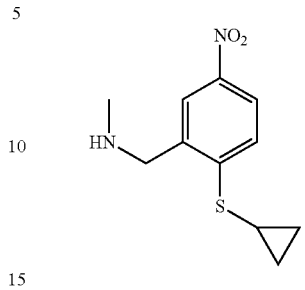

To a stirred solution of 2-(cyclopropylthio)-5-nitrobenzaldehyde (5 g, 22.40 mmol, see WO 2008/079759 for preparation) in MeOH (50 mL) was added methylamine (6.32 g, 67.2 mmol) dropwise and stirred for 1 h at 25° C. The reaction mixture was cooled to 0° C. and sodium borohydride (1.695 g, 44.8 mmol) was added portionwise with stirring. The reaction mixture was allowed to warm to rt and stirred overnight. The reaction mixture was concentrated under reduced pressure, diluted with EtOAc (250 mL), washed with water (2×100 mL), brine (1×100 mL) and dried (Na$_2$SO$_4$). Solvent was removed under reduced pressure to give Intermediate 6A (5 g, 20.98 mmol, 94% yield) as a orange oil. It was utilized in the subsequent step without any further purification. $^1$H NMR (400 MHz, chloroform-d) δ 8.11 (d, J=2.6 Hz, 1H), 8.04 (dd, J=8.8, 2.6 Hz, 1H), 7.64 (d, J=8.8 Hz, 1H), 3.69 (s, 2H), 2.40 (s, 3H), 2.13-2.09 (m, 1H), 1.18-1.12 (m, 2H), 0.73-0.67 (m, 2H); MS (ESI) m/z: 239.2 (M+H)$^+$.

Intermediate 6B: tert-Butyl 2-(cyclopropylthio)-5-nitrobenzyl(methyl)carbamate

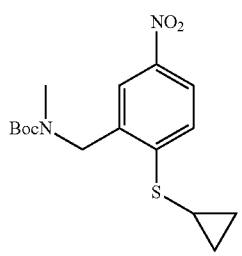 [SMILES: CN(Cc1cc([N+](=O)[O-])ccc1SC1CC1)C(=O)OC(C)(C)C]

BOC$_2$O (5.36 mL, 23.08 mmol) was added to a solution of Intermediate 6A (5 g, 20.98 mmol) and TEA (5.85 mL, 42.0 mmol) in CH$_2$Cl$_2$ (80 mL) and stirred overnight. The mixture was diluted with dichloromethane (80 mL), washed with water and brine, dried over Na$_2$SO$_4$ and concentrated in vacuo. The crude product was purified by flash chromatography (loading in chloroform, 0% to 50% ethyl acetate in hexane over 30 min using a 120 g silica gel cartridge) to yield Intermediate 6B (6.6 g, 19.50 mmol, 93% yield) as a pale yellow solid. $^1$H NMR (400 MHz, chloroform-d) δ 8.05 (d, J=8.3 Hz, 1H), 7.95-7.80 (m, 1H), 7.64 (d, J=8.8 Hz, 1H), 4.32 (br. s., 2H), 2.83 (s, 3H), 2.18-2.06 (m, 1H), 1.52 and 1.29 (s, 9H), 1.16 (d, J=6.2 Hz, 2H), 0.73-0.64 (m, 2H).

Intermediate 6C: tert-Butyl 5-amino-2-(cyclopropylthio)benzyl(methyl)carbamate

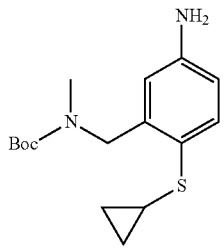 [SMILES: CN(Cc1cc(N)ccc1SC1CC1)C(=O)OC(C)(C)C]

Zinc (1.063 g, 16.25 mmol) was added to a mixture of Intermediate 6B (1 g, 2.95 mmol) and ammonium chloride (3.16 g, 59.1 mmol) in ethanol (10 mL). The mixture was stirred for 3 h at rt and concentrated. $Na_2CO_3$ (sat'd, 50 mL) and EtOAc (50 mL) was added and stirred for 1 h. The phases were separated and the aqueous layer was extracted with EtOAc (2×50 mL). The organics were combined, washed with brine, dried over $Na_2SO_4$ and concentrated. The crude product was purified by flash chromatography (loading in chloroform, 0% to 50% ethyl acetate in hexane over 30 min using a 40 g silica gel cartridge) to yield Intermediate 6C (600 mg, 1.945 mmol, 65.8% yield) as a yellow oil. $^1H$ NMR (400 MHz, chloroform-d) δ ppm 7.35 (1H, d, J=8.35 Hz), 6.58 (1H, dd, J=8.13, 2.42 Hz), 6.52 (1H, d, J=30.32 Hz), 4.45-4.61 (2H, m), 3.68 (2H, br. s.), 2.75-2.91 (3H, m), 2.03-2.15 (1H, m), 1.41-1.55 (9H, m), 0.83-0.97 (2H, m), 0.64 (2H, q, J=4.54 Hz).

Intermediate 6

Intermediate 6C (600 mg, 1.945 mmol) was stirred with 4.0 N HCl in dioxane (5 mL, 20.00 mmol) for 2 h. The solution was concentrated to yield Intermediate 6 (540 mg, 1.920 mmol, 99% yield) as a brown solid. MS (ESI) m/z: 209.1 $(M+H)^+$. $^1H$ NMR (400 MHz, DMSO-$d_6$) δ ppm 9.24-9.46 (2H, m), 7.66 (1H, d, J=8.35 Hz), 7.15-7.43 (2H, m), 4.11 (2H, t, J=5.27 Hz), 2.56 (3H, t, J=4.83 Hz), 2.24-2.34 (1H, m), 1.06 (2H, d, J=5.71 Hz), 0.63 (2H, q, J=5.57 Hz).

Intermediate 7: (4-(1,1-Difluoro-2-hydroxyethyl)-3,5-dimethylphenyl)boronic acid

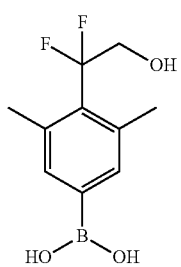

Intermediate 7A: Ethyl 2-(4-bromo-2,6-dimethylphenyl)-2,2-difluoroacetate

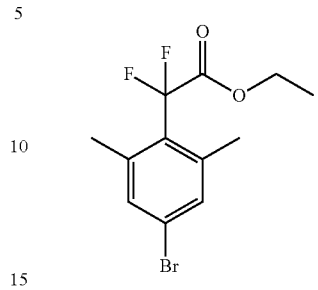

To a degassed solution of 5-bromo-2-iodo-1,3-dimethylbenzene (3.9 g, 12.54 mmol) and ethyl 2-bromo-2,2-difluoroacetate (3.22 ml, 25.08 mmol) in DMSO (30 ml) was added copper (3.19 g, 50.2 mmol). The reaction mixture was stirred at 60° C. for 3 h, then cooled to r.t. and filtered. The filtrate was diluted with EtOAc and water, extracted with EtOAc (3×). The combined organic layer was washed with brine, dried with $MgSO_4$, filtered and concentrated. The crude product was purified by flash chromatography to give Intermediate 7A (3.4 g, 11.07 mmol, 88% yield) as a colorless oil. $^1H$ NMR (400 MHz, chloroform-d) δ ppm 1.32 (t, J=7.03 Hz, 3H) 2.44 (t, J=4.17 Hz, 6H) 4.32 (q, J=7.18 Hz, 2H) 7.23 (s, 2H). $^{19}F$ NMR (376 MHz, chloroform-d) δ ppm −95.28 (br. s., 2F).

Intermediate 7B: 2-(4-Bromo-2,6-dimethylphenyl)-2,2-difluoroethanol

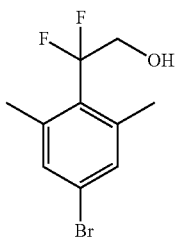

To a solution of Intermediate 7A (3.1 g, 10.09 mmol) in EtOH (30 ml) was added calcium chloride (0.336 g, 3.03 mmol). The resulting mixture was cooled to −10° C. and sodium borohydride (0.955 g, 25.2 mmol) was added. The mixture was then allowed to warm to rt and stand at rt. for 1 h. The reaction mixture was diluted with EtOAc and Sat. $NaHCO_3$, extracted with EtOAc (×3). The combined organic layer was dried ($MgSO_4$), concentrated to yield Intermediate 7B (2.68 g, 10.11 mmol, 100% yield) as a white solid. $^{19}F$ NMR (376 MHz, methanol-$d_3$) δ ppm −98.12 (br. s., 2F). $^1H$ NMR (400 MHz, methanol-$d_3$) δ ppm 2.42 (t, J=4.39 Hz, 6H) 3.92 (t, J=14.06 Hz, 2H) 7.26 (s, 2H).

Intermediate 7C: (2-(4-Bromo-2,6-dimethylphenyl)-2,2-difluoroethoxy)(tert-butyl)dimethylsilane

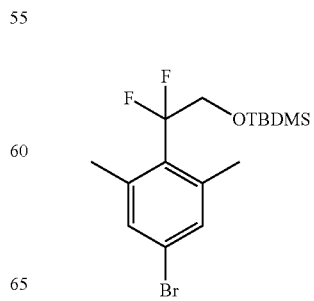

To a solution of Intermediate 7B (2.68 g, 10.11 mmol) and imidazole (1.376 g, 20.22 mmol) in DMF (30 ml) was added tert-butyl dimethylchlorosilane (1.828 g, 12.13 mmol). The mixture was stirred at rt overnight, diluted with EtOAc and sat. NaHCO₃. The organic layer was extracted by EtOAc (3×20 ml). The combined organic layer was washed with water and brine, dried (MgSO₄) and concentrated. The crude product was purified by flash chromatography to give Intermediate 7C (2.56 g, 66.8% yield) as a colorless oil. $^1$H NMR (400 MHz, chloroform-d) δ ppm −0.01 (s, 6H) 0.84 (s, 9H) 2.42 (t, J=4.61 Hz, 6H) 4.00 (t, J=13.18 Hz, 2H) 7.20 (s, 2H). $^{19}$F NMR (376 MHz, chloroform-d) δ ppm −95.94 (br. s., 2F).

Intermediate 7D: (4-(2-((tert-Butyldimethylsilyl)oxy)-1,1-difluoroethyl)-3,5-dimethylphenyl)boronic acid

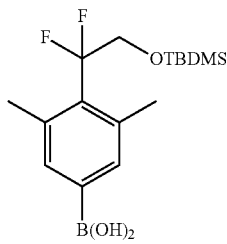 [SMILES: Cc1cc(B(O)O)cc(C)c1C(F)(F)CO[Si](C)(C)C(C)(C)C]

n-BuLi (1.6 M in hexanes, 1.236 ml, 1.977 mmol) was added to a solution of Intermediate 7C (500 mg, 1.318 mmol) in THF (5 ml) at −78° C. After 45 min, trimethyl borate (0.295 ml, 2.64 mmol) was added and the cooling bath was removed. The reaction mixture was warmed to rt, diluted with diethyl ether (300 mL), washed with 1.0 HCl, water and brine and concentrated. The crude product was purified by flash chromatography (loading in chloroform, 0 to 100% ethyl acetate in hexane over 30 min using a 12 g Isco column). Intermediate 7D (370 mg, 82% yield) was obtained as a white solid. $^1$H NMR (400 MHz, chloroform-d) δ ppm −0.03-0.02 (m, 6H) 0.82-0.88 (m, 9H) 2.57-2.63 (m, 6H) 4.10 (t, J=12.92 Hz, 2H) 7.86 (s, 2H).

Intermediate 7

To Intermediate 7D (370 mg, 1.075 mmol) at rt was added 10% acetonitrile in water containing 0.1% trifluoroacetic acid (10 ml). The mixture was stirred at rt overnight. LCMS indicated 50% conversion. trifluoroacetic acid (0.2 ml, 2.60 mmol) was added and the mixture was stirred at rt for 2 h. Solvent was removed under reduced pressure and the sample was lyophilized to give Intermediate 7 (200 mg, 0.870 mmol, 81% yield) as white lyophilate. $^1$H NMR (400 MHz, methanol-d₃) δ ppm 2.44 (t, J=4.61 Hz, 6H) 3.93 (t, J=14.28 Hz, 2H) 7.28 (s, 2H). 19F NMR (376 MHz, methanol-d₃) d ppm −98.73 (br. s., 2F).

Intermediate 8: 4-(Cyclopropylsulfonyl)-3-((methylamino)methyl)aniline hydrochloride

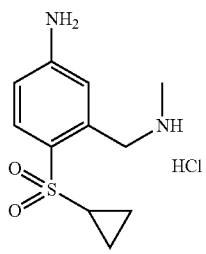 [SMILES: CNCc1cc(N)ccc1S(=O)(=O)C1CC1 ; Cl]

Intermediate 8A: tert-Butyl 2-(cyclopropylsulfonyl)-5-nitrobenzyl(methyl)carbamate

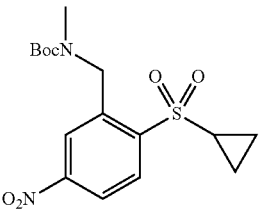 [SMILES: CN(Cc1cc([N+](=O)[O-])ccc1S(=O)(=O)C1CC1)C(=O)OC(C)(C)C]

To Intermediate 6B (10.7 g, 31.6 mmol) in CH₂Cl₂ (90 ml) at 0° C. was added mCPBA (10 g, 57.9 mmol). The reaction was stirred at rt for 4 h. Additional 2.0 g of mCPBA was added to the mixture and stirred for 1 h. The mixture was diluted with dichloromethane and washed with sat. NaHCO₃ and brine. The organic layer was separated and dried over sodium sulfate, filtered and concentrated. The crude product was purified by flash chromatography to give Intermediate 8A (10 g). $^1$H NMR (400 MHz, DMSO-d₆) δ ppm 1.09-1.20 (m, 4H) 1.24-1.55 (m, 9H) 2.92 (s, 3H) 3.09-3.21 (m, 1H) 4.93 (s, 2H) 7.99 (s, 1H) 8.16 (d, J=8.59 Hz, 1H) 8.33 (dd, J=8.59, 2.27 Hz, 1H).

Intermediate 8B: tert-Butyl 5-amino-2-(cyclopropylsulfonyl)benzyl(methyl)carbamate

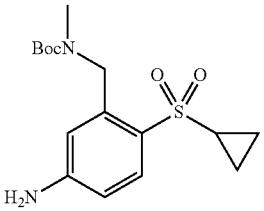

To Intermediate 8A (10.0 g, 27.0 mmol) in MeOH (250 ml) and EtOAc (150 ml) was added 10% Pd/C (0.5 g, 4.70 mmol) under a stream of nitrogen. The system was purged and degassed 3× with nitrogen, then the hydrogen balloon was introduced. The system was purged and degassed with hydrogen 3×. The mixture was stirred at rt overnight after addition of 0.5 mL of conc. HCl. The catalyst was filtered carefully over CELITE® under a stream of nitrogen and washed with methanol. The filtrate was concentrated and dried to give Intermediate 8B as an off-white solid (9.3 g). MS (ESI) (m/z) 341 [M+H]⁺; $^1$H NMR (400 MHz, DMSO-d₆) δ ppm 0.85-1.08 (m, 4H) 1.38 (d, J=48.37 Hz, 9H) 2.67-2.78 (m, J=4.40 Hz, 1H) 2.84 (s, 3H) 4.68 (s, 2H) 5.94-6.30 (m, 2H) 6.39 (s, 1H) 7.44 (d, J=8.79 Hz, 1H).

Intermediate 8

To Intermediate 8B (175 mg, 0.514 mmol) in EtOAc (1.5 mL) was added 4.0N HCl in dioxane (2.0 mL, 8.00 mmol). The mixture was stirred at rt for 40 min. Solvent was removed under reduced pressure to give Intermediate 8 as a white solid: $^1$H NMR (400 MHz, DMSO-d₆) δ ppm 0.95-1.05 (m, 4H) 2.57 (t, J=5.27 Hz, 3H) 2.89-2.96 (m, 1H) 3.55 (s, 3H)

4.24 (t, J=5.93 Hz, 2H) 6.68 (dd, J=8.35, 2.20 Hz, 1H) 6.74 (d, J=2.20 Hz, 1H) 7.48-7.54 (m, 1H) 8.92 (s, 2H).

Example 1

(2R,15R)-2-[(1-Aminoisoquinolin-6-yl)amino]-N,N,4,15,17-pentamethyl-3,12-dioxo-13-oxa-4,11-diazatricyclo[14.2.2.1⁶,¹⁰]henicosa-1(18),6,8,10 (21),16,19-hexaene-7-carboxamide trifluoroacetic acid salt

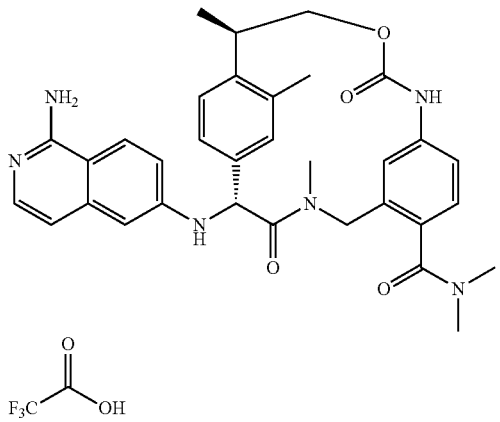

1A: tert-Butyl N-{6-[({[(5-amino-2-bromophenyl)methyl](methyl)carbamoyl}({4-[(2R)-1 hydroxypropan-2-yl]-3-methylphenyl})methyl)amino]isoquinolin-1-yl}-N-[(tert-butoxy)carbonyl]carbamate

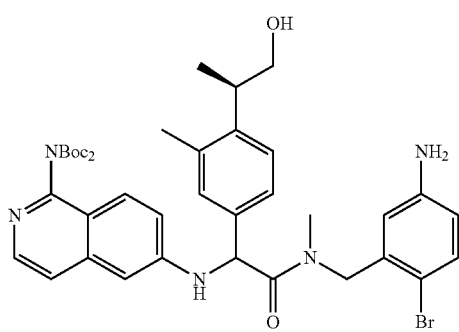

A solution of Intermediate 1 (0.699 g, 1.946 mmol), glyoxylic acid monohydrate (0.179 g, 1.946 mmol) and Intermediate 5B (0.600 g, 1.946 mmol) in DMF (3 mL) and acetonitrile (3 mL) was stirred at 80° C. for 1.5 h. The mixture was cooled to rt, diluted with DMF (2 mL). To this mixture were added sequentially 4-bromo-3-((methylamino)methyl)aniline (0.673 g, 2.335 mmol), BOP (0.947 g, 2.141 mmol) and TEA (1.628 mL, 11.68 mmol). The mixture was stirred at rt for 30 min. TBAF (1M in THF) (2.92 mL, 2.92 mmol) was added, and the reaction mixture was stirred at rt for 15 min. The reaction mixture was diluted with EtOAc, washed with water, brine and dried (Na₂SO₄). The solvent was removed under reduced pressure. The residues were redissolved in dichloromethane with ~3% MeOH, and was purified by Isco: (40 g) 1-15% MeOH/dichloromethane eluted at ~10% MeOH. Fractions were combined and concentrated under reduced pressure to give 1A (1.173 g, 1.538 mmol, 79% yield) as an orange glass. MS (ESI) m/z: 762.5 and 764.5 (M+H)⁺. Purity 90%; ¹H NMR was complicated by a pair of diastereomers and rotamers.

1B: tert-Butyl N-(6-{[(2R,15R)-7-bromo-4,15,20-trimethyl-3,12-dioxo-13-oxa-4,11-diazatricyclo[14.2.2.1⁶,¹⁰]henicosa-1(18),6,8,10 (21),16,19-hexaen-2-yl]amino}isoquinolin-1-yl)-N-[(tert-butoxy)carbonyl]carbamate

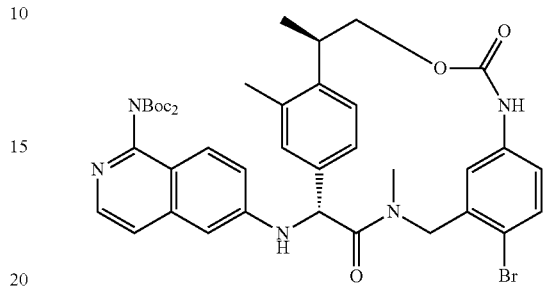

A solution of 1A (1.173 g, 1.538 mmol) in acetonitrile (8 mL), dichloromethane (8 mL) and DMPU (0.6 mL) was cooled to 0° C. To this solution was added phosgene (20% in toluene, 0.837 mL, 1.692 mmol). The mixture was stirred at 0° C. for 15 min. and then bubbled with Ar for 10 min to remove excess phosgene. The resulting solution was added dropwise over 3 h (via a syringe pump) into a solution of TEA (2.144 mL, 15.38 mmol) in dichloromethane (400 mL) at 40° C. The yellow solution was stirred for an additional 30 min. Reaction mixture was concentrated, suspended in EtOAc (250 mL), washed with water (2×200 mL), brine (1×100 ml) and dried (Na₂SO₄). EtOAc was removed under reduced pressure and the residue was purified by Isco: (40 g) 50-100% EtOAc/hexanes. Fractions were combined and concentrated under reduced pressure to give product as a mixture of diastereomers. The diastereoisomers were separated by chiral HPLC (Chiral OD 10 um 4.6×250 mm; sol. A heptane; sol. B 50% MeOH-50% EtOH) to give 1B (0.200 g, 0.254 mmol, 33.0% yield): MS (ESI) m/z: 788.1 [M+1]⁺; Purity 95%; ¹H NMR: (400 MHz, CD₃OD) δ ppm 8.04 (1H, d, J=5.50 Hz), 7.68 (1H, d, J=6.05 Hz), 7.60 (1H, d, J=9.34 Hz), 7.51 (1H, d, J=6.05 Hz), 7.46 (1H, d, J=7.70 Hz), 7.40 (1H, d, J=8.24 Hz), 7.27 (1H, dd, J=8.79, 2.20 Hz), 7.22 (1H, s), 6.87 (1H, d, J=2.20 Hz), 6.63 (1H, dd, J=8.52, 2.47 Hz), 5.99 (1H, d, J=2.20 Hz), 5.71 (1H, s), 5.35 (1H, d, J=17.04 Hz), 4.65 (1H, t, J=11.27 Hz), 3.95 (1H, dd, J=10.99, 4.40 Hz), 3.65 (1H, s), 3.44-3.53 (1H, m), 3.34 (3H, s), 2.31 (3H, s), 1.31 (3H, d, J=7.15 Hz), 1.27 (18H, s).

1C: Methyl (2R,15R)-2-[(1-{bis[(tert-butoxy)carbonyl]amino}isoquinolin-6-yl)amino]-4,15,17-trimethyl-3,12-dioxo-13-oxa-4,11-diazatricyclo[14.2.2.1⁶,¹⁰]henicosa-1(18),6,8,10 (21),16,19-hexaene-7-carboxylate

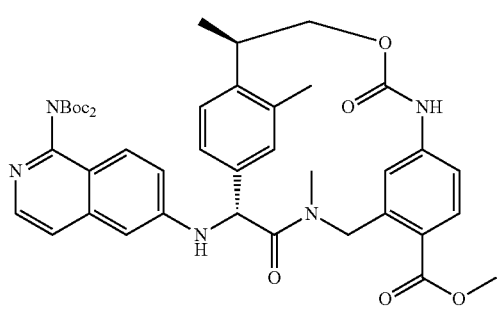

To a pressure flask charged with 1B (250 mg, 0.317 mmol), palladium(II) acetate (35.6 mg, 0.158 mmol), TEA (0.132 mL, 0.951 mmol) and dppp (65.4 mg, 0.158 mmol) was dissolved with DMSO (2 mL)/MeOH (1.000 mL). The resulting mixture was charged with carbon monoxide at 25 psi and then stirred at 80° C. under and atmosphere of CO overnight. Reaction mixture was cooled to rt, filtered and concentrated. The resulting residue was dissolved in EtOAc, washed with water. The aqueous layer was then back extracted. The organic layers were combined, washed with brine and dried (Na$_2$SO$_4$). The crude was purified on SQ16 column equilibrated with 1% MeOH in dichloromethane to give 1C (203 mg, 83% yield): MS (ESI) m/z: 768.4 [M+H]$^+$; $^1$H NMR (400 MHz, MeOD) δ ppm 7.94 (1H, d, J=5.77 Hz), 7.81 (1H, d, J=8.28 Hz), 7.58 (1H, d, J=7.03 Hz), 7.49 (1H, d, J=9.03 Hz), 7.41 (1H, d, J=5.77 Hz), 7.36 (1H, d, J=7.78 Hz), 7.16 (1H, dd, J=9.16, 2.13 Hz), 7.08 (1H, s), 6.78 (1H, d, J=1.76 Hz), 6.64 (1H, dd, J=8.28, 1.76 Hz), 6.14 (1H, s), 5.54-5.66 (2H, m), 4.52 (1H, t, J=10.92 Hz), 3.85 (1H, dd, J=10.54, 4.27 Hz), 3.74 (3H, s), 3.21 (2H, d, J=1.51 Hz), 3.20 (1H, br. s.), 2.18 (3H, s), 1.21 (4H, d, J=7.03 Hz), 1.15 (19H, s).

1D: (2R,15R)-2-[(1-{Bis[(tert-butoxy)carbonyl]amino}isoquinolin-6-yl)amino]-4,15,17-trimethyl-3,12-dioxo-13-oxa-4,11-diazatricyclo[14.2.2.1$^{6,10}$]henicosa-1(18),6,8,10 (21),16,19-hexaene-7-carboxylic acid

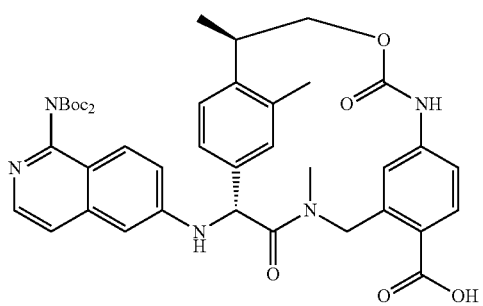

To a solution of 1C (25 mg, 0.033 mmol) in THF (1 mL) was added 1.0 N LiOH (0.5 mL) and the reaction mixture was stirred overnight. It was quenched with NH$_4$Cl, extracted with EtOAC, washed with brine and concentrated. The crude was purified by prep HPLC (Axia Luna 5 u C18 30×100 mm) to give 1D (14 mg, 57% yield): MS (ESI) m/z: =754.3 [M+H]$^+$.

Example 1

To a solution of 1D (8 mg, 10.61 μmol) at 0° C. in DMF (0.3 mL) and acetonitrile (0.300 mL) was added HATU (4.84 mg, 0.013 mmol) and N-methylmorpholine (1.750 μL, 0.016 mmol). The reaction was stirred for 5 min. Then 2M dimethylamine in THF (6.37 μL, 0.013 mmol) was added and the reaction was allowed to warm to rt and stirred for 4 h. The reaction mixture was diluted with water and extracted with EtOAc. The combined organic layer was washed with water, brine, dried (MgSO$_4$), and concentrated. The crude was purified by prep HPLC (Axia Luna 5 u C18 30×100 mm) to give the di-Boc intermediate. The di-Boc intermediate was treated with 1.5 mL of TFA and stirred for 30 min. The reaction mixture was then concentrated and purified by prep HPLC (Axia Luna 5 u C18 30×100 mm) to give Example 1 (2.9 mg, 39% yield): MS (ESI) m/z: 581.2 [M+H]$^+$; $^1$H NMR (400 MHz, MeOD) δ ppm 8.06 (1H, d, J=9.29 Hz), 7.61-7.71 (1H, m), 7.47 (1H, d, J=8.03 Hz), 7.33 (1H, d, J=7.03 Hz), 7.18-7.26 (2H, m), 7.13 (1H, d, J=8.03 Hz), 6.93 (1H, d, J=7.03 Hz), 6.84 (1H, d, J=2.26 Hz), 6.77 (1H, dd, J=8.03, 2.01 Hz), 6.14 (1H, s), 5.75 (1H, s), 5.27 (1H, s), 4.60-4.73 (1H, m), 4.01 (1H, dd, J=10.67, 4.39 Hz), 3.88 (1H, d, J=16.56 Hz), 3.44-3.58 (1H, m), 3.11 (3H, s), 2.94 (3H, s), 2.35 (3H, s), 1.33 (4H, d, J=7.03 Hz), 1.30 (2H, s); Analytical HPLC: (low pH, 254 nM) Sunfire C18 3.5 um, 4.6×150 mm, RT=4.59 min, 98% purity.

Example 2

(2R)-2-[(1-Amino-4-fluoroisoquinolin-6-yl)amino]-7-(cyclopropanesulfonyl)-14-hydroxy-4,17,20-trimethyl-4,11-diazatricyclo[14.2.2.1$^{6,10}$]henicosa-1(18),6,8,10 (21),16,19-hexaene-3,12-dione; trifluoroacetic acid

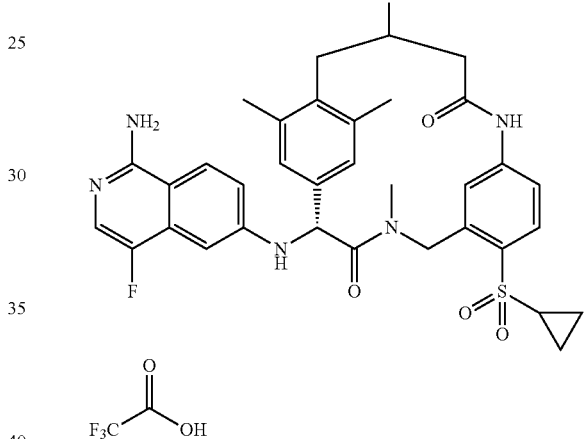

2A: Methyl 4-(4-bromo-2,6-dimethylphenyl)-3-hydroxybutanoate

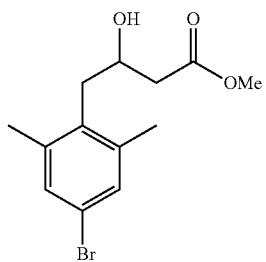 [SMILES: COC(=O)CC(O)Cc1c(C)cc(Br)cc1C]

DIBAL-H (8.66 mL, 12.99 mmol) was added dropwise to a solution of methyl 2-(4-bromo-2,6-dimethylphenyl)acetate (3.18 g, 12.37 mmol) in CH$_2$Cl$_2$ (60 mL) at −78° C. and stirred for 1 h. 1-(tert-Butyldimethylsilyloxy)-1-methoxyethene (4.05 mL, 18.55 mmol) followed by BF$_3$.OEt$_2$ (1.959 mL, 15.46 mmol) were added. The reaction was stirred at −78° C. for 20 min and then allowed to warm to rt. The reaction was quenched by the addition of 10 mL of 1.0 M HCl, extracted with dichloromethane. The combined organics were washed with brine, dried over Na₂SO₄ and concentrated in vacuo. The crude product was purified by flash chromatography (loading in chloroform, 0% to 50% ethyl acetate in hexane over 15 min using a 40 g silica gel cartridge) to yield 2A (2.5 g, 8.30 mmol, 67.1% yield) as a clear oil. ¹H NMR (500 MHz, chloroform-d) δ ppm 7.18 (2H, s), 4.20-4.28 (1H, m), 3.72 (3H, s), 2.91 (1H, dd, J=14.03, 8.25 Hz), 2.72-2.78 (2H, m), 2.53-2.57 (2H, m), 2.55 (2H, dd, J=40.03, 6.19 Hz), 2.33 (6H, s), 1.58 (2H, br. s.).

2B: Methyl 4-(4-bromo-2,6-dimethylphenyl)-3-((tert-butyldimethylsilyl)oxy)butanoate

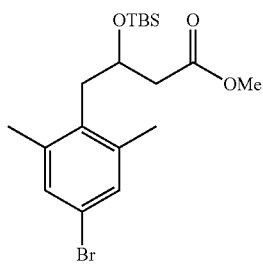 [SMILES: COC(=O)CC(Cc1c(C)cc(Br)cc1C)O[Si](C)(C)C(C)(C)C]

TBS-Cl (1291 mg, 4.28 mmol) was added to a solution of 2A (860 mg, 2.86 mmol) and imidazole (389 mg, 5.71 mmol) in dichloromethane (20 mL) and stirred overnight at rt. The reaction was diluted with EtOAc, washed with water and brine, dried over Na₂SO₄ and concentrated. The crude product was purified by flash chromatography (loading in chloroform, 0% to 50% ethyl acetate in hexane over 15 min using a 40 g silica gel cartridge) to yield 2B (830 mg, 1.998 mmol, 70.0% yield) as a clear oil. ¹H NMR (500 MHz, chloroform-d) δ ppm 7.15 (2H, s), 4.28-4.36 (1H, m), 3.68 (3H, s), 2.82 (2H, ddd, J=53.09, 13.89, 7.02 Hz), 2.53 (2H, ddd, J=57.43, 15.06, 6.19 Hz), 2.33 (6H, s), 0.80 (9H, s), −0.10 (3H, s), −0.32 (3H, s).

2C: (4-(2-Hydroxy-4-methoxy-4-oxobutyl)-3,5-dimethylphenyl)boronic acid

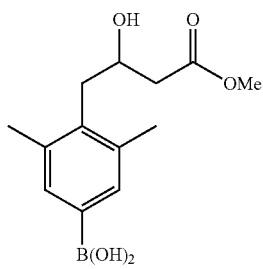 [SMILES: COC(=O)CC(O)Cc1c(C)cc(B(O)O)cc1C]

A mixture of 2B (400 mg, 0.963 mmol), potassium acetate (283 mg, 2.89 mmol), bis(neopentyl glycolato)diboron (326 mg, 1.444 mmol) and (1,1'-bis(diphenylphosphino)ferrocene)-dichloropalladium(II) (39.6 mg, 0.048 mmol) in dioxane (5 mL) was degassed with Ar. The reaction vessel was sealed and heated at 85° C. for 2 h. The mixture was cooled, diluted with EtOAc (100 mL), filtered and concentrated. The crude boronic ester was purified by flash chromatography (loading in chloroform, 0% to 100% ethyl acetate in hexane over 10 min using a 12 g silica gel cartridge). The resulting clear oil hydrolyzed to the boronic acid by a prep HPLC (0.1% TFA, MeOH, H₂O) to yield 2C (240 mg, 0.902 mmol, 94% yield). ¹H NMR (500 MHz, methanol-d₄) δ 7.44-7.06 (m, 2H), 4.78 (s, 3H), 4.22 (tdd, J=8.0, 6.1, 4.8 Hz, 1H), 3.66-3.52 (m, 2H), 2.98-2.71 (m, 2H), 2.58 and 2.23 (m, 6H).

2D: Methyl 4-{4-[({[5-amino-2-(cyclopropylsulfanyl)phenyl]methyl}(methyl)carbamoyl)[(1 {bis[(tert-butoxy)carbonyl]amino}-4-fluoroisoquinolin-6-yl)amino]methyl]-2,6-dimethylphenyl}-3-hydroxybutanoate

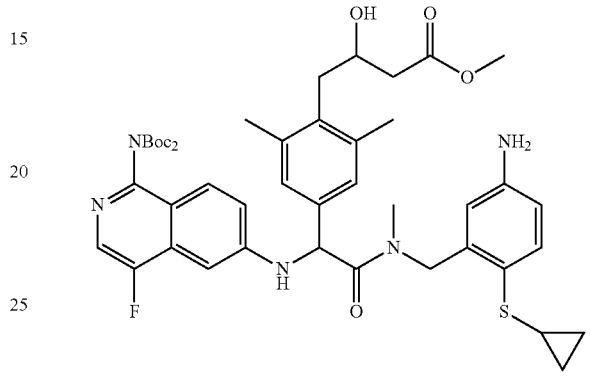

2C (100 mg, 0.376 mmol), Intermediate 3 (142 mg, 0.376 mmol), and glyoxylic acid monohydrate (34.6 mg, 0.376 mmol) were dissolved in acetonitrile (1.5 mL)/DMF (1.500 mL) and heated at 80° C. for 2 h. A solution of Intermediate 6 (106 mg, 0.376 mmol)) and TEA (0.157 mL, 1.127 mmol) in DMF (1.500 mL) was added followed by BOP (183 mg, 0.413 mmol) as a solid. The reaction mixture was stirred at rt for 3 h. The reaction mixture was diluted with EtOAc, washed with water and brine, dried over Na₂SO₄ and concentrated. The crude material was purified by column chromatography (0 to 100% EtOAc in hexanes then elute with 20% MeOH in dichloromethane) to yield 2D (210 mg, 0.248 mmol, 66.1% yield) as a yellow solid. MS (ESI) m/z: 846.7 (M+H)⁺.

2E: 4-{4-[({[5-Amino-2-(cyclopropylsulfanyl)phenyl]methyl}(methyl)carbamoyl)[(1-{bis[(tert-butoxy)carbonyl]amino}-4-fluoroisoquinolin-6-yl)amino]methyl]-2,6-dimethylphenyl}-3-hydroxybutanoic acid

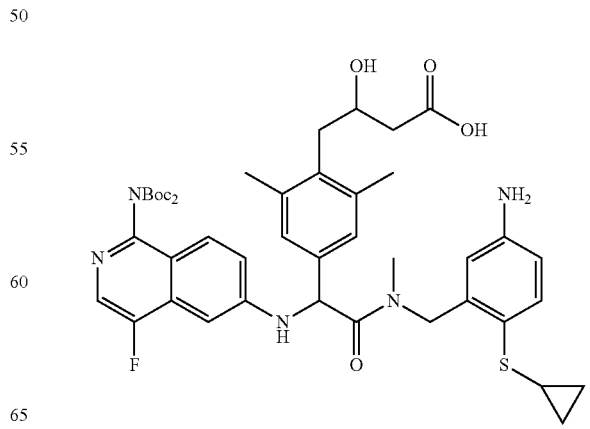

1.0 M LiOH (0.266 mL, 0.266 mmol) was added to a solution of 2D (225 mg, 0.266 mmol) in THF (2 mL) and stirred for 6 h at rt. HCl (0.266 mL, 1 M) was added and the mixture was extracted with EtOAc. The combined organics were washed with brine, dried over $Na_2SO_4$ and concentrated in vacuo. The product 2E was used without further purification. MS (ESI) m/z: 832.7 $(M+H)^+$.

2F: tert-Butyl N-[(tert-butoxy)carbonyl]-N-(6-{[(2R)-7-(cyclopropylsulfanyl)-14-hydroxy-4,17,20-trimethyl-3,12-dioxo-4,11-diazatricyclo[14.2.2.1$^{6,10}$]henicosa-1(18),6,8,10 (21),16,19-hexaen-2-yl]amino}-4-fluoroisoquinolin-1-yl)carbamate

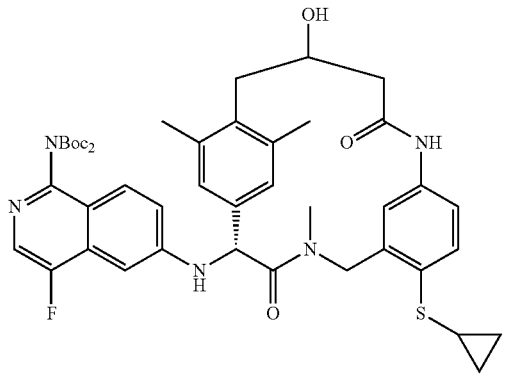

To a solution of BOP (234 mg, 0.529 mmol), TEA (0.074 mL, 0.529 mmol) and DMAP (129 mg, 1.058 mmol) in dichloromethane (10 mL) and DMF (10 mL) was added 2E in dichloromethane (10 mL) via a syringe pump over 10.0 h. The reaction was continued at rt for 4 h, quenched by water and extracted by EtOAc (×3). The combined organics were washed by brine, dried with $Na_2SO_4$ and concentrated. The crude product was purified by flash chromatography (loading in chloroform, 0% to 100% ethyl acetate in hexane over 10 min using a 4 g silica gel cartridge) to give a mixture of diastereoisomers (92 mg, 43% yield). The diastereoisomers were separated to give 2F (30 mg, 0.037 mmol, 32.6% yield) using a R,R-Welko-O 1 column (21.1 mm×250 mm, 10 micron, Regis Technologies, Inc.). MS (ESI) m/z: 814.7 $(M+H)^+$.

2G: tert-Butyl N-[(tert-butoxy)carbonyl]-N-(6-{[(2R)-7-(cyclopropanesulfonyl)-14-hydroxy-4,17,20-trimethyl-3,12-dioxo-4,11-diazatricyclo[14.2.2.1$^{6,10}$]henicosa-1(18),6,8,10 (21),16,19-hexaen-2-yl]amino}-4-fluoroisoquinolin-1-yl)carbamate

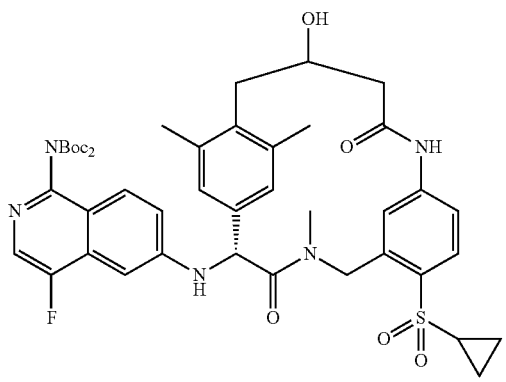

A solution of 2F (30 mg) in dichloromethane was treated with MCPBA (20 mg) at rt overnight. The reaction mixture was diluted with dichloromethane, washed with sat. $Na_2CO_3$, water and brine. The organics were dried over $Na_2SO_4$ and concentrated in vacuo. The crude product was purified by flash chromatography (loading in chloroform, 0% to 100% ethyl acetate in hexane over 10 min using a 4 g silica gel cartridge) to yield 2G (10 mg, 32.1% yield) as a brown film. MS (ESI) m/z: 846.7 $(M+H)^+$.

Example 2

TFA (1000 μL) was added to a solution of 2G (10 mg, 0.012 mmol) in dichloromethane (1000 μL) with 2 drops of water and stirred at rt for 2 h. The mixture was concentrated and purified by prep HPLC to yield Example 2 (10 mg, 0.012 mmol) as a white solid. MS (ESI) m/z: 646.5 $(M+H)^+$. $^1$H NMR (500 MHz, methanol-$d_4$) δ 8.12 (dd, J=9.2, 1.8 Hz, 1H), 7.79 (d, J=8.5 Hz, 1H), 7.50 (s, 1H), 7.47 (d, J=4.7 Hz, 1H), 7.28 (dd, J=9.2, 2.3 Hz, 1H), 6.99 (s, 1H), 6.91 (dd, J=8.4, 2.1 Hz, 1H), 6.87 (s, 1H), 6.57 (br. s., 1H), 5.82 (d, J=17.3 Hz, 1H), 5.73 (s, 1H), 4.71-4.65 (m, 1H), 4.26 (d, J=16.8 Hz, 1H), 3.21-3.14 (m, 1H), 3.02-2.92 (m, 2H), 2.79-2.71 (m, 1H), 2.68-2.61 (m, 1H), 2.57 (s, 3H), 2.35 (s, 3H).

Example 3

(2R,15R)-2-[(1-Amino-4-fluoroisoquinolin-6-yl)amino]-7-(ethanesulfonyl)-4,15,17-trimethyl-13-oxa-4,11-diazatricyclo[14.2.2.1$^{6,10}$]henicosa-1(18),6,8,10 (21),16,19-hexaene-3,12-dione; trifluoroacetic acid

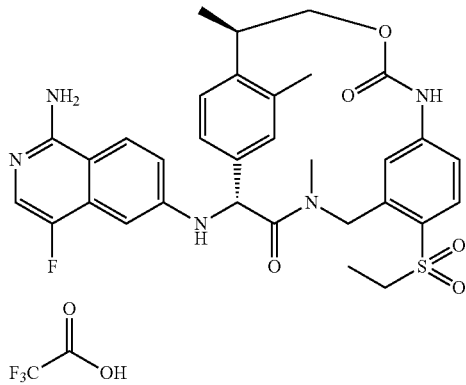

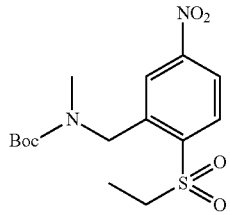 [SMILES: CCS(=O)(=O)c1ccc([N+](=O)[O-])cc1CN(C)C(=O)OC(C)(C)C]

3A: tert-Butyl 2-(ethylsulfonyl)-5-nitrobenzyl(methyl)carbamate m-CPBA (2.87 g, 12.80 mmol) was added to a solution of tert-butyl methyl(2-(methylthio)-5-nitrobenzyl)carbamate (2 g, 6.40 mmol) in dichloromethane (25 ml). The reaction was stirred at rt for 1 h. The reaction mixture was diluted with EtOAc (150 ml) and water, extracted with EtOAc (×3). The combined organic layer was washed with sat. $NaHCO_3$ (3×50 ml) and brine, dried with $Na_2SO_4$ and concentrated. The residue was purified by flash chromatography to give 3A (2.2 g, 6.14 mmol, 100% yield). $^1$H NMR (400 MHz, CDCl$_3$) δ ppm 8.11-8.36 (m, 3H) 4.92 (s, 2H) 4.12 (q, J=7.03 Hz, 2H) 3.04 (s, 3H) 1.50 (s, 9H) 1.33 (t, J=7.47 Hz, 3H).

3B: tert-Butyl
5-amino-2-(ethylsulfonyl)benzyl(methyl)carbamate

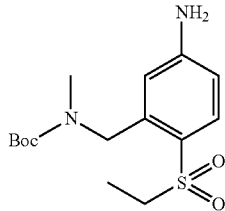

To a solution of 3A (2.2 g, 6.14 mmol) in MeOH (50 ml) and EtOAc (50.0 ml) was added 10% Pd on carbon (0.653 g, 0.614 mmol) and the mixture was stirred under a hydrogen balloon for 2 h. Pd/C was removed by filtration. The filtrate was concentrated to give 3B that was used for next step without further purification. $^1$H NMR (400 MHz, CDCl$_3$) δ ppm 7.75 (d, J=8.35 Hz, 1H) 6.58-6.67 (m, 1H) 6.52 (s, 1H) 4.78 (s, 2H) 3.04-3.13 (m, 2H) 2.94 (s, 3H) 1.45 (d, J=39.11 Hz, 9H) 1.26 (t, J=7.47 Hz, 3H).

3C:
4-(Ethylsulfonyl)-3-((methylamino)methyl)aniline hydrochloride

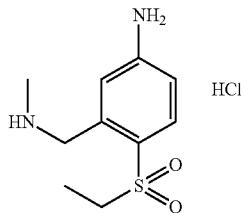

To a solution of 3B (2 g, 6.09 mmol) in EtOAc (30 mL) was added 4.0 N HCl in dioxane (30.4 mL, 122 mmol) and the mixture was stirred at r.t. for 2 h. Solvent was removed under reduced pressure to give 3C (1.8 g, 6.27 mmol, 99% yield) as a off white solid. $^1$H NMR (400 MHz, CD$_3$OD) δ ppm 7.79 (d, J=8.79 Hz, 1H) 7.03 (d, J=2.20 Hz, 1H) 6.96-7.02 (m, 1H) 4.33 (s, 2H) 3.24 (q, J=7.47 Hz, 2H) 2.75 (s, 3H) 1.24 (t, J=7.47 Hz, 3H).

3D: tert-Butyl N-(6-{[({[5-amino-2-(ethanesulfonyl)phenyl]methyl}(methyl)carbamoyl)({4-[(2R)-1-hydroxypropan-2-yl]-3-methylphenyl})methyl]amino}-4-fluoroisoquinolin-1-yl)-N-[(tert-butoxy)carbonyl]carbamate

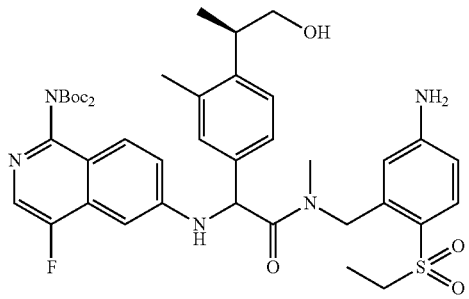

A mixture of Intermediate 3 (230 mg, 0.609 mmol), Intermediate 5 (130 mg, 0.670 mmol) and glyoxylic acid monohydrate (56.1 mg, 0.609 mmol) in DMF (2.0 mL) and acetonitrile (6.0 mL) was heated at 80° C. for 1.5 h. The reaction mixture was transfer to a flask containing 3C (161 mg, 0.609 mmol). To this solution was added DIEA (0.532 mL, 3.05 mmol) and BOP (270 mg, 0.609 mmol). The mixture was left stirring at rt over night. After removal of the solvent, the crude was purified by prep HPLC (Axia column 30 mm×100 cm). The desired fractions were combined and neutralized with sat. sodium bicarbonate. Acetonitrile was removed under vacuum. The residue was then extracted with methylene chloride. The organic layer was dried over sodium sulfate. After evaporation of solvent, 3D (303 mg, 0.382 mmol, 62.6% yield) was obtained as a white solid. MS (ESI) m/z: 794.7 (M+H)$^+$.

3E: tert-Butyl N-[(tert-butoxy)carbonyl]-N-(6-{[(2R,15R)-7-(ethanesulfonyl)-4,15,17-trimethyl-3,12-dioxo-13-oxa-4,11-diazatricyclo[14.2.2.1$^{6,10}$]henicosa-1(18),6,8,10 (21),16,19-hexaen-2-yl]amino}-4-fluoroisoquinolin-1-yl)carbamate

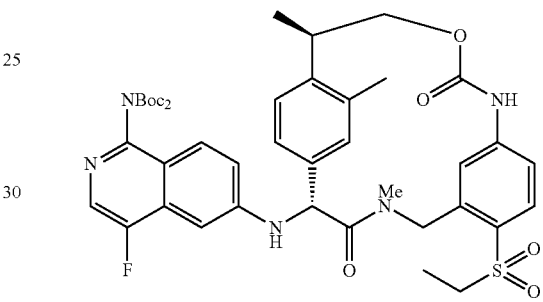

To a solution of 3D (303 mg, 0.382 mmol) in acetonitrile (7 mL) and dichloromethane (4 mL) at 0° C., was added phosgene solution (20% in toluene) (0.241 mL, 0.458 mmol) dropwise. The mixture was stirred at 0° C. for 40 min, then at rt for 10 min while extra phosgene was removed by bubbling Ar. The resulting solution was added dropwise via syringe pump into a solution of TEA (0.426 mL, 3.05 mmol) in dichloromethane (120 mL) at rt over 3.0 h. The solution was stirred at rt for additional 45 min. Solvent was removed and the crude was purified by prep HPLC to give a mixture of diastereoisomer (237 mg). The diastereoisomers were separated by chiral HPLC ((R,R)-Whelk-01 250×21.1 mm column) to give 3E (100 mg, 63.9% yield). MS (ESI) m/z: 820 [M+1]$^+$; $^1$H NMR (400 MHz, chloroform-d) δ ppm 1.29-1.41 (m, 24H) 2.21 (s, 3H) 3.18-3.33 (m, 2H) 3.33-3.39 (m, 3H) 3.38-3.48 (m, 1H) 3.95 (dd, J=10.77, 4.17 Hz, 1H) 4.28 (d, J=17.58 Hz, 1H) 4.67 (t, J=11.21 Hz, 1H) 5.43 (d, J=5.71 Hz, 1H) 5.65 (d, J=17.58 Hz, 1H) 6.39-6.48 (m, 2H) 6.63 (s, 1H) 6.76 (d, J=8.35 Hz, 1H) 6.85 (s, 1H) 7.03 (d, J=9.23 Hz, 1H) 7.08 (s, 1H) 7.50 (d, J=7.91 Hz, 1H) 7.56-7.65 (m, 2H) 7.85 (d, J=8.35 Hz, 1H) 8.05 (s, 1H). $^{19}$F NMR (376 MHz, chloroform-d) δ ppm −141.30 (br. s., 1F).

Example 3

To 3E (100 mg, 0.122 mmol) was added 4.0 N HCl in dioxane (3049 μL, 12.20 mmol). The reaction was stirred at rt over night. After removal of solvent, the crude was purified by prep HPLC (Luna Axia column 30 mm×75 cm, 5μ). The desired fractions were combined and lyophilized to give Example 3 (74.6 mg, 0.095 mmol, 78% yield) as a white lyophilate. MS (ESI) m/z: 620.5 (M+H)$^+$. $^1$H NMR (400

MHz, acetonitrile-d₃) δ ppm 7.83 (s, 1H) 7.70-7.77 (m, 2H) 7.66 (d, J=7.91 Hz, 1H) 7.44 (d, J=7.91 Hz, 1H) 7.15 (d, J=4.83 Hz, 1H) 7.09 (dd, J=9.01, 2.42 Hz, 1H) 7.00 (br. s., 1H) 6.94 (s, 1H) 6.78-6.85 (m, 3H) 6.35 (d, J=1.76 Hz, 1H) 5.59 (d, J=17.58 Hz, 2H) 4.56 (t, J=11.21 Hz, 1H) 4.09 (d, J=17.58 Hz, 1H) 3.90 (dd, J=10.55, 4.39 Hz, 1H) 3.33-3.43 (m, 1H) 3.15 (q, J=7.47 Hz, 2H) 2.14 (s, 3H) 1.24 (d, J=7.03 Hz, 3H) 1.14 (t, J=7.47 Hz, 3H); ¹⁹F NMR (376 MHz, acetonitrile-d₃) δ ppm −76.18 (s., 3F, TFA) −154.22 (s., 1F); Analytical HPLC (low pH, 254 nM): Sunfire, RT=6.38 min, 92% purity; XBridge, RT=5.53 min, 95% purity.

Example 4

(2R)-2-[(1-Aminoisoquinolin-6-yl)amino]-N-ethyl-15,15-difluoro-4,17,20-trimethyl-3,12-dioxo-N-(1,3-thiazol-2-ylmethyl)-13-oxa-4,11-diazatricyclo[14.2.2.1⁶,¹⁰]henicosa-1(18),6,8,10 (21),16,19-hexaene-7-carboxamide; trifluoroacetic acid

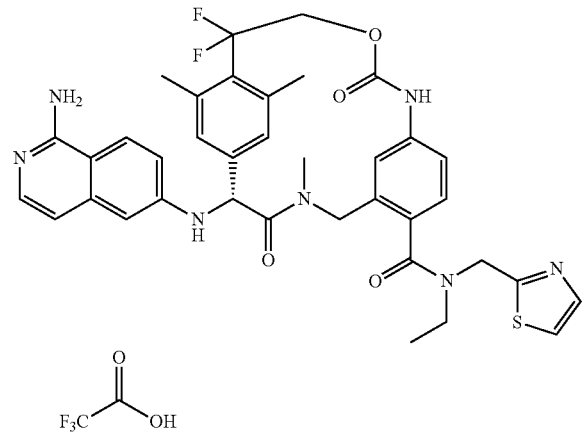

4A: tert-Butyl N-{6-[({[(5-amino-2-bromophenyl)methyl](methyl)carbamoyl}[4-(1,1-difluoro-2-hydroxyethyl)-3,5-dimethylphenyl]methyl)amino]isoquinolin-1-yl}-N-[(tert-butoxy)carbonyl]carbamate

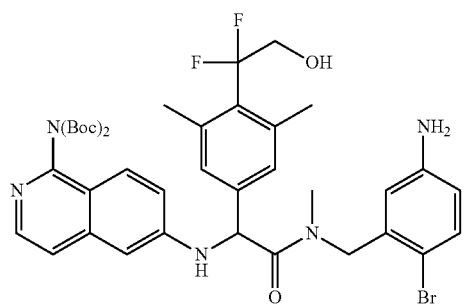

To a vial charged with Intermediate 1 (781 mg, 2.174 mmol) and Intermediate 7 (500 mg, 2.174 mmol) was added glyoxylic acid monohydrate (230 mg, 2.500 mmol) followed by acetonitrile (12 mL) and DMF (4 mL). The suspension was heated at 75° C. overnight. After it cooled to rt, 4-bromo-3-((methylamino)methyl)aniline HCl salt (751 mg, 2.61 mmol) was added, followed by additional DMF (8.000 mL) and DIEA (1.519 mL, 8.70 mmol). The reaction mixture was cooled to 0° C. HATU (909 mg, 2.391 mmol) was added. The reaction was stirred for 0.5 h then the cooling bath was removed and the reaction stirred for 2.5 h. The reaction was poured into 10% LiCl (100 mL) and extracted with EtOAc (3×100 mL). The combined organics were washed with 10% LiCl (100 mL), dried (Na₂SO₄), filtered and concentrated. The residue was chromatographed on Isco (120 g) eluting with 5 to 80% EtOAc/dichloromethane. Fractions containing desired material were rechromatographed using 0 to 10% MeOH/dichloromethane to give 4A (289 mg, 0.362 mmol, 16.64% yield) as a pale orange solid. MS and ¹H NMR are consistent with the desired product.

4B: tert-Butyl N-[6-({7-bromo-15,15-difluoro-4,17,20-trimethyl-3,12-dioxo-13-oxa-4,11-diazatricyclo[14.2.2.1⁶,¹⁰]henicosa-1(18),6,8,10 (21),16,19-hexaen-2-yl}amino)isoquinolin-1-yl]-N-[(tert-butoxy)carbonyl]carbamate

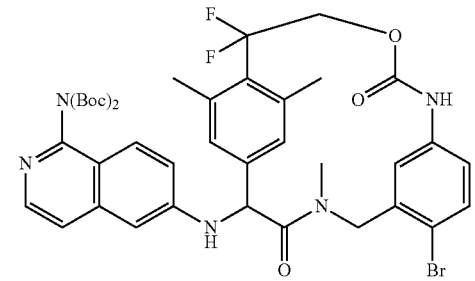

To a solution of 4A (289 mg, 0.362 mmol) in dichloromethane (5 mL) and acetonitrile (5.00 mL) at 0° C., was added phosgene (20% in toluene) (0.242 mL, 0.488 mmol). The reaction mixture was stirred at 0° C. for 15 min. Nitrogen was bubbled though the mixture for 0.5 h, then DMPU (~0.4 mL) was added. The resulting solution was added dropwise via a syringe pump into a solution of TEA (0.353 mL, 2.53 mmol) in dichloromethane (90 mL) at rt over 4 h, stirred for an additional 15 min and then evaporated. The crude product was purified by flash chromatography to give 4B (177 mg, 0.215 mmol, 59.3% yield) as a white solid. MS and ¹H NMR are consistent with the desired product.

4C: Methyl 2-[(1-{bis[(tert-butoxy)carbonyl]amino}isoquinolin-6-yl)amino]-15,15-difluoro-4,17,20-trimethyl-3,12-dioxo-13-oxa-4,11-diazatricyclo[14.2.2.1⁶,¹⁰]henicosa-1(18),6,8,10 (21),16,19-hexaene-7-carboxylate

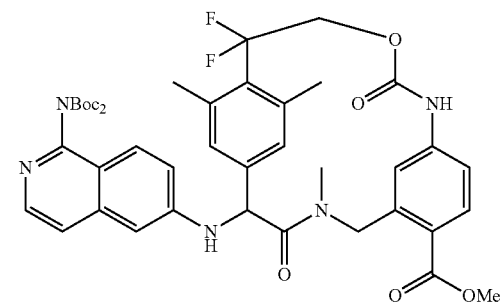

To a pressured-bottle charged with 4B (177 mg, 0.215 mmol), palladium(II) acetate (24.09 mg, 0.107 mmol), TEA (0.089 mL, 0.644 mmol) and DMSO (5 mL)/MeOH (2.500 mL) was added dppp (44.3 mg, 0.107 mmol). The resulting mixture was charged with carbon monoxide at 25 psi and stirred at 80° C. under an atmosphere of CO overnight. The reaction mixture was cooled to rt, filtered though CELITE® and concentrated to about ½ original volume. Water (50 mL) was added to the mixture and then extracted using 50% EtOAc/hexanes (3×). The combined organics were washed with water, dried with NaSO$_4$ then filtered and concentrated. The residue was purified on Isco (40 g) eluting with 0 to 30% EtOAc/dichloromethane to give 4C (130 mg, 0.162 mmol, 75% yield) as a white solid. MS and $^1$H NMR are consistent with the desired product.

4D: 2-[(1-{Bis[(tert-butoxy)carbonyl]amino}isoquinolin-6-yl)amino]-15,15-difluoro-4,17,20-trimethyl-3,12-dioxo-13-oxa-4,11-diazatricyclo[14.2.2.1$^{6,10}$]henicosa-1(18),6,8,10 (21),16,19-hexaene-7-carboxylic acid

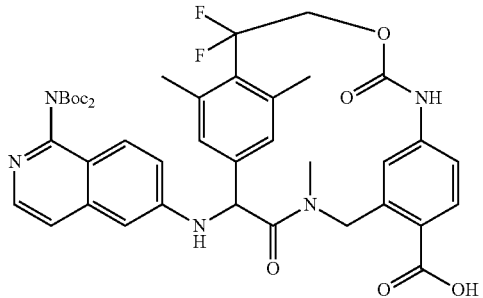

To a flask containing LiOH (38.7 mg, 1.617 mmol) was added water (8 mL). A solution of 4C (130 mg, 0.162 mmol) in dioxane (10 mL) was added and the reaction was stirred for 4.5 h. The reaction was partially evaporated to remove the dioxane then transferred to a funnel using H$_2$O (3 mL) and EtOAc (3 mL). To the mixture was added 1N sodium bisulfate (3.23 mL, 3.23 mmol) followed by extraction with EtOAc (4×8 mL). The combined organics were dried (Na$_2$SO$_4$), filtered and concentrated to leave 4D (128 mg, 90% yield) as a white solid. About 10% of the material is mono-boc compound by LC/MS. $^{19}$F and MS are consistent with the desired product.

4E: tert-Butyl N-[(tert-butoxy)carbonyl]-N-(6-{[(2R)-7-[ethyl(1,3-thiazol-2-ylmethyl)carbamoyl]-15,15-difluoro-4,17,20-trimethyl-3,12-dioxo-13-oxa-4,11-diazatricyclo[14.2.2.1^{6,10}]henicosa-1(18),6,8,10 (21),16,19-hexaen-2-yl]amino}isoquinolin-1-yl)carbamate

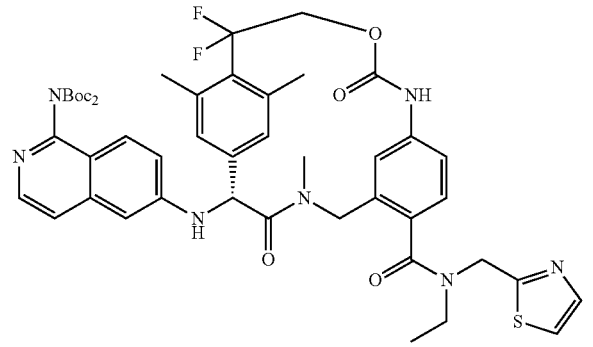

To a solution of 4D (64 mg, 0.081 mmol) in DMF (1.5 mL) was added ethyl-thiazol-2-ylmethyl-amine (13.83 mg, 0.097 mmol) followed by DIEA (0.028 mL, 0.162 mmol). The reaction was cooled to 0° C. and HATU (33.9 mg, 0.089 mmol) was added. Reaction was stirred for 15 min then allowed to warm to rt and stirred for 2 h. The reaction mixture was poured into EtOAc (25 mL), extracted with 10% LiCl (2×10 mL). The combined organics were dried (Na$_2$SO$_4$), filtered and evaporated. The residue was chromatographed on Isco (12 g) eluting with 0 to 100% EtOAc/dichloromethane to leave 58 mg of the mixture of diastereomers. The diastereomers were separated by a prep chiral HPLC (CHIRALCEL® R,R-Whelk-O1 250×21.1 mm) to give 4E (25.5 mg) as a white solid. MS is consistent with desired product.

Example 4

To a flask charged with 4E (23.5 mg, 0.026 mmol) was added TFA (1.5 mL) and the reaction was aged for 0.5 h. The solvent was removed on the rotovap and the residue purified by prep HPLC (YMC Sunfire 5 u C18 30×100 mm column). Fraction containing product was evaporated and lyophilized to give Example 4 (22 mg, 99% yield) as a white solid. $^1$H NMR is consistent with the desired product, although amide portion appears slightly obscured by rotamers. MS (ESI) m/z: 714.8 [M+1]$^+$.

Example 5

(2R)-2-[(1-Aminoisoquinolin-6-yl)amino]-7-(cyclopropanesulfonyl)-15,15-difluoro-4,17,20-trimethyl-13-oxa-4,11-diazatricyclo[14.2.2.1$^{6,10}$]henicosa-1(18),6,8,10 (21),16,19-hexaene-3,12-dione; trifluoroacetic acid

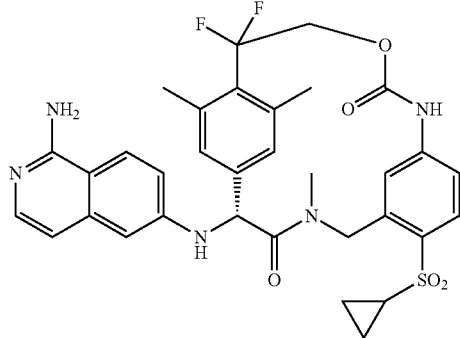

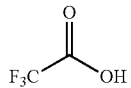

5A: tert-Butyl N-(6-{[({[5-amino-2-(cyclopropanesulfonyl)phenyl]methyl}(methyl)carbamoyl)[4-(1,1-difluoro-2-hydroxyethyl)-3,5-dimethylphenyl]methyl]amino}isoquinolin-1-yl)-N-[(tert-butoxy)carbonyl]carbamate

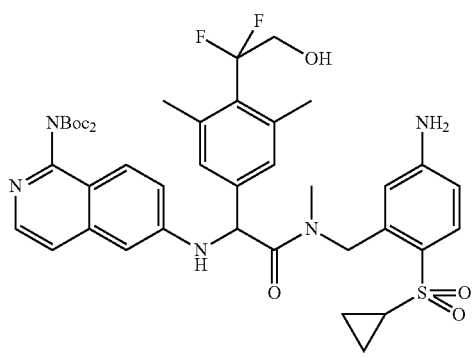

A mixture of Intermediate 7 (80 mg, 0.348 mmol), Intermediate 1 (125 mg, 0.348 mmol) and glyoxylic acid monohydrate (32.0 mg, 0.348 mmol) in DMF (0.3 mL)/acetonitrile (0.900 mL) was heated at 100° C. for 10 min in microwave reactor. A solution of Intermediate 8 (109 mg, 0.348 mmol) in DMF (2 mL) and DIEA (0.182 mL, 1.043 mmol) was added to the reaction mixture, followed by BOP (185 mg, 0.417 mmol) as a solid. The mixture was stirred at rt for 3 h. The reaction mixture was diluted with $CH_2Cl_2$ and 0.5 N HCl, extracted with $CH_2Cl_2$. The organic layer was washed with brine, dried over $Na_2SO_4$, filtered and concentrated. The crude product was purified by prep HPLC. The desired fractions were concentrated, diluted with EtOAc and washed with sat. $NaHCO_3$, dried over $Na_2SO_4$, filtered and concentrated to give 5A (100 mg, 0.121 mmol, 34.9% yield). MS (ESI) m/z: 824 [M+1]$^+$.

5B: tert-Butyl N-[(tert-butoxy)carbonyl]-N-(6-{[(2R)-7-(cyclopropanesulfonyl)-15,15-difluoro-4,17,20-trimethyl-3,12-dioxo-13-oxa-4,11-diazatricyclo[14.2.2.1$^{6,10}$]henicosa-1(18),6,8,10 (21),16,19-hexaen-2-yl]amino}isoquinolin-1-yl)carbamate

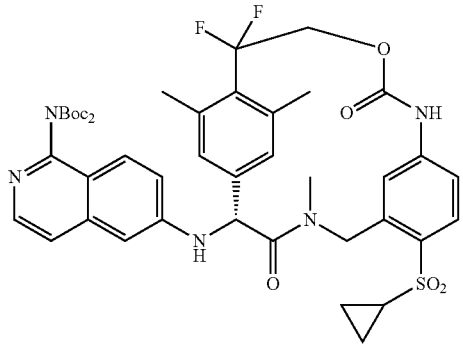

To a solution of 5B (160 mg, 0.194 mmol) in acetonitrile (6 mL) and dichloromethane (3 mL) at 0° C., was added phosgene solution (20% in toluene) (0.123 mL, 0.233 mmol) dropwise. The mixture was stirred at 0° C. for 20 min, then at rt for 15 min. The extra phosgene was removed by bubbling Ar though the reaction mixture (30 min). The resulting solution was added dropwise via syringe pump into a solution of TEA (0.217 mL, 1.554 mmol) in dichloromethane (40 ml) at rt over 3.0 h. The solution was stirred at rt overnight, quenched by 0.5 N HCl and extracted by $CH_2Cl_2$. The organic layer was washed with water, dried over sodium sulfate, filtered and concentrated. The crude product was purified by flash chromatography to afford a mixture of diastereoisomers (150 mg, 0.176 mmol, 91% yield). The diastereoisomers were separated by a prep chiral HPLC to give 5B (70 mg, 93% yield). MS and $^1$H NMR are consistent with the desired product.

Example 5

To a solution of 5B (60 mg, 0.071 mmol) in ethyl acetate (1 mL) was added 4 N HCl in dioxane (1.412 mL, 5.65 mmol). The mixture was stirred at rt for 3 h. Solvent was removed under reduced pressure. The crude product was purified by prep HPLC to afford Example 5 (19 mg, 0.025 mmol, 35.2% yield) after lyophilization. $^1$H NMR (400 MHz, acetonitrile-d$_3$) δ ppm 0.94-1.09 (m, 2H) 1.09-1.29 (m, 2H) 2.35 (d, J=10.55 Hz, 3H) 2.58 (d, J=7.91 Hz, 3H) 2.66-2.83 (m, 1H) 3.30 (s, 3H) 4.07-4.37 (m, 2H) 5.05-5.38 (m, 1H) 5.64 (br. s., 1H) 5.71 (d, J=17.58 Hz, 1H) 6.24 (s, 1H) 6.79 (br. s., 1H) 6.83 (d, J=6.59 Hz, 1H) 6.89 (dd, J=8.35, 1.76 Hz, 1H) 6.95 (br. s., 1H) 7.11-7.18 (m, 1H) 7.24-7.31 (m, 1H) 7.64 (br. s., 1H) 7.77 (d, J=8.35 Hz, 1H) 7.83 (d, J=9.23 Hz, 1H) 8.07 (s, 1H). $^{19}$F NMR (376 MHz, acetonitrile-d$_3$) δ ppm −97.18-−94.75 (m, 1F) −93.68-−91.47 (m, 1F) −76.23 (br. s., 3F); MS (ESI) m/z: 650.1 [M+1]$^+$. Analytical HPLC (low pH, 254 nM): Sunfire, RT=6.29, 100% purity; XBridge, RT=7.34, 100% purity.

Example 6

(2R,15R)-2-[(1-Amino-4-fluoroisoquinolin-6-yl)amino]-7-[(2S)-1-methoxypropane-2-sulfonyl]-4,15,17-trimethyl-13-oxa-4,11-diazatricyclo[14.2.2.1$^{6,10}$]henicosa-1(18),6,8,10 (21),16,19-hexaene-3,12-dione; trifluoroacetic acid

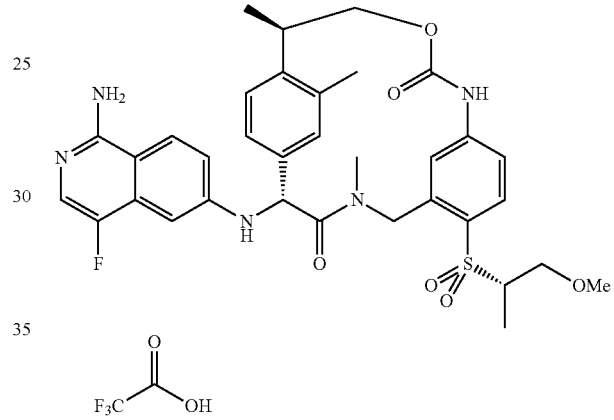

6A: Benzyl 2-chloro-5-nitrobenzyl(methyl)carbamate

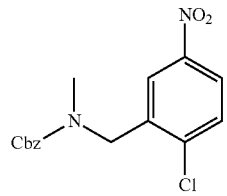 [SMILES: CN(Cc1cc([N+](=O)[O-])ccc1Cl)C(=O)OCc1ccccc1]

To a solution of 2-chloro-5-nitrobenzaldehyde (5 g, 26.9 mmol) in MeOH (100 mL), was added methylamine (33% in EtOH) (14.82 mL, 29.6 mmol). The mixture was stirred at rt for 1 h, cooled to 0° C. and treated with $NaBH_4$ (1.223 g, 32.3 mmol). The mixture was stirred at rt for 30 min, then was concentrated. The residue was dissolved in THF (50 mL), treated with water (20 mL) and sat. $NaHCO_3$ (20 mL). After stirring for 10 min, Cbz-Cl (4.62 mL, 32.3 mmol) was added dropwise. The mixture was stirred at rt over night. THF was removed under reduced pressure. The mixture was extracted with EtOAc (2×). The organic phase was washed with brine, dried ($Na_2SO_4$) and concentrated. The crude product was purified by flash chromatography (loaded in chloroform onto a 120 g column and eluted with a gradient from 0 to 50% ethyl acetate/hexanes) to give 6A (7.39 g, 22.08 mmol, 82% yield) as a white solid. MS (ESI) m/z: 335.1 [M+1]+; 1H NMR (400 MHz, chloroform-d) δ ppm 7.97-8.13 (m, 2H) 7.55 (d, J=7.53 Hz, 1H) 7.27-7.45 (m, 5H) 5.11-5.26 (m, 2H) 4.58-4.72 (m, 2H) 3.03 (br. s., 3H), 3:2 rotamers.

6B: Benzyl 2-mercapto-5-nitrobenzyl(methyl)carbamate

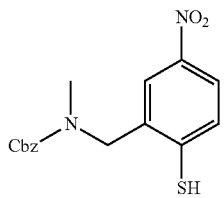 [SMILES: CN(Cc1cc([N+](=O)[O-])ccc1S)C(=O)OCc1ccccc1]

To a partially dissolved mixture of 6A (7.00 g, 20.91 mmol) in DMSO (40 mL), was added sodium sulfide (3.26 g, 41.8 mmol). The mixture was stirred at 50° C. for 45 min. The reaction mixture was cooled to rt, poured into water (500 mL). The mixture was extracted with EtOAc (3×). The combined organic phase was washed with water and brine, filtered though a pad of SiO$_2$ and concentrated to a red oil. The crude product was purified by flash chromatography (loaded in chloroform onto a 40 g column and eluted with a gradient from 0 to 100% ethyl acetate/hexanes). The desired fractions were collected, concentrated to give 6B (3.10 g, 9.33 mmol, 44.6% yield) as an orange solid. 1H NMR (400 MHz, chloroform-d) δ ppm 7.99 (d, J=7.15 Hz, 2H) 7.27-7.48 (m, 6H) 5.20 (br. s., 2H) 4.56 (br. s., 2H) 2.96 (br. s., 3H); MS (ESI) m/z: 333.1 [M+1]+.

6C: (S)-Benzyl 2-((1-methoxypropan-2-yl)thio)-5-nitrobenzyl(methyl)carbamate

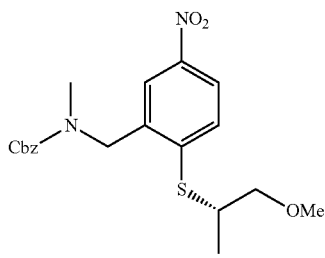 [SMILES: COC[C@H](C)Sc1ccc([N+](=O)[O-])cc1CN(C)C(=O)OCc1ccccc1]

To a solution of triphenylphosphine (355 mg, 1.354 mmol) in THF (4 mL) at 0° C., was added DIAD (0.263 mL, 1.354 mmol) dropwise. The mixture was stirred at 0° C. for 10 min affording a colorless suspension. A solution of 6B (300 mg, 0.903 mmol) and (R)-1-methoxypropan-2-ol (0.133 mL, 1.354 mmol) in THF (2 mL) was added dropwise. The resultant dark red solution was stirred at 0° C. for 0.5 h, then was allowed to slowly warm to rt over night. The reaction mixture was concentrated. The crude product was purified by flash chromatography (loaded in chloroform onto a 40 g column and eluted with a gradient from 0 to 40% ethyl acetate/hexanes) to afford 6C (396 mg, 108% yield) as yellow oil/semisolid. MS (ESI) m/z: 405.2 [M+1]+; 1H NMR (400 MHz, chloroform-d) δ ppm 8.07 (d, J=8.53 Hz, 1H) 7.96 (d, J=18.57 Hz, 1H) 7.32-7.51 (m, 6H) 5.11-5.26 (m, 2H) 4.59 (d, J=18.07 Hz, 2H) 3.58-3.68 (m, 1H) 3.47 (d, J=6.53 Hz, 2H) 3.37 (s, 3H) 2.99 (br. s., 3H) 1.40 (br. s., 3H).

6D: (S)-Benzyl 2-((1-methoxypropan-2-yl)sulfonyl)-5-nitrobenzyl(methyl)carbamate

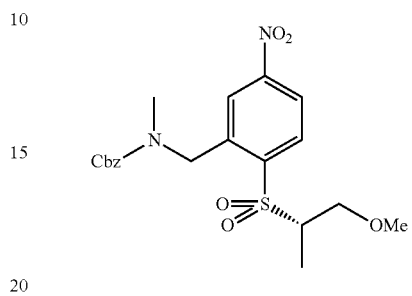

To a solution of 6C (362 mg, 0.895 mmol) in dichloromethane (8 mL) at rt was added m-CPBA (552 mg, 2.237 mmol). The mixture was stirred at rt over night, poured into 10% Na$_2$CO$_3$, extracted with dichloromethane (3×). The combined organic phase was dried (Na$_2$SO$_4$) and concentrated. The crude product was purified by flash chromatography (loaded in chloroform onto a 40 g column and eluted with a gradient from 0 to 75% ethyl acetate/hexanes) to give a colorless viscous oil. This material contains some DIAD byproduct and thus was further purified by prep HPLC to afford 6D (330 mg, 0.756 mmol, 84% yield) as a white solid. MS (ESI) m/z: 437.1 [M+1]+. 1H NMR (400 MHz, chloroform-d) δ ppm 8.08-8.27 (m, 3H) 7.16-7.44 (m, 5H) 5.08-5.26 (m, 2H) 4.90-5.04 (m, 2H) 3.30-3.74 (m, 3H) 3.09 (s, 3H) 3.01-3.18 (m, 3H) 1.27-1.45 (m, 3H) rotamers.

6E: (S)-4-((1-Methoxypropan-2-yl)sulfonyl)-3-((methylamino)methyl)aniline

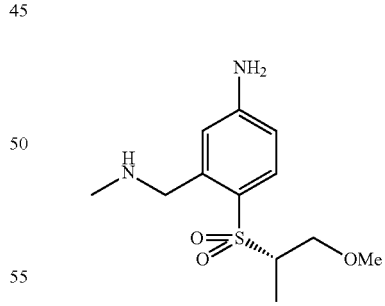

To a suspension of 6D (327 mg, 0.749 mmol) in MeOH (10 mL), was added 10% Pd—C (40 mg, 0.038 mmol). The mixture was evacuated and flushed with H$_2$ (3×), then was stirred under an atmosphere of H$_2$ for 7.5 h. The reaction mixture was filtered and concentrated to give 6E (203 mg, 99% yield) as a colorless semisolid. MS (ESI) m/z: 273.2 [M+1]+. 1H NMR (400 MHz, methanol-d$_4$) δ ppm 7.58 (d, J=8.78 Hz, 1H) 6.69 (d, J=2.51 Hz, 1H) 6.64 (dd, J=8.66, 2.38

Hz, 1H) 3.78-3.89 (m, 2H) 3.59-3.67 (m, 1H) 3.44-3.55 (m, 2H) 3.21 (s, 3H) 2.37 (s, 3H) 1.28 (d, J=6.78 Hz, 3H).

6F: tert-Butyl N-[6-({[({5-amino-2-[(2S)-1-methoxypropane-2-sulfonyl]phenyl}methyl)(methyl)carbamoyl]({4-[(2R)-1-hydroxypropan-2-yl]-3-methylphenyl})methyl}amino)-4-fluoroisoquinolin-1-yl]-N-[(tert-butoxy)carbonyl]carbamate

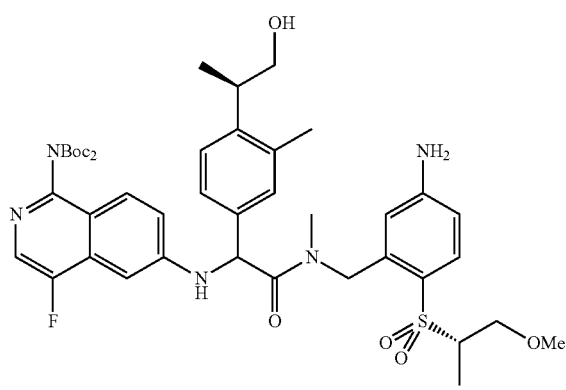

To a mixture of Intermediate 5 (56.6 mg, 0.291 mmol), Intermediate 3 (110 mg, 0.291 mmol) and glyoxylic acid monohydrate (26.8 mg, 0.291 mmol), were added DMF (1 mL) and acetonitrile (3 mL). The heterogeneous mixture was stirred at 80° C. for 1 h to give a brown solution, which was cooled to rt. To this mixture were added 6E (95 mg, 0.35 mmol), DMF (3.00 mL), TEA (0.162 mL, 1.166 mmol), and BOP (142 mg, 0.321 mmol). The mixture was stirred at rt for 2 h, partitioned between EtOAc and H$_2$O. The aqueous phase was extracted with EtOAc (2×). The combined organic phase was washed with 10% aq. LiCl (2×) and brine, dried (Na$_2$SO$_4$) and concentrated. The crude product was purified by flash chromatography (loaded in dichloromethane onto a 24 g column and eluted with a gradient from 0 to 10% methanol/methylene chloride). The desired product was freeze-dried from dioxane to give 6F (206 mg, 0.246 mmol, 84% yield) as an off-white solid. MS (ESI) m/z: 838.5 [M+1]$^+$. $^1$H NMR: complicated by 1:1 mixture of diastereomers and amide isomers.

Example 6

To a solution of 6F (203 mg, 0.242 mmol) in acetonitrile (1 mL) and dichloromethane (3 mL) at 0° C., was added phosgene (20% in toluene) (0.120 mL, 0.242 mmol). The mixture was stirred at 0° C. for 15 min, then was bubbled with Ar for 20 min. The solution was added dropwise to TEA (0.236 mL, 1.696 mmol) in dichloromethane (100 mL) at rt over 3.5 h. The reaction mixture was stirred for 30 min, then was concentrated. The crude product was purified by flash chromatography (loaded in dichloromethane onto a 40 g column and eluted with a gradient from 0 to 10% methanol/methylene chloride) to give a mixture of diastereoisomers. The diastereomers were separated by a prep chiral HPLC (R,R-Whelk-O column 21.1×250 mm). The fractions corresponding to the second peak were concentrated, treated with TFA (2 mL) for 20 min. The mixture was concentrated and the product was purified by prep HPLC to afford Example 6 (47.7 mg, 0.061 mmol, 50.4% yield) as an off-white solid after lyophilization. MS (ESI) m/z: 664.3 [M+1]$^+$. $^1$H NMR (400 MHz, methanol-d$_4$) δ ppm 8.10 (dd, J=9.29, 2.01 Hz, 1H) 7.75 (d, J=8.53 Hz, 1H) 7.67 (dd, J=8.03, 1.76 Hz, 1H) 7.49 (d, J=8.03 Hz, 1H) 7.44 (d, J=5.02 Hz, 1H) 7.28 (dd, J=9.29, 2.26 Hz, 1H) 7.08 (s, 1H) 6.97 (d, J=1.76 Hz, 1H) 6.85 (dd, J=8.53, 2.01 Hz, 1H) 6.44 (t, J=2.38 Hz, 1H) 5.77 (s, 1H) 5.68 (d, J=17.57 Hz, 1H) 4.64 (t, J=11.04 Hz, 1H) 4.21 (d, J=17.57 Hz, 1H) 3.99 (dd, J=10.67, 4.39 Hz, 1H) 3.67-3.75 (m, 1H) 3.58-3.67 (m, 2H) 3.50 (ddd, J=11.36, 7.09, 4.39 Hz, 1H) 3.39 (s, 3H) 3.23 (s, 3H) 2.30 (s, 3H) 1.34 (d, J=7.28 Hz, 3H) 1.30 (d, J=6.53 Hz, 3H). Analytical HPLC (low pH, 254 nM): Sunfire, RT=5.92, 99% purity; XBridge, RT=7.34, 99.9% purity.

Example 7

(2R,15R)-2-[(1-Aminoisoquinolin-6-yl)amino]-7-(azetidine-1-carbonyl)-4,15,17-trimethyl-13-oxa-4, 11-diazatricyclo[14.2.2.1$^{6,10}$]henicosa-1(18),6,8,10 (21),16,19-hexaene-3,12-dione; trifluoroacetic acid

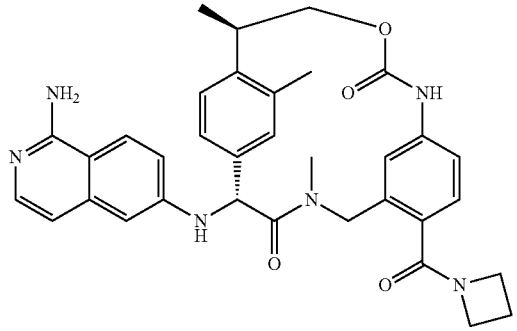

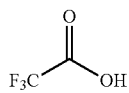

To a solution of 1D (10 mg, 0.016 mmol) at 0° C. in DMF (0.3 mL) and acetonitrile (0.300 mL) was added HATU (7.13 mg, 0.019 mmol) and N-methylmorpholine (2.58 µL, 0.023 mmol). The reaction was stirred for 5 min. Then azetidine (1.721 µL, 0.016 mmol) was added and the reaction was allowed to warm to rt and stirred for 4 h. The reaction mixture was diluted with water and extracted with EtOAc (3×). The combined organic layer was washed with water and brine, dried (MgSO$_4$), and concentrated.

The residue was purified by prep HPLC. The desired fractions were concentrated and treated with 1.5 mL of TFA at rt for 30 min. The mixture was concentrated and the product was purified by prep HPLC to afford Example 7 (1.1 mg, 10% yield). $^1$H NMR (400 MHz, MeOD) δ ppm 8.05 (1H, d, J=9.03 Hz), 7.59-7.72 (1H, m), 7.46 (1H, d, J=8.03 Hz), 7.31 (1H, d, J=7.03 Hz), 7.11-7.28 (3H, m), 6.92 (1H, d, J=7.28 Hz), 6.84 (1H, d, J=2.26 Hz), 6.72 (1H, dd, J=8.03, 2.01 Hz), 6.16 (1H, s), 5.73 (1H, s), 5.38 (1H, d, J=17.07 Hz), 4.16 (4H, d, J=7.03 Hz), 4.07 (1H, d, J=17.32 Hz), 3.98 (1H, dd, J=10.79, 4.52 Hz), 3.42-3.55 (2H, m), 2.32 (5H, s), 1.32 (3H, d, J=7.03 Hz).

Example 8

(2R,15R)-2-[(1-Amino-4-fluoroisoquinolin-6-yl)amino]-4,15,17-trimethyl-7-(propane-2-sulfonyl)-13-oxa-4,11-diazatricyclo[14.2.2.1$^{6,10}$]henicosa-1(18),6,8,10 (21),16,19-hexaene-3,12-dione; trifluoroacetic acid

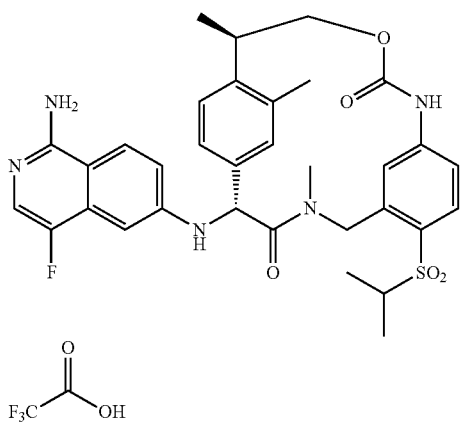

8A: tert-Butyl 5-amino-2-(isopropylsulfonyl)benzyl (methyl)carbamate

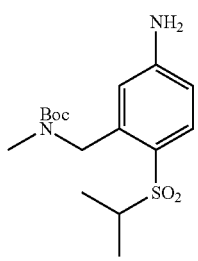 [SMILES: CC(C)S(=O)(=O)c1ccc(N)cc1CN(C)C(=O)OC(C)(C)C]

To a 500 mL round-bottomed flask was added tert-butyl 2-(isopropylsulfonyl)-5-nitrobenzyl(methyl)carbamate (2.6 g, 6.98 mmol, see WO 2008/079836 for preparation) and MeOH (200 ml) to give a colorless solution. Pd/C (0.074 g, 0.698 mmol) was added. The mixture was stirred under a hydrogen balloon at rt overnight. Pd/C was removed by filtration and the filtrate was concentrated to give 8A (2.18 g, 91% yield).

8B: 4-(Isopropylsulfonyl)-3-((methylamino)methyl) aniline

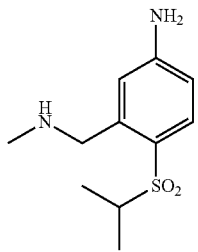 [SMILES: CNCc1cc(N)ccc1S(=O)(=O)C(C)C]

To a solution of 8A (1 g, 2.92 mmol) in ethyl acetate (10 ml) was added 4N HCl (29.2 ml, 117 mmol) and the mixture was stirred at r.t. for 4 h. Solvent was removed under reduced pressure to yield 8B (920 mg, 2.92 mmol, 100% yield) as a yellow solid. $^1$H NMR (500 MHz, methanol-d$_3$) δ ppm 1.27 (d, J=6.60 Hz, 6H) 3.26-3.41 (m, 1H) 3.66 (s, 3H) 4.28 (s, 2H) 6.79-6.91 (m, 2H) 7.68 (d, J=8.80 Hz, 1H).

8C: tert-Butyl N-(6-{[({[5-amino-2-(propane-2-sulfonyl)phenyl]methyl}(methyl)carbamoyl)({4-[(2R)-1-hydroxypropan-2-yl]-3-methylphenyl})methyl]amino}-4-fluoroisoquinolin-1-yl)-N-[(tert-butoxy)carbonyl]carbamate

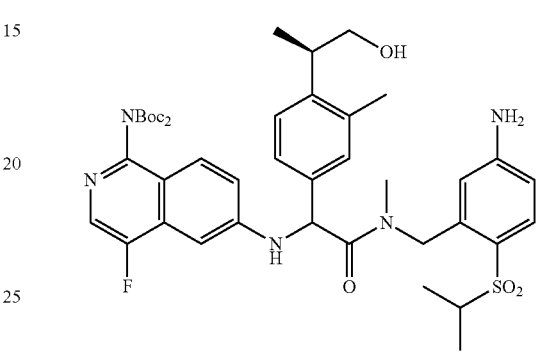

A mixture of Intermediate 5 (70 mg, 0.361 mmol), Intermediate 3 (136 mg, 0.361 mmol) and glyoxylic acid monohydrate (33.2 mg, 0.361 mmol) in DMF (0.25 mL)/acetonitrile (0.750 mL) was heated at 80° C. for 2 h. Then a solution of 8B (136 mg, 0.433 mmol) in DMF (2 mL) and DIEA (0.189 mL, 1.082 mmol) was added, followed by BOP (191 mg, 0.433 mmol) as a solid. The mixture was stirred at rt overnight. The crude product was purified by prep HPLC to give 8C (228 mg, 0.282 mmol, 78% yield). MS (ESI) m/z: 808 [M+1]$^+$.

8D: tert-Butyl N-[(tert-butoxy)carbonyl]-N-(4-fluoro-6-{[(2R,15R)-4,15,17-trimethyl-3,12-dioxo-7-(propane-2-sulfonyl)-13-oxa-4,11-diazatricyclo[14.2.2.1$^{6,10}$]henicosa-1(18),6,8,10 (21),16,19-hexaen-2-yl]amino}isoquinolin-1-yl)carbamate

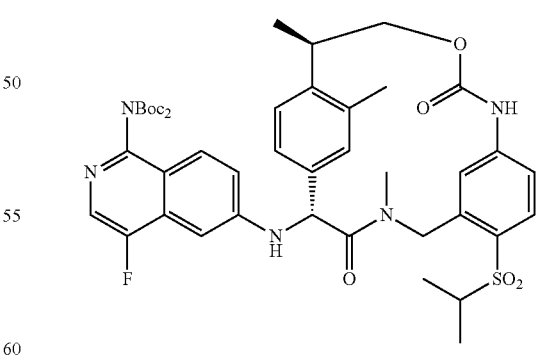

To a solution of 8C (228 mg, 0.282 mmol) in acetonitrile (10 mL) and dichloromethane (5 mL) at 0° C., was added phosgene solution (20% in toluene) (0.178 mL, 0.339 mmol) dropwise. The mixture was stirred at 0° C. for 20 min, then at rt for 15 min. The extra phosgene was removed by bubbling Ar though the reaction mixture (15 min). The resulting solution was added dropwise via syringe pump into a stirred solution of TEA (0.315 mL, 2.258 mmol) in dichloromethane (80 ml) at rt over 3.0 h. The reaction was quenched by 0.5 N HCl and extracted with CH₂Cl₂. The organic layer was collected, washed with water and dried over sodium sulfate, then concentrated. The crude product was purified by flash chromatography to give a mixture of diastereoisomers (235 mg). The diastereomers (165 mg) were separated by a prep chiral HPLC (R,R-Whelk-O column 21.1×250 mm) to give 8D (54 mg, 0.065 mmol, 32.7% yield). MS (ESI) m/z: 883 [M+1]⁺. ¹H NMR (400 MHz, chloroform-d) δ ppm 1.26 (d, J=6.59 Hz, 3H) 1.28-1.37 (m, 21H) 1.42 (d, J=6.59 Hz, 3H) 2.09 (s, 3H) 3.27-3.42 (m, 5H) 3.90 (dd, J=10.77, 3.73 Hz, 1H) 4.30 (d, J=17.58 Hz, 1H) 4.63 (t, J=10.99 Hz, 1H) 5.43 (d, J=5.71 Hz, 1H) 5.68 (d, J=18.02 Hz, 1H) 6.36 (s, 1H) 6.55 (d, J=5.71 Hz, 1H) 6.75 (d, J=8.35 Hz, 1H) 6.86 (s, 1H) 7.01 (d, J=9.23 Hz, 1H) 7.04-7.12 (m, 2H) 7.45-7.54 (m, 2H) 7.61 (d, J=7.91 Hz, 1H) 7.77 (d, J=8.35 Hz, 1H) 8.03 (s, 1H). ¹⁹F NMR (376 MHz, chloroform-d) δ ppm -141.12 (br. s., 1F).

Example 8

To a solution of 8D (85 mg, 0.102 mmol) in ethyl acetate (1 ml) was added 4N HCl in dioxane (1.529 ml, 6.12 mmol) and the mixture was stirred at rt overnight. Solvent was removed under reduced pressure and the crude product was purified by prep HPLC to give Example 8 (51 mg, 0.065 mmol, 64.0% yield) after lyophilization. MS (ESI) m/z: 634.5 (M+H)⁺. ¹H NMR (400 MHz, acetonitrile-d₃) δ ppm 1.21 (t, J=6.59 Hz, 6H) 1.28 (d, J=7.03 Hz, 3H) 2.19 (s, 3H) 3.29 (s, 3H) 3.29-3.49 (m, 2H) 3.94 (dd, J=10.55, 4.39 Hz, 1H) 4.14 (d, J=17.58 Hz, 1H) 4.58 (t, J=10.99 Hz, 1H) 5.64 (d, J=17.58 Hz, 2H) 6.36 (d, J=1.76 Hz, 1H) 6.85 (dd, J=8.57, 1.98 Hz, 1H) 6.92 (s, 1H) 6.99 (s, 1H) 7.18 (dd, J=9.01, 2.42 Hz, 1H) 7.29 (d, J=4.83 Hz, 1H) 7.47 (d, J=7.91 Hz, 1H) 7.69 (dd, J=7.91, 1.76 Hz, 1H) 7.74 (d, J=8.35 Hz, 1H) 7.76-7.86 (m, 2H). ¹⁹F NMR (376 MHz, acetonitrile-d₃) δ ppm -154.29 (br. s., 1F) -76.30 (s, 3F); Analytical HPLC (low pH, 254 nM): Sunfire, RT=6.28, 95.6% purity; XBridge, RT=5.66, 100% purity.

Example 9

(2R,15R)-2-[(1-Amino-8-fluoroisoquinolin-6-yl)amino]-7-(cyclopropanesulfonyl)-4,15,17-trimethyl-13-oxa-4,11-diazatricyclo[14.2.2.1⁶,¹⁰]henicosa-1(18),6,8,10 (21),16,19-hexaene-3,12-dione; trifluoroacetic acid

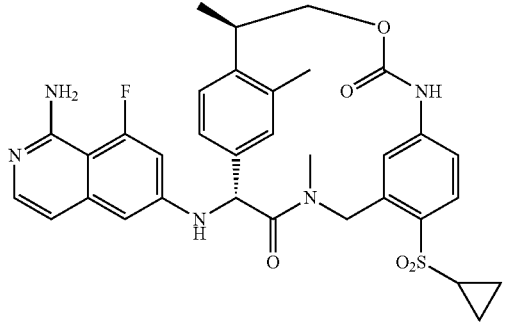

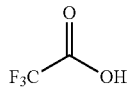

9A: tert-Butyl N-(6-{[({[5-amino-2-cyclopropanesulfonyl)phenyl]methyl}(methyl)carbamoyl)({4-[(2R)-1-hydroxypropan-2-yl]-3-methylphenyl})methyl]amino}-8-fluoroisoquinolin-1-yl)-N-[(tert-butoxy)carbonyl]carbamate

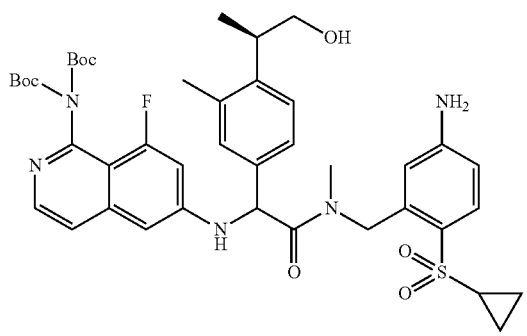 [SMILES: Cc1cc(C(Nc2cc(F)c3c(N(C(=O)OC(C)(C)C)C(=O)OC(C)(C)C)nccc3c2)C(=O)N(C)Cc2cc(N)ccc2S(=O)(=O)C2CC2)ccc1[C@@H](C)CO]

A mixture of Intermediate 2 (122 mg, 0.324 mmol), Intermediate 5B (100 mg, 0.324 mmol) and glyoxylic acid monohydrate (29.9 mg, 0.324 mmol) in DMF (0.5 mL) and acetonitrile (1.5 mL) was heated at 70° C. overnight. To the reaction mixture was added Intermediate 8 (0.100 g, 0.320 mmol) and DIEA (0.279 mL, 1.600 mmol) in DMF (1.0 mL), followed by BOP (0.18 g, 0.40 mmol). The mixture was stirred at rt overnight. To the solution was added 0.5N HCl and extracted with dichloromethane (3×). The organic layer was washed with brine and dried over sodium sulfate. The crude product was purified by flash chromatography to give 9A (0.2 g, 78% yield). MS (ESI) m/z: 806.6 [M+1]⁺.

9B: tert-Butyl N-[(tert-butoxy)carbonyl]-N-(6-{[(15R)-7-(cyclopropanesulfonyl)-4,15,17-trimethyl-3,12-dioxo-13-oxa-4,11-diazatricyclo[14.2.2.1⁶,¹⁰]henicosa-1(18),6,8,10(21),16,19-hexaen-2-yl]amino}-8-fluoroisoquinolin-1-yl)carbamate

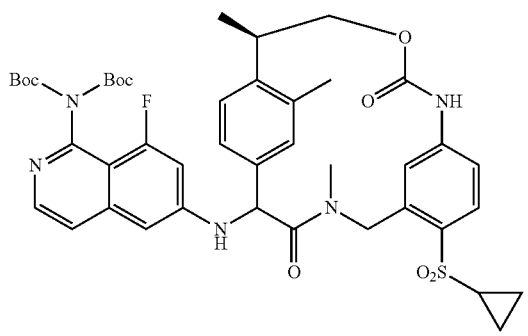 [SMILES: Cc1cc2ccc1[C@@H](C)COC(=O)Nc1ccc(S(=O)(=O)C3CC3)c(c1)CN(C)C(=O)C2Nc1cc(F)c2c(N(C(=O)OC(C)(C)C)C(=O)OC(C)(C)C)nccc2c1]

To a solution of 9A (0.2 g, 0.248 mmol) in acetonitrile (15 mL) and dichloromethane (5 mL) at 0° C., was added phosgene solution (20% in toluene) (0.157 mL, 0.298 mmol). The mixture was stirred at 0° C. for 30 min, then at rt for 30 min.

Extra phosgene was removed by bubbling Ar though the reaction mixture for 20 min. The mixture was diluted with methylene chloride (5 mL), then was added dropwise via a syringe pump into a stirred solution of TEA (0.277 mL, 1.985 mmol) in dichloromethane (60 mL) at rt over 2.5 h. To the reaction mixture was added 0.5 N HCl (30 mL) and dichloromethane. The organic layer was collected and aqueous was extracted with $CH_2Cl_2$. The organic layers were combined and washed with brine and dried over sodium sulfate. The solvent was removed and the crude 9B (0.2 g) was taken to the next step without purification. MS (ESI) m/z: 832.1 [M+1]$^+$.

Example 9

To 9B (0.2 g, 0.240 mmol) in dichloromethane (2 mL) was added 4M HCl in dioxane (2 mL, 8.00 mmol). The reaction was stirred at rt for 2 h. Additional 4M HCl (1.0 mL) was added and the reaction was left at rt over night. Solvent was removed and the crude was purified using a prep HPLC (C18 PHENOMENEX® Luna column 30 mm×100 mm, 5µ). The desired fractions were concentrated and the material was further purified by a prep chiral HPLC (equipped with a Chiral OD column) to give Example 9 (7.2 mg, 9.2% yield). MS (ESI) (m/z): 632.4 (M+H)$^+$. $^1$H NMR (400 MHz, MeOD) δ ppm 0.95-1.15 (m, 2H) 1.14-1.27 (m, 2H) 1.32 (t, J=7.33 Hz, 3H) 2.29 (s, 3H) 3.36-3.40 (m, 3H) 3.44-3.55 (m, 1H) 3.97 (dd, J=10.86, 4.29 Hz, 1H) 4.28 (d, J=17.68 Hz, 1H) 4.62 (t, J=10.99 Hz, 1H) 5.63 (s, 1H) 5.75 (d, J=17.43 Hz, 1H) 6.41 (d, J=2.02 Hz, 1H) 6.51 (d, J=2.27 Hz, 1H) 6.64-6.78 (m, 2H) 6.81 (dd, J=8.46, 2.15 Hz, 1H) 7.10 (d, J=1.52 Hz, 1H) 7.41-7.54 (m, 2H) 7.63 (dd, J=7.83, 1.77 Hz, 1H) 7.71 (d, J=8.34 Hz, 1H); $^{19}$F NMR (376 MHz, MeOD) δ ppm −115.25 (s, 1F); Analytical HPLC (low pH, 254 nM): Sunfire, RT=5.97 min, 97% purity; XBridge, RT=6.59 min, 98% purity.

Example 10

(2R)-2-[(2R,15R)-2-[(1-Amino-4-fluoroisoquinolin-6-yl)amino]-4,15,17-trimethyl-3,12-dioxo-13-oxa-4,11-diazatricyclo[14.2.2.1$^{6,10}$]henicosa-1(18),6,8,10(21),16,19-hexaen-7-yl]-4,4-difluorobutanoic acid; trifluoroacetic acid

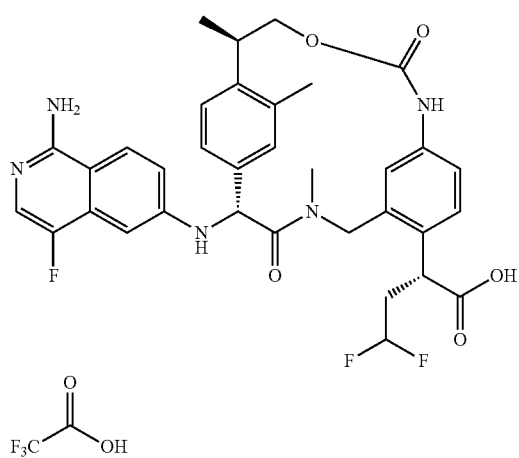

10A: Diethyl 2-(2-((((benzyloxy)carbonyl)(methyl)amino)methyl)-4-nitrophenyl)malonate

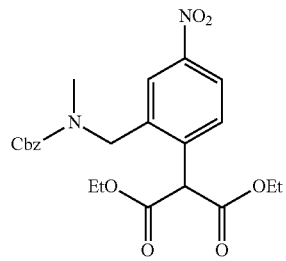 [SMILES: CCOC(=O)C(C(=O)OCC)c1ccc([N+](=O)[O-])cc1CN(C)C(=O)OCc1ccccc1]

To sodium hydride (60% dispersion) (1.885 g, 47.1 mmol), was added DMSO (20 mL). The mixture was stirred for 5 min, then diethyl malonate (7.15 mL, 47.1 mmol) was added. The reaction mixture was stirred at rt for 15 min to give a clear colorless solution. To this mixture was added a solution of benzyl 2-fluoro-5-nitrobenzyl(methyl)carbamate (3 g, 9.43 mmol) in DMSO (1 mL) dropwise. The orange reaction mixture was stirred at rt for 1 h, then at 65° C. for 3 h. The reaction mixture was cooled to rt, quenched with sat. NH$_4$Cl. The mixture was diluted with EtOAc. The organic phase was washed with H$_2$O (2×) and brine, dried (Na$_2$SO$_4$) and concentrated. The crude product was purified by flash chromatography (loaded in chloroform onto a 120 g column and eluted with a gradient from 0 to 30% ethyl acetate/hexanes) to give 10A (3.88 g, 8.46 mmol, 90% yield). MS (ESI) m/z: 458.9 (M+H)$^+$.

10B: Ethyl 2-(2-((((benzyloxy)carbonyl)(methyl)amino)methyl)-4-nitrophenyl)acetate

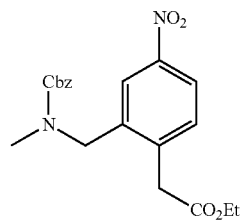 [SMILES: CCOC(=O)Cc1ccc([N+](=O)[O-])cc1CN(C)C(=O)OCc1ccccc1]

10A (3.22 g, 7.02 mmol) was dissolved in DMSO (25 mL), lithium chloride (0.596 g, 14.05 mmol) and water (0.152 mL, 8.43 mmol) were added. The reaction mixture was stirred at 130° C. for 3 h, then was cooled to rt, diluted with EtOAc (250 mL), washed with water (2×100 mL), brine (1×100 mL) and dried (Na$_2$SO$_4$). EtOAc was removed under reduced pressure and the crude product was purified by flash chromatography to give 10B (850 mg, 31.3% yield); MS (ESI) m/z: 386.9 (M+H)$^+$.

10C: Ethyl 2-(2-((((benzyloxy)carbonyl)(methyl)amino)methyl)-4-nitrophenyl)-4,4-difluorobutanoate

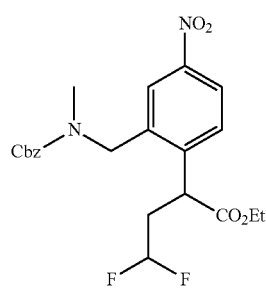 [SMILES: CCOC(=O)C(CC(F)F)c1ccc([N+](=O)[O-])cc1CN(C)C(=O)OCc1ccccc1]

To a solution of 10B (345 mg, 0.893 mmol) in THF (5 mL) at −78° C., was added LDA (2 M, heptane, THF and ethylbenzene) (0.536 mL, 1.071 mmol). The red/black mixture was stirred at −78° C. for 20 min, then a solution of 2,2-difluoroethyl trifluoromethanesulfonate (210 mg, 0.982 mmol) in THF (0.5 mL) was added dropwise. The reaction was removed from the cooling bath and was stirred at rt for 4 h. The reaction mixture was quenched with sat. NH$_4$Cl, diluted with EtOAc. The organic phase was washed with H$_2$O and brine, dried (Na$_2$SO$_4$) and concentrated. The crude product was purified by flash chromatography (loaded in chloroform onto a 12 g column and eluted with a gradient from 0 to 50% ethyl acetate/hexanes) to give 10C (70 mg, 0.155 mmol, 17.41% yield) pale yellow oil. MS (ESI) m/z: 450.9 (M+H)$^+$. $^1$H NMR (400 MHz, chloroform-d) δ ppm 8.15 (d, J=7.91 Hz, 1H) 7.97-8.11 (m, 1H) 7.50 (d, J=7.47 Hz, 1H) 7.24-7.43 (m, 5H) 5.10-5.29 (m, 2H) 4.57-4.87 (m, 2H) 4.00-4.39 (m, 3H) 2.91 (br. s., 3H) 2.57-2.87 (m, 1H) 2.19 (s, 1H) 1.05-1.33 (m, 3H).

10D: (R)-Ethyl 2-(2-((((benzyloxy)carbonyl)(methyl)amino)methyl)-4-nitrophenyl)-4,4-difluorobutanoate

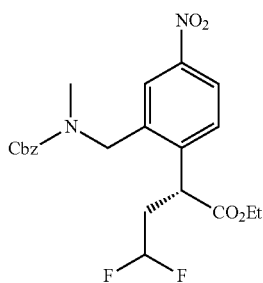 [SMILES: CCOC(=O)[C@H](CC(F)F)c1ccc([N+](=O)[O-])cc1CN(C)C(=O)OCc1ccccc1]

10C (312 mg, 0.693 mmol) was separated by a prep chiral HPLC to give 10D (115 mg, 0.255 mmol, 36.9% yield).

10E: (R)-Ethyl 2-(4-amino-2-((methylamino)methyl)phenyl)-4,4-difluorobutanoate

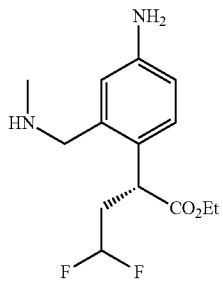 [SMILES: CCOC(=O)[C@H](CC(F)F)c1ccc(N)cc1CNC]

10D (115 mg, 0.255 mmol) was dissolved in MeOH (5 mL) containing HCl (93 mg, 2.55 mmol). 10% Pd/C was added. The reaction mixture was stirred under a hydrogen balloon for 12 h. Pd/C was removed by filtration and the filtrate was concentrated under reduced pressure to give 10E (93 mg, 0.259 mmol, 101% yield).

10F: Ethyl (2S)-2-[4-amino-2-({2-[(1-{bis[(tert-butoxy)carbonyl]amino}-4-fluoroisoquinolin-6-yl)amino]-2-{4-[(2R)-1-hydroxypropan-2-yl]-3-methylphenyl}-Nmethylacetamido}methyl)phenyl]-4,4-difluorobutanoate

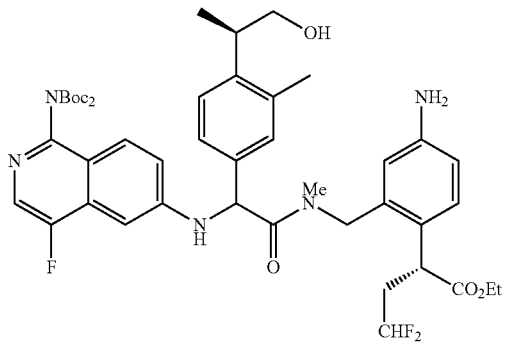

Intermediate 3 (90 mg, 0.239 mmol), Intermediate 5 (46.4 mg, 0.239 mmol) and glyoxylic acid monohydrate (22.00 mg, 0.239 mmol) were dissolved in DMF (1 mL) and acetonitrile. The solution was stirred at 80° C. for 2 h. The mixture was cooled to rt. To this mixture were added sequentially 10E (86 mg, 0.239 mmol), BOP (127 mg, 0.287 mmol), followed by TEA (0.167 mL, 1.195 mmol). The mixture was stirred at rt for 1 h, concentrated, purified by flash chromatography to give 10F (196 mg, 0.230 mmol, 96% yield). MS (ESI) m/z: 852.1 (M+H)$^+$.

10G: Ethyl (2S)-2-[(2R,15R)-2-[(1-{bis[(tert-butoxy)carbonyl]amino}-4-fluoroisoquinolin-6-yl)amino]-4,15,17-trimethyl-3,12-dioxo-13-oxa-4,11-diazatricyclo[14.2.2.1$^{6,10}$]henicosa-1(18),6,8,10(21),16,19-hexaen-7-yl]-4,4-difluorobutanoate

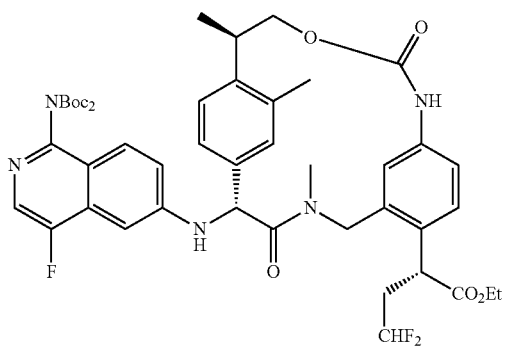

A solution of 10F (196 mg, 0.230 mmol) in acetonitrile (4 mL) and dichloromethane (2 mL) was cooled to 0° C. To this solution was added phosgene (20% in toluene) (0.137 mL, 0.276 mmol). The mixture was stirred at 0° C. for 5 min, and at rt for 1 h. The mixture was bubbled with Ar for 10 min to remove excess phosgene. The resulting solution was added dropwise over 3 h via a syringe pump into a solution of TEA (0.321 mL, 2.301 mmol) in CH$_2$Cl$_2$ (60 mL) at rt. The solution was stirred for 16 h. Solvent was removed under reduced pressure and the crude product was purified by flash chromatography to give a mixture of diastereoisomers (62 mg, 0.071 mmol, 30.7% yield). The diastereoisomers were separated by a prep chiral HPLC equipped with a OD column to give 10G (31 mg, 0.035 mmol, 47.0% yield). MS (ESI) m/z: 878.8 (M+H)$^+$.

Example 10

To 10G (31 mg, 0.035 mmol) dissolved in THF (1.5 mL) was add LiOH (1 mL, 1.000 mmol). The mixture was stirred at rt for 16 h. The reaction was acidified with 1NHCl, extracted with EtOAc, washed with brine, dried over Na$_2$SO$_4$, concentrated and dried under vacuum. The residue was stirred with TFA (1 mL) for 30 min, concentrated and purified by prep HPLC to give Example 10 (7.0 mg, 9.07 µmol, 25.7% yield). MS (ESI) m/z: 649.9 (M+H)$^+$. $^1$H NMR (400 MHz, methanol-d$_4$) δ ppm 8.11 (d, J=9.34 Hz, 1H) 7.67 (d, J=8.25 Hz, 1H) 7.42-7.51 (m, 2H) 7.31 (dd, J=9.07, 2.47 Hz, 1H) 7.15-7.22 (m, 2H) 7.00 (br. s., 1H) 6.73 (dd, J=8.24, 2.20 Hz, 1H) 6.00 (s, 1H) 5.80 (s, 1H) 5.45 (d, J=16.49 Hz, 1H) 4.65 (t, J=10.99 Hz, 1H) 4.15 (d, J=16.49 Hz, 1H) 3.96 (dd, J=10.72, 4.12 Hz, 1H) 3.87-3.93 (m, 1H) 3.44-3.56 (m, 1H) 3.34 (s, 3H) 2.58-2.72 (m, 1H) 2.33 (s, 3H) 2.14-2.28 (m, 1H) 1.26-1.35 (m, 3H); Analytical HPLC (low pH, 254 nM): Sunfire, RT=5.90 min, 100% purity; XBridge, RT=6.78 min, 100% purity.

Example 11

(2R,15R)-2-[(1-Amino-8-fluoroisoquinolin-6-yl) amino]-7-(cyclopropanesulfonyl)-8-fluoro-4,15,17-trimethyl-13-oxa-4,11-diazatricyclo[14.2.2.1$^{6,10}$] henicosa-1(18),6,8,10 (21),16,19-hexaene-3,12-dione; trifluoroacetic acid

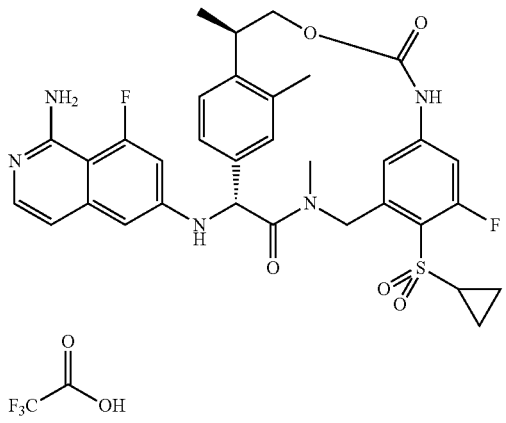

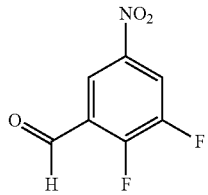 [SMILES: O=Cc1cc([N+](=O)[O-])cc(F)c1F]

11A: 2,3-Difluoro-5-nitrobenzaldehyde

To a solution of 2,3-difluorobenzaldehyde (2.9 g, 20.41 mmol) in conc. sulfuric acid (18 mL, 324 mmol) at 0° C., was added nitric acid (70%) (3.6 mL, 56.4 mmol) dropwise. The reaction mixture was removed from the ice bath and was stirred at rt for 3 h. The reaction mixture was poured onto ice, then was diluted to ~350 mL with H$_2$O. The aqueous was extracted with EtOAc (3×). The combined organic phase was washed with sat. NaHCO$_3$ and brine, dried (Na$_2$SO$_4$) and concentrated. The crude product was dissolved in EtOAc (10 mL), then was diluted with hexanes (40 mL). The solution was filtered though a 1" pad of SiO$_2$, then the pad was rinsed with 20% EtOAc/hexanes. The filtrate was concentrated. The resultant oil was dissolved in chloroform and hexanes, loaded onto a 150 g column and eluted with a gradient from 0 to 15% EtOAc/hexanes to give 11A (1.345 g, 7.19 mmol, 35.2% yield) as a colorless oil.

11B: 2-(Cyclopropylthio)-3-fluoro-5-nitrobenzaldehyde

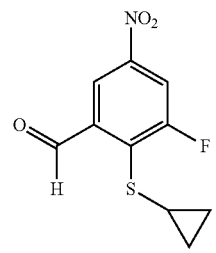 [SMILES: O=Cc1cc([N+](=O)[O-])cc(F)c1SC1CC1]

To cyclopropylmagnesium bromide (0.5 M, THF) (20 mL, 10.00 mmol) was added sulfur (321 mg, 10.00 mmol). The mixture was stirred at 50° C. for 1 h. The solution was cooled to 0° C., then was treated with lithium aluminum hydride (190 mg, 5.00 mmol). The reaction mixture was stirred at 50° C. for 30 min, then was cooled to 0° C. The reaction was quenched with H$_2$O (0.3 mL), then was treated with 5% aq. H$_2$SO$_4$ (20 mL). The mixture was stirred at rt for 10 min, then was filtered though a pad of CELITE®. The pad was rinsed with Et$_2$O. The filtrate was partitioned, the organic phase was washed with H$_2$O, sat. NaHCO$_3$ and brine, dried (Na$_2$SO$_4$) and filtered. The solution of the cyclopropyl thiol was used as is. This solution was added to a solution of 11A (748 mg, 4.00 mmol) and TEA (1.394 mL, 10.00 mmol) in DMF (20 mL) at rt. The mixture was stirred at rt for 1.5 h, then was diluted with EtOAc. The organic phase was washed with H$_2$O, 10% LiCl and brine, dried (Na$_2$SO$_4$), filtered though a 1" pad of SiO$_2$ and concentrated to yield 11B (965 mg, 4.00 mmol, 100% yield) as a brown oil. $^1$H NMR (400 MHz, chloroform-d) δ ppm 10.49 (1H, s), 8.52 (1H, dd, J=2.5, 1.3 Hz), 8.13 (1H, dd, J=9.0, 2.5 Hz), 2.49-2.62 (1H, m), 0.99-1.07 (2H, m), 0.70-0.77 (2H, m).

11C: tert-Butyl 2-(cyclopropylthio)-3-fluoro-5-nitrobenzyl(methyl)carbamate

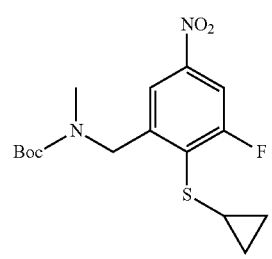 [SMILES: CN(Cc1cc([N+](=O)[O-])cc(F)c1SC1CC1)C(=O)OC(C)(C)C]

To a solution of 11B (0.965 g, 4.00 mmol) in MeOH (20 mL) was added methylamine (33% in EtOH) (0.598 mL, 4.80 mmol). The mixture was stirred at rt for 1.5 h, then was cooled to 0° C. sodium borohydride (0.182 g, 4.80 mmol) was added, then the mixture was stirred at rt for 1 h, then was concentrated. The resultant residue was taken up in THF (20 mL) and was treated with sat. NaHCO$_3$ (10 mL). The mixture was stirred at rt for 10 min, then was treated with Boc$_2$O (1.048 g, 4.80 mmol). The mixture was stirred at rt for 2 h. The THF was removed in vacuo, then the aqueous phase was extracted with EtOAc. The organic phase was washed with H$_2$O and brine, dried (Na$_2$SO$_4$) and concentrated. The crude product was purified by flash chromatography (loaded in chloroform onto a 80 g column and eluted with a gradient from 0 to 50% ethyl acetate/hexanes) to give 11C (1.05 g, 2.95 mmol, 73.6% yield) as an yellow oil. MS (ESI) m/z: 379.1 [M+Na]$^+$; $^1$H NMR (400 MHz, chloroform-d) δ ppm 7.78-7.94 (2H, m), 4.57 (2H, br. s.), 2.90 (3H, s), 2.49 (1H, qd, J=7.2, 4.3 Hz), 1.38-1.53 (9H, m), 0.92-0.98 (2H, m), 0.62-0.68 (2H, m).

11D: tert-Butyl 2-(cyclopropylsulfonyl)-3-fluoro-5-nitrobenzyl(methyl)carbamate

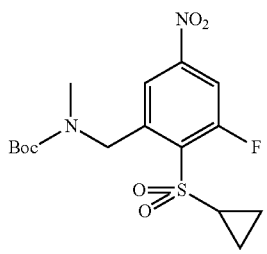 [SMILES: CN(Cc1cc([N+](=O)[O-])cc(F)c1S(=O)(=O)C1CC1)C(=O)OC(C)(C)C]

To a solution of 11C (1.09 g, 3.06 mmol) in dichloromethane (15 mL) at rt was added m-CPBA (77%) (2.056 g, 9.17 mmol). The mixture was stirred at rt for 23 h. The reaction mixture was diluted with EtOAc, then was washed with sat. Na$_2$CO$_3$ (2×) and brine, dried (Na$_2$SO$_4$) and concentrated. The crude product was purified by flash chromatography (loaded in chloroform onto an 80 g column and eluted with a gradient from 0 to 50% ethyl acetate/hexanes) to give 11D (989 mg, 2.55 mmol, 83% yield) as a pale yellow solid. MS (ESI) m/z: 411.1 [M+Na]$^+$. $^1$H NMR (400 MHz, chloroform-d) δ ppm 7.97 (2H, d, J=9.0 Hz), 4.96 (2H, s), 2.99 (3H, s), 2.87-2.97 (1H, m), 1.33-1.53 (11H, m), 1.15 (2H, q, J=6.5 Hz).

11E: 4-(Cyclopropylsulfonyl)-3-fluoro-5-((methylamino)methyl)aniline hydrochloride

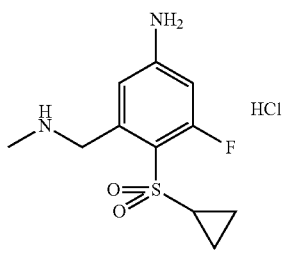 [SMILES: CNCc1cc(N)cc(F)c1S(=O)(=O)C1CC1 ; Cl]

To a fine suspension of 11D (985 mg, 2.54 mmol) in MeOH (10 mL) was added 10% Pd—C (50 mg, 0.047 mmol). The mixture was evacuated and flushed with hydrogen (3×), then was stirred under an atmosphere of hydrogen for 22 h. The reaction mixture was filtered and concentrated to afford a colorless solid. The solid was suspended in 4N HCl in dioxane (6 mL, 24.00 mmol). The suspension was stirred at rt for 1 h, then concentrated to give 11E (840 mg, 2.54 mmol, 100% yield) as an off-white solid. MS (ESI) m/z: 259.1 [M+1]$^+$. $^1$H NMR (400 MHz, MeOD) δ ppm 6.60 (1H, d, J=2.0 Hz), 6.54 (1H, dd, J=13.6, 2.3 Hz), 4.31 (2H, s), 2.87-2.97 (1H, m), 2.75 (3H, s), 1.24-1.31 (2H, m), 1.05-1.13 (2H, m).

11F: tert-Butyl N-(6-{[({[5-amino-2-(cyclopropanesulfonyl)-3-fluorophenyl]methyl}(methyl)carbamoyl)({4-[(2R)-1-hydroxypropan-2-yl]-3-methylphenyl})methyl]amino}-8-fluoroisoquinolin-1-yl)-N-[(tert-butoxy)carbonyl]carbamate

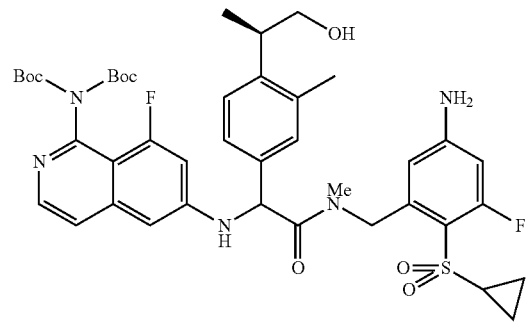 [SMILES: Cc1cc(C(Nc2cc(F)c3c(N(C(=O)OC(C)(C)C)C(=O)OC(C)(C)C)nccc3c2)C(=O)N(C)Cc2cc(N)cc(F)c2S(=O)(=O)C2CC2)ccc1[C@@H](C)CO]

Intermediate 2 (120 mg, 0.318 mmol), Intermediate 5 (61.7 mg, 0.318 mmol) and glyoxylic acid monohydrate (29.3 mg, 0.318 mmol) were dissolved in DMF (3 mL) and acetonitrile. The solution was stirred at 80° C. for 2 h. The mixture was cooled to rt. To this mixture were added sequentially 11E (126 mg, 0.382 mmol), BOP (155 mg, 0.350 mmol), followed by TEA (0.222 mL, 1.590 mmol). The mixture was stirred at rt for 1 h, quenched with water, extracted with EtOAc. The organic layer was washed with brine, dried, concentrated and purified by flash chromatography to give 11F (166 mg, 0.201 mmol, 63.4% yield). MS (ESI) m/z: 824.1 [M+1]$^+$.

11G: tert-Butyl N-[(tert-butoxy)carbonyl]-N-(6-{[(2R,15R)-7-(cyclopropanesulfonyl)-8-fluoro-4,15,17-trimethyl-3,12-dioxo-13-oxa-4,11-diazatricyclo[14.2.2.1$^{6,10}$]henicosa-1(18),6,8,10 (21),16,19-hexaen-2-yl]amino}-8-fluoroisoquinolin-1-yl)carbamate

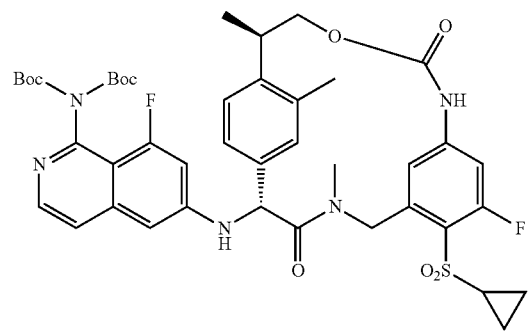 [SMILES: Cc1cc2ccc1[C@@H](C)COC(=O)Nc1cc(F)c(S(=O)(=O)C3CC3)c(c1)CN(C)C(=O)[C@@H]2Nc1cc(F)c2c(N(C(=O)OC(C)(C)C)C(=O)OC(C)(C)C)nccc2c1]

A solution of 11F (163 mg, 0.198 mmol) in acetonitrile (3 mL) and dichloromethane (6 mL) was cooled to 0° C. To this solution was added phosgene (20% in toluene) (0.108 mL, 0.218 mmol). The mixture was stirred at 0° C. for 5 min, and rt for 1 h. The mixture was bubbled with Ar for 10 min to remove excess phosgene. The resulting solution was added dropwise over 3 h via a syringe pump into a solution of TEA (0.276 mL, 1.978 mmol) in CH$_2$Cl$_2$ (260 mL) at rt. The solution was stirred for 16 h. Solvent was removed and the crude product was purified by flash chromatography to give a mixture of diastereoisomers (102 mg, 60.7% yield). The diastereoisomers were separated by a prep chiral HPLC equipped with an IA column to give 11G (43 mg, 0.051 mmol, 43.0% yield). MS (ESI) m/z: 850.1 [M+1]$^+$.

Example 11

11G (43 mg, 0.051 mmol) was stirred with TFA (2 mL, 0.051 mmol) for 2 h at rt, concentrated and purified by prep HPLC to give Example 11 (30 mg, 0.038 mmol, 75% yield). MS (ESI) m/z: 650.1 [M+1]$^+$. $^1$H NMR (500 MHz, methanol-d$_4$) δ ppm 7.66 (1H, dd, J=8.0, 1.7 Hz), 7.48 (1H, d, J=8.0 Hz), 7.29 (1H, d, J=7.2 Hz), 7.08 (1H, s), 6.94 (1H, dd, J=16.0, 1.9 Hz), 6.87 (1H, dd, J=7.2, 2.2 Hz), 6.69 (1H, d, J=1.4 Hz), 6.61 (1H, dd, J=12.1, 1.9 Hz), 6.21 (1H, s), 5.73 (1H, d, J=17.9 Hz), 5.70 (1H, s), 4.61 (1H, t, J=11.0 Hz), 4.19 (1H, d, J=17.9 Hz), 3.94-4.02 (1H, m), 3.46-3.57 (1H, m), 3.33 (3H, s), 2.88-3.05 (1H, m), 2.29 (3H, s), 1.34 (3H, d, J=7.2 Hz), 1.27-1.31 (2H, m), 1.04-1.11 (2H, m); Analytical HPLC (low pH, 254 nM): Sunfire, RT=6.08, 100% purity; XBridge, RT=7.25, 97% purity.

Example 12

Trifluoroacetic acid diethyl [(15R)-2-[(1-aminoisoquinolin-6-yl)amino]-4,15,20-trimethyl-3,12-dioxo-13-oxa-4,11-diazatricyclo[14.2.2.16,10]henicosa-1(18),6,8,10(21),16,19-hexaen-7-yl]phosphonate

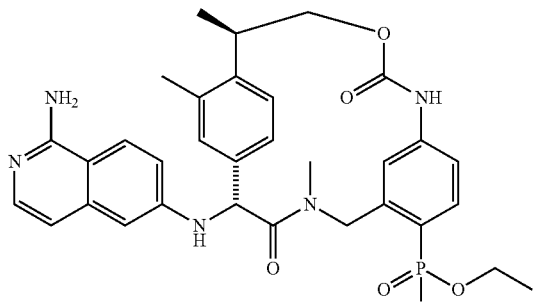

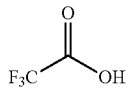

12A: tert-Butyl 5-amino-2-bromobenzyl(methyl)carbamate

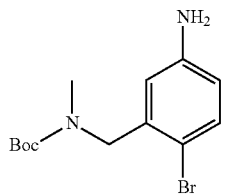 [SMILES: CN(Cc1cc(N)ccc1Br)C(=O)OC(C)(C)C]

Zinc (1.042 g, 15.93 mmol) was added to a mixture of tert-butyl 2-bromo-5-nitrobenzyl(methyl)carbamate (1 g, 2.90 mmol) and ammonium chloride (3.10 g, 57.9 mmol) in ethanol (10 mL). The mixture was stirred for 3 h at rt. The mixture was concentrated. Na$_2$CO$_3$ (sat., 50 mL) and EtOAc (50 mL) was added and stirred for 1 h. The phases were separated and the aqueous layer was extracted with EtOAc (2×50 mL). The organics were combined, washed with brine, dried over Na$_2$SO$_4$ and concentrated. The crude product was purified by flash chromatography (loading in chloroform, 0% to 50% ethyl acetate in hexane over 30 min using a 40 g silica gel cartridge) to yield 12A (0.785 g, 2.490 mmol, 86% yield) as a yellow oil.

12B: tert-Butyl 2-bromo-5-((tert-butoxycarbonyl)amino)benzyl(methyl)carbamate

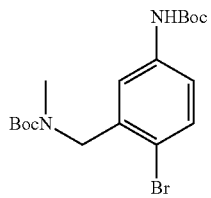

To a flask was added 12A (0.785 g, 2.490 mmol) and di-tert-butyl dicarbonate (2.72 g, 12.45 mmol). The mixture was stirred at 80° C. for 4 h. Solvent was removed and the crude product was purified by flash chromatography to give 12B (0.74 g, 1.782 mmol, 71.5% yield). $^1$H NMR (400 MHz, chloroform-d) δ ppm 7.40-7.47 (m, 1H) 7.34 (s, 1H) 7.02 (d, J=22.41 Hz, 1H) 6.49 (s, 1H) 4.46 (d, J=18.89 Hz, 2H) 2.85 (d, J=13.18 Hz, 3H) 1.37-1.54 (m, 18H).

12C: tert-Butyl 5-((tert-butoxycarbonyl)amino)-2-(diethoxyphosphoryl)benzyl(methyl)carbamate

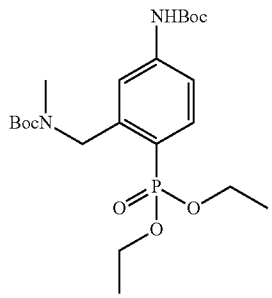 [SMILES: CCOP(=O)(OCC)c1ccc(NC(=O)OC(C)(C)C)cc1CN(C)C(=O)OC(C)(C)C]

A solution of 12B (25 mg, 0.060 mmol), bis(tri-t-butylphosphine)palladium (0) (3.08 mg, 6.02 μmol), Et₃N (0.042 mL, 0.301 mmol) and diethyl phosphite (0.039 mL, 0.301 mmol) in toluene (0.6 mL) was degassed with Ar by evacuating and filling (4×). The sealed vessel was stirred for 2 days at 105° C. The reaction mixture was concentrated and purified by column chromatography (0 to 30% EtOAc in hexanes) to yield 12C (15 mg, 0.032 mmol, 52.7% yield).

12D: Diethyl(4-amino-2-((methylamino)methyl)phenyl)phosphonate hydrochloride

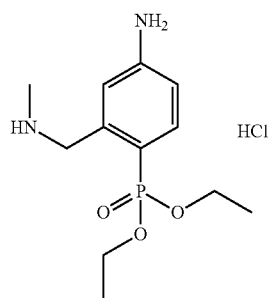 [SMILES: CCOP(=O)(OCC)c1ccc(N)cc1CNC ; Cl]

HCl in dioxane (4.0 M, 1 mL) was added to 12C (100 mg, 0.212 mmol) and stirred at rt for 1 h. The reaction mixture was concentrated to yield 12D (70 mg, 0.203 mmol, 96% yield) as a yellow solid.

12E: tert-Butyl N-(6-{[({[5-amino-2-diethoxyphosphoryl)phenyl]methyl}(methyl)carbamoyl)({4-[(2R)-1-hydroxypropan-2-yl]-3-methylphenyl})methyl]amino}isoquinolin-1-yl)-N-[(tert-butoxy)carbonyl]carbamate

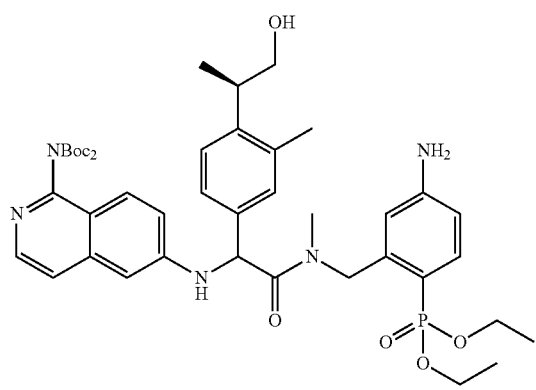

Intermediate 5 (0.06 g, 0.309 mmol), Intermediate 1 (0.083 g, 0.232 mmol), and glyoxylic acid monohydrate (0.021 g, 0.232 mmol) were dissolved in acetonitrile (0.8 mL)/DMF (0.800 mL) and heated at 80° C. for 2 h. A solution of 12D (0.08 g, 0.232 mmol)) and TEA (0.097 mL, 0.695 mmol) in DMF (0.800 mL) was added followed by BOP (0.113 g, 0.255 mmol) as a solid. The reaction mixture was stirred at rt for 3 h, then diluted with EtOAc, washed with water and brine, dried over Na₂SO₄ and concentrated. The crude was purified by column chromatography (0 to 100% EtOAc in hexanes then elute with 20% MeOH in dichloromethane) to yield 12E (135 mg, 0.165 mmol, 71.0% yield) as a yellow solid. MS (ESI) m/z: 820.1 (M+H)⁺.

12F: tert-Butyl N-[(tert-butoxy)carbonyl]-N-(6-{[(15R)-7-(diethoxyphosphoryl)-4,15,20-trimethyl-3,12-dioxo-13-oxa-4,11-diazatricyclo[14.2.2.1$^{6,10}$]henicosa-1(18),6,8,10(21),16,19-hexaen-2-yl]amino}isoquinolin-1-yl)carbamate

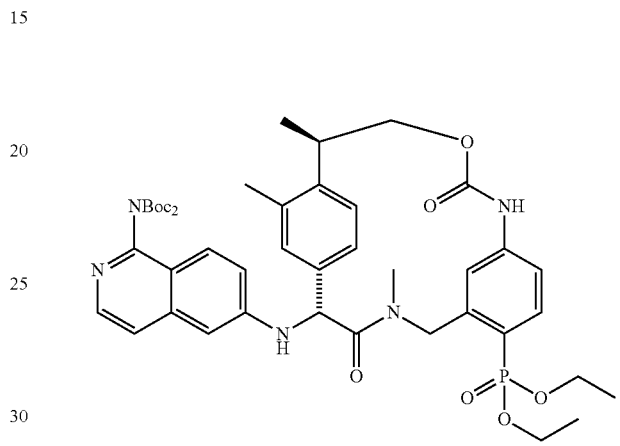

Phosgene (78 mg, 0.159 mmol, 20% in toluene) was added dropwise to a solution of 12E (130 mg, 0.159 mmol) in acetonitrile (1.5 mL)/CH₂Cl₂ (1.5 mL) at 0° C. The bath was removed the mixture was stirred at rt for 30 min. Ar was bubbled though the solution to remove excess phosgene and then the mixture was added to a solution of TEA (0.110 mL, 0.793 mmol) in CH₂Cl₂ (25 mL) at 40° C. over 5 h. The reaction was stirred at rt for overnight, quenched with H₂O (1 mL) and MeOH (5 mL) and then concentrated. The crude product was purified by flash chromatography (loading in dichloromethane, 0% to 100% ethyl to give a mixture of diastereoisomers. The diastereoisomers were separated by a prep chiral HPLC (CHIRALCEL® AD-H, 2.0 cm×25 cm, 5μ) to give 12F (50 mg, 0.059 mmol, 37.3% yield). MS (ESI) m/z: 846.2 (M+H)⁺.

Example 12

4.0 N HCl in dioxane (1 mL, 4.00 mmol) was added to 12F (50 mg, 0.059 mmol) and the reaction was stirred at rt for 1 h. The mixture was concentrated and purified by prep HPLC to yield Example 12 (24 mg, 59.7% yield) as a white solid. MS (ESI) m/z: 646.1 (M+H)⁺. ¹H NMR (400 MHz, methanol-d₃) δ ppm 9.39 (1H, s), 8.04 (1H, d, J=9.23 Hz), 7.74 (1H, dd, J=14.06, 8.35 Hz), 7.67 (1H, dd, J=7.91, 1.32 Hz), 7.47 (1H, d, J=7.91 Hz), 7.31 (1H, d, J=7.03 Hz), 7.19 (1H, dd, J=9.23, 2.20 Hz), 7.16 (1H, s), 6.92 (1H, d, J=7.03 Hz), 6.84 (1H, d), 6.76-6.82 (1H, m), 6.22-6.29 (1H, m), 5.74 (1H, s), 5.67 (1H, d, J=17.14 Hz), 4.63 (1H, t, J=10.99 Hz), 4.06-4.14 (4H, m), 3.96-4.02 (1H, m), 3.43-3.55 (1H, m), 3.35 (3H, s), 2.30 (3H, s), 1.29-1.38 (8H, m).

Example 13

(2R)-2-[(2R,15R)-2-[(1-Amino-4-fluoroisoquinolin-6-yl)amino]-4,15,17-trimethyl-3,12-dioxo-13-oxa-4,11-diazatricyclo[14.2.2.1$^{6,10}$]henicosa-1(18),6,8,10(21),16,19-hexaen-7-yl]butanoic acid; trifluoroacetic acid

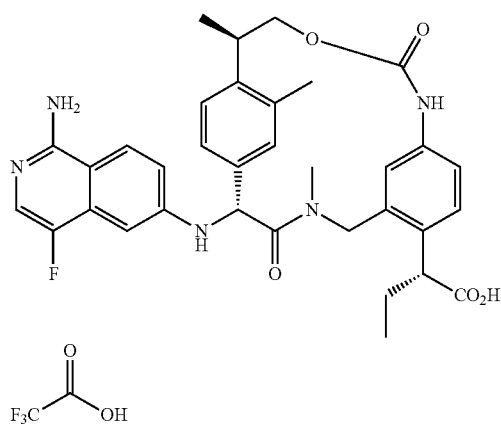

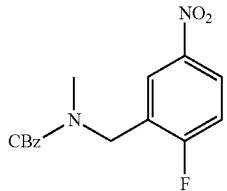

13A: Benzyl 2-fluoro-5-nitrobenzyl(methyl)carbamate

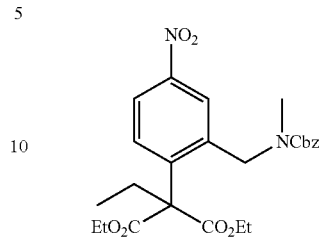

To a flask with 2-fluoro-5-nitrobenzaldehyde (2 g, 11.83 mmol) in MeOH (60 mL) was added methylamine (33% in EtOH, 2.94 mL, 23.65 mmol). The reaction mixture was stirred at rt for 2 h, cooled to 0° C. Sodium borohydride (0.895 g, 23.65 mmol) was added and the mixture was stirred at rt for 1 h. Solvent was removed and the residue was suspended in THF (60.0 mL) and water (30.0 mL). The mixture was treated with sodium bicarbonate (2.98 g, 35.5 mmol), cooled to 0° C., and then CBZ-Cl (2.195 mL, 15.37 mmol) was added dropwise. The mixture was stirred rt overnight. The solvent was removed and the residue was dissolved in EtOAc. The organic layer was washed with water, brine, dried over sodium sulfate and concentrated in vacuo. The crude product was purified by flash chromatography to give 13A (3.6 g, 11.31 mmol, 96% yield) as a yellow oil. MS (ESI) (m/z): 341 (M+Na)$^+$. $^1$H NMR (400 MHz, chloroform-d) δ ppm 8.04-8.28 (m, 2H) 7.28-7.50 (m, 5H) 7.21 (t, J=8.34 Hz, 1H) 5.19 (d, J=8.84 Hz, 2H) 4.51-4.68 (m, 2H) 3.01 (br. s., 3H).

13B: Diethyl 2-(2-((((benzyloxy)carbonyl)(methyl)amino)methyl)-4-nitrophenyl)-2-ethylmalonate

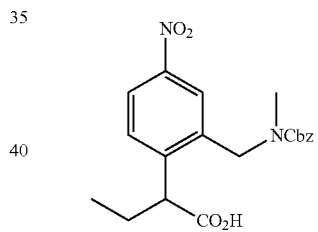

To a flask with sodium hydride (207 mg, 8.64 mmol) was added DMSO (5 mL). The mixture was stirred at rt for 5 min. Diethyl 2-ethylmalonate (1626 mg, 8.64 mmol) in DMSO (5 mL) was added. After 20 min stirring, 13A (550 mg, 1.728 mmol) in DMSO (5 mL) was added. The reaction mixture was heated at 65° C. over night. The reaction was quenched with water, extracted with EtOAc. The organic layer was dried over sodium sulfate and concentrated. The crude product was purified by flash chromatography to give 13B (820 mg, 98% yield). MS (ESI) m/z: 486.9 (M+H)$^+$. $^1$H NMR (400 MHz, chloroform-d) δ ppm 8.00-8.12 (m, 2H) 7.49 (d, J=8.79 Hz, 1H) 7.24-7.45 (m, 5H) 5.11-5.32 (m, 2H) 4.57 (d, J=16.26 Hz, 2H) 4.10-4.33 (m, 4H) 2.89 (d, J=3.95 Hz, 3H) 2.44 (t, J=7.25 Hz, 2H) 1.15-1.34 (m, 6H) 0.81-1.05 (m, 3H).

13C: 2-(2-((((Benzyloxy)carbonyl)(methyl)amino)methyl)-4-nitrophenyl)butanoic acid

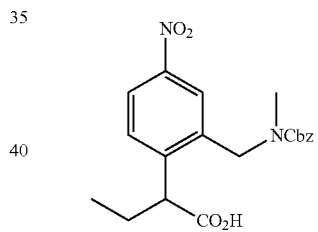

13B (820 mg, 1.685 mmol) was dissolved in EtOH (20 mL), sodium hydroxide (8.43 mL, 16.85 mmol) was added. The reaction mixture was stirred at 100° C. for 1 h. The mixture was concentrated, acidified to pH 2 with 1N HCl; extracted with EtOAc. The organic layer was washed with brine, dried and concentrated gave 13C (620 mg, 1.605 mmol, 95% yield). MS (ESI) m/z: 386.9 (M+H)$^+$.

13D: (R)-Methyl 2-(2-((((benzyloxy)carbonyl)(methyl)amino)methyl)-4-nitrophenyl)butanoate

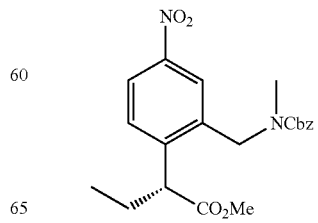

To a solution of the 13C (623 mg, 1.612 mmol) in benzene (10 mL) and MeOH (3.33 mL) at rt was added trimethylsilyl diazomethane (2M, 1.612 mL, 3.22 mmol). The reaction mixture was stirred at rt for 1 h, concentrated and purified by flash chromatography to give a racemate (503 mg, 78% yield). The racemate was separated by a prep chiral HPLC to give 13D (225 mg, 45.9% yield). MS (ESI) m/z: 400.9 (M+H)+.

13E: (R)-Methyl 2-(4-amino-2-((methylamino)methyl)phenyl)butanoate

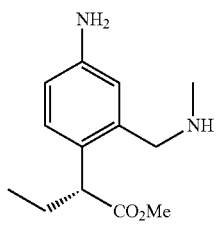 [SMILES: CC[C@@H](C(=O)OC)c1ccc(N)cc1CNC]

13D (103 mg, 2.81 mmol) was dissolved in MeOH (5 mL). 10% Pd/C was added. The reaction mixture was stirred under a hydrogen balloon for 3 h. Pd/C was removed by filtration and the filtrate was concentrated under reduced pressure to give 13E (169 mg, 0.547 mmol, 97% yield). MS (ESI) m/z: 237.0 (M+H)+.

13F: Methyl (2R)-2-[4-amino-2-({2-[(1-{bis[(tert-butoxy)carbonyl]amino}-4-fluoroisoquinolin-6-yl)amino]-2-{4-[(2R)-1-hydroxypropan-2-yl]-3-methylphenyl}-N-methylacetamido}methyl)phenyl]butanoate

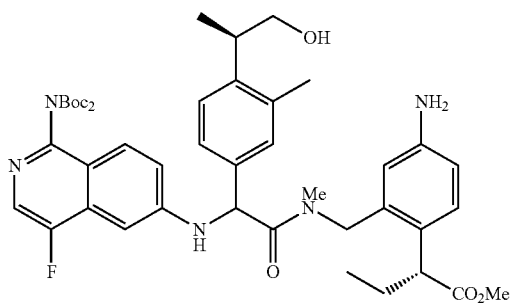

Intermediate 3 (170 mg, 0.450 mmol), Intermediate 5 (87 mg, 0.450 mmol) and glyoxylic acid monohydrate (41.5 mg, 0.450 mmol) were dissolved in DMF (1 mL) and acetonitrile. The solution was stirred at 80° C. for 2 h. The mixture was cooled to rt. To this mixture were added sequentially 13E (167 mg, 0.541 mmol), BOP (219 mg, 0.495 mmol) and TEA (0.314 mL, 2.252 mmol). The mixture was stirred at rt for 1 h. The reaction mixture was concentrated, purified by prep HPLC to give 13F (286 mg, 0.357 mmol, 79% yield). MS (ESI) m/z: 802.8 (M+H)+.

13G: Methyl (2R)-2-[(2R,15R)-2-[(1-{bis[(tert-butoxy)carbonyl]amino}-4-fluoroisoquinolin-6-yl)amino]-4,15,17-trimethyl-3,12-dioxo-13-oxa-4,11-diazatricyclo[14.2.2.1^{6,10}]henicosa-1(18),6,8,10(21),16,19-hexaen-7-yl]butanoate

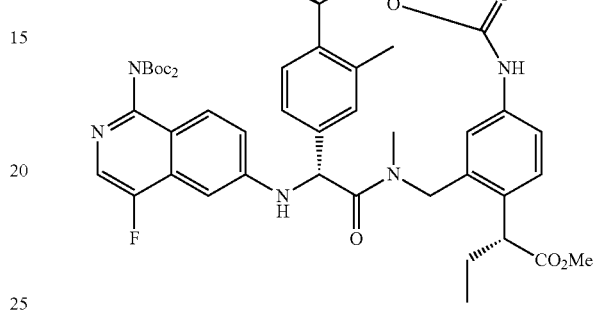

A solution of 13F (235 mg, 0.293 mmol) in acetonitrile (4 mL) and dichloromethane (2 mL) was cooled to 0° C. To this solution was added phosgene (20% in toluene, 0.159 mL, 0.322 mmol). The mixture was stirred at 0° C. for 5 min, and rt for 1 h. The mixture was bubbled with Ar for 10 min to remove excess phosgene. The resulting solution was added dropwise over 3 h via a syringe pump into a solution of TEA (0.408 mL, 2.93 mmol) in $CH_2Cl_2$ (100 mL) at rt. The solution was stirred at rt for 16 h. The reaction mixture was concentrated and purified by flash chromatography to give a mixture of diastereoisomers (198 mg, 82% yield). The diastereoisomers (169 mg, 0.204 mmol) were separated by a prep chiral HPLC to give 13G (80 mg, 47.3% yield). MS (ESI) m/z: 827.9 (M+H)+.

13H: (2R)-2-[(2R,15R)-2-[(1-{Bis[(tert-butoxy)carbonyl]amino}-4-fluoroisoquinolin-6-yl)amino]-4,15,17-trimethyl-3,12-dioxo-13-oxa-4,11-diazatricyclo[14.2.2.1^{6,10}]henicosa-1(18),6,8,10(21),16,19-hexaen-7-yl]butanoic acid

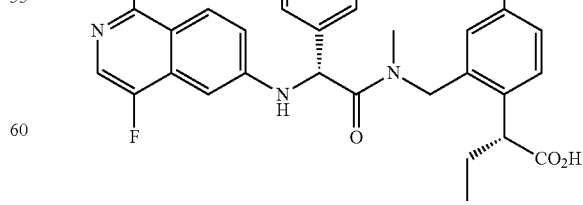

To a solution of 13G (62 mg, 0.075 mmol) in THF (2 mL) was added LiOH (2 mL, 2.000 mmol). The reaction mixture was stirred at rt for 2 days, concentrated and acidified with 1N HCl. The mixture was extracted with EtOAc, washed with brine, dried over Na$_2$SO$_4$, concentrated to give 13H (60 mg, 98% yield).

Example 13

13H (12 mg, 0.015 mmol) was stirred with TFA (2 mL) for 15 min, concentrated and purified by prep HHLC to give Example 13 (9 mg, 83% yield). MS (ESI) m/z: 614.0 (M+H)$^+$. $^1$H NMR (400 MHz, methanol-d$_4$) δ ppm 8.08-8.16 (m, 1H) 7.63-7.71 (m, 1H) 7.42-7.52 (m, 2H) 7.30 (dd, J=9.34, 2.20 Hz, 1H) 7.19-7.24 (m, 2H) 6.99 (s, 1H) 6.71 (dd, J=8.24, 2.20 Hz, 1H) 5.95 (s, 1H) 5.80 (s, 1H) 5.47 (d, J=16.49 Hz, 1H) 4.64 (t, J=10.99 Hz, 1H) 4.13 (d, J=16.49 Hz, 1H) 3.95 (dd, J=10.99, 4.40 Hz, 1H) 3.58 (t, J=7.42 Hz, 1H) 3.43-3.55 (m, 1H) 2.29-2.40 (m, 3H) 1.98-2.13 (m, 1H) 1.75 (ddd, J=13.88, 7.15, 7.01 Hz, 1H) 1.25-1.39 (m, 3H) 0.84-1.03 (m, 3H). Analytical HPLC (low pH, 254 nM): Sunfire, RT=5.73 min, 99.9% purity; XBridge, RT=6.49 min, 99.7% purity.

Example 14

(2R,15R)-2-[(1-Aminoisoquinolin-6-yl)amino]-N,N-diethyl-4,15,17-trimethyl-3,12-dioxo-13-oxa-4,11-diazatricyclo[14.2.2.1$^{6,10}$]henicosa-1(18),6,8,10(21),16,19-hexaene-7-carboxamide; trifluoroacetic acid

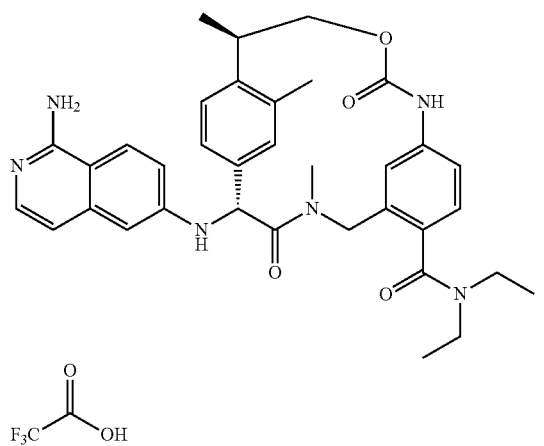

To a solution of 1D (12 mg, 0.016 mmol) at 0° C. in DMF (0.3 mL) and acetonitrile (0.300 mL) was added HATU (7.40 mg, 0.019 mmol) and N-methylmorpholine (2.67 µL, 0.024 mmol). The reaction was stirred for 5 min. Then diethylamine (2.54 µL, 0.024 mmol) was added and the reaction was allowed to warm to rt and stirred for 4 h. The reaction mixture was diluted with water and extracted with EtOAc (3×). The combined organic layer was washed with water and brine, dried (MgSO$_4$) and concentrated. The residue was purified by prep HPLC to give a di-Boc intermediate. The di-Boc intermediate was treated with 1.5 mL of TFA for 30 min. The reaction mixture was then concentrated and purified by prep HPLC to afford Example 14 (3.4 mg, 29% yield). $^1$H NMR (400 MHz, MeOD) δ ppm 7.99-8.11 (1H, m), 7.65 (1H, dd, J=7.78, 1.76 Hz), 7.46 (1H, d, J=8.03 Hz), 7.31 (1H, d, J=7.03 Hz), 7.15-7.26 (2H, m), 7.10 (1H, d, J=8.03 Hz), 6.91 (1H, d, J=7.03 Hz), 6.83 (1H, d, J=2.26 Hz), 6.76 (1H, dd, J=8.03, 1.76 Hz), 6.10 (1H, s), 5.73 (1H, s), 5.25 (1H, br. s.), 4.65 (1H, t, J=11.04 Hz), 3.99 (1H, dd, J=10.79, 4.27 Hz), 3.87 (1H, br. s.), 3.59 (1H, d, J=1.00 Hz), 3.42-3.56 (2H, m), 2.33 (3H, s), 1.27-1.37 (3H, m), 1.25 (3H, t, J=7.15 Hz), 1.10 (3H, t, J=7.03 Hz).

Example 15

1-[(2R,15R)-2-[(1-Amino-4-fluoroisoquinolin-6-yl)amino]-4,15,20-trimethyl-3,12-dioxo-13-oxa-4,11-diazatricyclo[14.2.2.1$^{6,10}$]henicosa-1(18),6,8,10(21),16,19-hexaen-7-yl]cyclopropane-1-carboxylic acid; trifluoroacetic acid

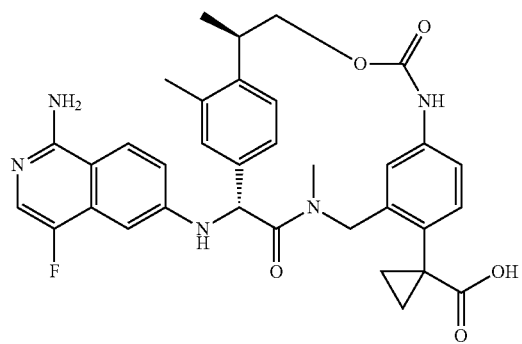

15A: Diethyl 2-(2-((((benzyloxy)carbonyl)(methyl)amino)methyl)-4-nitrophenyl)malonate

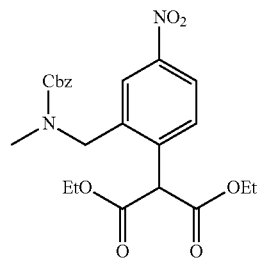 [SMILES: CCOC(=O)C(C(=O)OCC)c1ccc([N+](=O)[O-])cc1CN(C)C(=O)OCc1ccccc1]

Benzyl 2-bromo-5-nitrobenzyl(methyl)carbamate (3.000 g, 7.91 mmol), copper(i) iodide (0.301 g, 1.582 mmol), L-proline (0.364 g, 3.16 mmol) and cesium carbonate (5.16 g, 15.82 mmol) were mixed in a pressure vial and degassed (3×). A solution of diethyl malonate (1.501 mL, 9.89 mmol) in DMSO (10 mL) was added, the reaction mixture was degassed again and stirred at 50° C. for 3 days. The cooled reaction mixture was partitioned between EtOAc (100 mL) and NH$_4$Cl (aq. std.; 100 mL). The organic layer was washed with brine (2×50 mL) and dried (Na$_2$SO$_4$). EtOAc was removed under reduced pressure and the residue was purified by flash chromatography (0-40% EtOAc/hexane). Fractions were combined and concentrated under reduced pressure to give 15A (2.668 g, 5.82 mmol, 73.6% yield) as a colorless syrup. MS (ESI) m/z: 459.2 [M+1]$^+$. $^1$H NMR: (400 MHz, CDCl$_3$) δ ppm 8.18 (1H, d, J=8.53 Hz), 8.09 (1H, br. s.), 7.72

(1H, d, J=7.28 Hz), 7.36 (5H, d, J=15.81 Hz), 5.20 (3H, br. s.), 4.67 (2H, br. s.), 4.07-4.28 (4H, m), 2.81 (3H, s), 1.24 (6H, t, J=7.15 Hz).

15B: Ethyl 2-(2-((((benzyloxy)carbonyl)(methyl) amino)methyl)-4-nitrophenyl)acetate

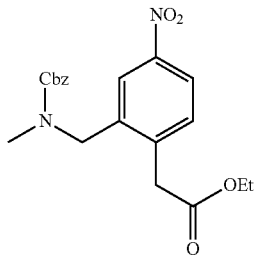 [SMILES: CCOC(=O)Cc1ccc([N+](=O)[O-])cc1CN(C)C(=O)OCc1ccccc1]

15A (2.668 g, 5.82 mmol) was dissolved in DMSO (30 mL), lithium chloride (0.493 g, 11.64 mmol) and water (0.105 mL, 5.82 mmol) were added. The reaction mixture was stirred at 130° C. for 3 h, cooled to rt, diluted with EtOAc (150 mL), washed with water (2×50 mL), brine (1×50 mL) and dried (Na$_2$SO$_4$). EtOAc was removed under reduced pressure and the residue was purified by flash chromatography (0-60% EtOAc/hexanes). Fractions were combined and concentrated under reduced pressure to give 15B (2.062 g, 92% yield) as a yellowish oil. MS (ESI) m/z: 387.2 [M+1]$^+$. $^1$H NMR: (400 MHz, CDCl$_3$) δ ppm 8.11 (1H, d, J=8.34 Hz), 8.06 (1H, br. s.), 7.28-7.46 (6H, m), 5.20 (2H, br. s.), 4.55-4.69 (2H, m), 4.13 (2H, d, J=6.82 Hz), 3.64-3.86 (2H, m), 2.92 (3H, s), 1.24 (3H, td, J=7.07, 2.53 Hz).

15C: Ethyl 2-(4-amino-2-((((benzyloxy)carbonyl) (methyl)amino)methyl)phenyl)acetate

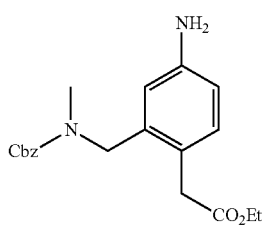 [SMILES: CCOC(=O)Cc1ccc(N)cc1CN(C)C(=O)OCc1ccccc1]

To a solution of 15B (2.062 g, 5.34 mmol) in methanol (30 mL) and THF (5 mL) was added zinc (dust) (3.49 g, 53.4 mmol) and ammonium chloride (5.71 g, 107 mmol). The resulting solution was stirred at rt for 18 h. MeOH was removed under reduced pressure, to the residue Na$_2$CO$_3$ (aq, 100 mL) and EtOAc (250 mL) were added, and the suspension was stirred vigorously for 10 min, filtered though glass frit, solid residue was washed with EtOAc (3×150 mL). Combined EtOAc fractions were washed with std. Na$_2$CO$_3$ (aq, 2×100 mL), water (2×100 mL), brine (1×100 mL) and dried (Na$_2$SO$_4$). EtOAc was removed under reduced pressure and the residue was purified by flash chromatography (0-100% EtOAc/hexanes). Fractions were combined and concentrated under reduced pressure to give 15C (1.546 g, 4.34 mmol, 81% yield) as an amber oil. MS (ESI) m/z: 357.2 [M+1]$^+$. $^1$H NMR: (400 MHz, CDCl$_3$) δ ppm 7.28-7.47 (5H, m), 7.00 (1H, d, J=7.28 Hz), 6.56 (1H, d, J=8.03 Hz), 6.38-6.52 (1H, m), 5.13-5.22 (2H, m), 4.48 (2H, br. s.), 4.08 (2H, br. s.), 3.44-3.58 (2H, m), 2.85 (3H, d, J=17.82 Hz), 1.21 (3H, d, J=7.03 Hz).

15D: Ethyl 2-(2-(((tert-butoxycarbonyl)(methyl) amino)methyl)-4-((tert-butoxycarbonyl)amino)phenyl)acetate

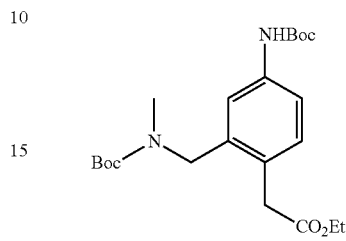

15C (1.546 g, 4.34 mmol) was mixed with BOC-anhydride (4.73 g, 21.69 mmol) and heated at 85° C. for 2 h. The reaction mixture was cooled to rt and diluted with EtOH (30 mL). Additional amount of BOC-anhydride (2.367 g, 10.84 mmol) and Pd—C (0.462 g, 0.434 mmol) were added to the reaction mixture, the reaction mixture was degassed (3× vacuum/Ar) and hydrogenated (1 atm) for 1 h. The reaction mixture was filtered though a membrane filter, EtOH was removed under reduced pressure. The residue was purified by flash chromatography (0-40% EtOAc/hexanes). Fractions were combined and concentrated under reduced pressure to give mixture of di-Boc and mono-Boc material. The obtained material was dissolved in EtOH (anhydr., 30 mL), and then potassium carbonate (1.798 g, 13.01 mmol) was added. The reaction mixture was stirred for 30 h at rt, and then at 65° C. for 3 h. The reaction mixture was cooled at rt, filtered though a pad of CELITE®. EtOH was removed under reduced pressure. The residue was purified by flash chromatography (0-35% EtOAc/hexanes) to give 15D (0.792 g, 43.2% yield) as colorless foam. MS (ESI) m/z: 423.2 [M+1]$^+$. $^1$H NMR: (400 MHz, CDCl$_3$) δ ppm 7.32 (1H, br. s.), 7.15 (1H, d, J=8.08 Hz), 7.11 (1H, br. s.), 6.50 (1H, br. s.), 4.46 (2H, br. s.), 4.12 (2H, q, J=7.16 Hz), 3.60 (2H, s), 2.76 (3H, br. s.), 1.41-1.57 (18H, m), 1.23 (3H, t, J=7.07 Hz).

15E: Ethyl 2-(2-(((tert-butoxycarbonyl)(methyl) amino)methyl)-4-((tert-butoxycarbonyl)amino)phenyl)acrylate

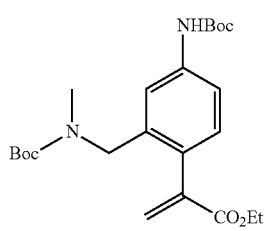 [SMILES: C=C(C(=O)OCC)c1ccc(NC(=O)OC(C)(C)C)cc1CN(C)C(=O)OC(C)(C)C]

15D (0.573 g, 1.356 mmol) was dissolved in toluene (5 mL), and to the resulting solution were sequentially added potassium carbonate (0.375 g, 2.71 mmol), paraformaldehyde (0.407 g, 13.56 mmol) and tris(3,6-dioxaheptyl)amine (tda-1) (0.043 mL, 0.136 mmol). The reaction mixture was stirred at 85° C. for 10 h. The reaction mixture was diluted with EtOAc (20 mL) and water (10 mL) and stirred for 15 min. The organic phase was separated, washed with water (3×10 mL), brine (1×10 mL) and dried (Na$_2$SO$_4$). EtOAc was removed under reduced pressure and the residue was purified flash chromatography (0-35% EtOAc/hexanes). Fractions were combined and concentrated under reduced pressure to give 15E (0.187 g, 31.7% yield) as a colorless syrup. MS (ESI) m/z: 435.1 [M+1]$^+$. $^1$H NMR: (400 MHz, CDCl$_3$) δ ppm 7.40 (1H, d, J=5.77 Hz), 7.06 (2H, d, J=8.28 Hz), 6.50 (1H, s), 5.67 (1H, d, J=1.76 Hz), 4.27-4.39 (2H, m), 4.21 (2H, q, J=7.03 Hz), 2.61-2.77 (3H, m), 1.38-1.55 (18H, m), 1.26 (3H, t, J=7.03 Hz).

15F: Ethyl 1-(2-(((tert-butoxycarbonyl)(methyl) amino)methyl)-4-((tert-butoxycarbonyl)amino)phenyl)cyclopropanecarboxylate

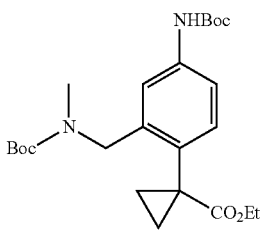 [SMILES: CCOC(=O)C1(c2ccc(NC(=O)OC(C)(C)C)cc2CN(C)C(=O)OC(C)(C)C)CC1]

To a suspension of sodium hydride (60% suspension in mineral oil) (0.019 g, 0.473 mmol) in DMSO (2.5 mL), was added trimethylsulfoxonium iodide (0.284 g, 1.291 mmol). The mixture was stirred at rt for 2 h. To the solution was added 15E (0.187 g, 0.430 mmol) in DMSO (2.5 mL) to give a yellow solution. The mixture was stirred at rt for 1 h, quenched with sat. NH$_4$Cl (10 mL), extracted with EtOAc (4×15 mL). Combined organic phase was washed with water (2×10 mL), brine (1×10 mL) and dried (Na$_2$SO$_4$). EtOAc was removed under reduced pressure and the residue was purified by flash chromatography (0-40% EtOAc/hexanes). Fractions were combined and concentrated under reduced pressure to give 15F (0.173 g, 90% yield) as a colorless syrup. MS (ESI) m/z: 449.1 [M+1]$^+$. $^1$H NMR: (400 MHz, CDCl$_3$) δ ppm 7.34-7.50 (1H, m), 7.20 (1H, d, J=8.08 Hz), 6.83-6.96 (1H, m), 6.44 (1H, br. s.), 4.51 (2H, br. s.), 4.07 (2H, q, J=7.16 Hz), 2.82 (3H, br. s.), 1.35-1.72 (22H, m), 1.15 (3H, t, J=7.07 Hz).

15G: Ethyl 1-(4-amino-2-((methylamino)methyl) phenyl)cyclopropanecarboxylate hydrochloride

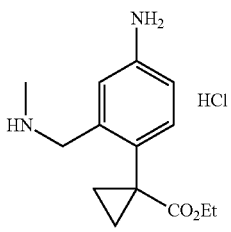 [SMILES: CCOC(=O)C1(c2ccc(N)cc2CNC)CC1 ; Cl]

15F (0.173 g, 0.386 mmol) was dissolved in EtOAc (3 mL) and dichloromethane (2 mL), then HCl (4M in dioxane) (2 mL, 8.00 mmol) was added. The reaction mixture was stirred for 6 h at rt. The solvent was removed under reduced pressure, and the residue was dried under high vacuum to give 15G (0.123 g, 99% yield) as an off-white solid. MS (ESI) m/z: 249.1[M+1]$^+$. $^1$H NMR: (400 MHz, CD$_3$OD) δ ppm 7.69 (1H, d, J=2.27 Hz), 7.59 (1H, d, J=8.34 Hz), 7.42 (1H, dd, J=8.34, 2.27 Hz), 4.38 (2H, s), 4.14 (2H, q, J=7.07 Hz), 2.84 (3H, s), 1.83 (2H, d, J=3.03 Hz), 1.31-1.39 (2H, m), 1.20 (3H, t, J=7.20 Hz).

15H: Ethyl 1-[4-amino-2-({2-[(1-{bis[(tert-butoxy) carbonyl]amino}-4-fluoroisoquinolin-6-yl)amino]-2-{4-[(2R)-1-hydroxypropan-2-yl]-3-methylphenyl}-N-methylacetamido}methyl)phenyl]cyclopropane-1-carboxylate

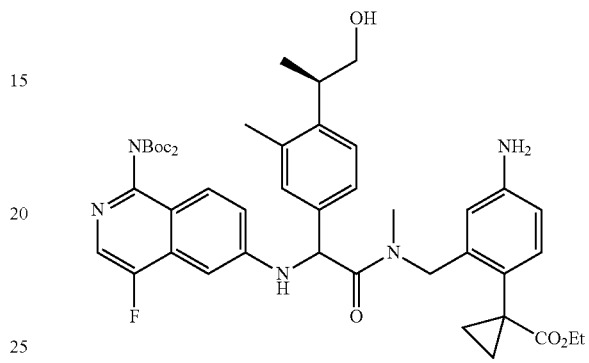

Intermediate 5 (0.074 g, 0.383 mmol), glyoxylic acid monohydrate (0.035 g, 0.383 mmol) and Intermediate 3 (0.145 g, 0.383 mmol) were dissolved in DMF (1 mL) and acetonitrile (2 mL). The reaction mixture was stirred at 80° C. for 1.5 h, cooled to rt and diluted with DMF (1 mL). To this solution were added sequentially 15G (0.123 g, 0.383 mmol), BOP (0.186 g, 0.421 mmol) and TEA (0.320 mL, 2.297 mmol). The mixture was stirred at rt for 30 min, quenched with water (0.5 mL). The reaction mixture was diluted with EtOAc (150 mL), washed with water (4×50 mL), brine (1×50 mL) and dried (Na$_2$SO$_4$) and concentrated. The crude product was purified by flash chromatography (1-20% MeOH/dichloromethane). Fractions were combined and concentrated under reduced pressure to give 15H (0.254 g, 0.312 mmol, 82% yield) as an orange solid after lyophilization. MS (ESI) m/z: 814.3 [M+1]$^+$. $^1$H NMR: complicated by a pair of diastereomers and rotamers.

15I: Ethyl 1-[(2R,15R)-2-[(1-{bis[(tert-butoxy)carbonyl]amino}-4-fluoroisoquinolin-6-yl)amino]-4,15,20-trimethyl-3,12-dioxo-13-oxa-4,11-diazatricyclo[14.2.2.1$^{6,10}$]henicosa-1(18),6,8,10 (21),16,19-hexaen-7-yl]cyclopropane-1-carboxylate

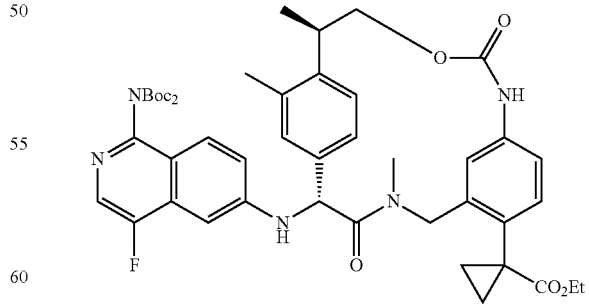

A solution of 15H (0.254 g, 0.312 mmol) in acetonitrile (5 mL) and dichloromethane (5 mL) was cooled to 0° C. To this solution was added phosgene (20% in toluene, 0.162 mL, 0.328 mmol). The mixture was stirred at 0° C. for 15 min. The mixture was bubbled with Ar for 25 min to remove excess phosgene and HCl. The resulting solution was added dropwise over 5 h via a syringe pump into a solution of TEA (0.435 mL, 3.12 mmol) in dichloromethane (200 mL) at rt. The solution was stirred for an additional 30 min. The reaction mixture was concentrated. The residue was purified by flash chromatography (1-15% MeOH/dichloromethane). Fractions were combined and concentrated under reduced pressure to give di-Boc protected intermediate (0.157 g, 60%) as a diastereomeric mixture. The diastereomers were separated by a prep chiral HPLC (CHIRALCEL® OD 10 um 4.6×250 mm) to give 15I (0.058 g, 0.069 mmol, 44.3% yield) as a yellowish powder. MS (ESI) m/z: 840.2 [M+1]$^+$. $^1$H NMR: (400 MHz, CD$_3$OD) δ ppm 7.97 (1H, d, J=2.51 Hz), 7.66 (1H, dd, J=7.91, 1.63 Hz), 7.57 (1H, dd, J=9.29, 1.76 Hz), 7.46 (1H, d, J=8.03 Hz), 7.33 (1H, dd, J=9.29, 2.26 Hz), 7.24 (1H, s), 7.15 (1H, d, J=8.03 Hz), 6.93 (1H, d, J=2.01 Hz), 6.67 (1H, dd, J=8.16, 2.13 Hz), 5.98 (1H, d, J=2.01 Hz), 5.72 (1H, s), 5.51 (1H, d, J=16.81 Hz), 4.65 (1H, t, J=11.04 Hz), 4.09 (2H, q, J=7.03 Hz), 3.93-3.98 (1H, m), 3.90 (1H, d, J=16.81 Hz), 3.65 (1H, s), 3.41-3.53 (1H, m), 2.29 (3H, s), 1.56-1.68 (2H, m), 1.24-1.36 (23H, m), 1.17 (3H, t, J=7.15 Hz).

Example 15

15I (58 mg, 0.069 mmol) was dissolved in MeOH (1.5 mL), THF (1.5 mL) and water (0.6 mL). The reaction mixture was stirred for 10 min and LiOH (41.3 mg, 1.726 mmol) was added. After stirring at rt for 24 h, the reaction mixture was acidified to pH-4.0 with saturated citric acid, and most of the solvent was removed under reduced pressure. The residue was dissolved in DMSO/MeOH, and was purified by prep HPLC (Axia Luna 5 u C18 30×100 mm). The desired fractions were combined and concentrated. The Boc-intermediate was treated with TFA (1.5 mL) at rt for 15 mL. TFA was removed under reduced pressure, and the residue was purified by prep HPLC to give Example 15 (14.37 mg, 0.019 mmol, 28.2% yield) as a white solid. MS (ESI) m/z: 612.2 [M+1]$^+$. $^1$H NMR: (400 MHz, CD$_3$OD) δ ppm 8.09 (1H, dd, J=9.29, 2.01 Hz), 7.65 (1H, dd, J=8.03, 1.76 Hz), 7.45 (1H, d, J=8.03 Hz), 7.42 (1H, d, J=5.02 Hz), 7.28 (1H, dd, J=9.29, 2.26 Hz), 7.21 (1H, s), 7.16 (1H, d, J=8.28 Hz), 6.97 (1H, s), 6.67 (1H, dd, J=8.03, 2.26 Hz), 5.97 (1H, d, J=2.01 Hz), 5.77 (1H, s), 5.54 (1H, d, J=16.82 Hz), 4.64 (1H, t, J=10.92 Hz), 3.89-4.00 (2H, m), 3.43-3.53 (1H, m), 3.28 (3H, s), 2.32 (3H, s), 1.64 (2H, br. s.), 1.31 (3H, d, J=7.03 Hz), 1.20 (2H, br. s.); Analytical HPLC (low pH, 254 nM): Sunfire, RT=5.24, 98.4% purity; XBridge, RT=6.29, 99.4% purity.

Example 16

(2R,15R)-2-[(1-Aminoisoquinolin-6-yl)amino]-7-(cyclopropanesulfonyl)-15-(difluoromethyl)-4,17-dimethyl-13-oxa-4,11-diazatricyclo[14.2.2.1$^{6,10}$] henicosa-1(18),6,8,10 (21),16,19-hexaene-3,12-dione; trifluoroacetic acid

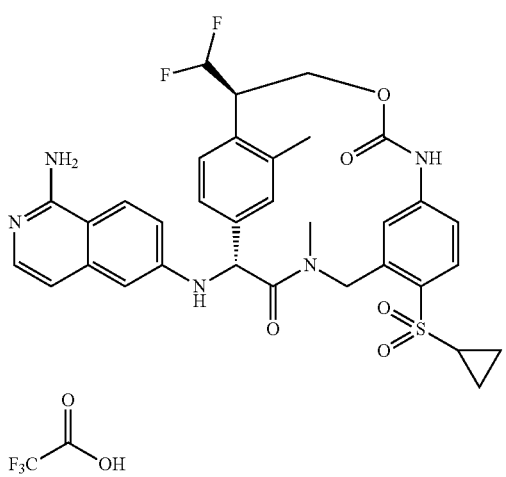

16A: 1-Allyl-4-bromo-2-methylbenzene

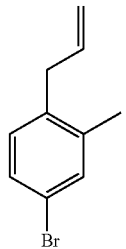

To a solution of 4-bromo-1-iodo-2-methylbenzene (8.41 mL, 58.9 mmol) in THF (200 mL) in a 1.0 L flask under Ar at −20° C., was added isopropylmagnesium chloride (2M, THF) (52.5 mL, 105 mmol) though a dropping funnel. The reaction was stirred for 20 min at −20° C. A solution of lithium chloride (6.00 g, 141 mmol) and copper(I) cyanide (6.33 g, 70.7 mmol) in THF (140 mL) (stirred 15 min at rt to dissolve the LiCl) was cannulated to the above solution. The pale green solution was stirred for 10 min at −10° C., then allyl bromide (15.30 mL, 177 mmol) was added. The mixture was stirred at −10° C. for 30 min. The reaction was quenched with 0.5 N HCl and the solvent was evaporated. The residue was redissolved in diethyl ether/ethylacetate and organic phase was washed with 1N HCl, H$_2$O, brine and dried over sodium sulfate. After evaporation of solvent, the crude product was purified by flash chromatography (0% to 15% EtOAc in hexanes). The desired fractions were combined and concentrated to give 16A (12.10 g, 97% yield). $^1$H NMR (400 MHz, chloroform-d) δ ppm 7.15-7.25 (m, 2H) 6.92 (d, J=8.24 Hz, 1H) 5.83 (dddd, J=16.97, 10.37, 6.18, 6.05 Hz, 1H) 5.00 (d, J=9.89 Hz, 1H) 4.85-4.94 (m, 1H) 3.23 (d, J=6.60 Hz, 2H) 2.18 (s, 3H).

16B: 2-(4-Bromo-2-methylphenyl)acetic acid

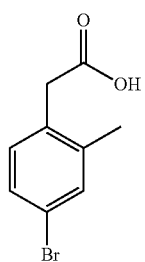

To a solution of 16A (12 g, 56.8 mmol) in CCl$_4$ (200 mL), acetonitrile (200 mL) and water (300 mL) at rt was added ruthenium (III) chloride hydrate (1.474 g, 7.11 mmol) and sodium periodate (48.6 g, 227 mmol). The suspension was stirred vigorously for 5.0 h. The solvent was removed under vacuum. The residue was filtered though wet CELITE®, washed with EtOAc. The mixture was further extracted with EtOAc (3×400 mL). The volume of organic layers was reduced to ca 500 mL, washed with sat. sodium sulfite/with conc. HCl (pH ca 2-3). The organic layer was dried over sodium sulfate and concentrated. After evaporation of solvent, 16B (11.47 g, 50.1 mmol, 88% yield) was obtained as a white solid. $^1$H NMR (400 MHz, CDCl$_3$) δ ppm 2.27 (s, 3H) 3.60 (s, 2H) 7.04 (d, J=7.91 Hz, 1H) 7.28 (dd, J=8.13, 1.98 Hz, 1H) 7.32 (s, 1H).

16C: (S)-4-Benzyl-3-(2-(4-bromo-2-methylphenyl)acetyl)oxazolidin-2-one

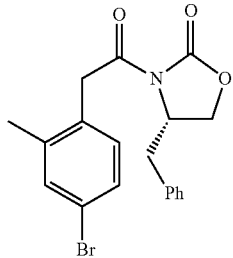 [SMILES: Cc1cc(Br)ccc1CC(=O)N1C(=O)OC[C@@H]1Cc1ccccc1]

To 16B (11 g, 48.0 mmol) in CH$_2$Cl$_2$ (200 ml) was added oxalyl chloride (7.36 ml, 84 mmol) and DMF (0.112 ml, 1.441 mmol). The reaction was stirred at rt for 2 h. The solvent was removed and chased with ethyl acetate (2×). The residue was dried under high vac for 1.5 h. To (S)-4-benzyloxazolidin-2-one (10.21 g, 57.6 mmol) in THF (200 ml) at −78° C. was added n-butyllithium (1.6 M in hexanes, 36.0 ml, 57.6 mmol). The reaction was stirred for 25 min at −78° C. Then the above acylchloride dissolved in THF (100 mL) was added. The reaction was stirred at −78° C. for 1 h and then at rt for 15 min. Sat ammonium chloride was added to quench the reaction and ethyl acetate to dilute the reaction. The organic layer was then washed with water, brine, dried over sodium sulfate and concentrated. The crude product was purified by flash chromatography (0-50% ethyl acetate/hexanes). The desired fractions were combined and concentrated to give 16C (14.1 g, 36.3 mmol, 76% yield) as a white solid. $^1$H NMR (400 MHz, chloroform-d) δ ppm 7.38 (d, J=1.77 Hz, 1H) 7.27-7.38 (m, 4H) 7.16-7.23 (m, 2H) 7.06 (d, J=8.08 Hz, 1H) 4.64-4.76 (m, 1H) 4.14-4.36 (m, 4H) 3.32 (dd, J=13.26, 3.16 Hz, 1H) 2.79 (dd, J=13.39, 9.60 Hz, 1H) 2.26-2.32 (m, 3H).

16D: (S)-4-Benzyl-3-((R)-3-(benzyloxy)-2-(4-bromo-2-methylphenyl)propanoyl)oxazolidin-2-one

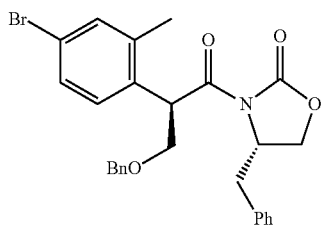

To a solution of 16C (2.0 g, 5.15 mmol) in CH$_2$Cl$_2$ (20 ml) was added TiCl$_4$ (6.18 ml, 6.18 mmol) at 0° C. to form a yellow solution. DIEA (1.080 ml, 6.18 mmol) was added at 0° C. to form a blue solution. The mixture was stirred at 0° C. for 1 h. Benzyl chloromethyl ether (1.428 ml, 10.30 mmol) was added and stirring was continued for 2 h at 0° C. at which point the blue turn to brownish red solution. The reaction was quenched with water, diluted with EtOAc. The aqueous layer was extracted with EtOAc. The combined organic extracts were washed with sat. NaHCO$_3$ and brine, dried over sodium sulfate and concentrated. The crude product was purified by flash chromatography (0-50% ethyl acetate/hexanes). The fractions containing the product was combined, concentrated to give 16D (2.4 g, 4.72 mmol, 92% yield) as a semi solid. $^1$H NMR (400 MHz, chloroform-d) δ ppm 2.41 (d, J=6.05 Hz, 3H) 2.78-2.93 (m, 1H) 3.30 (d, J=13.19 Hz, 1H) 3.43-3.57 (m, 1H) 4.01-4.23 (m, 3H) 4.46-4.81 (m, 3H) 5.36-5.53 (m, 1H) 7.01-7.16 (m, 1H) 7.18-7.41 (m, 12H).

16E: (R)-3-(Benzyloxy)-2-(4-bromo-2-methylphenyl)propanoic acid

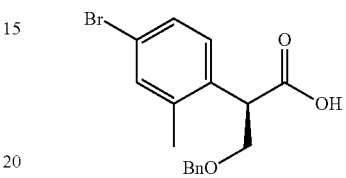

To a solution of 16D (11.2 g, 22.03 mmol) in THF (70 ml) and water (20 ml) at 0° C. was added a solution of lithium peroxide [prepared by adding hydrogen peroxide (11.25 ml, 110 mmol) to lithium hydroxide (1.387 g, 33.0 mmol) in water (20 ml)] dropwise. The mixture was stirred at 0° C. for 1 h, then quenched with sat. sodium sulfite, and organic solvent was removed under reduced pressure. The remaining solution was diluted by 50 ml of water and extracted with dichloromethane (2×20 ml). The aqueous layer was acidified using conc. HCl. The solution was then extracted with ethyl acetate (3×). The organic extracts was combined and washed with brine and dried over sodium sulfate. The solution was filtered, concentrated and dried in vacuo to give 16E (8 g, 22.91 mmol, 104% yield) as an oil. MS (ESI) (m/z): 347, 349.4 (M−H)$^+$.

16F: (S)-3-(Benzyloxy)-2-(4-bromo-2-methylphenyl)propan-1-ol

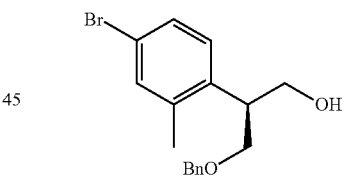

To 16E (8.0 g, 22.91 mmol), 4-methylmorpholine (3.02 mL, 27.5 mmol) in THF (100 mL) at −20° C. was added ethyl chloroformate (2.420 mL, 25.2 mmol). The mixture was stirred for 20 min. The cloudy reaction mixture was filtered. The filtrate was treated with sodium borohydride (1.213 g, 32.1 mmol) and MeOH (30 mL) slowly from −20° C. The mixture was stirred at −20° C. for 15 min. and then at rt for 1 h. The reaction was quenched with addition of sat. ammonium chloride. Organic solvent was removed under reduced pressure. The residue was partitioned between EtOAc/water. The organic layers were collected, washed with sat. sodium bicarbonate and brine, dried over sodium sulfate and concentrated. The crude product was purified by flash chromatography (0-40% ethyl acetate/hexanes). The desired fractions were combined and concentrated to give 16F (5.93 g, 17.69 mmol, 77% yield). MS (ESI) (m/z): 357, 359.4 (M+Na)$^+$. $^1$H NMR (400 MHz, chloroform-d) δ ppm 7.27-7.40 (m, 7H) 7.01 (d, J=8.34 Hz, 1H) 4.56 (s, 2H) 3.92-4.04 (m, 1H) 3.67-3.89 (m, 3H) 3.35-3.49 (m, 1H) 2.34 (s, 3H).

16G: (R)-3-(Benzyloxy)-2-(4-bromo-2-methylphenyl)propanal

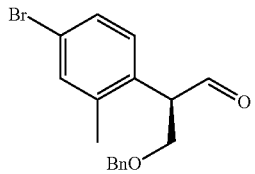 [SMILES: Cc1cc(Br)ccc1[C@@H](C=O)COCc1ccccc1]

To 16F (2.83 g, 8.44 mmol) in dichloromethane (60 ml) was added Dess-Martin periodinane (4.30 g, 10.13 mmol) at rt. The reaction was stirred at rt for 2 h. The mixture was filtered and the filtrate was concentrated. The crude product was purified by flash chromatography (0-30% ethyl acetate/hexanes). The desired fractions were combined, concentrated to give 16G (2.0 g, 6.00 mmol, 71.1% yield) as colorless oil. MS (ESI) (m/z): 331.3, 333.3 (M+H)$^+$. $^1$H NMR (400 MHz, chloroform-d) δ ppm 9.72 (s, 1H) 7.40 (d, J=1.77 Hz, 1H) 7.24-7.38 (m, 6H) 6.95 (d, J=8.08 Hz, 1H) 4.46-4.61 (m, 2H) 4.02-4.16 (m, 2H) 3.67-3.81 (m, 1H) 2.34 (s, 3H).

16H: (R)-1-(3-(Benzyloxy)-1,1-difluoropropan-2-yl)-4-bromo-2-methylbenzene

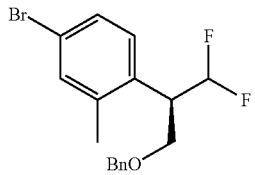 [SMILES: Cc1cc(Br)ccc1[C@H](COCc1ccccc1)C(F)F]

To 16G (0.205 g, 0.615 mmol) in CH$_2$Cl$_2$ (2 mL) at 0° C. was added bis(2-methoxyethyl)aminosulfur trifluoride (0.284 mL, 1.538 mmol) dropwise. The reaction was allowed to warm to rt and stirred overnight. Saturated sodium bicarbonate was added and the product was extracted with dichloromethane (2×). The organic layer was separated, dried over sodium sulfate and concentrated. The crude product was purified by flash chromatography (0-40% ethyl acetate/hexanes). The desired fractions were combined and concentrated to give 16H (0.19 g, 0.535 mmol, 87% yield) as a colorless oil. $^1$H NMR (400 MHz, chloroform-d) δ ppm 7.28-7.43 (m, 7H) 7.18 (d, J=8.34 Hz, 1H) 5.89-6.37 (m, 1H) 4.45-4.61 (m, 2H) 3.87 (dd, J=9.09, 7.07 Hz, 1H) 3.53-3.77 (m, 2H) 2.33 (s, 3H); $^{19}$F NMR (376 MHz, chloroform-d) δ ppm −125.44−−121.35 (m, 2F).

16I: (R)-(4-(3-(Benzyloxy)-1,1-difluoropropan-2-yl)-3-methylphenyl)boronic acid

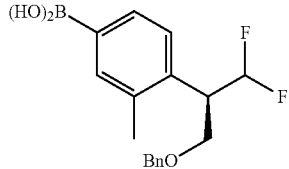 [SMILES: Cc1cc(B(O)O)ccc1[C@H](COCc1ccccc1)C(F)F]

16H (0.2 g, 0.563 mmol), bis(neopentyl glycolato)diboron (0.178 g, 0.788 mmol) and potassium acetate (0.138 g, 1.408 mmol) were dissolved in dioxane (1.5 mL) and DMSO (1.200 mL). The suspension was degassed and flushed with Ar (3×). PdCl$_2$(dppf)-CH$_2$Cl$_2$ (0.041 g, 0.051 mmol) was added. The reaction was heated at 90° C. in an oil bath for 3.0 h. The reaction mixture was cooled to rt, diluted with ethyl acetate. The organic layer was washed with brine (3×), dried over sodium sulfate and concentrated. The crude product was purified by flash chromatography (0-40% ethyl acetate/hexanes) to give the boronic ester. The boronic ester was hydrolyzed to acid under the prep HPLC purification condition. The desired fractions were collected, concentrated and dried to give 16I (0.13 g, 0.406 mmol, 72.1% yield). $^1$H NMR (400 MHz, MeOD) δ ppm 7.40-7.63 (m, 2H) 7.19-7.39 (m, 6H) 5.99-6.44 (m, 1H) 4.44-4.61 (m, 2H) 3.86-3.98 (m, 1H) 3.61-3.86 (m, 2H) 2.37 (s, 3H); $^{19}$F NMR (376 MHz, MeOD) δ ppm −126.25−−121.39 (m, 2F).

16J: (R)-(4-(1,1-Difluoro-3-hydroxypropan-2-yl)-3-methylphenyl)boronic acid

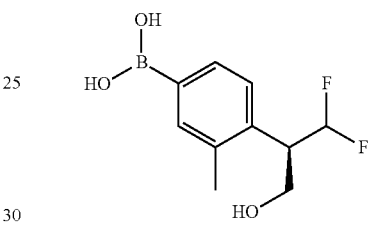

To 16I (0.13 g, 0.406 mmol) was added Pd/C (0.036 g, 0.338 mmol) and MeOH (10 mL) slowly under N$_2$. Then a H$_2$ balloon was introduced and system was degassed and flush with H$_2$ (3×) before letting it stir at rt overnight. The mixture was filtered and washed with MeOH (3×). The filtrate was evaporated and dried to give 16J (0.089 g, 0.387 mmol, 95% yield). $^1$H NMR (400 MHz, MeOD) δ ppm 7.41-7.52 (m, 2H) 7.32 (d, J=7.33 Hz, 1H) 5.95-6.40 (m, 1H) 4.02 (dd, J=10.99, 6.95 Hz, 1H) 3.86 (dd, J=10.99, 6.44 Hz, 1H) 3.56-3.74 (m, 1H) 2.39 (s, 3H); $^{19}$F NMR (376 MHz, MeOD) δ ppm −125.42−−122.40 (m, 2F).

16K: tert-Butyl N-(6-{[({[5-amino-2-(cyclopropanesulfonyl)phenyl]methyl}(methyl)carbamoyl)({4-[(2R)-1,1-difluoro-3-hydroxypropan-2-yl]-3-methylphenyl})methyl]amino}isoquinolin-1-yl)-N-[(tert-butoxy)carbonyl]carbamate

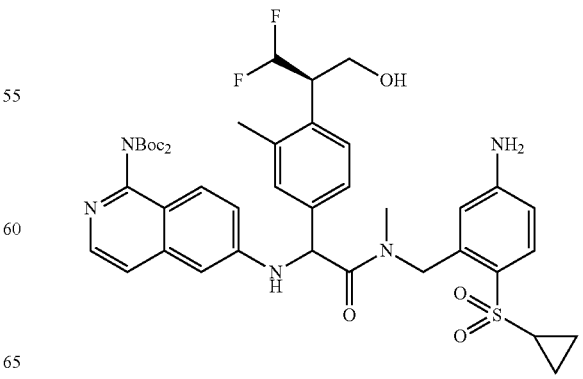

A mixture of Intermediate 1 (0.139 g, 0.387 mmol), 16J (0.089 g, 0.387 mmol) and glyoxylic acid monohydrate (0.037 g, 0.397 mmol) suspended in DMF (1 mL) and acetonitrile (3 mL) was heated at 80° C. in an oil bath for 2.0 h. After it cooled to rt, Intermediate 8 (0.121 g, 0.387 mmol) and DIEA (0.338 mL, 1.935 mmol) were added, followed by BOP (0.171 g, 0.387 mmol). The mixture was left stirring at rt over 2 days.

The solvent was removed under reduced pressure. The crude product was purified by flash chromatography (0-100% ethyl acetate/hexanes). The desired fractions were combined and concentrated to give 16K (0.144 g, 0.175 mmol, 45.2% yield). MS (ESI) (m/z): 824.0 (M+H)$^+$.

16L: tert-Butyl N-[(tert-butoxy)carbonyl]-N-(6-{[(2R,15R)-7-(cyclopropanesulfonyl)-15-(difluoromethyl)-4,17-dimethyl-3,12-dioxo-13-oxa-4,11-diazatricyclo[14.2.2.1$^{6,10}$]henicosa-1(18),6,8,10 (21),16,19-hexaen-2-yl]amino}isoquinolin-1-yl) carbamate

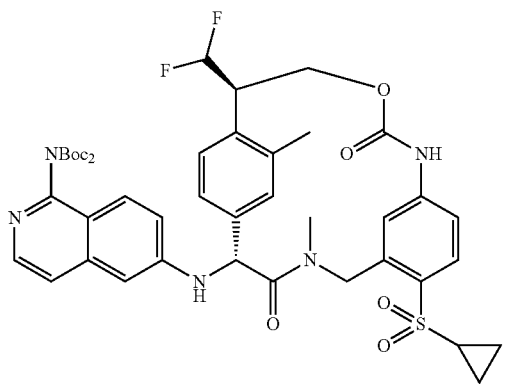

To a solution of 16K (0.144 g, 0.175 mmol) in acetonitrile (5 mL) and dichloromethane (2.5 mL) at 0° C. was added phosgene solution (20% in toluene, 0.101 mL, 0.192 mmol) dropwise. The mixture was stirred at 0° C. for 30 min. Extra phosgene was removed by bubbling Ar for 20 min. The resulting solution was added dropwise via syringe pump into a solution of TEA (0.195 mL, 1.398 mmol) in dichloromethane (60 mL) at rt over 3.0 h. The reaction mixture was stirred at rt over night. The solvent was removed and the crude product was purified by flash chromatography (0-80% ethyl acetate/hexanes). The desired fractions were collected, concentrated to give a mixture of diastereoisomers (0.12 g, 0.141 mmol, 81% yield). The diastereoisomers were separated using a prep chiral HPLC equipped with a Whelko-01 column to give 16L (34 mg, 48% yield). MS (ESI) (m/z): 850.0 (M+H)$^+$.

Example 16

To 16L (0.034 g, 0.040 mmol) in CH$_2$Cl$_2$ (1 mL) was added 4M HCl in dioxane (1.000 mL, 4.00 mmol). The reaction was stirred at rt for 2 h. The solvent was removed and the crude was purified using a prep HPLC equipped with a C18 PHENOMENEX® Luna column (30 mm×100 mm, 5µ). The desired fractions were combined, concentrated and lyophilized to give Example 16 (0.021 g, 0.027 mmol, 67.4% yield) as a white amorphous solid. MS (ESI) (m/z): 650.3 (M+H)$^+$. $^1$H NMR (400 MHz, MeOD) δ ppm 8.06 (d, J=9.09 Hz, 1H) 7.75 (d, J=8.34 Hz, 2H) 7.63 (d, J=7.83 Hz, 1H) 7.32 (d, J=7.07 Hz, 1H) 7.18-7.27 (m, 2H) 6.93 (d, J=7.07 Hz, 1H) 6.86 (dd, J=5.18, 2.15 Hz, 2H) 6.14-6.54 (m, 2H) 5.79 (t, J=8.72 Hz, 2H) 5.05 (t, J=10.86 Hz, 1H) 4.21-4.38 (m, 2H) 3.75-3.92 (m, 1H) 3.42 (s, 3H) 2.78-2.93 (m, 1H) 2.32 (s, 3H) 1.22-1.35 (m, 1H) 1.00-1.20 (m, 3H). $^{19}$F NMR (376 MHz, MeOD) δ ppm –76.11 (s, 3F from TFA) –125.87--109.88 (m, 2F); Analytical HPLC (low pH, 254 nM): Sunfire, RT=5.98 min, 98.8% purity; XBridge, RT=7.03 min, 97.9% purity.

Example 17

(2R,15R)-2-[(1-Aminoisoquinolin-6-yl)amino]-8-fluoro-7-[(2S)-2-hydroxypropoxy]-4,15,20-trimethyl-13-oxa-4,11-diazatricyclo[14.2.2.1$^{6,10}$]henicosa-1(18),6,8,10 (21),16,19-hexaene-3,12-dione; trifluoroacetic acid

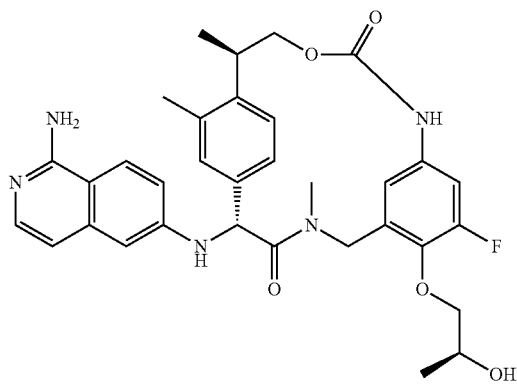

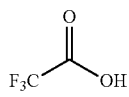

17A: (S)-Methyl 2-((tert-butyldimethylsilyl)oxy)propanoate

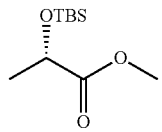

To a solution of (S)-methyl 2-hydroxypropanoate (1.00 g, 9.61 mmol) in DMF (10 mL) at rt, were added imidazole (0.981 g, 14.41 mmol) and TBS-Cl (1.737 g, 11.53 mmol). The mixture was stirred at rt for 3 h. The reaction mixture was diluted with hexanes. The organic phase was washed with water (2×) and brine, dried (Na$_2$SO$_4$) and concentrated. The crude product was purified by flash chromatography (0 to 10% ethyl acetate/hexanes) to give 17A (1.73 g, 7.92 mmol, 82% yield) as a colorless oil. $^1$H NMR (400 MHz, chloroform-d) δ ppm 4.34 (q, J=6.7 Hz, 1H) 3.72 (s, 3H) 1.40 (d, J=6.8 Hz, 3H) 0.90 (s, 8H) 0.09 (d, J=10.8 Hz, 6H).

17B: (S)-2-((tert-Butyldimethylsilyl)oxy)propan-1-ol

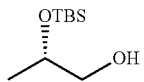

To a solution of 17A (1.33 g, 6.09 mmol) in THF (20 mL) at 0° C., was added lithium borohydride (0.531 g, 24.36 mmol). The resultant suspension was stirred at rt for 7 h. The reaction was cooled to 0° C., then was quenched with sat. NH₄Cl (5 mL). The mixture was diluted with H₂O and hexanes. The reaction mixture was acidified with 1 N HCl, then was extracted with hexanes (3×). The combined organic phase was washed with brine, dried (Na₂SO₄), and concentrated. The crude product was purified by flash chromatography (0 to 60% ethyl acetate/hexanes) to give 17B (980 mg, 5.15 mmol, 85% yield) as a colorless oil. MS (ESI) m/z: 191.2 [M+1]⁺. ¹H NMR (400 MHz, chloroform-d) δ ppm 3.87-3.96 (m, J=6.3, 6.3, 6.3, 6.3, 3.6 Hz, 1H) 3.51 (ddd, J=11.0, 7.7, 3.6 Hz, 1 H) 3.37 (ddd, J=11.1, 6.3, 5.1 Hz, 1H) 1.93 (dd, J=7.8, 5.3 Hz, 1H) 1.12 (d, J=6.3 Hz, 3H) 0.90 (s, 9H) 0.09 (s, 6H).

17C: 3-Fluoro-2-hydroxy-5-nitrobenzaldehyde

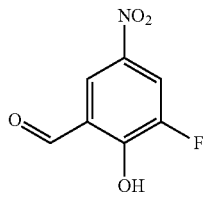 [SMILES: O=Cc1cc([N+](=O)[O-])cc(F)c1O]

To a flask with 3-fluoro-2-hydroxybenzaldehyde (5.00 g, 35.7 mmol) in acetic acid (10 mL, 175 mmol), was added nitric acid (conc., 10 mL, 244 mmol) at 0° C. The mixture was stirred 0° C. for 30 min, quenched with ice, extracted with EtOAc (3×30 mL). The combined organic layer was washed with brine, dried (Na₂SO₄) and concentrated to give 17C (5.457 g, 29.5 mmol, 83% yield) as a yellow solid.

17D: tert-Butyl 3-fluoro-2-hydroxy-5-nitrobenzyl(methyl)carbamate

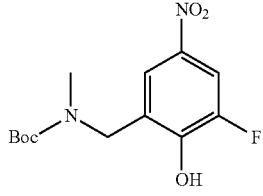

To a solution of 17C (5.965 g, 32.2 mmol) in MeOH (150 mL), methylamine (33% in EtOH) (5.21 mL, 41.9 mmol) was added dropwise and stirred rt for 1 h. The reaction mixture was cooled to 0° C., sodium borohydride (1.463 g, 38.7 mmol) was added portionwise and the mixture was stirred at rt for 1 h. The reaction mixture was diluted by water (50 mL) and THF (50 mL), then di-tert-butyl dicarbonate (8.44 g, 38.7 mmol) and sodium bicarbonate (8.12 g, 97 mmol) was added. The mixture was stirred rt for 1 h. Most of THF and MeOH were removed under reduced pressure. The pH was adjusted to ~5.0 with 1 M HCl. The mixture was extracted with EtOAc (3×20 mL), washed with water, brine, dried (Na₂SO₄).

EtOAc was removed under reduced pressure and the residue was purified by flash chromatography (0-60% EtOAc/hexanes). Fractions were combined and concentrated under reduced pressure to give 17D (5.992 g, 19.95 mmol, 61.9% yield) as an off-white solid. MS (ESI) m/z: 245.0 [M+1]⁺–tBu. ¹H NMR: (400 MHz, CDCl₃) δ ppm 7.97 (1H, dd, J=10.16, 2.64 Hz), 7.86-7.92 (1H, m), 4.38 (2H, s), 2.94 (3H, s), 1.50 (9H, s).

17E: tert-Butyl 2-(benzyloxy)-3-fluoro-5-nitrobenzyl (methyl)carbamate

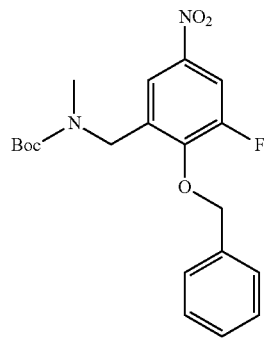 [SMILES: CN(Cc1cc([N+](=O)[O-])cc(F)c1OCc1ccccc1)C(=O)OC(C)(C)C]

17D (2.500 g, 8.33 mmol) and (bromomethyl)benzene (1.483 mL, 12.49 mmol) were dissolved in acetone (40 mL). Cesium carbonate (5.43 g, 16.65 mmol) was added, and the reaction mixture was stirred at 50° C. for 4 h. The reaction mixture was filtered, the filter cake was washed with acetone (3×25 mL). Organic fractions were combined, and the solvent was removed under reduced pressure. The residue was purified by flash chromatography (0-50% EtOAc/hexanes). Fractions were combined and concentrated under reduced pressure to give 17E (2.789 g, 7.14 mmol, 86% yield) as a white solid. MS (ESI) m/z: 391.0 [M+1]⁺. ¹H NMR: (400 MHz, CDCl₃) δ ppm 7.94 (1H, d, J=11.54 Hz), 7.77-7.90 (1H, m), 7.39 (5H, s), 5.31 (2H, br. s.), 4.25-4.50 (2H, m), 2.78 (3H, s), 1.35-1.55 (9H, m).

17F: tert-Butyl 5-amino-2-(benzyloxy)-3-fluorobenzyl(methyl)carbamate

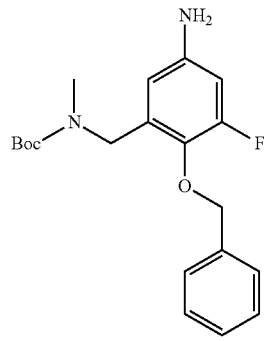 [SMILES: CN(Cc1cc(N)cc(F)c1OCc1ccccc1)C(=O)OC(C)(C)C]

To a solution of 17E (2.789 g, 7.14 mmol) in methanol (40 mL) and THF (10 mL) was added zinc (dust) (4.67 g, 71.4 mmol) and ammonium chloride (7.64 g, 143 mmol). The resulting solution was stirred at rt for 30 min, then at 40° C. overnight. MeOH was removed under reduced pressure, Na₂CO₃ (aq, 100 mL) and EtOAc (150 mL) were added, and the suspension was stirred vigorously for 10 min. The mixture was filtered though glass frit, solid residue was washed with EtOAc (3×150 mL). Combined EtOAc fractions were washed with sat. Na$_2$CO$_3$ (aq, 2×50 mL), water (2×50 mL), brine (1×50 mL) and dried (Na$_2$SO$_4$). EtOAc was removed under reduced pressure and the residue was purified by flash chromatography (0-100% EtOAc/hexanes). Fractions were combined and concentrated under reduced pressure to give 17F (2.566 g, 7.12 mmol, 100% yield) as a yellowish oil, which solidified upon standing. MS (ESI) m/z: 361.1 [M+1]$^+$. $^1$H NMR: (400 MHz, CDCl$_3$) δ ppm 7.30-7.46 (5H, m), 6.37 (1H, dd, J=12.55, 2.76 Hz), 6.11-6.30 (1H, m), 4.94 (2H, s), 4.20-4.39 (2H, m), 3.58 (2H, s), 2.70 (3H, d, J=7.53 Hz), 1.36-1.54 (9H, m).

17G: 4-(Benzyloxy)-3-fluoro-5-((methylamino)methyl)aniline hydrochloride

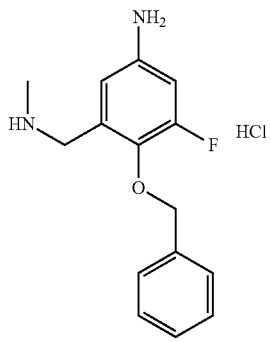 [SMILES: CNCc1cc(N)cc(F)c1OCc1ccccc1 ; Cl]

17F (2.566 g, 7.12 mmol) was dissolved in dichloromethane (40 mL), then HCl (4M in dioxane) (10 mL, 40.0 mmol) was added. The reaction mixture was stirred for 1 h at rt. The solvent was removed under reduced pressure, and the residue was dried under high vacuum to give 17G (2.265 g, 6.80 mmol, 95% yield) as an off-white solid. MS (ESI) m/z: 261.1 [M+1]$^+$. $^1$H NMR: (400 MHz, CD$_3$OD) δ ppm 7.30-7.53 (7H, m), 5.33 (2H, s), 4.07 (2H, s), 2.65 (3H, s).

17H: tert-Butyl N-(6-{[({[5-amino-2-(benzyloxy)-3-fluorophenyl]methyl}(methyl)carbamoyl)({4-[(2R)-1-hydroxypropan-2-yl]-3-methylphenyl})methyl]amino}isoquinolin-1-yl)-N-[(tert-butoxy)carbonyl]carbamate

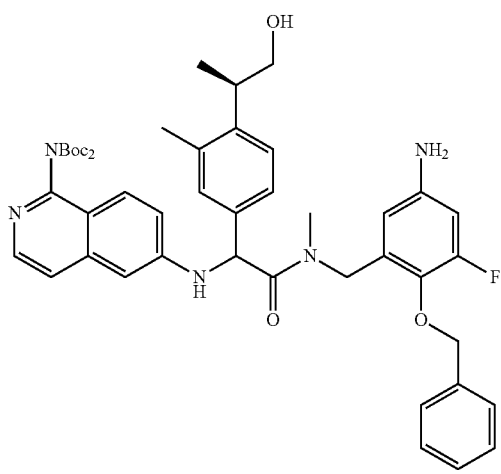

Intermediate 5 (1.000 g, 5.15 mmol), glyoxylic acid monohydrate (0.474 g, 5.15 mmol) and Intermediate 1 (1.852 g, 5.15 mmol) were dissolved in DMF (15 mL) and acetonitrile (20 mL). The reaction mixture was stirred at 80° C. for 1.5 h, then cooled to rt and diluted with DMF (5 mL). To this solution were added sequentially 17G (2.061 g, 6.18 mmol), BOP (2.507 g, 5.67 mmol) and TEA (4.31 mL, 30.9 mmol). The mixture was stirred at rt for 30 min, then quenched with water (0.5 mL). The reaction mixture was diluted with EtOAc (450 mL), washed with water (4×250 mL) and brine (250 mL), dried (Na$_2$SO$_4$) and concentrated. The crude product was purified by flash chromatography (1-20% MeOH/dichloromethane) to give 17H (2.795 g, 3.46 mmol, 67.1% yield) as an orange glass, which was lyophilized to a yellowish powder. MS (ESI) m/z: 808.2 [M+1]$^+$. $^1$H NMR was complicated by a pair of diastereomers and rotamers.

17I: tert-Butyl N-(6-{[(2R,15R)-7-(benzyloxy)-8-fluoro-4,15,20-trimethyl-3,12-dioxo-13-oxa-4,11-diazatricyclo[14.2.2.1$^{6,10}$]henicosa-1(18),6,8,10 (21),16,19-hexaen-2-yl]amino}isoquinolin-1-yl)-N-[(tert-butoxy)carbonyl]carbamate

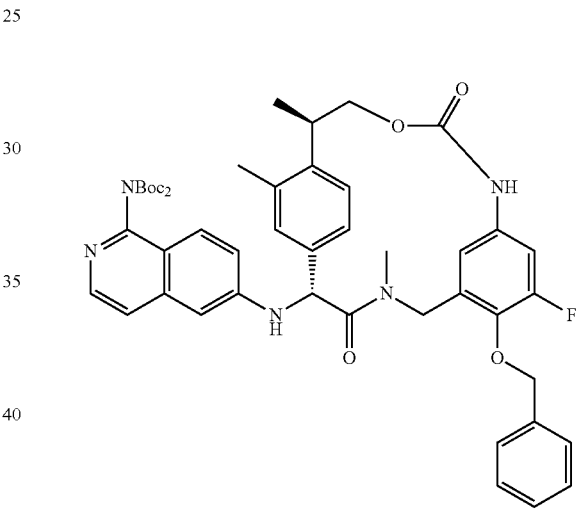

A solution of 17H (1.000 g, 1.238 mmol) in acetonitrile (10 mL) and dichloromethane (10 mL) was cooled to 0° C. To this solution was added phosgene (20% in toluene, 0.673 mL, 1.361 mmol). The mixture was stirred at 0° C. for 15 min, then bubbled with Ar for 60 min to remove excess phosgene and HCl. The resulting solution was added dropwise over 14 h via syringe pump into a solution of TEA (1.725 mL, 12.38 mmol) in dichloromethane (300 mL) at rt. The solution was stirred for an additional 30 min. Solvent was removed under reduced pressure. The crude product was purified by flash chromatography (1-15% MeOH/dichloromethane). Fractions were combined and concentrated under reduced pressure to give di-Boc protected intermediate (0.782 g, 76%) as a diastereomeric mixture. The diastereoisomers were separated by a prep chiral HPLC (Chiracel OD-H column, 21.1×250 mm) to give 17I (0.227 g, 0.272 mmol, 44.0% yield) as a yellow solid. MS (ESI) m/z: 834.2 [M+1]$^+$. $^1$H NMR: (400 MHz, CD$_3$OD) δ ppm 8.04 (1H, d, J=6.02 Hz), 7.60-7.69 (2H, m), 7.56 (1H, d, J=6.02 Hz), 7.28-7.45 (7H, m), 7.22 (1H, s), 6.87 (1H, d, J=2.01 Hz), 6.56 (1H, dd, J=12.17, 2.38 Hz), 5.61-5.71 (2H, m), 5.31 (1H, d, J=17.07 Hz), 5.00-5.10 (2H, m), 4.64 (1H, t, J=10.92 Hz), 3.95 (1H, dd, J=10.67, 4.39 Hz), 3.61-3.74 (3H, m), 3.40-3.56 (2H, m), 3.17 (3H, s), 2.31 (3H, s), 1.20-1.33 (21H, m).

17J: tert-Butyl N-[(tert-butoxy)carbonyl]-N-(6-{[(2R,15R)-8-fluoro-7-hydroxy-4,15,20-trimethyl-3,12-dioxo-13-oxa-4,11-diazatricyclo[14.2.2.1$^{6,10}$]henicosa-1(18),6,8,10(21),16,19-hexaen-2-yl]amino}isoquinolin-1-yl)carbamate

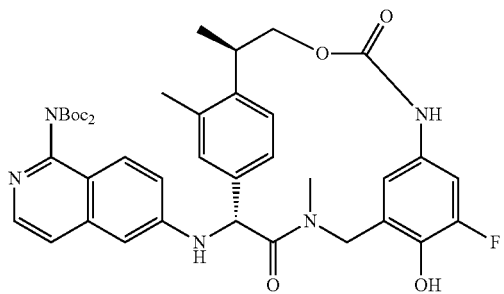

17I (0.227 g, 0.272 mmol) was dissolved in methanol (10 mL), degassed (3×Ar/vacuum). Then, Pd—C (0.029 g, 0.027 mmol) was added, and the reaction mixture was degassed again (3× Ar/vacuum). The resulting suspension was stirred under hydrogen (1 atm, balloon) for 1 h. The reaction mixture was filtered though a membrane filter, washed with MeOH (2×2 mL). MeOH was removed under reduced pressure to give 17J (0.199 g, 0.268 mmol, 98% yield) as a yellowish glass, which was lyophilized to give as a yellow solid. MS (ESI) m/z: 744.3 [M+1]$^+$. $^1$H NMR: (400 MHz, CD$_3$OD) δ ppm 8.04 (1H, d, J=5.77 Hz), 7.58-7.69 (2H, m), 7.50 (1H, d, J=6.02 Hz), 7.43 (1H, d, J=7.78 Hz), 7.24-7.30 (2H, m), 6.86 (1H, d, J=2.01 Hz), 6.50 (1H, dd, J=11.29, 2.01 Hz), 5.71 (1H, s), 5.56 (1H, br. s.), 5.36 (1H, d, J=17.32 Hz), 4.67 (1H, t, J=10.92 Hz), 3.86-3.99 (2H, m), 3.65 (2H, s), 3.41-3.55 (1H, m), 3.28 (3H, br. s.), 2.34 (3H, s), 1.23-1.36 (21H, m).

Example 17

To Ph$_3$P (88 mg, 0.336 mmol) in THF (1 mL) at 0° C. was added DIAD (0.065 mL, 0.336 mmol) dropwise within 5 min. The reaction mixture was stirred for 10 min at 0° C. Then, a solution of 17J (50 mg, 0.067 mmol) and 17B (64.0 mg, 0.336 mmol, dried over MS 4A) in THF (0.5 ml) was added to the reaction mixture dropwise within 5 min. The resulting suspension was stirred at 0° C. for 15 min, then warmed to rt over 1 h and continued stirring at rt for 2 h. THF was removed under reduced pressure, and the residue was purified by prep HPLC (Axia Luna 5 u C18 30×100 mm column; sol. A 10% MeCN-90% H$_2$O-0.1% TFA; sol. B 90% MeCN-10% H$_2$O-0.1% TFA). The desired fractions left overnight in HPLC solvent (0.1% TFA) resulted in deprotection of the TBS group. The solvent was removed, and the residue was coevaporated with MeCN (3×). $^1$H NMR and orthogonal HPLC showed a mixture of two compounds which was further separated by a prep chiral HPLC to give Example 17 (13.09 mg, 0.018 mmol, 26.5% yield) as a white solid. MS (ESI) m/z: 602.2 [M+1]$^+$. $^1$H NMR: (400 MHz, CD$_3$OD) δ ppm 8.89 (1H, s), 8.04 (1H, d, J=9.29 Hz), 7.64 (1H, d, J=7.78 Hz), 7.44 (1H, d, J=7.78 Hz), 7.30 (1H, d, J=7.03 Hz), 7.08-7.24 (2H, m), 6.90 (1H, d, J=7.03 Hz), 6.83 (1H, d, J=2.01 Hz), 6.53 (1H, dd, J=12.30, 2.26 Hz), 5.73 (1H, s), 5.68 (1H, br. s.), 5.42 (1H, d, J=17.32 Hz), 4.65 (1H, t, J=11.04 Hz), 3.86-4.09 (5H, m), 3.41-3.55 (1H, m), 2.33 (3H, s), 1.30 (3H, d, J=7.03 Hz), 1.23 (3H, d, J=6.53 Hz). Analytical HPLC (low pH, 254 nM): Sunfire, RT=5.51, 97.5% purity; XBridge, RT=6.37, 99% purity.

Example 18

1-({[(2R,15R)-2-[(1-Aminoisoquinolin-6-yl)amino]-8-fluoro-4,15,20-trimethyl-3,12-dioxo-13-oxa-4,11-diazatricyclo[14.2.2.1$^{6,10}$]henicosa-1(18),6,8,10(21),16,19-hexaen-7-yl]oxy}methyl)cyclopropane-1-carbonitrile; trifluoroacetic acid

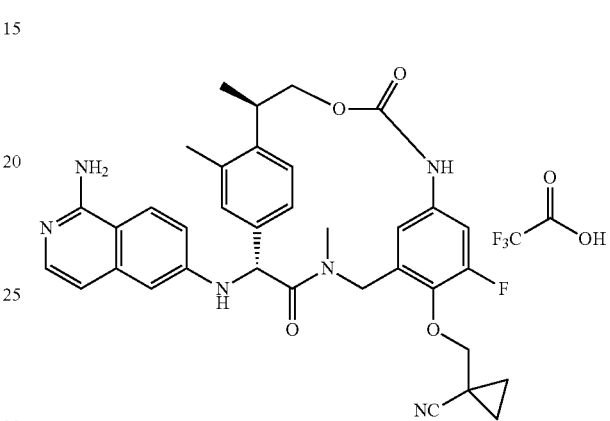

18A: (1-Cyanocyclopropyl)methyl 4-methylbenzenesulfonate

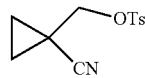

TsCl (7.25 g, 38 mmol) was added in one portion to a stirred solution of 1-(hydroxymethyl)cyclopropanecarbonitrile (3.1 h, 32 mmol) in dichloromethane (75 mL) at 0° C. Et$_3$N (4.1 g, 40 mmol) was added. The reaction mixture was stirred at rt over night. The mixture was diluted with dichloromethane, washed with water, 0.5 N NaOH, brine. The organic extract was dried over MgSO$_4$, filtered and concentrated in vacuo. The crude product was purified by flash chromatography to give 18A (6.43 g, 81% yield) as a white solid.

Example 18

17J (45 mg, 0.060 mmol) was dissolved in acetone (0.8 mL), and cesium carbonate (99 mg, 0.302 mmol) was added. To the solution was added 18A (15.96 mg, 0.064 mmol) in acetone (0.25 mL). The reaction mixture was stirred at rt for 24 h, then quenched slowly with a few drops of HCl (4 M in dioxane). The solvent was removed under reduced pressure, the residue was dissolved in HCl (4 M in dioxane; 1.5 mL) and stirred at rt for 45 min. The solvent was removed and the residue was purified by prep HPLC to give Example 18 (23.7 mg, 0.031 mmol, 51.8% yield) as a white solid. MS (ESI) m/z: 623.4 [M+1]$^+$. $^1$H NMR: (400 MHz, CD$_3$OD) δ ppm 8.94 (1H, s), 8.03 (1H, d, J=9.29 Hz), 7.65 (1H, dd, J=7.91, 1.63 Hz), 7.45 (1H, d, J=7.78 Hz), 7.28 (1H, d, J=7.03 Hz), 7.19-7.22 (2H, m), 6.88 (1H, d, J=7.03 Hz), 6.82 (1H, d, J=2.26 Hz), 6.54 (1H, dd, J=12.17, 2.38 Hz), 5.73 (2H, br. s.), 5.48 (1H, d, J=17.32 Hz), 4.65 (1H, t, J=11.04 Hz), 3.92-4.11 (4H, m), 3.42-3.54 (1H, m), 2.32 (3H, s), 1.35 (2H, d, J=2.26 Hz), 1.30 (3H, d, J=7.03 Hz), 1.06-1.18 (2H, m). Analytical HPLC (low pH, 254 nM): Sunfire, RT=5.27, 95.6% purity; XBridge, RT=6.33, 97.4% purity.

Example 19

(2R,15R)-2-[(1-Amino-4-fluoroisoquinolin-6-yl)amino]-7-(cyclopropanesulfonyl)-4,15,17-trimethyl-13-oxa-4,11-diazatricyclo[14.2.2.1$^{6,10}$]henicosa-1(18),6,8,10 (21),16,19-hexaene-3,12-dione; trifluoroacetic acid

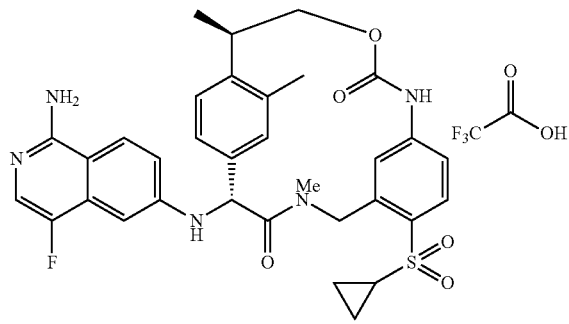

19A: tert-Butyl N-(6-{[({[5-amino-2-(cyclopropanesulfonyl)phenyl]methyl}(methyl)carbamoyl)({4-[(2R)-1-hydroxypropan-2-yl]-3-methylphenyl})methyl]amino}-4-fluoroisoquinolin-1-yl)-N-[(tert-butoxy)carbonyl]carbamate

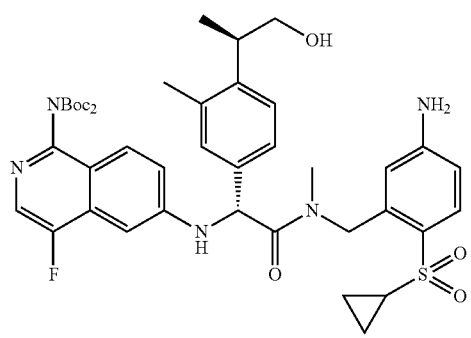

A mixture of Intermediate 3 (119 mg, 0.315 mmol), Intermediate 5 (61.2 mg, 0.315 mmol) and glyoxylic acid monohydrate (29.0 mg, 0.315 mmol) suspended in DMF (1.0 mL) and acetonitrile (3.0 mL) was heated at 80° C. in an oil bath for 1.5 h. After it was cooled to rt, Intermediate 8 (87 mg, 0.315 mmol) in DMF (1.0 mL) and DIEA (0.275 mL, 1.577 mmol) was added, followed by BOP (139 mg, 0.315 mmol). The mixture was stirred at rt over night. The solvent was removed under reduced pressure. The crude was purified by prep HPLC. The desired fractions were combined, concentrated, dissolved in methylene chloride, washed with sat. sodium carbonate. The organic extract was then washed with brine and dried over sodium sulfate. After evaporation of solvent, 19A (135 mg, 0.168 mmol, 53.1% yield) was obtained as a white solid. MS (ESI) m/z: 806.6 (M+H)$^+$.

19B: tert-Butyl N-[(tert-butoxy)carbonyl]-N-(6-{[(2R,15R)-7-(cyclopropanesulfonyl)-4,15,17-trimethyl-3,12-dioxo-13-oxa-4,11-diazatricyclo[14.2.2.1$^{6,10}$]henicosa-1(18),6,8,10 (21),16,19-hexaen-2-yl]amino}-4-fluoroisoquinolin-1-yl) carbamate

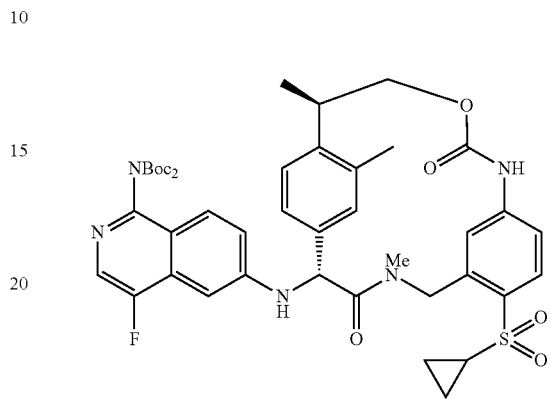

To a solution of 19A (135 mg, 0.168 mmol) in acetonitrile (6 mL) and dichloromethane (3 mL) at 0° C., was added phosgene solution (20% in toluene, 0.106 mL, 0.201 mmol) dropwise. The mixture was stirred at 0° C. for 40 min, then at rt for 10 min. Extra phosgene was removed by bubbling Ar for 20 min. The crude was redissolved in acetonitrile (1.0 mL) and dichloromethane (1.0 mL), and was added dropwise via syringe pump into a solution of TEA (0.187 mL, 1.340 mmol) in dichloromethane (60 mL) at rt over 3.0 h. The solution was stirred at rt over night. The solvent was removed and the crude residue was purified using a prep HPLC equipped with a C18 PHENOMENEX® Luna Axia column (30 mm×75 cm, 5µ). The desired fractions were collected and concentrated to give a mixture of diastereoisomers (114 mg). The diastereoisomers were separated by a prep chiral HPLC [(R,R)-Whelk-01 250×21.1 mm column] to give 19B (48 mg, 0.058 mmol, 34.4% yield). MS (ESI) m/z: 832.6 (M+H)$^+$.

Example 19

To 19B (48 mg, 0.058 mmol) was added 4.0 N HCl in dioxane (1442 µL, 5.77 mmol). The mixture was stirred at rt for 3.5 h. Solvent was removed. The crude was purified using a prep HPLC equipped with a C18 PHENOMENEX® Luna Axia column (30 mm×75 cm, 5µ). The desired fractions were concentrated and lyophilized to give Example 19 (39 mg, 0.052 mmol, 90% yield). MS (ESI) m/z: 632.1 (M+H)$^+$. $^1$H NMR (400 MHz, acetonitrile-d$_3$) δ ppm 7.74-7.81 (m, 2H) 7.71 (d, J=8.35 Hz, 1H) 7.64-7.69 (m, 1H) 7.45 (d, J=7.91 Hz, 1H) 7.21 (d, J=4.83 Hz, 1H) 7.13 (dd, J=9.23, 2.20 Hz, 1H) 6.98 (s, 1H) 6.88 (s, 1H) 6.81 (dd, J=8.35, 1.76 Hz, 1H) 6.30 (d, J=1.76 Hz, 1H) 5.70 (d, J=17.14 Hz, 1H) 5.65 (d, J=3.95 Hz, 1H) 4.56 (t, J=10.99 Hz, 1H) 4.18 (d, J=17.58 Hz, 1H) 3.91 (dd, J=10.55, 4.39 Hz, 1H) 3.39 (ddd, J=11.32, 7.14, 4.39 Hz, 1H) 3.27 (s, 3H) 2.63-2.72 (m, 1H) 2.17 (s, 3H) 1.25 (d, J=7.03 Hz, 3H) 1.05-1.20 (m, 2H) 0.93-1.04 (m, 2H); $^{19}$F NMR (376 MHz, acetonitrile-d$_3$) δ ppm −76.17 (s, 3F, TFA) −154.37 (br. s., 1F); Analytical HPLC (low pH, 254 nM): Sunfire, RT=6.62 min, 97.6% purity; XBridge, RT=5.49 min, 100% purity.

Example 20

(2R,15R)-2-[(1-Amino-8-fluoroisoquinolin-6-yl)amino]-8-fluoro-4,15,17-trimethyl-7-(propane-2-sulfonyl)-13-oxa-4,11-diazatricyclo[14.2.2.1$^{6,10}$]henicosa-1(18),6,8,10 (21),16,19-hexaene-3,12-dione; trifluoroacetic acid

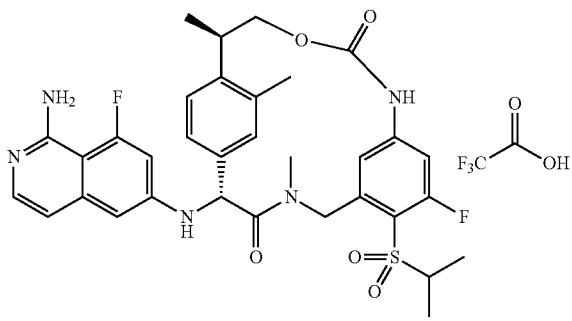

20A:
3-Fluoro-2-(isopropylthio)-5-nitrobenzaldehyde

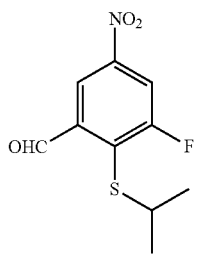 [SMILES: CC(C)Sc1c(F)cc([N+](=O)[O-])cc1C=O]

To a solution of 11A (51 mg, 0.273 mmol) in DMF (1 mL), were added TEA (0.057 mL, 0.409 mmol) and propane-2-thiol (0.030 mL, 0.327 mmol). The mixture was stirred at rt for 1 h, then was diluted with EtOAc. The organic phase was washed with H$_2$O (2×), 10% LiCl and brine, dried (Na$_2$SO$_4$), filtered though a 1" pad of SiO$_2$ and concentrated to give 20A (64 mg, 0.263 mmol, 97% yield) as a yellow oil. $^1$H NMR (400 MHz, chloroform-d) δ ppm 10.69 (1H, s), 8.57 (1H, dd, J=2.4, 1.1 Hz), 8.15 (1H, dd, J=8.5, 2.5 Hz), 3.72 (1H, dt, J=13.4, 6.7 Hz), 1.33 (6H, d, J=6.0 Hz).

20B: tert-Butyl 3-fluoro-2-(isopropylthio)-5-nitrobenzyl(methyl)carbamate

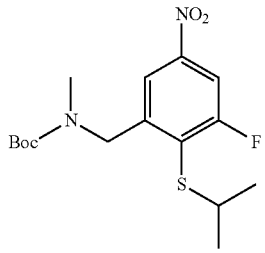

To a solution of 20A (635 mg, 2.61 mmol) in MeOH (10 mL), was added methylamine (33% in EtOH) (0.390 mL, 3.13 mmol). The mixture was stirred at rt for 3 h, then was cooled to 0° C. and treated with NaBH$_4$ (119 mg, 3.13 mmol). The reaction was stirred at 0° C. for 2 h, then was concentrated. The residue was dissolved in THF (10 mL), treated with H$_2$O (10 mL) and sat. NaHCO$_3$ (10 mL). After stirring for 10 min, Boc$_2$O (684 mg, 3.13 mmol) was added. The mixture was stirred at rt for 2 h, then the THF was evaporated. The mixture was extracted with EtOAc (2×). The organic phase was washed with H$_2$O and brine, dried (Na$_2$SO$_4$) and concentrated. The crude product was purified by flash chromatography (loaded in chloroform onto a 40 g column and eluted with a gradient from 0 to 40% ethyl acetate/hexanes) to give 20B (864 mg, 2.411 mmol, 92% yield) as a pale yellow oil. MS (ESI) m/z: 381.1 [M+1]$^+$. $^1$H NMR (400 MHz, chloroform-d) δ ppm 7.80-7.94 (2H, m), 4.68 (2H, d, J=20.6 Hz), 3.60-3.71 (1H, m), 2.92 (3H, d, J=10.5 Hz), 1.53 (5H, s), 1.43 (4H, br. s.), 1.27 (6H, d, J=6.3 Hz), 3:2 ratio of rotamers.

20C: tert-Butyl 3-fluoro-2-(isopropylsulfonyl)-5-nitrobenzyl(methyl)carbamate

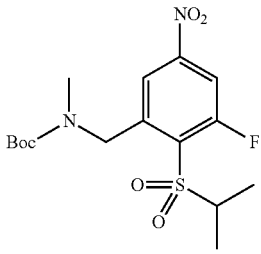 [SMILES: CC(C)S(=O)(=O)c1c(F)cc([N+](=O)[O-])cc1CN(C)C(=O)OC(C)(C)C]

To a solution of 20B (860 mg, 2.399 mmol) in dichloromethane (12 mL) at rt, was added m-CPBA (70%) (1479 mg, 6.00 mmol). The mixture was stirred at rt for 20 h. Additional m-CPBA (70%) (500 mg, 2.028 mmol) was added and the mixture was allowed to stir at rt for 24 h. The reaction mixture was diluted with EtOAc, washed with sat. Na$_2$CO$_3$ (2×) and brine, dried (Na$_2$SO$_4$) and concentrated. The crude product was purified by flash chromatography (loaded in chloroform onto a 40 g column and eluted with a gradient from 0 to 40% ethyl acetate/hexanes) to give 20C (867 mg, 2.221 mmol, 93% yield) as a colorless glass. MS (ESI) m/z: 391.1 [M+1]$^+$. $^1$H NMR (400 MHz, chloroform-d) δ ppm 7.90-8.08 (2H, m), 4.99 (2H, s), 3.56 (1H, ddd, J=13.2, 6.5, 6.4 Hz), 3.00 (3H, s), 1.52 (5H, br. s.), 1.40 (6H, d, J=7.0 Hz), 1.37 (4H, br. s.) ~1:1 rotamers.

20D: 3-Fluoro-4-(isopropylsulfonyl)-5-((methylamino)methyl)aniline hydrochloride

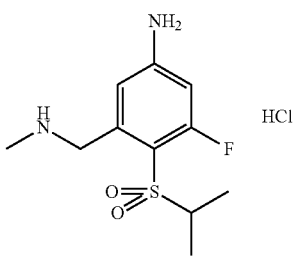 [SMILES: CNCc1cc(N)cc(F)c1S(=O)(=O)C(C)C ; Cl]

To a solution of 20D (864 mg, 2.213 mmol) in MeOH (10 mL), was added Pd—C (10%) (50 mg, 0.047 mmol). The mixture was evacuated and flushed with H$_2$ (3×), then was stirred under a balloon of H₂ for 5 h. The mixture was filtered and concentrated. The resultant foam was dissolved in 4N HCl in dioxane (5 mL, 20.00 mmol). The solution immediately became a suspension, which was stirred at rt for 1.5 h and concentrated to give 20D (737 mg, 2.212 mmol, 100% yield) as a white solid. MS (ESI) m/z: 261.1 [M+1]⁺. ¹H NMR (400 MHz, MeOD) δ ppm 6.61 (1H, d, J=2.3 Hz), 6.53 (1H, dd, J=13.6, 2.3 Hz), 4.27 (2H, s), 3.43 (1H, ddd, J=13.7, 6.8, 6.7 Hz), 2.75 (3H, s), 1.31 (6H, d, J=6.3 Hz).

20E: tert-Butyl N-(6-{[({[5-amino-3-fluoro-2-(propane-2-sulfonyl)phenyl]methyl}(methyl)carbamoyl) ({4-[(2R)-1-hydroxypropan-2-yl]-3-methylphenyl}) methyl]amino}-8-fluoroisoquinolin-1-yl)-N-[(tert-butoxy)carbonyl]carbamate

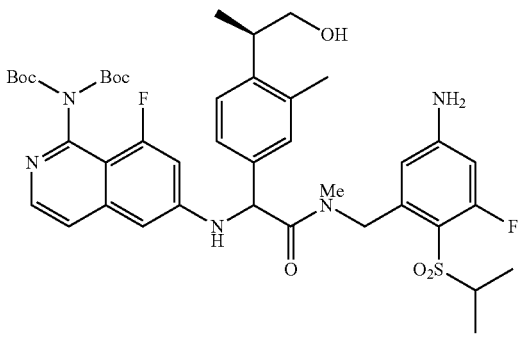 [SMILES: Cc1cc(C(Nc2cc(F)c3c(N(C(=O)OC(C)(C)C)C(=O)OC(C)(C)C)nccc3c2)C(=O)N(C)Cc2cc(N)cc(F)c2S(=O)(=O)C(C)C)ccc1[C@@H](C)CO]

Intermediate 2 (120 mg, 0.318 mmol), Intermediate 5 (61.7 mg, 0.318 mmol) and glyoxylic acid monohydrate (29.3 mg, 0.318 mmol) were dissolved in DMF (3 mL) and acetonitrile. The solution was stirred at 80° C. for 2 h. The mixture was cooled to rt. To this mixture were added sequentially 20D (117 mg, 0.350 mmol), BOP (155 mg, 0.350 mmol) and TEA (0.222 mL, 1.590 mmol). The mixture was stirred at rt for 1 h, quenched with water, extracted with EtOAc. The extract was washed with brine, dried (Na₂SO₄) and concentrated. The crude product was purified by flash chromatography (0-90% EtOAc in hexanes) to give 20E (130 mg, 0.157 mmol, 49.5% yield). MS (ESI) m/z: 826.2 [M+1]⁺.

20F: tert-Butyl N-[(tert-butoxy)carbonyl]-N-(8-fluoro-6-{[(2R,15R)-8-fluoro-4,15,17-trimethyl-3, 12-dioxo-7-(propane-2-sulfonyl)-13-oxa-4,11-diazatricyclo[14.2.2.1⁶,¹⁰]henicosa-1(18),6,8,10 (21),16, 19-hexaen-2-yl]amino}isoquinolin-1-yl)carbamate

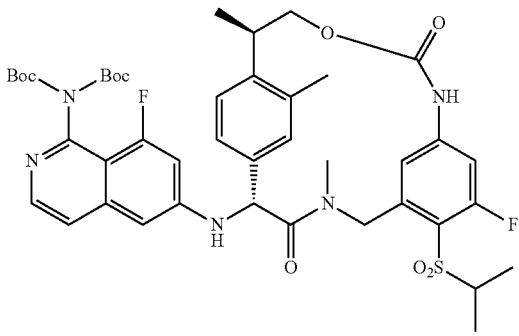 [SMILES: Cc1cc2ccc1[C@@H](C)COC(=O)Nc1cc(F)c(S(=O)(=O)C(C)C)c(c1)CN(C)C(=O)[C@@H]2Nc1cc(F)c2c(N(C(=O)OC(C)(C)C)C(=O)OC(C)(C)C)nccc2c1]

A solution of 20E (123 mg, 0.149 mmol) in acetonitrile (3 mL) and dichloromethane (6 mL) was cooled to 0° C. To this solution was added phosgene (20% in toluene, 0.081 mL, 0.164 mmol). The mixture was stirred at 0° C. for 5 min, and rt for 1 h. The mixture was bubbled with Ar for 10 min to remove excess phosgene. The resulting solution was added dropwise over 3 h via a syringe pump into a solution of TEA (0.208 mL, 1.489 mmol) in CH₂Cl₂ (260 mL) at rt. The solution was stirred at rt for 16 h. The solvent was concentrated and the crude product was purified by flash chromatography to give a mixture of diastereoisomers (60 mg, 47.3% yield). The diastereoisomers were separated by a prep chiral HPLC to give 20F (22 mg, 0.026 mmol, 37.9% yield).

Example 20

20F (21 mg, 0.025 mmol) was stirred with TFA (1 mL) for 30 min at rt. The mixture was concentrated and purified by prep HPLC to give Example 20 (17 mg, 0.022 mmol, 89% yield). MS (ESI) m/z: 652.1 [M+1]⁺. ¹H NMR (500 MHz, methanol-d₄) δ ppm 7.66 (1H, dd, J=8.0, 1.7 Hz), 7.48 (1H, d, J=7.7 Hz), 7.29 (1H, d, J=7.2 Hz), 7.07 (1H, s), 6.93 (1H, dd, J=16.0, 1.9 Hz), 6.86 (1H, dd, J=7.2, 1.9 Hz), 6.68 (1H, s), 6.60 (1H, dd, J=12.1, 1.9 Hz), 6.24 (1H, br. s.), 5.67-5.75 (2H, m), 4.61 (1H, t, J=11.0 Hz), 4.21 (1H, d, J=17.9 Hz), 3.93-4.02 (1H, m), 3.42-3.57 (2H, m), 3.34 (3H, s), 2.28 (3H, s), 1.34 (3H, s), 1.30-1.34 (6H, m). Analytical HPLC (low pH, 254 nM): Sunfire, RT=6.14, 99.7% purity; XBridge, RT=7.20, 96% purity.

Example 21

(2R,15R)-2-[(1-Aminoisoquinolin-6-yl)amino]-7-[(2S)-2-cyclopropyl-2-hydroxyethoxy]-8-fluoro-4, 15,20-trimethyl-13-oxa-4,11-diazatricyclo[14.2.2.16, 10]henicosa-1(18),6,8,10 (21),16,19-hexaene-3,12-dione; trifluoroacetic acid

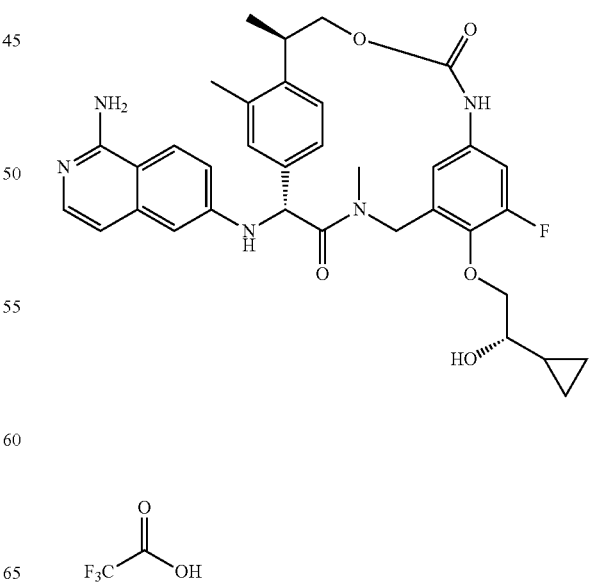

21A: 2-Bromo-1-cyclopropylethanone

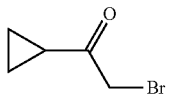

To a solution of 1-cyclopropylethanone (18.85 mL, 201 mmol) in MeOH (120 mL) at 0° C. was added bromine (10.40 mL, 202 mmol) dropwise. The reaction mixture was stirred at 0° C. for 1 h, rt for 30 min, and quenched by addition of water. The mixture was extracted with ether (3×100 mL). The organic layer was washed with sat. sodium bicarbonate and brine, dried over MgSO$_4$ and concentrated to give 21A (32.5 g, 199 mmol, 99% yield) as a light brown oil.

21B: tert-Butyl 2-(2-cyclopropyl-2-oxoethoxy)-3-fluoro-5-nitrobenzyl(methyl)carbamate

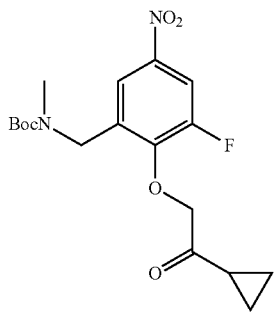 [SMILES: CN(Cc1cc([N+](=O)[O-])cc(F)c1OCC(=O)C1CC1)C(=O)OC(C)(C)C]

To a solution of 17D (1.15 g, 3.83 mmol) in DMF (10 mL) was added 21A (1.486 g, 3.69 mmol), K$_2$CO$_3$ (2.65 g, 19.15 mmol). The mixture was stirred 60° C. for 2 h, quenched with water, extracted with EtOAc (2×). The extract was dried over sodium sulfate and concentrated. The crude product was purified by flash chromatography to give 21B (1.486 g, 3.69 mmol, 96% yield). MS (ESI) m/z: 383.2 (M+H)$^+$.

21C: tert-Butyl 2-(2-cyclopropyl-2-hydroxyethoxy)-3-fluoro-5-nitrobenzyl(methyl)carbamate

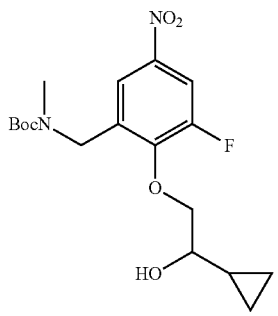 [SMILES: CN(Cc1cc([N+](=O)[O-])cc(F)c1OCC(O)C1CC1)C(=O)OC(C)(C)C]

21B (1.47 g, 3.84 mmol) was dissolved in MeOH (15 mL) at 0° C. NaBH$_4$ (0.175 g, 4.61 mmol) was added. The reaction mixture was stirred rt for 1 h. quenched with water, extracted with EtOAc (2×). The extract was dried over sodium sulfate and concentrated. The crude was purified by prep HPLC. To give 21C (830 mg, 2.159 mmol, 56.2% yield). MS (ESI) m/z: 385.4 (M+H)$^+$. $^1$H NMR (400 MHz, chloroform-d) δ ppm 7.95 (dd, J=11.86, 2.20 Hz, 1H) 7.88 (s, 1H) 4.70 (d, J=11.86 Hz, 1H) 4.51 (s, 3H) 4.35 (d, J=13.62 Hz, 1H) 4.20 (t, J=7.91 Hz, 1H) 3.21 (t, J=7.47 Hz, 1H) 2.75 (s, 3H) 1.45 (s, 9H) 0.90 (dd, J=8.13, 4.17 Hz, 1H) 0.49-0.61 (m, 2H) 0.41 (td, J=9.23, 4.83 Hz, 1H) 0.22-0.29 (m, 1H).

21D: (S)-tert-Butyl 2-(2-cyclopropyl-2-hydroxyethoxy)-3-fluoro-5-nitrobenzyl(methyl)carbamate

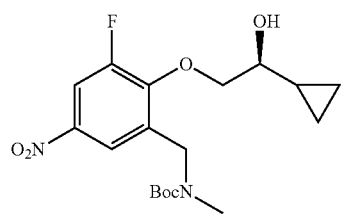 [SMILES: CN(Cc1cc([N+](=O)[O-])cc(F)c1OC[C@@H](O)C1CC1)C(=O)OC(C)(C)C]

21C (200 mg, 0.520 mmol) was separated by a prep chiral HPLC. The 2nd peak was concentrated to give 21D (82 mg, 0.213 mmol, 41.0% yield). The absolute stereochemistry is undetermined.

21E: (S)-Benzyl 2-(2-cyclopropyl-2-hydroxyethoxy)-3-fluoro-5-nitrobenzyl(methyl)carbamate

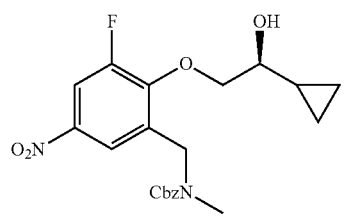 [SMILES: CN(Cc1cc([N+](=O)[O-])cc(F)c1OC[C@@H](O)C1CC1)C(=O)OCc1ccccc1]

To 21D (88 mg, 0.229 mmol) in EtOAc (2 mL) was added 4.0 M HCl in dioxane (1.5 mL, 6.00 mmol). The mixture was stirred rt for 1 h, concentrated. The residue was dissolved in DMF (10 ml). N-(benzyloxycarbonyloxy) succinimide (62.8 mg, 0.252 mmol) was added, followed by N,N-diisopropylethylamine (0.120 mL, 0.687 mmol). The mixture was stirred rt for 16 h, then was quenched with water, extracted with EtOAc (3×30 ml). The organic layer was washed with brine, dried (Na$_2$SO$_4$) and concentrated. The crude product was purified by flash chromatography (0-60% EtOAc in hexane) to give 21E (99 mg, 103% yield). MS (ESI) m/z: 419.3 (M+H)$^+$.

21F: (S)-Benzyl 2-(2-((tert-butyldimethylsilyl)oxy)-2-cyclopropylethoxy)-3-fluoro-5-nitrobenzyl(methyl)carbamate

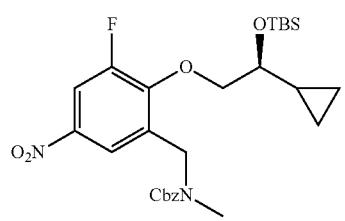 [SMILES: CN(Cc1cc([N+](=O)[O-])cc(F)c1OC[C@@H](O[Si](C)(C)C(C)(C)C)C1CC1)C(=O)OCc1ccccc1]

To a solution of 21E (99 mg, 0.237 mmol) in DMF (3 mL), was added tert-butyldimethylsilyl chloride (178 mg, 1.183 mmol) and imidazole (81 mg, 1.183 mmol). The reaction mixture was stirred at rt for 60 h., then was quenched with water, extracted with EtOAc (2×). The organic layer was washed with brine, dried (Na$_2$SO$_4$) and concentrated. The crude product was purified by flash chromatography to give 21F (92 mg, 0.173 mmol, 73.0% yield). MS (ESI) m/z: 533.4 (M+H)$^+$.

21G: (S)-4-(2-((tert-Butyldimethylsilyl)oxy)-2-cyclopropylethoxy)-3-fluoro-5-((methylamino)methyl)aniline

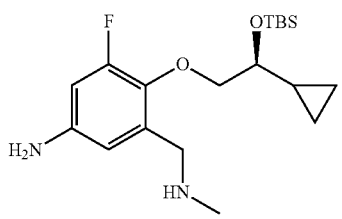

To a solution of 21F (92 mg, 0.173 mmol) in MeOH (5 mL) was added 10% Pd—C (50 mg, 0.047 mmol). The mixture was evacuated and flushed with H$_2$ (3×), then was stirred under a balloon of H$_2$ for 5 h. The mixture was filtered and concentrated to give 21G (62 mg, 0.168 mmol, 97% yield). MS (ESI) m/z: 369.4 (M+H)$^+$.

21H: tert-Butyl N-[6-({[({5-amino-2-[(2S)-2-[(tert-butyldimethylsilyl)oxy]-2-cyclopropylethoxy]-3-fluorophenyl}methyl)(methyl)carbamoyl]({4-[(2R)-1-hydroxypropan-2-yl]-3-methylphenyl})methyl}amino)isoquinolin-1-yl]-N-[(tert-butoxy)carbonyl]carbamate

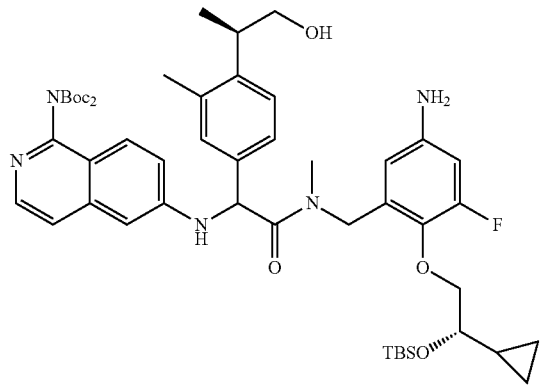

Intermediate 5 (33 mg, 0.170 mmol), glyoxylic acid monohydrate (15.66 mg, 0.170 mmol) and Intermediate 1 (61.1 mg, 0.170 mmol) were dissolved in DMF (1 mL) and acetonitrile. The solution was stirred at 80° C. for 2 h. The mixture was cooled to rt. To this mixture were added sequentially TEA (0.119 mL, 0.850 mmol), 21G (62.7 mg, 0.170 mmol) and BOP (90 mg, 0.204 mmol). The mixture was stirred at rt for 30 min. The reaction mixture was concentrated, purified by prep HPLC to give 21H (62 mg, 0.068 mmol, 39.8% yield) as light yellow solid. MS (ESI) m/z: 916.8 (M+H)$^+$.

21I: tert-Butyl N-[(tert-butoxy)carbonyl]-N-(6-{[(2R,15R)-7-[(2S)-2-cyclopropyl-2-hydroxyethoxy]-8-fluoro-4,15,20-trimethyl-3,12-dioxo-13-oxa-4,11-diazatricyclo[14.2.2.1$^{6,10}$]henicosa-1(18),6,8,10 (21),16,19-hexaen-2-yl]amino}isoquinolin-1-yl)carbamate

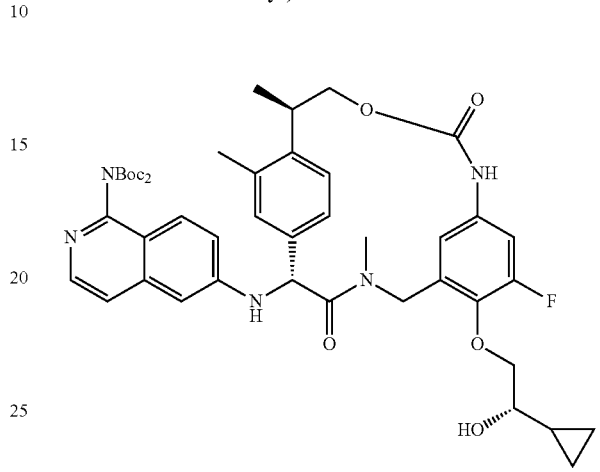

A solution of 21H (62 mg, 0.069 mmol) in acetonitrile (2 mL) and dichloromethane (2 mL) was cooled to 0° C. To this solution was added phosgene (20% in toluene, 0.038 mL, 0.076 mmol). The mixture was stirred at 0° C. for 5 min, and rt for 20 min. The mixture was bubbled with Ar for 10 min to remove excess phosgene. The resulting solution was added dropwise over 3 h via a syringe pump into a solution of TEA (0.096 mL, 0.690 mmol) in CH$_2$Cl$_2$ (60 mL) at rt. The solution was stirred at rt for 16 h. The solvent was removed under reduced pressure, and the residue was mixed with THF (3 mL) and TBAF (2 mL, 1M), the solution was stirred rt for 1 h. The mixture was concentrated and purified by flash chromatography (0-90% EtOAc in Hex) to give s mixture of diastereoisomers (38 mg, 0.046 mmol, 66.5% yield). The diastereomers were separated by a prep chiral HPLC (R,R-Whelk-O column 21.1×250 mm) to give 21I (16 mg, 0.019 mmol, 42.1% yield). MS (ESI) m/z: 828.7 (M+H)$^+$.

Example 21

To a solution of 21I (16 mg, 0.019 mmol) in EtOAc (2 mL) was added 4.0 M HCl in dioxane (2 mL, 8.00 mmol). The mixture was stirred rt for 4 h, then concentrated and purified by prep HPLC to give Example 21 (8.2 mg, 10.83 μmol, 56.1% yield). MS (ESI) m/z: 628.5 (M+H)$^+$. $^1$H NMR (400 MHz, methanol-d$_4$) δ ppm 8.04 (d, J=9.34 Hz, 1 H) 7.63 (d, J=8.24 Hz, 1H) 7.43 (d, J=8.25 Hz, 1H) 7.30 (d, J=7.15 Hz, 1H) 7.16-7.24 (m, 2H) 6.90 (d, J=7.15 Hz, 1H) 6.83 (d, J=2.20 Hz, 1H) 6.52 (dd, J=12.37, 2.47 Hz, 1H) 5.73 (s, 1H) 5.66 (s, 1H) 5.43 (d, J=17.04 Hz, 1H) 4.65 (t, J=11.27 Hz, 1H) 4.09-4.18 (m, 1H) 3.99-4.08 (m, 2H) 3.96 (dd, J=10.44, 4.40 Hz, 1H) 3.48 (ddd, J=11.13, 7.01, 4.40 Hz, 1H) 3.28 (s, 3H) 3.15 (ddd, J=11.27, 7.70, 3.57 Hz, 1H) 2.32 (s, 3H) 1.29 (d, J=7.15 Hz, 3H) 0.91-1.02 (m, 1H) 0.48-0.57 (m, 2H) 0.33-0.41 (m, 1H) 0.23-0.33 (m, 1H). Analytical HPLC (low pH, 254 nM): Sunfire, RT=6.49 min, 97.6% purity; XBridge, RT=5.53 min, 100% purity.

Example 22

(15R)-2-[(1-Aminoisoquinolin-6-yl)amino]-4,15,17-trimethyl-7-(2-methylpropane-2-sulfonyl)-13-oxa-4,11-diazatricyclo[14.2.2.1⁶,¹⁰]henicosa-1(18),6,8,10(21),16,19-hexaene-3,12-dione; trifluoroacetic acid

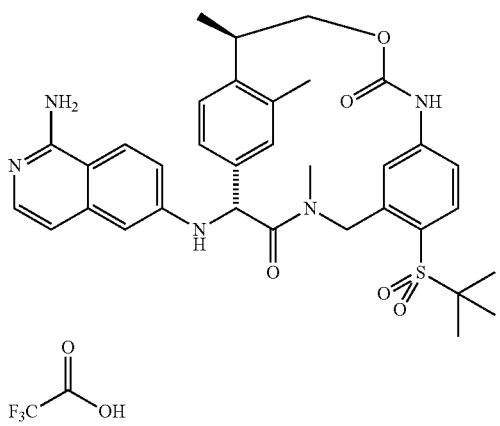

22A: tert-Butyl 2-(tert-butylsulfonyl)-5-nitrobenzyl (methyl)carbamate

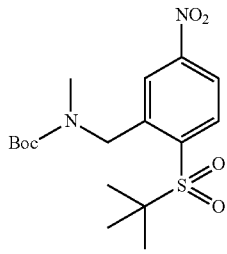

To a solution of tert-butyl 2-(tert-butylthio)-5-nitrobenzyl (methyl)carbamate (3 g, 8.46 mmol) in dichloromethane (60 mL) at 0° C., was added mCPBA (4.74 g, 21.16 mmol). The suspension was stirred at rt for 2 h. The mixture was filtered and the precipitate was rinsed with CH₂Cl₂ (3×10 mL). The combined dichloromethane solution was washed with 10% aq. K₂CO₃ (3×) and brine, dried (Na₂SO₄) and concentrated. The crude product was purified by flash chromatography (0 to 70% ethyl acetate/hexanes) to give 22A (2.5 g, 76% yield). MS (ESI) m/z: 387.5 (M+H)⁺. ¹H NMR (400 MHz, DMSO-d₆) δ ppm 8.30-8.40 (1H, m), 8.14 (1H, d, J=8.79 Hz), 8.01 (1H, s), 4.89 (2H, s), 2.88 (3H, s), 1.32-1.53 (9H, m), 1.30 (9H, s).

22B: tert-Butyl 5-amino-2-(tert-butylsulfonyl)benzyl (methyl)carbamate

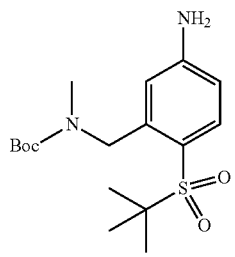 [SMILES: CN(Cc1cc(N)ccc1S(=O)(=O)C(C)(C)C)C(=O)OC(C)(C)C]

A mixture of 22A (2.5 g, 6.47 mmol) and Pd/C (0.25 g, 0.235 mmol) in MeOH (30 mL) were stirred under H₂ (50 psi) overnight. The reaction was filtered and concentrated. The crude product was purified by flash chromatography (0% to 100% ethyl acetate in hexane) to yield 22B (1.6 g, 4.49 mmol, 69.4% yield) as a white solid. MS (ESI) m/z: 357.5 (M+H)⁺. ¹H NMR (400 MHz, DMSO-d₆) δ ppm 7.41 (1H, d, J=8.79 Hz), 6.53 (1H, d, J=8.79 Hz), 6.38 (1H, br. s.), 6.26 (2H, d, J=12.74 Hz), 4.66 (2H, s), 2.80 (3H, s), 1.29-1.56 (9H, m), 1.21 (9H, s).

22C: 4-(tert-Butylsulfonyl)-3-((methylamino)methyl)aniline hydrochloride

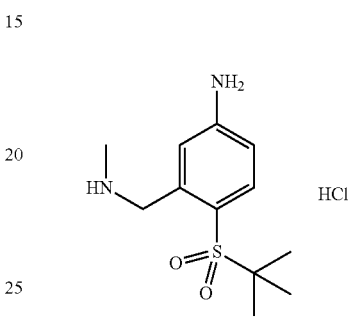

HCl (4 M in dioxane, 5 mL) was added to 22B (500 mg, 1.403 mmol) and stirred at rt for 1 h. The reaction was concentrated to yield 22C (460 mg, 1.397 mmol, 100% yield) as a white solid. MS (ESI) m/z: 257.3 (M+H)⁺. ¹H NMR (400 MHz, DMSO-d₆) δ ppm 8.93 (2H, br. s.), 7.51 (1H, d, J=8.79 Hz), 6.76 (1H, d, J=2.20 Hz), 6.72 (1H, dd, J=8.79, 2.20 Hz), 4.17 (2H, t, J=5.71 Hz), 2.53 (3H, t, J=5.27 Hz), 1.21 (9H, s).

22D: tert-Butyl N-(6-{[({[5-amino-2-(2-methylpropane-2-sulfonyl)phenyl]methyl}(methyl)carbamoyl)({4-[(2R)-1-hydroxypropan-2-yl]-3-methylphenyl})methyl]amino}isoquinolin-1-yl)-N-[(tert-butoxy)carbonyl]carbamate

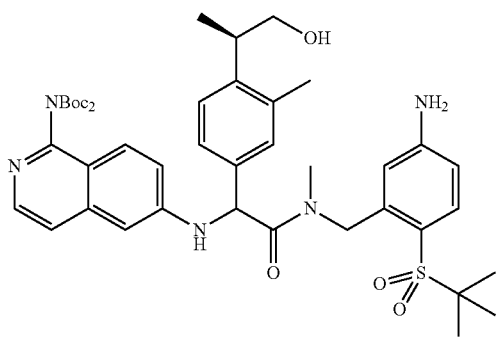

Intermediate 5 (147 mg, 0.759 mmol), Intermediate 1 (300 mg, 0.835 mmol) and glyoxylic acid monohydrate (77 mg, 0.835 mmol) were dissolved in acetonitrile (2 mL)/DMF (2.000 mL) and heated at 100° C. in the microwave for 10 min. A solution of 22C (250 mg, 0.759 mmol) and TEA (0.317 mL, 2.278 mmol) in DMF (2.000 mL) was added, followed by BOP (369 mg, 0.835 mmol) as a solid. The reaction mixture was stirred at rt for 3 h. The reaction mixture was diluted with EtOAc, washed with water and brine, dried over Na₂SO₄ and concentrated. The crude material was purified by column chromatography (0 to 20% MeOH in CH$_2$Cl$_2$) to yield 22D (303 mg, 0.377 mmol, 49.6% yield). MS (ESI) m/z: 804.6 (M+H)$^+$.

22E: tert-Butyl N-[(tert-butoxy)carbonyl]-N-(6-{[(15R)-4,15,17-trimethyl-7-(2-methylpropane-2-sulfonyl)-3,12-dioxo-13-oxa-4,11-diazatricyclo[14.2.2.1$^{6,10}$]henicosa-1(18),6,8,10 (21),16,19-hexaen-2-yl]amino}isoquinolin-1-yl)carbamate

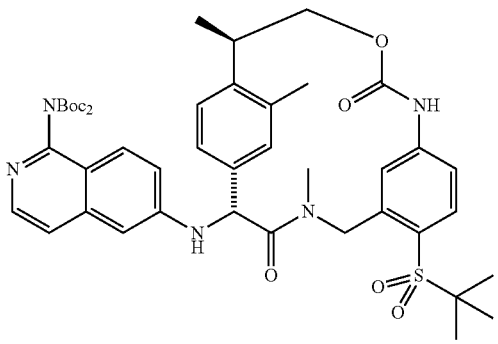

Phosgene (201 mg, 0.406 mmol) was added dropwise to a solution of 22D (297 mg, 0.369 mmol) in acetonitrile (4 mL)/CH$_2$Cl$_2$ (4 mL) at 0° C. The bath was removed and the mixture was stirred at rt for 30 min. Ar was bubbled though the solution (10 min) to remove excess phosgene. The resulting solution was added to a solution of TEA (0.257 mL, 1.847 mmol) in CH$_2$Cl$_2$ (40 mL) at 40° C. over 5 h via a syringe pump. The reaction was stirred at rt overnight, quenched with H$_2$O (1 mL) and MeOH (5 mL) and then concentrated. The crude product was purified by flash chromatography to give a mixture of diastereoisomers. The diastereomers were separated by a prep chiral HPLC (R,R-Whelk-O column 21.1× 250 mm) to give 22E (75 mg, 0.090 mmol, 24.46% yield). MS (ESI) m/z: 830.8 (M+H)$^+$.

Example 22

22E (75 mg, 0.090 mmol) was stirred with TFA (5 mL) for 30 min. The mixture was concentrated and the crude was purified by prep HPLC to yield Example 22 (50 mg, 0.070 mmol, 77% yield) as a white solid. MS (ESI) m/z: 630.4 (M+H)$^+$. $^1$H NMR (400 MHz, methanol-d$_3$) δ ppm 8.04 (1H, d, J=9.23 Hz), 7.73 (1H, d, J=8.79 Hz), 7.65-7.70 (1H, m), 7.48 (1H, d, J=7.91 Hz), 7.32 (1H, d, J=7.03 Hz), 7.19 (1H, dd, J=9.23, 2.20 Hz), 7.14 (1H, s), 6.92 (1H, d, J=7.03 Hz), 6.87 (1H, dd, J=8.35, 2.20 Hz), 6.83 (1H, d, J=2.20 Hz), 6.38 (1H, s), 5.67-5.80 (1H, m), 4.62 (1H, t, J=10.99 Hz), 4.30 (1H, d, J=18.02 Hz), 4.00 (1H, dd, J=10.99, 4.39 Hz), 3.66 (1H, s), 3.35 (3H, s), 2.31 (3H, s), 1.31-1.39 (12H, m). Analytical HPLC (low pH, 254 nM): Sunfire, RT=6.69 min, 99% purity; XBridge, RT=5.61 min, 97% purity.

Example 23

(2R,15R)-2-[(1-Aminoisoquinolin-6-yl)amino]-N-ethyl-4,15,17-trimethyl-3,12-dioxo-N-(1,3-thiazol-2-ylmethyl)-13-oxa-4,11-diazatricyclo[14.2.2.1$^{6,10}$]henicosa-1(18),6,8,10 (21),16,19-hexaene-7-carboxamide; trifluoroacetic acid

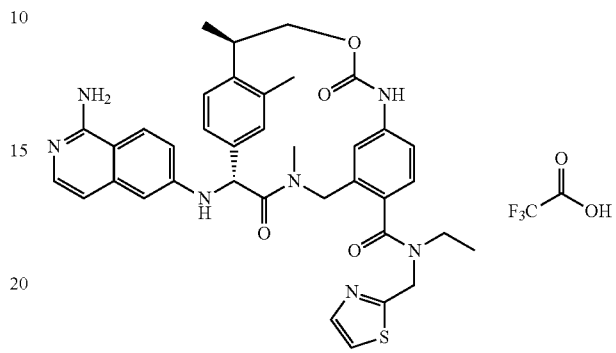

To a solution of 1D (7 mg, 9.46 μmol) in DMF (0.2 mL) and acetonitrile (0.200 mL) at 0° C. was added HATU (4.32 mg, 0.011 mmol) and N-methylmorpholine (1.560 μL, 0.014 mmol). The reaction was stirred for 5 min. Then N-(thiazol-2-ylmethyl)ethanamine (2.019 mg, 0.014 mmol) was added and the reaction was allowed to warm to room temperature and stirred for 4 h. The reaction mixture was diluted with water and extracted with EtOAc (3×). The combined organic layer was washed with water and brine, dried (MgSO$_4$), and concentrated. The residue was purified by prep HPLC. The desired fraction were collected and concentrated. The residue wash then treated with 1.5 mL of TFA and stirred for 30 min. The reaction mixture was concentrated and purified by prep HPLC to give Example 23 (5.0 mg, 67% yield). $^1$H NMR (400 MHz, MeOD) δ ppm 8.04 (1H, d, J=9.29 Hz), 7.74 (1H, d, J=2.76 Hz), 7.65 (1H, dd, J=8.03, 1.51 Hz), 7.58 (1H, d, J=3.01 Hz), 7.45 (1H, d, J=7.78 Hz), 7.31 (1H, d, J=7.28 Hz), 7.15-7.26 (3H, m), 6.90 (1H, d, J=7.28 Hz), 6.83 (1H, s), 6.77 (1H, d, J=7.78 Hz), 6.14 (1H, s), 5.73 (1H, s), 5.26 (1H, br. s.), 4.92-5.15 (2H, m), 4.64 (1H, t, J=10.92 Hz), 3.94-4.05 (1H, m), 3.42-3.59 (1H, m), 1.17-1.36 (5H, m), 1.11 (2H, t, J=6.90 Hz).

Example 24

(2R,15R)-2-[(1-Aminoisoquinolin-6-yl)amino]-7-(cyclopropanesulfonyl)-15-(fluoromethyl)-4,17-dimethyl-13-oxa-4,11-diazatricyclo[14.2.2.1$^{6,10}$]henicosa-1(18),6,8,10 (21),16,19-hexaene-3,12-dione; trifluoroacetic acid

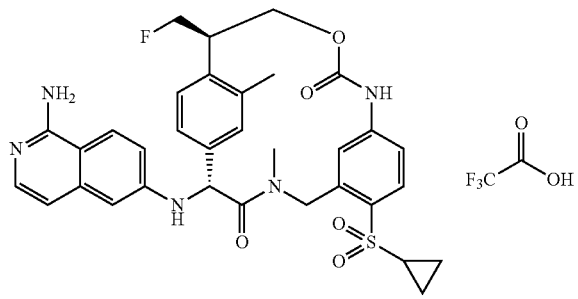 [SMILES: Cc1cc2ccc1[C@@H](CF)COC(=O)Nc1ccc(S(=O)(=O)C3CC3)c(c1)CN(C)C(=O)[C@@H]2Nc1ccc2c(N)nccc2c1 ; O=C(O)C(F)(F)F]

24A: (R)-3-(Benzyloxy)-2-(4-bromo-2-methylphenyl)propyl methanesulfonate

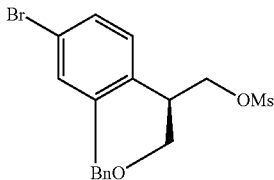

To 16F (0.6 g, 1.790 mmol) in CH$_2$Cl$_2$ (15 mL) was added triethylamine (0.299 mL, 2.148 mmol) and MsCl (0.167 mL, 2.148 mmol). The reaction was stirred at rt for 2 h. The solvent was removed and residue was redissolved in EtOAc. The solution was washed with water and brine, dried over sodium sulfate and concentrated. The crude product was purified by flash chromatography (0-40% ETOAc/hexanes) to give 24A (0.74 g, 1.790 mmol, 100% yield) as an oil. $^1$H NMR (400 MHz, chloroform-d) δ ppm 7.28-7.40 (m, 7H) 7.13 (d, J=8.34 Hz, 1H) 4.39-4.59 (m, 4H) 3.69 (d, J=5.81 Hz, 2H) 3.52-3.62 (m, 1H) 2.85 (s, 3H) 2.33 (s, 3H).

24B: (R)-1-(1-(Benzyloxy)-3-fluoropropan-2-yl)-4-bromo-2-methylbenzene

To 24A (0.74 g, 1.790 mmol) in tBuOH (10 mL) was added TBAF (1.0 M in THF, 5.37 mL, 5.37 mmol). The mixture was stirred at 80° C. for 2 h. Ethyl ether was added and the mixture was filtered. The filtrate was evaporated and the crude product was purified by flash chromatography (0-30% EtOAc/hexanes) to give 24B (0.46 g, 1.364 mmol, 76% yield) as colorless oil. $^1$H NMR (400 MHz, chloroform-d) δ ppm 7.27-7.43 (m, 7H) 7.13 (d, J=8.34 Hz, 1H) 4.74 (d, J=5.56 Hz, 1H) 4.62 (d, J=5.56 Hz, 1H) 4.47-4.59 (m, 2H) 3.71-3.81 (m, 1H) 3.60-3.70 (m, 1H) 3.37-3.57 (m, 1H) 2.33 (s, 3H); $^{19}$F NMR (376 MHz, chloroform-d) δ ppm −224.19 (s, 1F).

24C: (R)-(4-(1-(Benzyloxy)-3-fluoropropan-2-yl)-3-methylphenyl)boronic acid

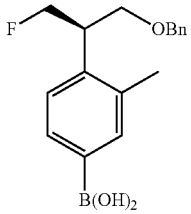 [SMILES: Cc1cc(B(O)O)ccc1[C@@H](CF)COCc1ccccc1]

To a solution of 24B (0.46 g, 1.364 mmol) in THF (7 mL) at −78° C., was added a solution of n-BuLi (2.2 mL, 3.52 mmol) dropwise. The mixture was stirred at −78° C. for 15 min, then was treated with trimethyl borate (0.456 mL, 4.09 mmol). The reaction was stirred at −78° C. for 15 min, then was allowed to warm to rt and stir for 3 h. The reaction mixture was diluted with EtOAc (30 mL), treated with 1N HCl (20 mL). The mixture was stirred at rt for 1 h. The phases were separated, then the aqueous layer was extracted with EtOAc. The combined organic phase was washed with H$_2$O and brine, dried (Na$_2$SO$_4$) and concentrated. The crude product was purified by flash chromatography (0 to 80% EtOAc/hexanes) to give 24C (0.2 g, 0.662 mmol, 48.5% yield). $^1$H NMR (400 MHz, chloroform-d) δ ppm 7.97-8.10 (m, 2H) 7.28-7.44 (m, 6H) 4.82 (d, J=5.56 Hz, 1H) 4.71 (d, J=5.56 Hz, 1H) 4.53-4.59 (m, 2H) 3.56-3.90 (m, 3H) 2.47 (s, 3H); $^{19}$F NMR (376 MHz, chloroform-d) δ ppm −223.99 (s, 1F).

24D: (R)-(4-(1-Fluoro-3-hydroxypropan-2-yl)-3-methylphenyl)boronic acid

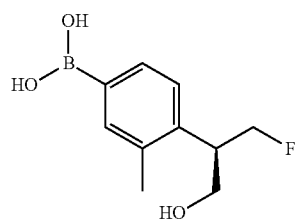

To 24C (0.2 g, 0.662 mmol) was added Pd/C (0.070 g, 0.662 mmol) and MeOH (10 mL) under N$_2$. The reaction was flush with N$_2$ and degassed (3×). Then H$_2$ balloon was introduced and system was degassed and flush with H$_2$ (3×) before letting it stir at rt overnight. The mixture was filtered and washed with MeOH (3×). The filtrate was evaporated and dried under vacuo to give 24D (0.1 g, 0.472 mmol, 71.3% yield). $^1$H NMR (400 MHz, MeOD) δ ppm 7.36-7.46 (m, 2H) 7.23 (d, J=7.83 Hz, 1H) 4.68-4.78 (m, 1H) 4.56-4.67 (m, 1H) 3.66-3.93 (m, 2H) 3.37-3.53 (m, 1H) 2.31-2.46 (m, 3H); $^{19}$F NMR (376 MHz, MeOD) δ ppm −229.52—222.26 (m, 1F).

24E: tert-Butyl N-(6-{[({[5-amino-2-(cyclopropanesulfonyl)phenyl]methyl}(methyl)carbamoyl)({4-[(2R)-1-fluoro-3-hydroxypropan-2-yl]-3-methylphenyl})methyl]amino}isoquinolin-1-yl)-N-[(tert-butoxy)carbonyl]carbamate

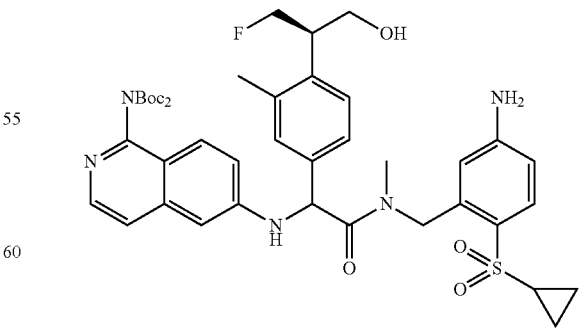

A mixture of Intermediate 1 1080 (0.076 g, 0.212 mmol), 24D (0.045 g, 0.212 mmol) and glyoxylic acid monohydrate (0.020 g, 0.218 mmol) suspended in DMF (0.5 mL) and acetonitrile (1.5 mL) was heated at 80° C. in an oil bath for 2.0 h. After it was cooled to rt, Intermediate 8 (0.066 g, 0.212 mmol) and DIEA (0.185 mL, 1.061 mmol) was added, followed by BOP (0.094 g, 0.212 mmol). The mixture was left stirring at rt overnight. The solvent was removed under reduced pressure, the crude residue was redissolved in dichloromethane and washed with brine (3×) and dried over sodium sulfate. The crude product was purified by flash chromatography (0-100% EtOAc/hexanes) to give 24E (0.103 g, 0.128 mmol, 60.2% yield). MS (ESI) (m/z): 806.3 (M+H)+.

24F: tert-Butyl N-[(tert-butoxy)carbonyl]-N-(6-{[(2R,15R)-7-(cyclopropanesulfonyl)-15-(fluoromethyl)-4,17-dimethyl-3,12-dioxo-13-oxa-4,11-diazatricyclo[14.2.2.1$^{6,10}$]henicosa-1(18),6,8,10 (21),16, 19-hexaen-2-yl]amino}isoquinolin-1-yl)carbamate

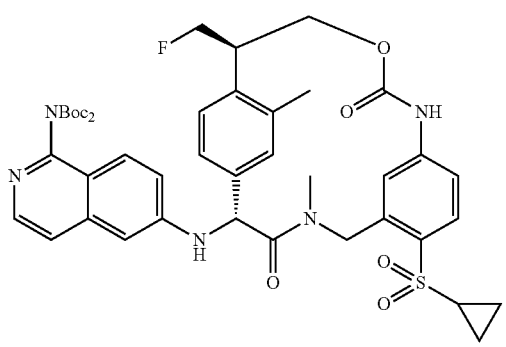

To a solution of 24E (0.1 g, 0.124 mmol) in acetonitrile (5 mL) and dichloromethane (2.5 mL) at 0° C., was added phosgene solution (20% in toluene, 0.072 mL, 0.136 mmol) dropwise. The mixture was stirred at 0° C. for 30 min. Extra phosgene was removed by bubbling Ar for 20 min. The crude was then added dropwise via syringe pump into a solution of TEA (0.138 mL, 0.993 mmol) in dichloromethane (60 mL) at rt over 3.0 h. The solution was stirred at rt over night. Solvent was removed, and the crude product was purified by flash chromatography (0-80% EtOAc/hexanes) to give a mixture of diastereoisomers (0.1 g, 0.120 mmol, 97% yield). The diastereomers were separated by a prep chiral HPLC (R,R-Whelk-O column 21.1×250 mm) to give 24F (38 mg, 76% yield). MS (ESI) (m/z): 831.9 (M+H)+.

Example 24

To 24F (0.038 g, 0.046 mmol) in CH$_2$Cl$_2$ (1 mL) was added 4.0 M HCl in dioxane (1.142 mL, 4.57 mmol). The reaction was stirred at rt for 2 h. The solvent was removed and the sample was purified using a prep HPLC equipped with a C18 PHENOMENEX® Luna column (30 mm×100 mm, 5μ). The desired fractions were combined and lyophilized to give Example 24 (0.025 g, 0.033 mmol, 71.2% yield) as a white amorphous solid. MS (ESI) (m/z): 632.3 (M+H)+. $^1$H NMR (400 MHz, MeOD) δ ppm 8.05 (d, J=9.09 Hz, 1H) 7.74 (d, J=8.59 Hz, 1H) 7.65-7.72 (m, 1H) 7.48 (d, J=7.83 Hz, 1H) 7.32 (d, J=7.07 Hz, 1H) 7.13-7.24 (m, 2H) 6.92 (d, J=7.07 Hz, 1H) 6.79-6.89 (m, 2H) 6.40 (d, J=1.77 Hz, 1H) 5.74-5.84 (m, 2H) 4.83-4.98 (m, 3H) 4.20-4.36 (m, 2H) 3.62-3.84 (m, 1H) 3.40 (s, 3H) 2.79-2.93 (m, 1H) 2.32 (s, 3H) 1.22-1.31 (m, 1H) 0.98-1.18 (m, 3H); $^{19}$F NMR (376 MHz, MeOD) δ ppm −77.55 (br. s., 3F from TFA) −224.04 (s, 1F); Analytical HPLC (low pH, 254 nM): Sunfire, RT=5.74 min, 99% purity; XBridge, RT=6.81 min, 97% purity.

Example 25

(2R,15R)-2-[(1-Amino-7-fluoroisoquinolin-6-yl) amino]-7-(cyclopropanesulfonyl)-18-fluoro-20-methoxy-4,15-dimethyl-13-oxa-4,11-diazatricyclo [14.2.2.1$^{6,10}$]henicosa-1(18),6,8,10 (21),16,19-hexaene-3,12-dione; trifluoroacetic acid

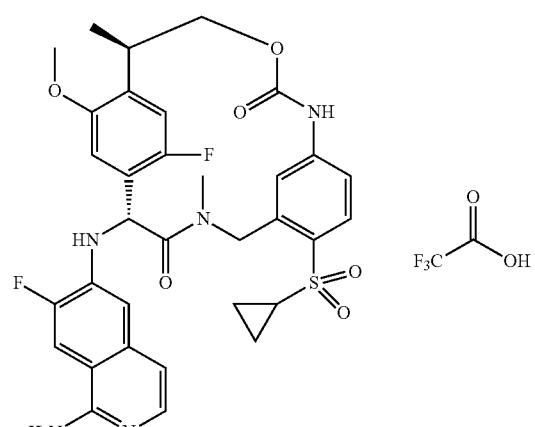

25A: (R)-2-(5-Fluoro-2-methoxyphenyl)propan-1-ol

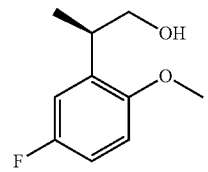

2-(5-Fluoro-2-methoxyphenyl)propan-1-ol (34.5 g, 187 mmol) was separated by prep chiral HPLC to give 25A (11.9 g, 64.6 mmol, 34.5% yield) with ~98% ee.

25B: (R)-tert-Butyl(2-(5-fluoro-2-methoxyphenyl) propoxy)dimethylsilane

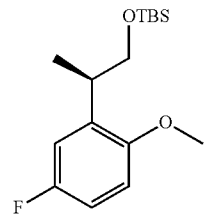

Imidazole (3.55 g, 52.1 mmol) and tert-butyldimethylchlorosilane (10.21 g, 33.9 mmol) were added to a solution of 25A (4.8 g, 26.1 mmol) in CH$_2$Cl$_2$ (125 mL) and stirred overnight at rt. The reaction mixture was diluted with EtOAc (150 mL), washed with water and brine, dried over Na$_2$SO$_4$ and concentrated in vacuo. The crude product was purified by flash chromatography (loading in chloroform, 0% to 20% ethyl acetate in hexane) to yield 25B as a clear oil.

25C: (R)-(2-Fluoro-4-(1-hydroxypropan-2-yl)-5-methoxyphenyl)boronic acid

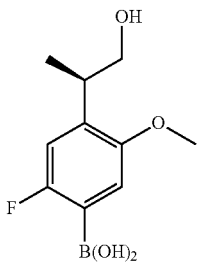

To a solution of 25B (1.12 g, 3.75 mmol) in THF (20 mL) was dropwise added sec-butyllithium (3.22 mL, 4.50 mmol) at −78° C. and stirred at −78° C. for 10 min. Triisopropyl borate (1.743 mL, 7.50 mmol) was added and the mixture was slowly warmed up to r.t. overnight. The reaction was quenched by 6.0 ml of 1N HCl and the mixture was stirred at r.t. for 4 h. TBS is ~60% removed. Addition 4 ml of 1 N HCl was gassed and the mixture was heated at 50° C. for 1 h. The mixture was concentrated and purified by prep HPLC to yield 25C (700 mg, 3.07 mmol, 82% yield) as a white solid. MS (ESI) m/z: 227.5 (M−H)$^+$. $^1$H NMR (400 MHz, methanol-d$_3$) δ ppm 6.87-6.94 (2H, m), 3.81 (3H, s), 3.70 (1H, dd, J=10.77, 5.93 Hz), 3.51 (1H, dd, J=10.55, 7.47 Hz), 3.32-3.37 (1H, m), 1.22 (3H, d, J=7.03 Hz).

25D: tert-Butyl N-(6-{[({[5-amino-2-(cyclopropane-sulfonyl)phenyl]methyl}(methyl)carbamoyl)({2-fluoro-4-[(2R)-1-hydroxypropan-2-yl]-5-methoxyphenyl})methyl]amino}-7-fluoroisoquinolin-1-yl)-N-[(tert-butoxy)carbonyl]carbamate

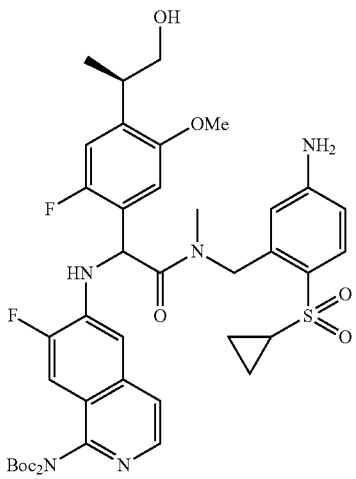

25C (0.075 g, 0.329 mmol), Intermediate 4 (0.124 g, 0.329 mmol) and glyoxylic acid monohydrate (0.033 g, 0.362 mmol) were dissolved in acetonitrile (1 mL)/DMF (1.000 mL) and heated at 80° C. for 3 h. A solution of Intermediate 8 (0.103 g, 0.329 mmol)) and TEA (0.138 mL, 0.987 mmol) in DMF (1.000 mL) was added followed by BOP (0.160 g, 0.362 mmol). The reaction mixture was stirred at rt for 3 h. The reaction mixture was diluted with EtOAc, washed with water and brine, dried over Na$_2$SO$_4$ and concentrated. The crude product was purified by flash chromatography (loading in chloroform, 0% to 100% ethyl acetate in hexane over 15 min using a 12 g silica gel cartridge) to yield 25D (155 mg, 0.185 mmol, 56.1% yield) as a yellow solid. MS (ESI) m/z: 840.4 (M+H)$^+$.

25E: tert-Butyl N-[(tert-butoxy)carbonyl]-N-(6-{[(2R,15R)-7-(cyclopropanesulfonyl)-18-fluoro-20-methoxy-4,15-dimethyl-3,12-dioxo-13-oxa-4,11-diazatricyclo[14.2.2.1$^{6,10}$]henicosa-1(18),6,8,10(21),16,19-hexaen-2-yl]amino}-7-fluoroisoquinolin-1-yl)carbamate

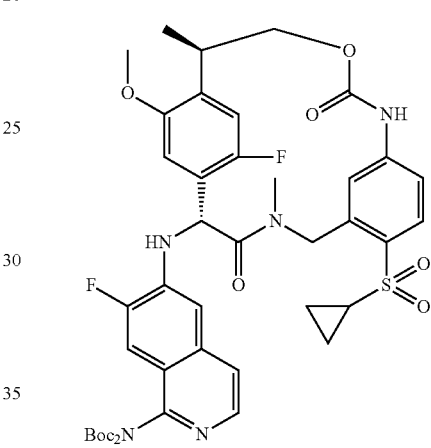

Phosgene (87 mg, 0.176 mmol) was added dropwise to a solution of 25D (148 mg, 0.176 mmol) in acetonitrile (2.5 mL)/CH$_2$Cl$_2$ (2.5 mL) at 0° C. The mixture was stirred at rt for 30 min. Ar was bubbled though the solution (10 min) to remove excess phosgene, and then the mixture was added to a solution of TEA (0.123 mL, 0.881 mmol) in CH$_2$Cl$_2$ (25 mL) at 40° C. over 5 h. The reaction was stirred at rt overnight, quenched with H$_2$O (1 mL) and MeOH (5 mL) and then concentrated. The crude product was purified by flash chromatography (loading in chloroform, 0% to 100% ethyl acetate in hexane over 15 min using a 12 g silica gel cartridge). The diastereomers were separated by a prep chiral HPLC (R,R-Whelk-O column 21.1×250 mm) to give 25E (20 mg, 0.023 mmol, 13.11% yield).

Example 25

TFA (1.000 mL) was added to a solution of 25E (20 mg, 0.023 mmol) in CH$_2$Cl$_2$ (1 mL) and stirred at rt for 1 h. The reaction mixture was concentrated and purified by prep HPLC to yield Example 25 (12 mg, 0.017 mmol, 73.4% yield) as a white solid. MS (ESI) m/z: 666.5 (M+H)$^+$. $^1$H NMR (400 MHz, methanol-d$_3$) δ ppm 8.04 (1H, d, J=12.74 Hz), 7.76 (1H, d, J=8.35 Hz), 7.40 (1H, d, J=7.47 Hz), 7.30 (1H, d, J=10.99 Hz), 6.97 (2H, dd, J=7.69, 5.05 Hz), 6.86 (1H, dd, J=8.57, 1.98 Hz), 6.71 (1H, d, J=6.15 Hz), 6.64 (1H, d, J=2.20 Hz), 6.13 (1H, s), 5.84 (1H, d, J=17.58 Hz), 4.55 (1H, t, J=10.99 Hz), 4.36 (1H, d, J=17.58 Hz), 3.91-4.00 (1H, m), 3.70-3.82 (1H, m), 3.55 (3H, s), 3.35 (3H, s), 2.84-2.95 (1H, m), 1.26 (3H, d, J=7.03 Hz), 1.05-1.22 (3H, m); Analytical HPLC (low pH, 254 nM): Sunfire, RT=6.40 min, 95% purity; XBridge, RT=5.73 min, 97% purity.

Example 26

(2R,15R)-2-[(1-Amino-7-fluoroisoquinolin-6-yl)amino]-7-(cyclopropanesulfonyl)-4,15,17-trimethyl-13-oxa-4,11-diazatricyclo[14.2.2.1$^{6,10}$]henicosa-1(18),6,8,10(21),16,19-hexaene-3,12-dione; trifluoroacetic acid

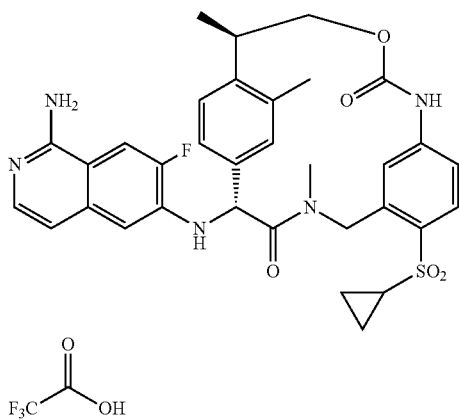

26A: tert-Butyl N-(6-{[({[5-amino-2-(cyclopropanesulfonyl)phenyl]methyl}(methyl)carbamoyl)({4-[(2R)-1-hydroxypropan-2-yl]-3-methylphenyl})methyl]amino}-7-fluoroisoquinolin-1-yl)-N-[(tert-butoxy)carbonyl]carbamate

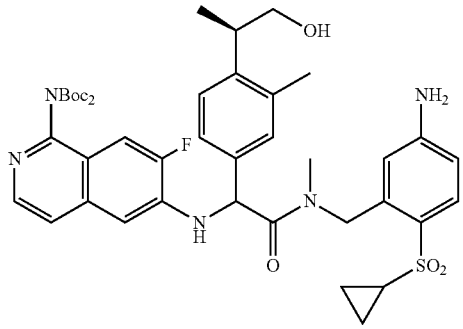

A mixture of Intermediate 5 (61.7 mg, 0.318 mmol), Intermediate 4 (120 mg, 0.318 mmol) and glyoxylic acid monohydrate (29.3 mg, 0.318 mmol) in DMF (0.25 mL)/acetonitrile (0.750 mL) was heated at 80° C. for 2 h. Then a solution of Intermediate 8 (106 mg, 0.382 mmol) in DMF (2 mL) and DIEA (0.167 mL, 0.954 mmol) was added at rt, followed by BOP (169 mg, 0.382 mmol) as a solid. The mixture was stirred at rt for 1.5 h. The mixture was diluted with CH$_2$Cl$_2$ and 0.5 N HCl, extracted with CH$_2$Cl$_2$. The organic layer was washed with brine, dried over Na$_2$SO$_4$ and concentrated. The crude product was purified by prep HPLC to give 26A (80 mg, 0.099 mmol, 31.2% yield). $^1$H NMR was complicated. $^{19}$FNMR (376 MHz, acetonitrile-d$_3$) ppm −130.36 (s, 1F).

26B: tert-Butyl N-[(tert-butoxy)carbonyl]-N-(6-{[(2R,15R)-7-(cyclopropanesulfonyl)-4,15,17-trimethyl-3,12-dioxo-13-oxa-4,11-diazatricyclo[14.2.2.1$^{6,10}$]henicosa-1(18),6,8,10(21),16,19-hexaen-2-yl]amino}-7-fluoroisoquinolin-1-yl)carbamate

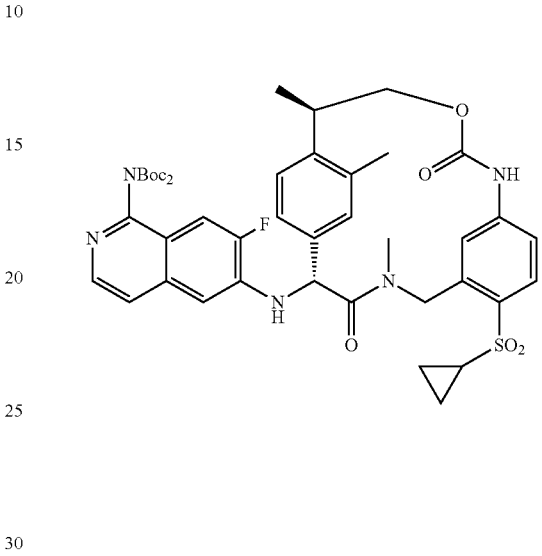

To a solution of 26A (80 mg, 0.099 mmol) in acetonitrile (6 mL) and dichloromethane (3 mL) at 0° C., was added phosgene solution (20% in toluene, 0.063 mL, 0.119 mmol) dropwise. The mixture was stirred at 0° C. for 40 min, then at rt for 30 min. Extra phosgene was removed by bubbling Ar though the reaction mixture (30 min). The mixture was added dropwise via syringe pump into a solution of TEA (0.111 mL, 0.794 mmol) in dichloromethane (40 ml) at rt over 3.0 h. The solution was stirred at rt overnight, quenched with 0.5 N HCl, extracted with CH$_2$Cl$_2$. The organic layer was washed with water and dried over sodium sulfate, then concentrated. The crude residue was purified by flash chromatography (30-100% EtOAc/hexanes) to give a mixture of diastereoisomers (70 mg, 0.084 mmol, 85% yield). The diastereomers were separated by a prep chiral HPLC (R,R-Whelk-O column 21.1×250 mm) to give 26B (30 mg, 0.036 mmol, 42.9% yield). MS (ESI) m/z: [M+1]$^+$. $^{19}$F NMR (376 MHz, CDCl$_3$) d ppm −128.71 (s, 1F).

Example 26

To a solution of 26B (30 mg, 0.036 mmol) in ethyl acetate (1 ml) was added 4.0 M HCl in dioxane (0.721 ml, 2.88 mmol). The mixture was stirred at rt overnight. Solvent was removed under reduced pressure and the crude was purified by prep HPLC to give Example 2 (19 mg, 0.024 mmol, 67.1% yield). MS (ESI) m/z: 632.4 [M+1]$^+$. $^1$H NMR (400 MHz, acetonitrile-d$_3$) δ ppm 7.92 (d, J=12.64 Hz, 1H) 7.64-7.73 (m, 2H) 7.44 (d, J=7.70 Hz, 1H) 7.29 (d, J=7.15 Hz, 1H) 6.93-6.99 (m, 2H) 6.90 (d, J=7.15 Hz, 1H) 6.69-6.84 (m, 1H) 6.34 (s, 1H) 5.69-5.77 (m, 2H) 4.54-4.58 (m, 1H) 4.23 (d, J=17.59 Hz, 1H) 3.91 (dd, J=10.44, 4.40 Hz, 1H) 3.38-3.49 (m, 1H) 3.31 (s, 3H) 2.74-2.88 (m, 1H) 2.21 (s, 3H) 1.25 (d, J=6.60 Hz, 3H) 0.97-1.13 (m, 4H); $^{19}$F NMR (376 MHz, acetonitrile-d$_3$) δ ppm −131.68 (s, 1F); Analytical HPLC (low pH, 254 nM): Sunfire, RT=6.67, 94.3% purity; XBridge, RT=5.48, 99.7% purity.

Example 27

(2R,15R)-2-[(1-Aminoisoquinolin-6-yl)amino]-8-fluoro-7-{[(3R,4S)-4-hydroxyoxolan-3-yl]oxy}-4,15,17-trimethyl-13-oxa-4,11-diazatricyclo[14.2.2.1$^{6,10}$]henicosa-1(18),6,8,10(21),16,19-hexaene-3,12-dione; trifluoroacetic acid

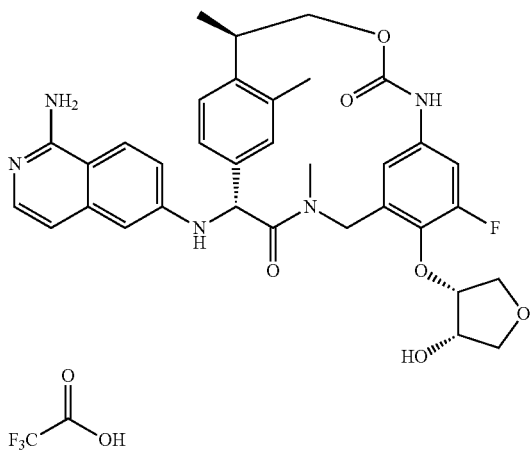

27A:
2-Fluoro-6-((methylamino)methyl)-4-nitrophenol

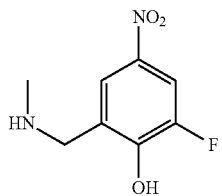

To a solution of 17C (2.65 g, 14.32 mmol) in MeOH (100 mL), methylamine (33% in EtOH, 1.960 mL, 15.75 mmol) was added dropwise and stirred rt for 1 h. The reaction mixture was cooled to 0° C., sodium borohydride (0.596 g, 15.75 mmol) was added portionwise and the mixture was stirred at rt for 1 h. The reaction was quenched with 0.5 N HCl, extracted with EtOAc (3×20 mL), washed with water, brine, dried (Na$_2$SO$_4$). EtOAc was removed under reduced pressure and the residue was purified by flash chromatography to give 27A (3.8 g, 18.98 mmol, 133% yield) yellow solid. MS (ESI) m/z: 201.2 (M+H)$^+$.

27B: Benzyl 3-fluoro-2-hydroxy-5-nitrobenzyl(methyl)carbamate

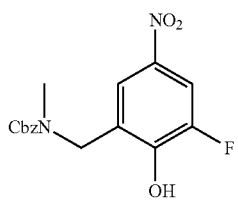 [SMILES: CN(Cc1cc([N+](=O)[O-])cc(F)c1O)C(=O)OCc1ccccc1]

To a flask containing 27A (1.6 g, 7.99 mmol), DIEA (2.088 ml, 11.99 mmol) in DMF (10 ml), was added N-(benzyloxycarbonyloxy) succinimide (2.19 g, 8.79 mmol). The mixture was stirred at rt for 1 h. The reaction was quenched with H$_2$O and then extracted with EtOAc (3×). The organic layer was washed with brine, dried over Na$_2$SO$_4$ and concentrated. The crude was purified by flash column chromatography (0-60% EtOAc/hexanes) to give 27B (1.8 g, 5.38 mmol, 67.4% yield). MS (ESI) m/z: 335.2 (M+H)$^+$.

27C: Benzyl 3-fluoro-2-(((3R,4R)-4-hydroxytetrahydrofuran-3-yl)oxy)-5-nitrobenzyl(methyl)carbamate

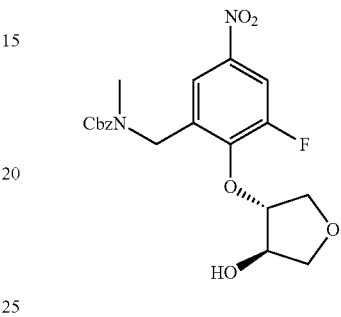

27B (680 mg, 2.034 mmol) was mixed with 3,6-dioxabicyclo[3.1.0]hexane (876 mg, 10.17 mmol), and K$_2$CO$_3$ (1546 mg, 11.19 mmol) in acetonitrile (1 mL) and H$_2$O (1 mL) in a sealed tube. The mixture was stirred at 100° C. for 20 h. The reaction was quenched with H$_2$O then extracted with EtOAc (2×) and concentrated. The residue was purified by flash column chromatography (0-90% EtOAc/hexanes) to give a mixture of diastereomers as yellow oil. The diastereomers were further separated by a prep chiral HPLC equipped with a OJ Column to give the first peak 27C (181 mg, 0.431 mmol, 21.17% yield). The relative stereochemistry of hydroxyether is trans however absolute stereochemistry is undetermined MS (ESI) m/z: 421.2 (M+H)$^+$.

27D: (3S,4R)-4-(2-((((Benzyloxy)carbonyl)(methyl)amino)methyl)-6-fluoro-4-nitrophenoxy)tetrahydrofuran-3-yl 4-nitrobenzoate

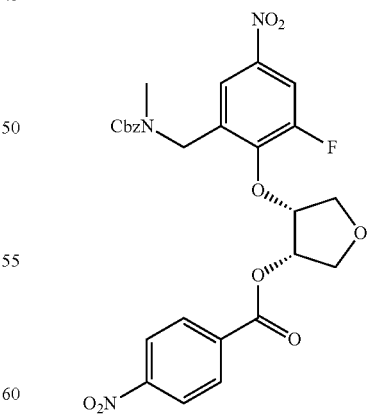

Intermediate 27C (250 mg, 0.595 mmol) was mixed with 4-nitrobenzoic acid (447 mg, 2.68 mmol), PPh$_3$ (741 mg, 2.82 mmol) in THF (1.5 mL) and stirred at rt for 10 min. The reaction was cooled to 0° C., then DIAD (0.589 mL, 2.97 mmol) was added. After stirring at rt for 16 h, the reaction was quenched with H₂O and extracted with EtOAc (2×). The organic extracts were washed with brine, dried (Na₂SO₄) and concentrated. The residue was purified by flash column chromatography to give 27D (268 mg, 0.471 mmol, 79% yield) as a white foam. The relative stereochemistry of hydroxyether is cis however absolute stereochemistry is undetermined MS (ESI) m/z: 570.4 (M+H)⁺.

27E: Benzyl 3-fluoro-2-(((3R,4S)-4-hydroxytetrahydrofuran-3-yl)oxy)-5-nitrobenzyl(methyl)carbamate

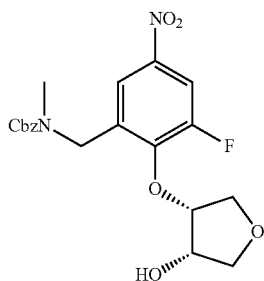 [SMILES: CN(Cc1cc([N+](=O)[O-])cc(F)c1O[C@@H]1COC[C@@H]1O)C(=O)OCc1ccccc1]

To 27D (250 mg, 0.439 mmol) in MeOH (5 mL) was added KOH (0.878 mL, 0.878 mmol) and the reaction was stirred at rt for 2 h. The reaction was concentrated and acidified with 1N HCl after addition of H₂O. The sample was extracted with EtOAc (2×) and the extracts was washed with sat. NaHCO₃ and brine. The solvent was removed and the residue was purified by flash column chromatography (0-60% EtOAc/hexanes) to afford 27E (172 mg, 0.409 mmol, 93% yield). MS (ESI) m/z: 421.4 (M+H)⁺. ¹H NMR (400 MHz, CDCl₃)) δ ppm 7.83-8.07 (m, 2H) 7.33 (s, 5H) 5.14 (s, 2H) 4.92-5.03 (m, 1H) 4.78 (d, J=7.91 Hz, 1H) 4.70 (d, J=14.94 Hz, 1H) 4.49-4.60 (m, 1H) 4.39 (d, J=6.15 Hz, 1H) 4.06-4.19 (m, 1H) 3.90-4.03 (m, 2H) 3.65-3.78 (m, 1H) 2.84 (s, 3H).

27F: Benzyl 2-(((3R,4S)-4-((tert-butyldimethylsilyl)oxy)tetrahydrofuran-3-yl)oxy)-3-fluoro-5-nitrobenzyl(methyl)carbamate

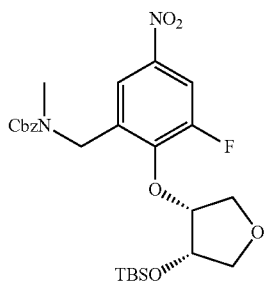 [SMILES: CN(Cc1cc([N+](=O)[O-])cc(F)c1O[C@@H]1COC[C@@H]1O[Si](C)(C)C(C)(C)C)C(=O)OCc1ccccc1]

To 27E (171 mg, 0.407 mmol) in DMF (3 mL) was added TBS-Cl (307 mg, 2.034 mmol) and imidazole (138 mg, 2.034 mmol). The reaction was stirred at rt for 16 h, then quenched with H₂O and extracted with EtOAc (2×). The solvent was removed and the residue was purified by flash column chromatography (0-60% EtOAc/hexanes) to give 27F (215 mg, 0.402 mmol, 99% yield). MS (ESI) m/z: 535.4 (M+H)⁺.

27G: 4-(((3R,4S)-4-((tert-Butyldimethylsilyl)oxy)tetrahydrofuran-3-yl)oxy)-3-fluoro-5-((methylamino)methyl)aniline

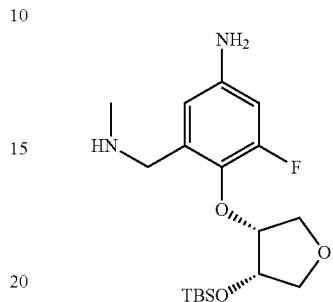

To 27F (138 mg, 0.372 mmol, 93% yield) in MeOH (5 mL) was added 10% Pd/C (50 mg) and the mixture was hydrogenated (1 atm) for 4 h at rt. The mixture was filtered and concentrated to give 27G (138 mg, 0.372 mmol, 93% yield) as a colorless oil. MS (ESI) m/z: 371.4 (M+H)⁺.

27H: tert-Butyl N-{6-[({[(5-amino-2-{[(3R,4S)-4-[(tert-butyldimethylsilyl)oxy]oxolan-3-yl]oxy}-3-fluorophenyl)methyl](methyl)carbamoyl}({4-[(2R)-1-hydroxypropan-2-yl]-3-methylphenyl})methyl)amino]isoquinolin-1-yl}-N-[(tert-butoxy)carbonyl]carbamate

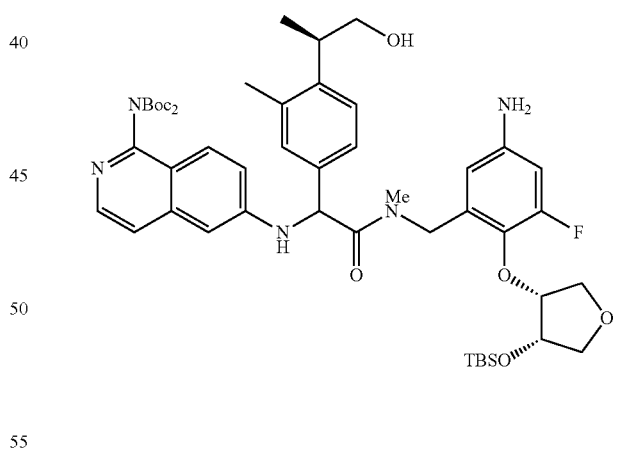

Intermediate 5 (65 mg, 0.335 mmol), glyoxylic acid monohydrate (30.8 mg, 0.335 mmol) and Intermediate 1 (120 mg, 0.335 mmol) were dissolved in DMF (1 mL). The solution was stirred at 80° C. for 2 h then allowed to cool to rt. To this mixture were added sequentially TEA (0.140 mL, 1.005 mmol), 27G (137 mg, 0.368 mmol) and BOP (178 mg, 0.402 mmol). The mixture was stirred at rt for 1.5 h and concentrated. The residue was purified by prep HPLC to give 27H (195 mg, 0.212 mmol, 63.4% yield) as light yellow solid. MS (ESI) m/z: 918.9 (M+H)⁺.

155

27I: tert-Butyl N-[(tert-butoxy)carbonyl]-N-(6-{[(2R,15R)-8-fluoro-7-{[(3R,4S)-4-hydroxyoxolan-3-yl]oxy}-4,15,20-trimethyl-3,12-dioxo-13-oxa-4,11-diazatricyclo[14.2.2.1⁶,¹⁰]henicosa-1(18),6,8,10(21),16,19-hexaen-2-yl]amino}isoquinolin-1-yl)carbamate

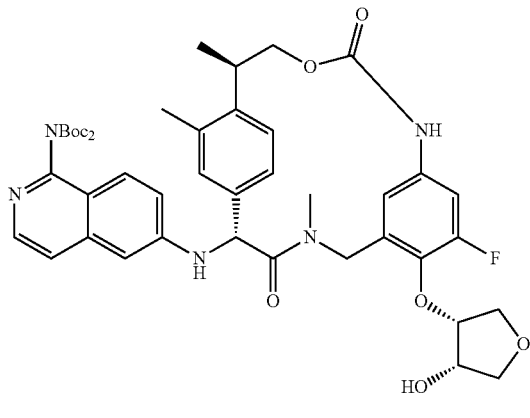

To 27H (195 mg, 0.212 mmol) in acetonitrile (2 mL) and dichloromethane (2 mL) cooled to 0° C., was added phosgene (20% in toluene, 0.116 mL, 0.234 mmol). The mixture was stirred at 0° C. for 5 min, and then at rt for 20 min. The reaction was bubbled with Ar for 10 min to remove excess phosgene. The resulting solution was added dropwise over 3 h via a syringe pump into a solution of TEA (0.296 mL, 2.124 mmol) in dichloromethane (60 mL) and stirred at rt for 20 h. The reaction mixture was concentrated and the residue was dissolved in THF (5 mL). TBAF (2 mL, 1 M in THF) was added and the solution was stirred at rt for 2 h. The solvent was removed and the residue was purified by flash column chromatography (0-90% EtOAc/hexanes) to give a mixture of diastereoisomers (113 mg, 0.120 mmol, 56.4% yield). The diastereomers were separated by a prep chiral HPLC to yield 27I (22 mg, 0.027 mmol, 19.47% yield). MS (ESI) m/z: 830.7 (M+H)⁺. The active isomer has a cis relative stereochemistry at the hydroxyether, however, its absolute stereochemistry is undetermined.

Example 27

To 27I (22 mg, 0.027 mmol) in EtOAc (2 mL), was added HCl (2 mL, 8.00 mmol) and stirred at rt for 3 h. The sample was concentrated and purified by prep HPLC to give Example 27 (18 mg, 0.024 mmol, 90% yield). MS (ESI) m/z: 630.6 (M+H)⁺. ¹H NMR (400 MHz, CD₃OD) δ ppm 8.03 (d, J=9.34 Hz, 1H) 7.63 (d, J=8.24 Hz, 1H) 7.43 (d, J=8.25 Hz, 1H) 7.29 (d, J=7.15 Hz, 1H) 7.16-7.22 (m, 2H) 6.88 (d, J=7.15 Hz, 1H) 6.81 (d, J=2.20 Hz, 1H) 6.53 (dd, J=12.64, 2.20 Hz, 1H) 5.72 (s, 1H) 5.69 (s, 1H) 5.37 (d, J=17.59 Hz, 1H) 4.71-4.75 (m, 1H) 4.65 (t, J=10.99 Hz, 1H) 4.36-4.44 (m, 1H) 4.14 (d, J=17.04 Hz, 1H) 3.93-4.00 (m, 4H) 3.75 (dd, J=8.52, 6.32 Hz, 1H) 3.43-3.52 (m, 1H) 3.29 (s, 3H) 2.32 (s, 3H) 1.29 (d, J=6.60 Hz, 3H). Anal HPLC (low pH, 254 nM): Sunfire, RT=5.64 min, 98.5% purity; XBridge, RT=4.80 min, 98.9% purity.

156

Example 28

(2R,15R)-2-[(1-Aminoisoquinolin-6-yl)amino]-8-fluoro-7-(3-methoxypropoxy)-4,15,20-trimethyl-13-oxa-4,11-diazatricyclo[14.2.2.1⁶,¹⁰]henicosa-1(18),6,8,10 (21),16,19-hexaene-3,12-dione; trifluoroacetic acid

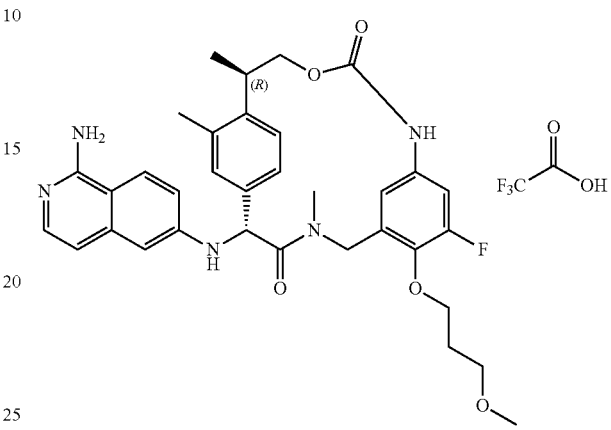

28A: tert-Butyl 5-amino-3-fluoro-2-(3-methoxypropoxy)benzyl(methyl)carbamate

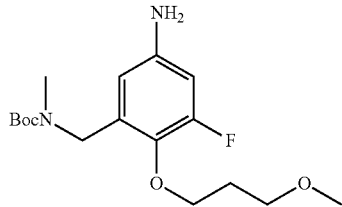 [SMILES: COCCCOc1c(F)cc(N)cc1CN(C)C(=O)OC(C)(C)C]

DIAD was added to a solution of 17D (751 mg, 2.5 mmol), 3-methoxypropan-1-ol (496 mg, 5.50 mmol), triphenylphosphine (1443 mg, 5.50 mmol) in THF (5 mL) at 0° C. The reaction mixture was stirred at 0° C. for 30 min, and rt for 16 h. The mixture was concentrated and purified by flash chromatography (0-50% EtOAc in hexanes) to give a light yellow solid. The obtained solid was dissolved in MeOH (20 mL) and THF (5 mL). Zinc (1635 mg, 25.00 mmol) and ammonium chloride (2.64 mL, 75 mmol) was added. The reaction mixture was stirred rt for 2 h. After aqueous work up and extraction, the crude product was purified by flash chromatography to give 28A (900 mg, 2.63 mmol, 105% yield). MS (ESI) m/z: 343.1 (M+H)⁺.

28B: (R)-tert-Butyl 5-(((2-(4-bromo-2-methylphenyl)propoxy)carbonyl)amino)-3-fluoro-2-(3-methoxypropoxy)benzyl(methyl)carbamate

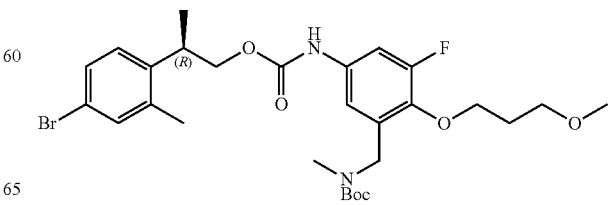

To a solution of 28A (902 mg, 2.63 mmol), sodium bicarbonate (2213 mg, 26.3 mmol) in CH$_2$Cl$_2$ (10 ml) at 0° C., phosgene (20% in toluene, 2.61 ml, 5.27 mmol) was added. The mixture was stirred 0° C. for 30 min, rt for 1 h, filtered, and concentrated. The residue was dissolved in CH$_2$Cl$_2$ (10 ml) at 0° C., TEA (0.719 ml, 5.27 mmol) was added, followed by Intermediate 5A (604 mg, 2.63 mmol, WO 2008/079836). The mixture was stirred rt for 1 h, quenched with water, and extracted with EtOAc (2×20 mL). The combined organic layer was washed with 1N HCl and brine, dried (Na$_2$SO$_4$) and concentrated. The crude product was purified by flash chromatography (0-40% EtOAc in hexanes) to give 28B (1.2 g, 2.008 mmol, 76% yield). MS (ESI) m/z: 597.3 (M+H)$^+$.

28C: (R)-Benzyl 5-(((2-(4-bromo-2-methylphenyl)propoxy)carbonyl)amino)-3-fluoro-2-(3-methoxypropoxy)benzyl(methyl)carbamate

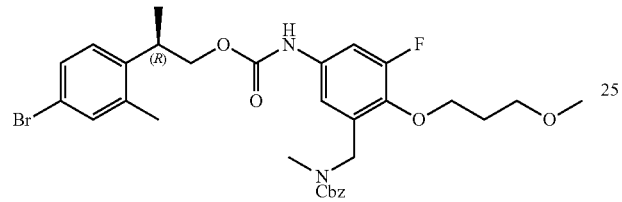

To a solution of 28B (450 mg, 0.753 mmol) in EtOAc (6 mL), was added HCl (4N, 6 mL). The mixture was stirred rt for 2 h, and concentrated. The residue was dissolved in DMF (10 ml), N,N-diisopropylethylamine (0.525 ml, 3.01 mmol) was added, followed by N-(benzyloxycarbonyloxy) succinimide (206 mg, 0.828 mmol). The mixture was stirred rt for 1 h, quenched with water, extracted with EtOAc (3×30 ml). The organic layer was washed with brine, dried (Na$_2$SO$_4$) and concentrated. The crude product was purified by flash chromatography (0-60% EtOAc in hexanes) to give 28C (376 mg, 0.595 mmol, 79% yield). MS (ESI) m/z: 631.0 (M+H)$^+$.

28D: (R)-(4-(1-(((3-((((Benzyloxy)carbonyl)(methyl)amino)methyl)-5-fluoro-4-(3-methoxypropoxy)phenyl)carbamoyl)oxy)propan-2-yl)-3-methylphenyl) boronic acid

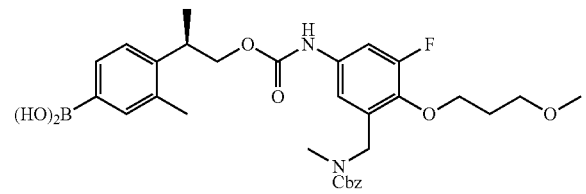 [SMILES: COCCCOc1c(F)cc(NC(=O)OC[C@H](C)c2ccc(B(O)O)cc2C)cc1CN(C)C(=O)OCc1ccccc1]

To a tube was added 28C (373 mg, 0.591 mmol), 5,5,5',5'-tetramethyl-2,2'-bi(1,3,2-dioxaborinane) (160 mg, 0.709 mmol), potassium acetate (145 mg, 1.477 mmol), Pd(dppf)Cl$_2$ (97 mg, 0.118 mmol) in DMSO (1.5 ml). The tube was filled with Ar, sealed and stirred at 85° C. for 2 h. The mixture was quenched with water, extracted with EtOAc (3×20 ml). The combined organic layer was filtered though silica gel and concentrated. The crude product was purified by flash chromatography to give 28D (210 mg, 0.352 mmol, 59.6% yield). MS (ESI) m/z: 597.3 (M+H)$^+$.

28E: 2-((1-(Bis(tert-butoxycarbonyl)amino)isoquinolin-6-yl)amino)-2-(4-((R)-1-(((3-fluoro-4-(3-methoxypropoxy)-5-((methylamino)methyl)phenyl)carbamoyl)oxy)propan-2-yl)-3-methylphenyl)acetic acid

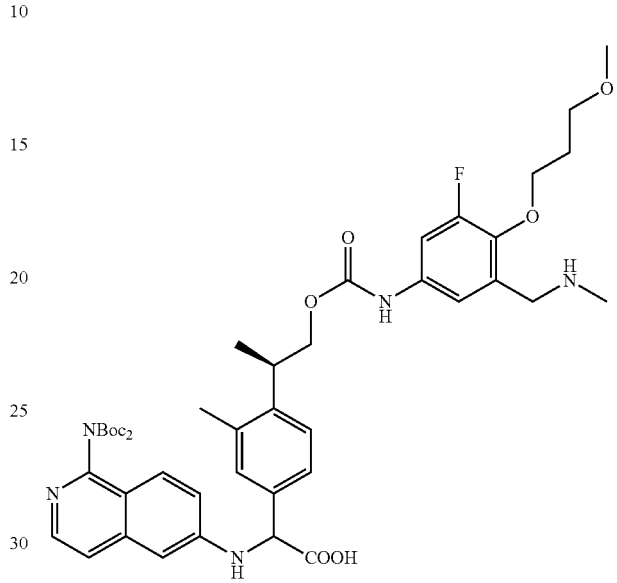

To a flask was added 28D (208 mg, 0.349 mmol), Intermediate 1 (138 mg, 0.384 mmol), glyoxylic acid monohydrate (32.1 mg, 0.349 mmol) in CH$_3$CN (3 ml) and DMF (0.5 ml). The mixture was stirred at 85° C. for 2 h. The mixture was concentrated and purified by prep HPLC. The desired fractions were combined, concentrated. The residue was dissolved in MeOH (8 mL), and 10% Pd/C was added. The mixture was hydrogenated at 40 psi for 6 h. The mixture was filtered and concentrated to give 28E (188 mg, 0.225 mmol, 64.6% yield). MS (ESI) m/z: 834.5 (M+H)$^+$.

Example 28

To a solution of BOP (199 mg, 0.451 mmol), 4-dimethylaminopyridine (138 mg, 1.127 mmol) in CH$_2$Cl$_2$ (40 mL), was added a solution of 28E (188 mg, 0.225 mmol) in DMF (10 mL) dropwise via a syringe pump for 6 h. The mixture was stirred rt for 16 h, concentrated and purified by prep HPLC. The desired fractions were combined, concentrated. The residue was dissolved in EtOAc (5 mL). HCl (4.0 N, 5 mL) was added and the mixture was stirred rt for 3 h. The mixture was concentrated and the residue was purified by a prep chiral HPLC equipped with an OD column to yield Example 28 (20 mg, 0.023 mmol, 10.41% yield). MS (ESI) m/z: 616.2 (M+H)$^+$. $^1$H NMR (400 MHz, acetonitrile-d$_3$) δ ppm 7.84 (s, 2H) 7.79 (d, J=8.79 Hz, 1H) 7.65 (dd, J=7.91, 1.76 Hz, 1H) 7.42 (d, J=7.91 Hz, 1H) 7.28 (s, 1H) 7.20-7.24 (m, 1H) 7.12 (dd, J=9.23, 2.20 Hz, 1H) 7.08 (d, J=1.76 Hz, 1H) 6.74-6.83 (m, 2H) 6.53 (dd, J=12.30, 2.20 Hz, 1H) 5.62 (s, 2H) 5.32 (d, J=17.14 Hz, 1H) 4.60 (t, J=10.99 Hz, 1H) 4.04 (t, J=5.93 Hz, 2H) 3.91 (dd, J=10.99, 4.39 Hz, 1H) 3.85 (d, J=17.14 Hz, 1H) 3.51 (t, J=6.37 Hz, 2H) 3.35-3.43 (m, 1H) 3.28 (s, 3H) 3.19 (s, 3H) 2.22 (s, 3H) 1.25 (d, J=7.03 Hz, 3H);

Analytical HPLC (low pH, 254 nM): Sunfire, RT=6.85 min, 99.4% purity; XBridge, RT=5.75 min, 99.4% purity.

Example 29

(2R,15R)-2-[(1-Amino-7-fluoroisoquinolin-6-yl)amino]-7-(cyclopropanesulfonyl)-8-fluoro-4,15,17-trimethyl-13-oxa-4,11-diazatricyclo[14.2.2.1$^{6,10}$]henicosa-1(18),6,8,10 (21),16,19-hexaene-3,12-dione; trifluoroacetic acid

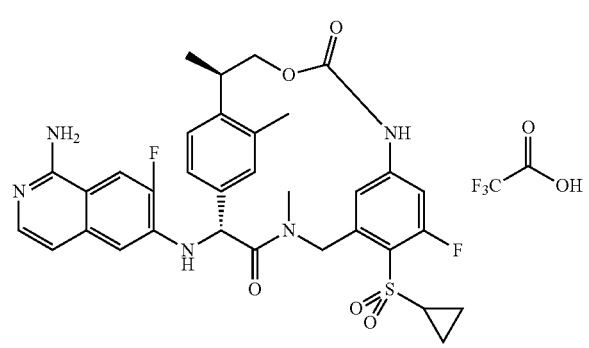 [SMILES: Cc1cc2ccc1[C@@H](C)COC(=O)Nc1cc(F)c(S(=O)(=O)C3CC3)c(c1)CN(C)C(=O)[C@@H]2Nc1cc2ccnc(N)c2cc1F ; O=C(O)C(F)(F)F]

29A: tert-Butyl N-(6-{[({[5-amino-2-(cyclopropanesulfonyl)-3-fluorophenyl]methyl}(methyl)carbamoyl)({4-[(2R)-1-hydroxypropan-2-yl]-3-methylphenyl})methyl]amino}-7-fluoroisoquinolin-1-yl)-N-[(tert-butoxy)carbonyl]carbamate

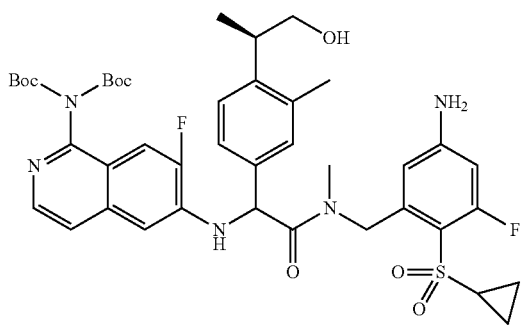 [SMILES: Cc1cc(C(Nc2cc3ccnc(N(C(=O)OC(C)(C)C)C(=O)OC(C)(C)C)c3cc2F)C(=O)N(C)Cc2cc(N)cc(F)c2S(=O)(=O)C2CC2)ccc1[C@@H](C)CO]

Intermediate 4 (120 mg, 0.318 mmol), Intermediate 5 (61.7 mg, 0.318 mmol) and glyoxylic acid monohydrate (29.3 mg, 0.318 mmol) were dissolved in DMF (3 mL) and acetonitrile. The solution was stirred at 80° C. for 2 h, then allowed to cool to rt. To this mixture were added sequentially 11E (126 mg, 0.382 mmol), BOP (155 mg, 0.350 mmol) and TEA (0.222 mL, 1.590 mmol). The mixture was stirred at rt for 1 h, quenched with water, extracted with EtOAc. The extract was washed with brine, dried (Na$_2$SO$_4$) and concentrated. The crude product was purified by flash chromatography to give 29A (136 mg, 0.165 mmol, 51.9% yield). MS (ESI) m/z: 824.2 [M+1]$^+$.

29B: tert-Butyl N-[(tert-butoxy)carbonyl]-N-(6-{[(2R,15R)-7-(cyclopropanesulfonyl)-8-fluoro-4,15,17-trimethyl-3,12-dioxo-13-oxa-4,11-diazatricyclo[14.2.2.1$^{6,10}$]henicosa-1(18),6,8,10 (21),16,19-hexaen-2-yl]amino}-7-fluoroisoquinolin-1-yl)carbamate

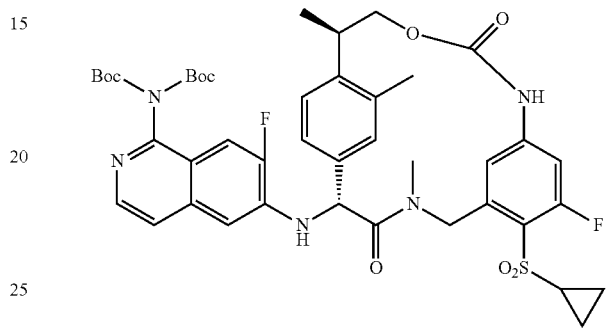

A solution of 29A (133 mg, 0.161 mmol) in acetonitrile (3 mL) and dichloromethane (6 mL) was cooled to 0° C. To this solution was added phosgene (20% in toluene, 0.088 mL, 0.178 mmol). The mixture was stirred at 0° C. for 5 min, and rt for 1 h. The mixture was bubbled with Ar for 10 min to remove excess phosgene. The resulting solution was added dropwise over 3 h via a syringe pump into a solution of TEA (0.225 mL, 1.614 mmol) in CH$_2$Cl$_2$ (260 mL). The solution was stirred for 16 h, concentrated and purified by flash chromatography to give a mixture of diastereoisomers (96 mg, 0.113 mmol, 70.0% yield). The diastereoisomers were separated by a prep chiral HPLC equipped with a IA column to give 29B (44 mg, 0.052 mmol, 46.3% yield). MS (ESI) m/z: 850.2 [M+1]$^+$. $^1$H NMR (500 MHz, methanol-d$_4$) δ ppm 8.09 (1H, d, J=5.8 Hz), 7.77 (1H, d, J=7.7 Hz), 7.53 (1H, d, J=6.1 Hz), 7.50 (1H, d, J=8.0 Hz), 7.42 (1H, d, J=11.8 Hz), 7.00-7.09 (2H, m), 6.61 (2H, dd, J=12.1, 1.9 Hz), 6.24 (1H, s), 5.76 (1H, d, J=17.9 Hz), 5.72 (1H, t, J=2.9 Hz), 4.62 (1H, t, J=11.1 Hz), 4.21 (1H, d, J=17.9 Hz), 3.96 (1H, dd, J=10.6, 4.3 Hz), 3.47 (1H, ddd, J=11.4, 7.0, 4.4 Hz), 3.32-3.38 (3H, m), 2.97 (1H, dd, J=4.8, 3.2 Hz), 2.22-2.33 (3H, m), 1.25-1.37 (24H, m), 1.03-1.13 (2H, m).

Example 29

29B (44 mg, 0.052 mmol) was stirred with TFA (2 mL, 0.052 mmol) for 1 h at rt. The mixture was concentrated and purified by prep HPLC to give Example 29 (32 mg, 0.041 mmol, 80% yield). MS (ESI) m/z: 650.1 [M+1]$^+$. $^1$H NMR (500 MHz, methanol-d$_4$) δ ppm 7.99 (1H, d, J=12.7 Hz), 7.76 (1H, dd, J=8.0, 1.7 Hz), 7.49 (1H, d, J=8.0 Hz), 7.35 (1H, d, J=7.2 Hz), 7.01 (2H, dd, J=4.8, 3.2 Hz), 6.96 (1H, d, J=6.9 Hz), 6.61 (1H, dd, J=12.0, 2.1 Hz), 6.22 (1H, d, J=1.1 Hz), 5.69-5.79 (2H, m), 4.62 (1H, t, J=11.0 Hz), 4.20 (1H, d, J=17.9 Hz), 3.98 (1H, dd, J=10.7, 4.4 Hz), 3.48 (1H, ddd, J=11.3, 7.1, 4.4 Hz), 3.34 (3H, s), 2.94-3.02 (1H, m), 2.27 (3H, s), 1.26-1.36 (5H, m), 1.03-1.16 (2H, m). Analytical HPLC (low pH, 254 nM): Sunfire, RT=6.20, 99.5% purity; XBridge, RT=7.40, 99.6% purity.

Example 30

(2R,15R)-2-[(1-Aminoisoquinolin-6-yl)amino]-8-fluoro-7-{[(2R)-1-hydroxypropan-2-yl]oxy}-4,15,20-trimethyl-13-oxa-4,11-diazatricyclo[14.2.2.1⁶,¹⁰]henicosa-1(18),6,8,10 (21),16,19-hexaene-3,12-dione; trifluoroacetic acid

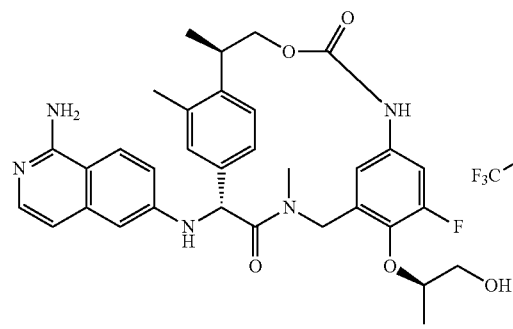

To Ph₃P (88 mg, 0.336 mmol) in THF (1 mL) at 0° C., was added DIAD (0.065 mL, 0.336 mmol) dropwise over 5 min. The reaction mixture was stirred at 0° C. for 10 min. A solution of 17J (50 mg, 0.067 mmol) and 17B (64.0 mg, 0.336 mmol) (dried over MS 4A) in THF (0.5 ml) was added to the reaction mixture dropwise over 5 min. The resulting suspension was stirred at 0° C. for 15 min, then warmed to rt over 1 h and continued stirring at rt for 2 h. THF was removed under reduced pressure, and the residue was purified by prep HPLC (Axia Luna 5 u C18 30×100 mm column; sol. A 10% MeCN-90% H₂O-0.1% TFA; sol. B 90% MeCN-10% H₂O-0.1% TFA). The desired fractions left overnight in HPLC solvent (0.1% TFA) resulted in deprotection of the TBS group. The solvent was removed, and the residue was chased with MeCN (3×). ¹H NMR and orthogonal HPLC showed a mixture of two compounds which was further separated by a prep chiral HPLC to give Example 17 (13.09 mg, 26.5% yield) as a major product, and Example 30 (4.11 mg, 58.19% yield) as a minor product. Example 30: MS (ESI) m/z: 602.2 [M+1]⁺. ¹H NMR: (400 MHz, CD₃OD) δ ppm 8.05 (1H, d, J=9.03 Hz), 7.63 (1H, d, J=7.78 Hz), 7.44 (1H, d, J=8.03 Hz), 7.31 (1H, d, J=7.03 Hz), 7.17-7.25 (2H, m), 6.91 (1H, d, J=7.28 Hz), 6.83 (1H, d, J=2.01 Hz), 6.53 (1H, dd, J=12.30, 2.26 Hz), 5.73 (1H, s), 5.66 (1H, s), 5.37 (1H, d, J=17.32 Hz), 4.65 (1H, t, J=10.92 Hz), 4.28-4.38 (1H, m), 4.06 (1H, d, J=17.32 Hz), 3.96 (1H, dd, J=10.67, 4.39 Hz), 3.63 (2H, d, J=4.52 Hz), 3.43-3.54 (1H, m), 3.28 (3H, s), 2.34 (3H, s), 1.29 (6H, dd, J=11.04, 6.78 Hz). Analytical HPLC (low pH, 254 nM): Sunfire, RT=5.43, 95.9% purity; XBridge, RT=6.22, 99% purity.

Example 31

(2R,15R)-2-[(1-Aminoisoquinolin-6-yl)amino]-7-(cyclopropanesulfonyl)-4,15,20-trimethyl-13-oxa-4,11-diazatricyclo[14.2.2.1⁶,¹⁰]henicosa-1(18),6,8,10 (21),16,19-hexaene-3,12-dione; trifluoroacetic acid

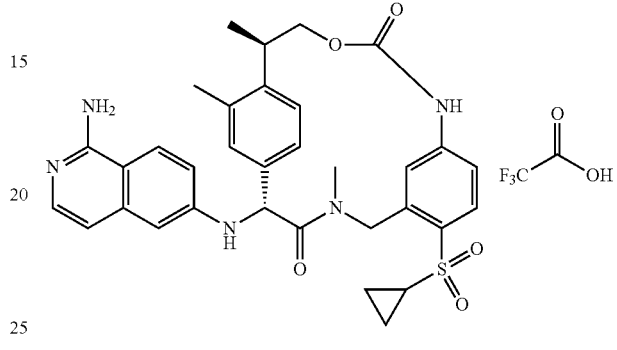

31A: tert-Butyl N-(6-{[({[5-amino-2-(cyclopropanesulfonyl)phenyl]methyl}(methyl)carbamoyl)({4-[(2R)-1-hydroxypropan-2-yl]-3-methylphenyl})methyl]amino}isoquinolin-1-yl)-N-[(tert-butoxy)carbonyl]carbamate

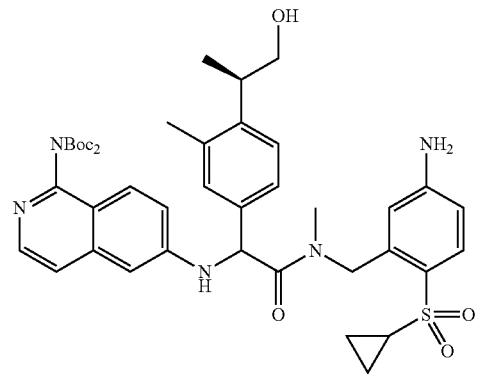

Intermediate 5 (0.210 g, 1.082 mmol), glyoxylic acid monohydrate (0.100 g, 1.082 mmol) and Intermediate 1 (0.389 g, 1.082 mmol) were dissolved in DMF (2 mL) and acetonitrile. The reaction mixture was stirred at 80° C. for 1.5 h, then allowed to cooled to rt. To this solution were added sequentially Intermediate 8 (0.339 g, 1.082 mmol), BOP (0.527 g, 1.191 mmol) and TEA (0.905 mL, 6.49 mmol). The mixture was stirred at rt for 30 min. The reaction mixture was quenched with water (0.5 mL), diluted with EtOAc (150 mL), washed with water (4×50 mL), brine (1×50 mL) and dried (Na₂SO₄). Then the solvent was removed under reduced pressure. The crude product was purified by flash chromatography to give 31A (0.657 g, 0.834 mmol, 77% yield) as an orange glass, which was lyophilized to give a powder. MS (ESI) m/z: 788.2 [M+1]⁺. ¹H NMR: complicated by a pair of diastereomers and rotamers.

Example 31

A solution of 31A (0.657 g, 0.834 mmol) in acetonitrile (5 mL) and dichloromethane (5 mL) was cooled to 0° C. To this solution, was added phosgene (20% in toluene, 0.433 mL, 0.875 mmol). The mixture was stirred at 0° C. for 15 min, then bubbled with Ar for 25 min to remove excess phosgene and HCl. The resulting solution was added dropwise over 5 h via a syringe pump into a solution of TEA (1.162 mL, 8.34 mmol) in dichloromethane (200 mL). The solution was stirred for an additional 30 min, then the solvent was removed and the crude product was purified by flash chromatography (1-15% MeOH/dichloromethane). Desired fractions were combined and concentrated under reduced pressure to give di-Boc protected intermediate (0.498 g, 73%) as a diastereomeric mixture. The diastereomers were separated by a prep chiral HPLC (R,R-Whelk-O column 21.1×250 mm). Desired fractions were combined and concentrated under reduced pressure. The residue was treated with TFA (2.5 mL) for 15 min at rt. TFA was removed under reduced pressure and the residue was purified by prep HPLC to give Example 31 (115.78 mg, 0.157 mmol, 37.6% yield) as white solid. MS (ESI) m/z: 614.1 [M+1]$^+$. $^1$H NMR: (400 MHz, CD$_3$OD) δ ppm 9.50 (1H, s), 8.05 (1H, d, J=9.29 Hz), 7.73 (1H, d, J=8.53 Hz), 7.68 (1H, dd, J=7.91, 1.63 Hz), 7.48 (1H, d, J=8.03 Hz), 7.32 (1H, d, J=7.03 Hz), 7.20 (1H, dd, J=9.16, 2.38 Hz), 7.11 (1H, s), 6.92 (1H, d, J=7.03 Hz), 6.80-6.86 (2H, m), 6.42 (1H, t, J=2.38 Hz), 5.78 (1H, d, J=17.57 Hz), 5.74 (1H, s), 4.64 (1H, t, J=11.04 Hz), 4.30 (1H, d, J=17.57 Hz), 3.99 (1H, dd, J=10.79, 4.27 Hz), 3.46-3.55 (1H, m), 3.40 (3H, s), 2.81-2.92 (1H, m), 2.31 (3H, s), 1.34 (3H, d, J=7.03 Hz), 1.22-1.30 (1H, m), 1.01-1.17 (3H, m). Analytical HPLC (low pH, 254 nM): Sunfire, RT=5.89, 97.8% purity; XBridge, RT=6.96, 98.4% purity.

Example 32

(2R,15R)-2-[(1-Aminoisoquinolin-6-yl)amino]-7-[(1,3-difluoropropan-2-yl)oxy]-8-fluoro-4,15,20-trimethyl-13-oxa-4,11-diazatricyclo[14.2.2.1$^{6,10}$]henicosa-1(18),6,8,10 (21),16,19-hexaene-3,12-dione; trifluoroacetic acid

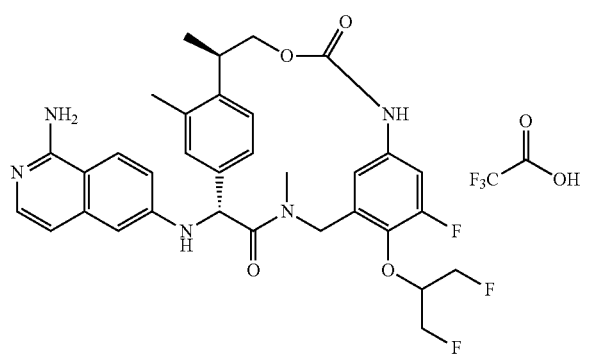 [SMILES: Cc1cc2ccc1[C@@H](C)COC(=O)Nc1cc(F)c(OC(CF)CF)c(c1)CN(C)C(=O)[C@@H]2Nc1ccc2c(N)nccc2c1 ; O=C(O)C(F)(F)F]

To Ph$_3$P (88 mg, 0.336 mmol) in THF (1 mL) at 0° C., was added DIAD (0.065 mL, 0.336 mmol) dropwise over 5 min. The reaction mixture was stirred at 0° C. for 10 min. A solution of 17J (50 mg, 0.067 mmol) and 1,3-difluoropropan-2-ol (0.026 mL, 0.336 mmol) (0.026 mL, 0.336 mmol) (dried over MS 4A) in THF (0.5 ml) was added to the reaction mixture dropwise over 5 min. The resulting suspension was stirred at 0° C. for 15 min, then warmed to rt over 1 h and continued stirring at rt for 2 h. THF was removed under reduced pressure, and the residue was purified by prep HPLC. Desired fractions were combined and concentrated under reduced pressure. The residue was treated with TFA (2.0 mL) for 15 min at rt. TFA was removed under reduced pressure and the residue was purified by prep HPLC to give Example 32 (23.8 mg, 0.032 mmol, 47.9% yield) as a white solid. MS (ESI) m/z: 622.2 [M+1]$^+$. $^1$H NMR: (400 MHz, CD$_3$OD) δ ppm 8.95 (1H, br. s.), 8.03 (1H, d, J=2.76 Hz), 7.65 (1H, d, J=7.53 Hz), 7.45 (1H, d, J=5.02 Hz), 7.30 (1H, d, J=7.03 Hz), 7.20 (2H, br. s.), 6.87-6.95 (1H, m), 6.82 (1H, br. s.), 6.56 (1H, d, J=12.30 Hz), 5.73 (2H, br. s.), 5.42 (1H, d, J=17.32 Hz), 4.70-4.82 (2H, m), 4.46-4.70 (4H, m), 3.87-4.04 (2H, m), 3.42-3.58 (1H, m), 2.32 (3H, br. s.), 1.30 (3H, d, J=6.78 Hz). Analytical HPLC (low pH, 254 nM): Sunfire, RT=6.32, 99.5% purity; XBridge, RT=7.34, 97.4% purity.

Example 33

(2R,15R)-2-[(1-Aminoisoquinolin-6-yl)amino]-8-fluoro-7-{[(2S)-1-hydroxypropan-2-yl]oxy}-4,15,20-trimethyl-13-oxa-4,11-diazatricyclo[14.2.2.1$^{6,10}$]henicosa-1(18),6,8,10 (21),16,19-hexaene-3,12-dione; trifluoroacetic acid

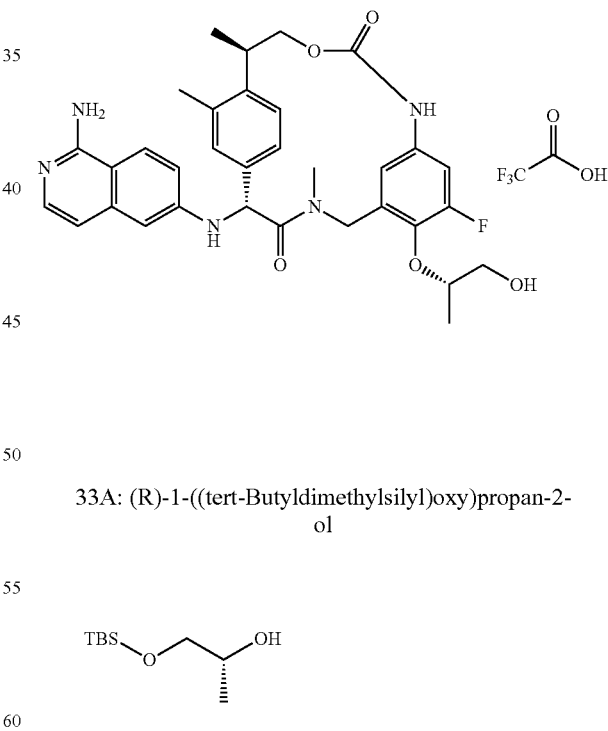

33A: (R)-1-((tert-Butyldimethylsilyl)oxy)propan-2-ol

To a solution of (s)-(+)-1,2-propanediol (2.0 g, 26.3 mmol) in DMF (5 mL) was added TBS-Cl (5.94 g, 39.4 mmol) and imidazole (2.147 g, 31.5 mmol). The reaction was stirred at 25° C. for 18 h. The reaction mixture was partitioned between ethyl acetate and sat. ammonium chloride. The organic phase was washed with sat ammonium chloride and brine, dried (MgSO4) and concentrated in vacuo. The crude product was purified by flash chromatography to give 33A (4.0 g, 80% yield) as a colorless oil.

33B: (S)-Benzyl 2-((1-((tert-butyldimethylsilyl)oxy) propan-2-yl)oxy)-3-fluoro-5-nitrobenzyl(methyl) carbamate

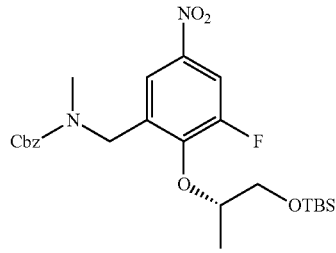 [SMILES: C[C@@H](CO[Si](C)(C)C(C)(C)C)Oc1c(F)cc([N+](=O)[O-])cc1CN(C)C(=O)OCc1ccccc1]

To a solution of 27B (400 mg, 1.197 mmol), 33A (251 mg, 1.316 mmol) and triphenylphosphine (345 mg, 1.316 mmol) in THF (10 mL) at 0° C., was added DIAD (0.256 mL, 1.316 mmol) dropwise. The reaction mixture was allowed to slowly warm to rt and stirred for 16 h, then was concentrated. The crude product was purified by flash chromatography (0 to 40% ethyl acetate/hexanes) to give 33B (577 mg, 1.139 mmol, 95% yield) as colorless oil. MS (ESI) m/z: 507.1[M+1]$^+$. $^1$H NMR (400 MHz, chloroform-d) δ ppm 7.78-7.94 (2H, m) 7.27-7.43 (5H, m) 5.17 (2H, d, J=20.1 Hz) 4.46-4.74 (3H, m) 3.65-3.81 (2H, m) 2.97 (3H, d, J=15.8 Hz) 1.31 (3H, t, J=7.0 Hz) 0.81 (9H, d, J=7.0 Hz) −0.05-0.04 (6H, m) rotamers.

33C: (S)-4-((1-((tert-Butyldimethylsilyl)oxy)propan-2-yl)oxy)-3-fluoro-5-((methylamino)methyl)aniline

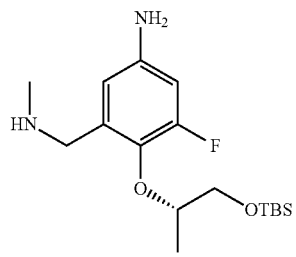 [SMILES: CNCc1cc(N)cc(F)c1O[C@@H](C)CO[Si](C)(C)C(C)(C)C]

To a degassed solution of 33B (573 mg, 1.131 mmol) in MeOH (10 mL), was added 10% Pd—C (50 mg, 0.047 mmol). The mixture was evacuated and flushed with H$_2$ (3×), then was stirred under an atmosphere of H$_2$ for 8 h. The mixture was filtered and concentrated to give 33C (382 mg, 1.115 mmol, 99% yield) as a pale brown oil. MS (ESI) m/z: 343.1 [M+1]$^+$. $^1$H NMR (400 MHz, chloroform-d) δ ppm 6.40 (1H, d, J=1.8 Hz) 6.33 (1H, dd, J=12.5, 2.8 Hz) 4.20 (1H, sxt, J=5.7 Hz) 3.62-3.79 (4H, m) 3.53 (2H, br. s.) 2.40 (3H, s) 1.25 (3H, d, J=6.3 Hz) 0.89 (9H, s) 0.05 (6H, s).

33D: tert-Butyl N-{6-[({[(5-amino-2-{[(2S)-1-[(tert-butyldimethylsilyl)oxy]propan-2-yl]oxy}-3-fluorophenyl)methyl](methyl)carbamoyl}({4-[(2R)-1-hydroxypropan-2-yl]-3-methylphenyl})methyl)amino]isoquinolin-1-yl}-N-[(tert-butoxy)carbonyl]carbamate

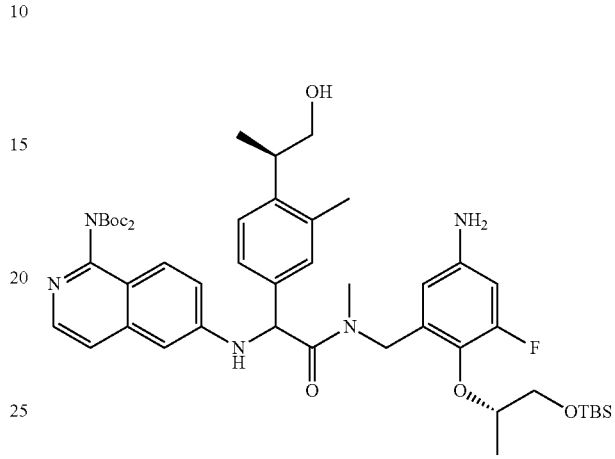

To Intermediate 5 (100 mg, 0.515 mmol), Intermediate 1 (185 mg, 0.515 mmol), and glyoxylic acid monohydrate (47.4 mg, 0.515 mmol), were added DMF (6.00 mL) and acetonitrile (6 mL). The mixture was stirred at 80° C. for 1 h, then was cooled to rt. To the mixture were added sequentially 33C (201 mg, 0.587 mmol), DMF (6.00 mL), TEA (0.215 mL, 1.546 mmol) and BOP (251 mg, 0.567 mmol). The reaction mixture was stirred at rt for 1 h, then was diluted with H$_2$O and extracted with EtOAc (3×). The extract was washed with brine, dried (Na$_2$SO$_4$) and concentrated. The crude product was purified by flash chromatography (1 to 15% MeOH/methylene chloride) to give 33D (422 mg, 0.474 mmol, 92% yield) as an orange foam. MS (ESI) m/z: 890.3 [M+1]$^+$. $^1$H NMR: complicated due to presence of diastereomers and amide rotamers.

Example 33

To a solution of 33D (417 mg, 0.468 mmol) in dichloromethane (10 mL) and acetonitrile (5 mL) at 0° C., was added phosgene (20% in toluene, 0.243 mL, 0.492 mmol) dropwise. The mixture was stirred at 0° C. for 20 min, then was removed from the cooling bath and bubbled with Ar for 20 min. This mixture was added dropwise via a syringe pump into a solution of TEA (0.392 mL, 2.81 mmol) in dichloromethane (190 mL) over 5 h. The reaction mixture was allowed to stir at rt for 11 h, and then concentrated. The crude product was purified by flash chromatography (1 to 15% MeOH/methylene chloride) to give a mixture of diastereoisomers. The diastereomers were separated by a prep chiral HPLC (R,R-Whelk-O column 21.1×250 mm). The desired fractions were combined and concentrated. The residue was treated with TFA (4 mL) for 15 min. The reaction mixture was concentrated and purified by prep HPLC to give Example 33 (52.9 mg, 0.074 mmol, 31.4% yield) white solid. MS (ESI) m/z: 602.2 [M+1]$^+$. $^1$H NMR (400 MHz, methanol-d$_4$) δ ppm 8.05 (1H, d, J=9.3 Hz) 7.64 (1H, dd, J=7.8, 1.8 Hz) 7.44 (1H, d, J=7.8 Hz) 7.31 (1H, d, J=7.0 Hz) 7.18-7.23 (2H, m) 6.91 (1H, d, J=7.3 Hz) 6.83 (1H, d, J=2.3 Hz) 6.53 (1H, dd, J=12.4, 2.4 Hz) 5.73 (1H, s) 5.66 (1H, br. s.) 5.37 (1H, d, J=17.1 Hz) 4.65 (1H, t, J=11.0 Hz) 4.27-4.38 (1H, m, J=5.7, 5.7, 5.7, 5.7, 5.4 Hz) 4.06 (1H, d, J=17.3 Hz) 3.96 (1H, dd, J=10.8, 4.3 Hz) 3.63 (2H, d, J=4.8 Hz) 3.43-3.55 (1H, m) 3.27 (3H, s) 2.34 (3H, s) 1.30 (3H, d, J=7.0 Hz) 1.27 (3H, d, J=6.3 Hz). Analytical HPLC (low pH, 254 nM): Sunfire, RT=5.5, 99.6% purity; XBridge, RT=6.16, 99.6% purity.

Example 34

(2R,15R)-2-[(1-Amino-7-fluoroisoquinolin-6-yl)amino]-8-fluoro-4,15,17-trimethyl-7-(propane-2-sulfonyl)-13-oxa-4,11-diazatricyclo[14.2.2.1^{6,10}]henicosa-1(18),6,8,10 (21),16,19-hexaene-3,12-dione; trifluoroacetic acid

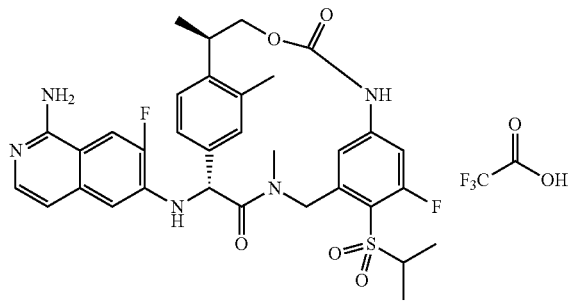 [SMILES: Cc1cc2ccc1[C@@H](C)COC(=O)Nc1cc(F)c(S(=O)(=O)C(C)C)c(c1)CN(C)C(=O)[C@@H]2Nc1cc2ccnc(N)c2cc1F ; O=C(O)C(F)(F)F]

34A: tert-Butyl N-(6-{[({[5-amino-3-fluoro-2-(propane-2-sulfonyl)phenyl]methyl}(methyl)carbamoyl)({4-[(2R)-1-hydroxypropan-2-yl]-3-methylphenyl})methyl]amino}-7-fluoroisoquinolin-1-yl)-N-[(tert-butoxy)carbonyl]carbamate

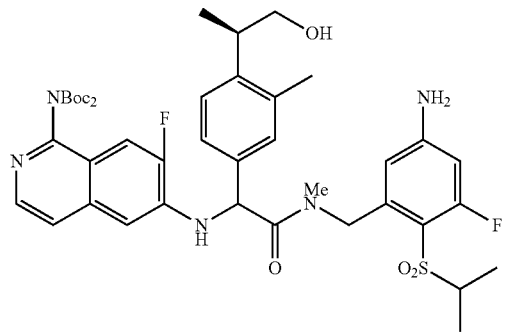

Intermediate 4 (155 mg, 0.411 mmol), Intermediate 5 (80 mg, 0.411 mmol) and 2 glyoxylic acid monohydrate (37.8 mg, 0.411 mmol) were dissolved in DMF (3 mL) and acetonitrile. The solution was stirred at 80° C. for 2 h, then allowed cooled to rt. To this mixture were added sequentially 20D (136 mg, 0.41 mmol), BOP (200 mg, 0.452 mmol) and TEA (0.286 mL, 2.053 mmol). The mixture was stirred at rt for 1 h, and then quenched with water, extracted with EtOAc. The extract was washed with brine, dried (Na$_2$SO$_4$) and concentrated. The crude product was purified by flash chromatography (0-90% EtOAc in hexanes) to give 34A (170 mg, 0.206 mmol, 50.1% yield) a colorless form. MS (ESI) m/z: 826.3 [M+1]$^+$.

34B: tert-Butyl N-[(tert-butoxy)carbonyl]-N-(7-fluoro-6-{[(2R,15R)-8-fluoro-4,15,17-trimethyl-3,12-dioxo-7-(propane-2-sulfonyl)-13-oxa-4,11-diazatricyclo[14.2.2.1^{6,10}]henicosa-1(18),6,8,10 (21),16,19-hexaen-2-yl]amino}isoquinolin-1-yl)carbamate

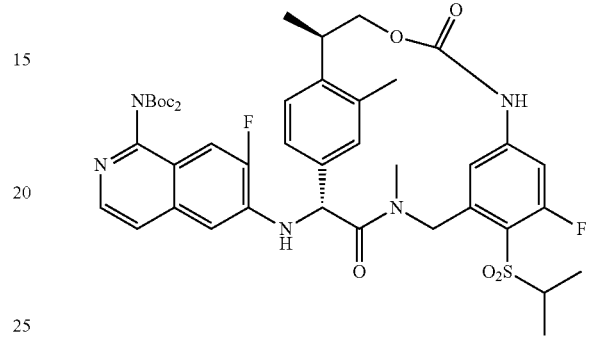

A solution of 34A (170 mg, 0.206 mmol) in acetonitrile (3 mL) and dichloromethane (6 mL) was cooled to 0° C. To this solution, was added phosgene (20% in toluene, 0.112 mL, 0.226 mmol). The mixture was stirred at 0° C. for 5 min, and rt for 1 h. The mixture was bubbled with Ar for 10 min to remove excess phosgene. The resulting solution was added dropwise over 3 h via syringe pump into a solution of TEA (0.287 mL, 2.058 mmol) in CH$_2$Cl$_2$ (260 mL). The solution was stirred for 16 h, and then concentrated and purified by flash chromatography to give a mixture of diastereoisomers (98 mg, 0.115 mmol, 55.9% yield). The diastereomers were separated by a prep chiral HPLC equipped with a OD column to give 34B (38 mg, 0.045 mmol, 38.8% yield). MS (ESI) m/z: 852.3 [M+1]$^+$. $^1$H NMR (500 MHz, methanol-d$_4$) δ ppm 8.10 (1H, d, J=5.8 Hz), 7.78 (1H, dd, J=7.8, 1.5 Hz), 7.55 (1H, d, J=5.8 Hz), 7.51 (1H, d, J=8.0 Hz), 7.41 (1H, d, J=12.1 Hz), 7.06 (1H, d, J=8.3 Hz), 7.04 (1H, d, J=1.7 Hz), 6.61 (1H, dd, J=12.0, 2.1 Hz), 6.27 (1H, d, J=1.1 Hz), 5.67-5.78 (2H, m), 4.63 (1H, t, J=11.0 Hz), 4.24 (1H, d, J=17.9 Hz), 3.98 (1H, dd, J=10.7, 4.4 Hz), 3.45-3.57 (2H, m), 3.34-3.41 (3H, m), 2.28 (3H, s), 1.38 (3H, d, J=6.9 Hz), 1.35 (3H, d, J=6.9 Hz), 1.33 (3H, d, J=6.9 Hz), 1.28 (18H, s).

Example 34

34B (42 mg, 0.049 mmol) was stirred with 1 mL of TFA for 30 min at rt. The mixture was concentrated and purified by prep HPLC to give Example 34 (30 mg, 0.039 mmol, 79% yield). MS (ESI) m/z: 652.2 [M+1]$^+$. $^1$H NMR (500 MHz, acetone-d$_6$) δ ppm 8.08 (1H, d, J=12.7 Hz), 7.93 (1H, d, J=8.0 Hz), 7.51 (1H, d, J=8.0 Hz), 7.37 (1H, d, J=6.9 Hz), 7.15 (1H, d, J=8.3 Hz), 7.02 (1H, s), 6.89 (2H, d, J=7.2 Hz), 6.73 (1H, dd, J=12.1, 1.9 Hz), 6.34 (1H, br. s.), 5.84-5.97 (1H, m), 5.78 (1H, d, J=17.9 Hz), 4.63 (1H, t, J=11.0 Hz), 4.23 (1H, d, J=17.9 Hz), 3.95 (1H, dd, J=10.7, 4.4 Hz), 3.47-3.58 (1H, m), 3.35-3.46 (4H, m), 2.22 (3H, s), 2.07-2.14 (1H, m), 1.38 (3H, d, J=6.6 Hz), 1.34 (3H, d, J=6.6 Hz), 1.30 (3H, d, J=6.9 Hz); Analytical HPLC (low pH, 254 nM): Sunfire, RT=6.29, 99.5% purity; XBridge, RT=7.31, 95.2% purity.

Example 35

(2R,15R)-2-[(1-Aminoisoquinolin-6-yl)amino]-8-fluoro-4,15,20-trimethyl-7-[2-(2-oxopyrrolidin-1-yl)ethoxy]-13-oxa-4,11-diazatricyclo[14.2.2.1⁶,¹⁰]henicosa-1(18),6,8,10 (21),16,19-hexaene-3,12-dione; trifluoroacetic acid

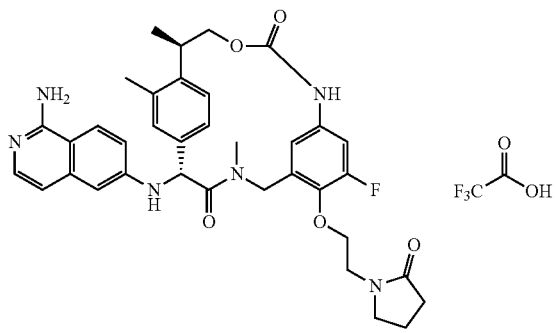 [SMILES: Cc1cc2ccc1[C@@H](C)COC(=O)Nc1cc(F)c(OCCN3CCCC3=O)c(c1)CN(C)C(=O)[C@@H]2Nc1ccc2c(N)nccc2c1 ; O=C(O)C(F)(F)F]

To Ph₃P (70.5 mg, 0.269 mmol) in THF (1 mL) at 0° C., was added DIAD (0.052 mL, 0.269 mmol) dropwise over 5 min. The reaction mixture was stirred at 0° C. for 10 min. A solution of 17J (40 mg, 0.054 mmol) and 1-(2-hydroxyethyl)pyrrolidin-2-one (34.7 mg, 0.269 mmol) (dried over MS 4A) in THF (0.5 ml) was added to the reaction mixture dropwise over 5 min. The resulting suspension was stirred at 0° C. for 15 min, then warmed to rt over 1 h and continued stirring at rt for 2 h. THF was removed under reduced pressure, and the residue was purified by prep HPLC. Desired fractions were combined and concentrated under reduced pressure. The residue was treated with TFA (2.0 mL) for 15 min at rt. TFA was removed under reduced pressure and the residue was purified by prep HPLC to give Example 35 (20.65 mg, 0.026 mmol, 48.0% yield) as a white solid. MS (ESI) m/z: 655.3 [M+1]. ¹H NMR: (400 MHz, CD₃OD) δ ppm 8.92 (1H, s), 8.04 (1H, d, J=9.03 Hz), 7.64 (1H, dd, J=7.78, 1.76 Hz), 7.44 (1H, d, J=8.03 Hz), 7.30 (1H, d, J=7.03 Hz), 7.19 (2H, d, J=2.01 Hz), 6.89 (1H, d, J=7.03 Hz), 6.82 (1H, d, J=2.26 Hz), 6.52 (1H, dd, J=12.42, 2.38 Hz), 5.73 (1H, s), 5.70 (1H, s), 5.33 (1H, d, J=17.07 Hz), 4.65 (1H, t, J=11.04 Hz), 4.08-4.26 (2H, m), 3.96 (1H, dd, J=10.79, 4.27 Hz), 3.89 (1H, d, J=17.32 Hz), 3.63-3.74 (1H, m), 3.53-3.63 (3H, m), 3.48 (1H, ddd, J=11.23, 6.96, 4.39 Hz), 2.38 (2H, t, J=8.28 Hz), 2.31 (3H, s), 1.98-2.09 (2H, m), 1.30 (3H, d, J=7.03 Hz). Analytical HPLC (low pH, 254 nM): Sunfire, RT=5.56, 97.5% purity; XBridge, RT=6.42, 96.1% purity.

Example 36

(2R,15R)-2-[(1-Aminoisoquinolin-6-yl)amino]-4,15,20-trimethyl-7-[1-(1H-1,2,3,4-tetrazol-5-yl)cyclopropyl]-13-oxa-4,11-diazatricyclo[14.2.2.1⁶,¹⁰]henicosa-1(18),6,8,10 (21),16,19-hexaene-3,12-dione; trifluoroacetic acid

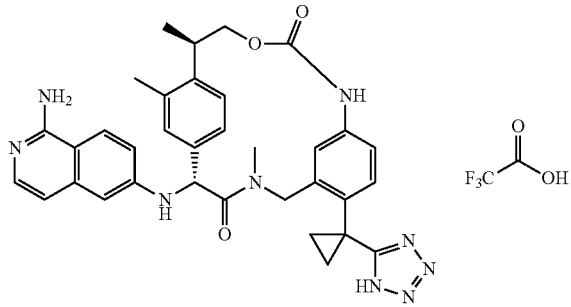 [SMILES: Cc1cc2ccc1[C@@H](C)COC(=O)Nc1ccc(C3(c4nnn[nH]4)CC3)c(c1)CN(C)C(=O)[C@@H]2Nc1ccc2c(N)nccc2c1 ; O=C(O)C(F)(F)F]

36A: Benzyl 2-bromo-5-nitrobenzyl(methyl)carbamate

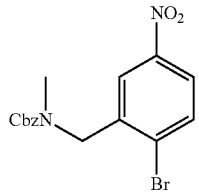 [SMILES: CN(Cc1cc([N+](=O)[O-])ccc1Br)C(=O)OCc1ccccc1]

To 1-(2-bromo-5-nitrophenyl)-N-methylmethanamine (7 g, 28.6 mmol, see WO 2008/079836 for preparation) in DMF (30 ml), was added N-(benzyloxycarbonyloxy) succinimide (8.54 g, 34.3 mmol) and N,N-diisopropylethylamine (9.98 ml, 57.1 mmol). The mixture was stirred rt for 1 h, then quenched with water, extracted with EtOAc (3×30 ml). The organic layer was washed with brine, dried (Na₂SO₄) and concentrated. The crude product was purified by flash chromatography (0-60% EtOAc in hexane) to yield 36A (10.66 g, 28.1 mmol, 98% yield). MS (ESI) m/z: 379.2 (M+H)⁺. ¹H NMR (400 MHz, chloroform-d) δ ppm 7.92-8.02 (m, 2H) 7.74 (d, J=6.15 Hz, 1H) 7.33-7.42 (m, 2H) 7.28 (s, 3H) 5.22 (s, 1H) 5.15 (s, 1H) 4.61 (d, J=18.46 Hz, 2H) 3.02 (s, 3H).

36B: Ethyl 2-(2-((((benzyloxy)carbonyl)(methyl)amino)methyl)-4-nitrophenyl)-2-cyanoacetate

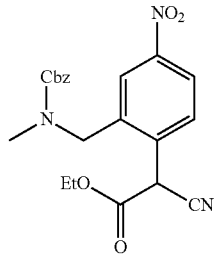 [SMILES: CCOC(=O)C(C#N)c1ccc([N+](=O)[O-])cc1CN(C)C(=O)OCc1ccccc1]

36A (3.000 g, 7.91 mmol), copper(I) iodide (0.301 g, 1.582 mmol), L-proline (0.364 g, 3.16 mmol) and cesium carbonate (5.16 g, 15.82 mmol) were mixed in a pressure vial and degassed (3× vacuum/Ar). Then, a solution of ethyl 2-cyanoacetate (1.059 mL, 9.89 mmol) in DMSO (10 mL) was added, the reaction mixture was degassed again and stirred at 50° C. for 3 days. The cooled reaction mixture was partitioned between EtOAc (100 mL) and sat. NH₄Cl (100 mL). The organic layer was washed with brine (2×50 mL) and dried (Na₂SO₄). EtOAc was removed under reduced pressure and the residue was purified by flash chromatography to give 36B (2.609 g, 6.34 mmol, 80% yield) as a yellowish syrup. MS (ESI) m/z: 412.2 [M+1]⁺. ¹H NMR: (400 MHz, CDCl₃) δ ppm 8.24 (1H, d, J=8.03 Hz), 8.14 (1H, br. s.), 7.79 (1H, d, J=8.53 Hz), 7.29-7.43 (5H, m), 5.67 (1H, br. s.), 5.18 (2H, s), 4.50-4.86 (2H, m), 4.14-4.29 (2H, m), 2.90 (3H, s), 1.27 (3H, t, J=7.15 Hz).

36C: Benzyl 2-(cyanomethyl)-5-nitrobenzyl(methyl)carbamate

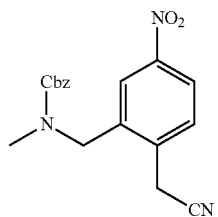 [SMILES: CN(Cc1cc([N+](=O)[O-])ccc1CC#N)C(=O)OCc1ccccc1]

36B (2.609 g, 6.34 mmol) was dissolved in DMSO (40 mL), lithium chloride (0.538 g, 12.68 mmol) and water (0.114 mL, 6.34 mmol) were added. The reaction mixture was stirred at 130° C. for 2 h, then cooled to rt, diluted with EtOAc (250 mL), washed with water (2×100 mL), brine (1×100 mL) and dried (Na$_2$SO$_4$). EtOAc was removed under reduced pressure and the residue was purified by flash chromatography (0-70% EtOAc/hexanes) to give 36C (1.803 g, 5.31 mmol, 84% yield) as a yellowish film. MS (ESI) m/z: 340.1 [M+1]$^+$. $^1$H NMR: (400 MHz, CDCl$_3$) δ ppm 8.20 (1H, d, J=7.07 Hz), 8.09 (1H, br. s.), 7.67 (1H, d, J=5.05 Hz), 7.29-7.46 (5H, m), 5.19 (2H, s), 4.59 (2H, br. s.), 3.91 (2H, br. s.), 2.94 (3H, br. s.).

36D: Benzyl 5-amino-2-(cyanomethyl)benzyl(methyl)carbamate

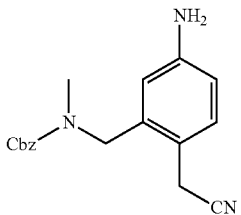 [SMILES: CN(Cc1cc(N)ccc1CC#N)C(=O)OCc1ccccc1]

To a solution of 36C (1.803 g, 5.31 mmol) in MeOH (30 mL) and THF (10 mL) was added zinc (dust) (3.47 g, 53.1 mmol) and ammonium chloride (5.68 g, 106 mmol). The resulting solution was stirred at rt for 2 h. MeOH was removed under reduced pressure. Na$_2$CO$_3$ (aq, 100 mL) and EtOAc (150 mL) was added, and the suspension was stirred vigorously for 10 min. The mixture was filtered through a glass frit, solid residue was washed with EtOAc (3×150 mL). Combined EtOAc fractions were washed with std. Na$_2$CO$_3$ (aq, 2×50 mL), water (2×50 mL), brine (1×50 mL) and dried (Na$_2$SO$_4$). EtOAc was removed under reduced pressure and the residue was purified by flash chromatography (0-100% EtOAc/hexanes) to give 36D (1.459 g, 4.72 mmol, 89% yield) as a yellowish oil. MS (ESI) m/z: 310.2 [M+1]$^+$. $^1$H NMR: (400 MHz, CDCl$_3$) δ ppm 7.29-7.46 (5H, m), 7.15 (1H, br. s.), 6.60 (1H, d, J=7.28 Hz), 6.35-6.55 (1H, m), 5.18 (2H, s), 4.44 (2H, s), 3.71 (2H, br. s.), 3.41-3.66 (2H, m), 2.85 (3H, br. s.).

36E: tert-Butyl 5-((tert-butoxycarbonyl)amino)-2-(cyanomethyl)benzyl(methyl)carbamate

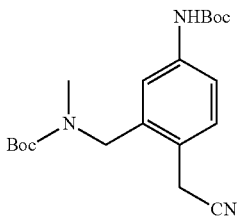 [SMILES: CN(Cc1cc(NC(=O)OC(C)(C)C)ccc1CC#N)C(=O)OC(C)(C)C]

36D (1.285 g, 4.15 mmol) was mixed with BOC-anhydride (4.53 g, 20.77 mmol) and heated at 85° C. for 2 h. The reaction mixture was cooled to rt and diluted with MeOH (30 mL). Additional amount of BOC-anhydride (2.266 g, 10.38 mmol) and Pd—C (0.442 g, 0.415 mmol) were added to the reaction mixture, the reaction mixture was degassed (3× vacuum/Ar) and hydrogenated (1 atm) for 1 h. The mixture was filtered though a membrane filter, MeOH was removed under reduced pressure. The residue was purified by flash chromatography (0-50% EtOAc/hexanes) to give 36E (1.276 g, 3.40 mmol, 82% yield) as a colorless foam. MS (ESI) m/z: 376.3 [M+1]$^+$. $^1$H NMR: (400 MHz, CDCl$_3$) δ ppm 7.28-7.39 (2H, m), 6.55 (1H, s), 5.30 (1H, s), 4.44 (2H, s), 3.71 (2H, br. s.), 2.76 (3H, br. s.), 1.45-1.57 (18H, m).

36F: tert-Butyl 5-((tert-butoxycarbonyl)amino)-2-(1-cyanovinyl)benzyl(methyl)carbamate

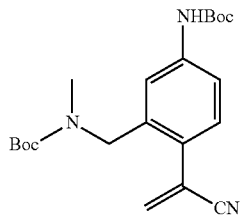 [SMILES: C=C(C#N)c1ccc(NC(=O)OC(C)(C)C)cc1CN(C)C(=O)OC(C)(C)C]

36E (0.344 g, 0.916 mmol) was dissolved in toluene (4 mL), and to the resulting solution were sequentially added potassium carbonate (0.253 g, 1.832 mmol), paraformaldehyde (0.275 g, 9.16 mmol) and tris(3,6-dioxaheptyl)amine (tda-1) (0.029 mL, 0.092 mmol). The reaction mixture was stirred at 85° C. for 10 h, then diluted with EtOAc (20 mL) and water (10 mL) and stirred for 15 min. The organic phase was separated, washed with water (3×10 mL), brine (1×10 mL) and dried (Na$_2$SO$_4$). EtOAc was removed under reduced pressure and the residue was purified by flash chromatography (0-40% EtOAc/hexanes) to give 36F (0.280 g, 0.723 mmol, 79% yield) as a colorless syrup, which solidified upon standing. MS (ESI) m/z: 388.3 [M+1]$^+$. $^1$H NMR: (400 MHz, CDCl$_3$) δ ppm 7.48 (1H, d, J=16.56 Hz), 7.20 (1H, d, J=8.28 Hz), 7.05-7.16 (1H, m), 6.63 (1H, br. s.), 6.22 (1H, s), 5.91 (1H, s), 4.55 (2H, s), 2.82 (3H, br. s.), 1.38-1.57 (18H, m).

36G: tert-Butyl 5-((tert-butoxycarbonyl)amino)-2-(1-cyanocyclopropyl)benzyl(methyl)carbamate

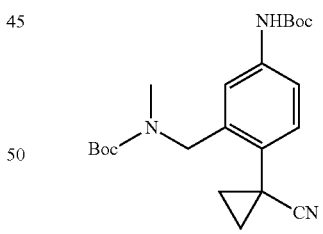

To a suspension of sodium hydride (0.019 g, 0.795 mmol) in DMSO (2 mL), was added trimethylsulfoxonium iodide (0.191 g, 0.867 mmol). The mixture was stirred at rt for 2 h. To the resultant clear solution was added to a solution of 36F (0.280 g, 0.723 mmol) in DMSO (2 mL) to give a yellow solution. The mixture was stirred at rt for 1 h, then at 60° C. for 5 h. Reaction mixture was quenched with sat. NH$_4$Cl (10 mL), extracted with EtOAc (4×25 mL). Combined organic phase was washed with water (2×25 mL), brine (1×25 mL) and dried (Na$_2$SO$_4$). EtOAc was removed under reduced pressure and the residue was purified by flash chromatography (0-40% EtOAc/hexanes) to give 36G (0.144 g, 0.359 mmol, 49.6% yield) as a colorless syrup. MS (ESI) m/z: 402.2

[M+1]+. 1H NMR: (400 MHz, CDCl3) δ ppm 7.33-7.58 (1H, m), 7.23 (1H, d, J=8.28 Hz), 6.91-7.11 (1H, m), 6.60-6.79 (1H, m), 4.71 (2H, br. s.), 2.82-2.98 (3H, m), 1.66 (2H, br. s.), 1.37-1.58 (18H, m), 1.19-1.32 (2H, m).

36H: 1-(4-Amino-2-((methylamino)methyl)phenyl) cyclopropanecarbonitrile hydrochloride

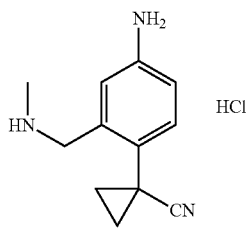

36G (0.254 g, 0.633 mmol) was dissolved in EtOAc (3 mL) and dichloromethane (2 mL), then HCl (4M in dioxane) (2 mL, 8.00 mmol) was added. The reaction mixture was stirred for 4 h at rt. The solvent was removed under reduced pressure, and the residue was dried under high vacuum to give 36H (0.170 g, 0.620 mmol, 98% yield) as an off-white solid. MS (ESI) m/z: 202.2 [M+1]+. 1H NMR: (400 MHz, CD3OD) δ ppm 7.70 (1H, d, J=2.01 Hz), 7.67 (1H, d, J=8.28 Hz), 7.45 (1H, dd, J=8.28, 2.01 Hz), 4.61 (2H, s), 2.92 (3H, s), 1.82-1.88 (2H, m), 1.50-1.57 (2H, m).

36I: tert-Butyl N-(6-{[({[5-amino-2-(1-cyanocyclopropyl)phenyl]methyl}(methyl)carbamoyl)({4-[(2R)-1-hydroxypropan-2-yl]-3-methylphenyl})methyl]amino}isoquinolin-1-yl)-N-[(tert-butoxy)carbonyl]carbamate

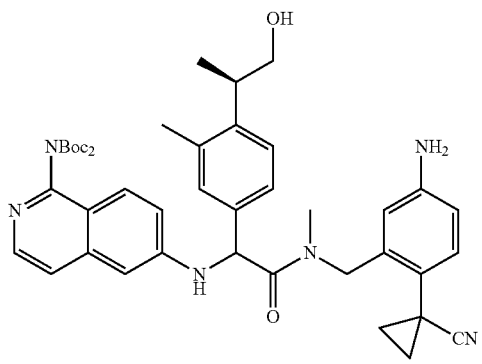

Intermediate 5 (0.126 g, 0.650 mmol), glyoxylic acid monohydrate (0.060 g, 0.650 mmol) and Intermediate 1 (0.234 g, 0.650 mmol) were dissolved in DMF (1 mL) and acetonitrile (2 mL). The reaction mixture was stirred at 80° C. for 1.5 h, then cooled to rt. To this solution were added sequentially 36H (0.170 g, 0.715 mmol), BOP (0.316 g, 0.715 mmol) and TEA (0.544 mL, 3.90 mmol). The mixture was stirred at rt for 30 min, quenched with water (0.5 mL), diluted with EtOAc (150 mL). The organic layer was washed with water (4×50 mL) and brine (1×50 mL), dried (Na2SO4) and concentrated. The crude product was purified by flash chromatography (1-20% MeOH/dichloromethane) to yield 36I (0.371 g, 0.495 mmol, 76% yield) as an orange glass, which was lyophilized to give yellowish powder. MS (ESI) m/z: 749.5 [M+1]+. 1H NMR: complicated by a pair of diastereomers and rotamers.

36J: tert-Butyl N-[(tert-butoxy)carbonyl]-N-(6-{[(2R,15R)-7-(1-cyanocyclopropyl)-4,15,20-trimethyl-3,12-dioxo-13-oxa-4,11-diazatricyclo[14.2.2.1⁶,¹⁰]henicosa-1(18),6,8,10(21),16,19-hexaen-2-yl]amino}isoquinolin-1-yl)carbamate

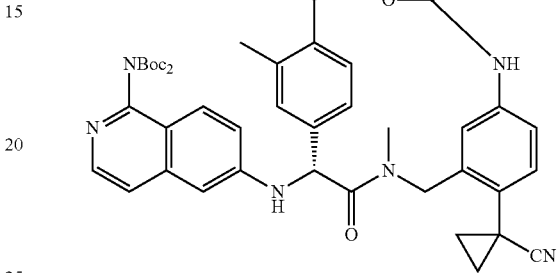

A solution of 36I (0.371 g, 0.495 mmol) in acetonitrile (5 mL) and dichloromethane (5 mL) was cooled to 0° C. To this solution, was added phosgene (20% in toluene, 0.257 mL, 0.520 mmol). The mixture was stirred at 0° C. for 15 min, then bubbled with Ar for 25 min to remove excess phosgene and HCl. The resulting solution was added dropwise over 5 h via a syringe pump into a solution of TEA (0.690 mL, 4.95 mmol) in dichloromethane (200 mL). The solution was stirred for an additional 30 min and then concentrated. The crude product was purified by flash chromatography (1-15% MeOH/dichloromethane) to give di-Boc protected intermediate (0.326 g, 85%) as a diastereomeric mixture. The diastereomers were separated by a prep chiral HPLC (CHIRALCEL® OD 10 um 4.6×250 mm) to yield 36J (0.141 g, 0.182 mmol, 73.5% yield) as a yellowish solid. MS (ESI) m/z: 775.3 [M+1]+. 1H NMR: (400 MHz, CD3OD) δ ppm 8.05 (1H, d, J=5.81 Hz), 7.68 (1H, dd, J=7.83, 1.77 Hz), 7.61 (1H, d, J=9.09 Hz), 7.52 (1H, d, J=5.81 Hz), 7.46 (1H, d, J=8.08 Hz), 7.27 (1H, dd, J=9.22, 2.15 Hz), 7.18-7.24 (2H, m), 6.88 (1H, d, J=2.02 Hz), 6.71 (1H, dd, J=8.08, 2.27 Hz), 6.11 (1H, d, J=2.02 Hz), 5.73 (1H, s), 5.67 (1H, d, J=16.93 Hz), 4.65 (1H, t, J=10.99 Hz), 4.14 (1H, d, J=16.93 Hz), 3.96 (1H, dd, J=10.86, 4.29 Hz), 3.40 (3H, s), 2.31 (3H, s), 1.27 (25H, s).

Example 36

36J (40 mg, 0.052 mmol) was dissolved in toluene (1 mL), and azidotributyltin (0.035 mL, 0.129 mmol) was added. The reaction mixture was degassed (3× vacuum/Ar), and stirred at 90° C. for 24 h. Toluene was removed under reduced pressure, and the residue was treated with TFA (1 mL) for 15 min at rt. TFA was removed under reduced pressure, and the residue was purified by prep HPLC to yield Example 36 (14.09 mg, 0.019 mmol, 36.2% yield) as a white solid. MS (ESI) m/z: 618.3 [M+1]+. 1H NMR: (400 MHz, CD3OD) δ ppm 9.05 (1H, s), 8.03 (1H, d, J=9.29 Hz), 7.65 (1H, dd, J=7.91, 1.63 Hz), 7.46 (1H, d, J=7.78 Hz), 7.35 (1H, d, J=8.28 Hz), 7.29 (1H, d, J=7.28 Hz), 7.19 (1H, dd, J=9.16, 2.38 Hz), 7.15 (1H, s), 6.89 (1H, d, J=7.03 Hz), 6.81 (1H, d, J=2.26 Hz), 6.77 (1H, dd, J=8.03, 2.01 Hz), 6.14 (1H, br. s.), 5.71 (1H, s), 5.27 (1H, d, J=16.81 Hz), 4.66 (1H, t, J=11.04 Hz), 3.97 (1H, dd, J=10.79, 4.27 Hz), 3.80 (1H, d, J=16.81 Hz), 3.42-3.57 (1H, m), 3.31-3.33 (3H, m), 2.31 (3H, s), 1.62-1.82 (2H, m), 1.49-1.59 (2H, m), 1.32 (3H, d, J=7.03 Hz); Analytical HPLC (low pH, 254 nM): Sunfire, RT=4.94, 98.7% purity; XBridge, RT=5.87, 97% purity.

Example 37

(2R,15R)-2-[(1-Aminoisoquinolin-6-yl)amino]-8-fluoro-7-{[(2S)-1-methoxypropan-2-yl]oxy}-4,15,20-trimethyl-13-oxa-4,11-diazatricyclo[14.2.2.1$^{6,10}$]henicosa-1(18),6,8,10 (21),16,19-hexaene-3,12-dione; trifluoroacetic acid

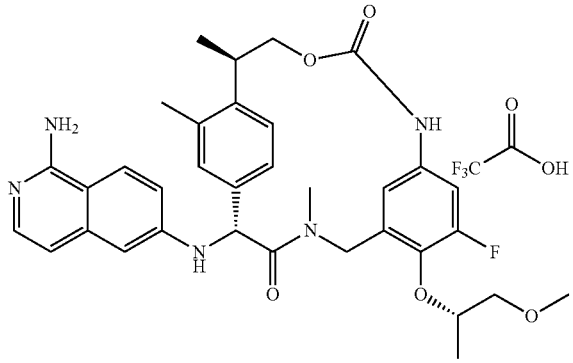

37A: (S)-3-Fluoro-4-((1-methoxypropan-2-yl)oxy)-5-((methylamino)methyl)aniline dihydrochloride

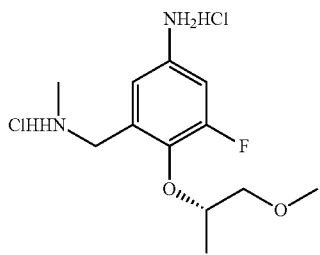

To a solution of 17D (556 mg, 1.852 mmol), (R)-1-methoxypropan-2-ol (367 mg, 4.07 mmol), triphenylphosphine (1068 mg, 4.07 mmol) in THF (5 mL) was added DIAD (0.81 mL, 4.07 mmol). The reaction mixture was stirred at 0° C. for 30 min, and at rt for 16 h. The mixture was concentrated and purified by flash chromatography. The desired fractions were combined and concentrated. The residue was dissolved in MeOH (30 mL) and THF (10 mL). Zinc (dust) (3.47 g, 53.1 mmol) and ammonium chloride (5.68 g, 106 mmol) were added. The resulting solution was stirred at rt for 2 h. MeOH was removed under reduced pressure. Na$_2$CO$_3$ (aq, 100 mL) and EtOAc (150 mL) was added, and the suspension was stirred vigorously for 10 min. The mixture was filtered through a glass frit, solid residue was washed with EtOAc (3×150 mL). Combined EtOAc fractions were washed with std. Na$_2$CO$_3$ (aq, 2×50 mL), water (2×50 mL), brine (1×50 mL) and dried (Na$_2$SO$_4$). EtOAc was removed under reduced pressure and the residue was dissolved in EtOAc (10 mL), treated with HCl (4M, 8 mL) for 2 h at rt. The solvent was removed under reduced pressure to yield 37A (520 mg, 1.650 mmol, 89% yield) as a yellow solid. MS (ESI) m/z: 244.3 (M+H)$^+$.

37B: (S)-Benzyl 5-amino-3-fluoro-2-((1-methoxypropan-2-yl)oxy)benzyl(methyl)carbamate

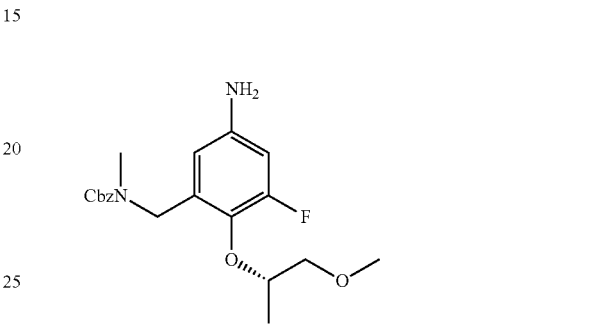

To a solution of 37A (472 mg, 1.497 mmol) and N,N-diisopropylethylamine (1.043 ml, 5.99 mmol) in DMF (10 ml), was added N-(benzyloxycarbonyloxy) succinimide (411 mg, 1.647 mmol). The mixture was stirred rt for 1 h, then quenched with water, extracted with EtOAc (3×30 ml). The organic layer was washed with brine, dried (Na$_2$SO$_4$) and concentrated. The crude product was purified by flash chromatography (0-60% EtOAc in hexanes) to give 37B (520 mg, 1.381 mmol, 92% yield). MS (ESI) m/z: 377.3 (M+H)$^+$.

37C: Benzyl 5-((((R)-2-(4-bromo-2-methylphenyl)propoxy)carbonyl)amino)-3-fluoro-2-(((S)-1-methoxypropan-2-yl)oxy)benzyl(methyl)carbamate

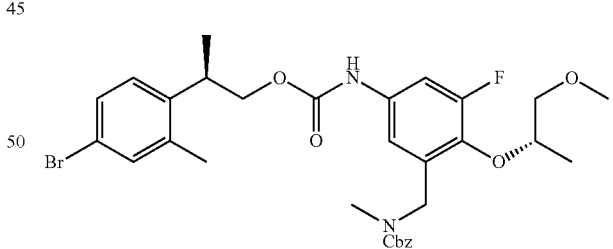

To a solution of 37B (510 mg, 1.355 mmol), sodium bicarbonate (1138 mg, 13.55 mmol) in CH$_2$Cl$_2$ (10 ml) at 0° C., was added phosgene (1340 mg, 2.71 mmol, 20% in toluene). The mixture was stirred 0° C. for 30 min, rt for 1 h, filtered, and concentrated. The residue was dissolved in CH$_2$Cl$_2$ (10 ml) at 0° C., DMAP (182 mg, 1.490 mmol) and TEA (0.370 ml, 2.71 mmol) was added, followed by Intermediate 5A (310 mg, 1.355 mmol). The mixture was stirred rt for 1 h, quenched with water, and extracted with EtOAc (2×20 mL). The combined organic layer was washed with 1N HCl, brine, dried (Na$_2$SO$_4$) and concentrated. The crude product was purified by flash chromatography (0-40% EtOAc in hexanes) to give 37C (810 mg, 1.283 mmol, 95% yield). MS (ESI) m/z: 631.3 (M+H)⁺.

37D: (4-((R)-1-(((3-((((Benzyloxy)carbonyl)(methyl)amino)methyl)-5-fluoro-4-(((S)-1-methoxypropan-2-yl)oxy)phenyl)carbamoyl)oxy)propan-2-yl)-3-methylphenyl)boronic acid

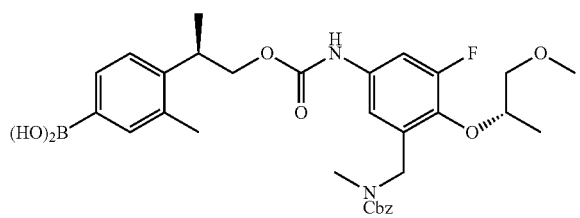 [SMILES: COC[C@H](C)Oc1c(F)cc(NC(=O)OC[C@H](C)c2ccc(B(O)O)cc2C)cc1CN(C)C(=O)OCc1ccccc1]

To a reaction tube was added 37C (480 mg, 0.76 mmol), 5,5,5',5'-tetramethyl-2,2'-bi(1,3,2-dioxaborinane) (206 mg, 0.912 mmol), KOAc (186 mg, 1.900 mmol), Pd(dppf)Cl₂ (125 mg, 0.152 mmol) in DMSO (1.5 ml). The tube was filled with Ar, sealed and stirred at 85° C. for 2 h. The mixture was quenched with water, and extracted with EtOAc. The combined organic layer was filtered though silica gel and concentrated. The crude product was purified by flash chromatography to give 37D (309 mg, 0.518 mmol, 68.2% yield). MS (ESI) m/z: 597.4 (M+H)⁺.

37E: 2-((1-(Bis(tert-butoxycarbonyl)amino)isoquinolin-6-yl)amino)-2-(4-((R)-1-(((3-fluoro-4-(((S)-1-methoxypropan-2-yl)oxy)-5-((methylamino)methyl)phenyl)carbamoyl)oxy)propan-2-yl)-3-methylphenyl)acetic acid

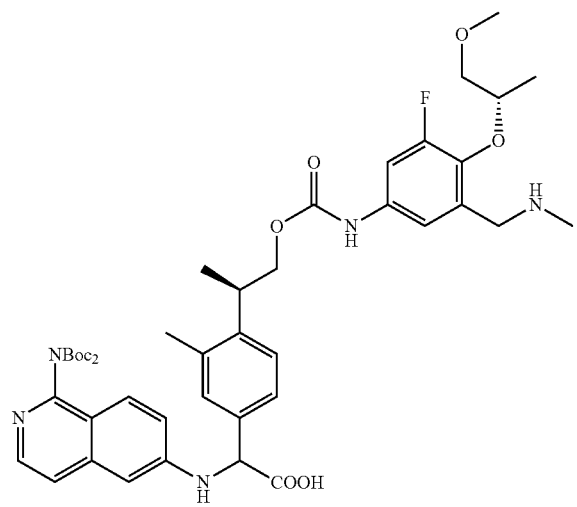

37D (309 mg, 0.518 mmol), Intermediate 1 (205 mg, 0.570 mmol), glyoxylic acid monohydrate (47.7 mg, 0.518 mmol) were dissolved in CH₃CN (3 ml) and DMF (0.5 ml). The mixture was stirred at 85° C. 20 h, then concentrated and purified by prep HPLC. The desired fractions were combined, concentrated. The residue was dissolved in THF (8 mL). 10% Pd/C was added and the mixture was hydrogenated at 40 psi for 3 h. The mixture was filtered, concentrated and purified by prep HPLC to give 37E (185 mg, 0.222 mmol, 42.8% yield). MS (ESI) m/z: 834.4 (M+H)⁺.

37F: tert-Butyl N-[(tert-butoxy)carbonyl]-N-(6-{[(15R)-8-fluoro-7-{[(2S)-1-methoxypropan-2-yl]oxy}-4,15,20-trimethyl-3,12-dioxo-13-oxa-4,11-diazatricyclo[14.2.2.1⁶,¹⁰]henicosa-1(18),6,8,10(21),16,19-hexaen-2-yl]amino}isoquinolin-1-yl)carbamate

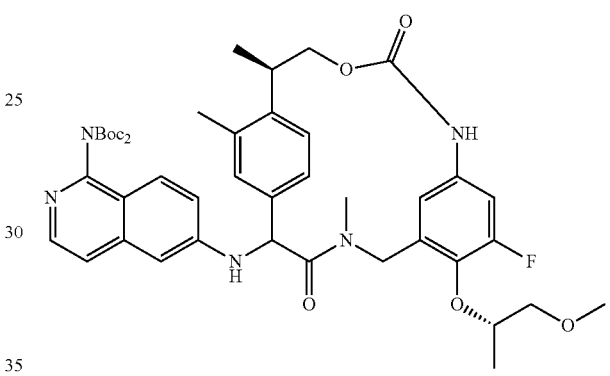

To a solution of BOP (196 mg, 0.444 mmol), 4-dimethylaminopyridine (136 mg, 1.109 mmol) in CH₂Cl₂ (40 mL), was added a solution of 37E (185 mg, 0.222 mmol) in DMF (10 mL) via a syringe pump over 6 h. The reaction mixture was stirred at rt for 16 h, then concentrated and purified by prep HPLC to give 37F (150 mg, 0.184 mmol, 83% yield) as a yellow solid. MS (ESI) m/z: 816.2 (M+H)⁺.

Example 37

37F (150 mg, 0.184 mmol) in EtOAc (3 mL) was treated with 4.0 M HCl in dioxane HCl (3 mL, 12.00 mmol) for 2 h at rt. The reaction mixture was concentrated. The residue was separated by a prep chiral HPLC (R,R-Whelk-O column 21.1×250 mm) to yield Example 37 (46 mg, 0.054 mmol, 0.450% yield). MS (ESI) m/z: 616.1 (M+H)⁺. ¹H NMR (400 MHz, acetonitrile-d₃) δ ppm 7.79 (d, J=9.23 Hz, 1H) 7.73 (s, 2H) 7.65 (dd, J=7.91, 1.76 Hz, 1H) 7.42 (d, J=7.91 Hz, 1H) 7.27 (s, 1H) 7.21-7.26 (m, 1H) 7.12 (dd, J=9.01, 2.42 Hz, 1H) 7.10 (s, 1H) 6.75-6.82 (m, 2H) 6.54 (dd, J=12.30, 2.64 Hz, 1H) 5.60-5.63 (m, 2H) 5.39 (d, J=17.14 Hz, 1H) 4.59 (t, J=10.99 Hz, 1H) 4.32-4.37 (m, 1H) 3.90-3.95 (m, 1H) 3.83 (d, J=17.14 Hz, 1H) 3.45-3.48 (m, 2H) 3.37-3.44 (m, 1H) 3.32 (s, 3H) 3.17 (s, 3H) 2.22-2.25 (m, 3H) 1.23-1.29 (m, 6H); Analytical HPLC (low pH, 254 nM): Sunfire, RT=6.91 min, 99.5% purity; XBridge, RT=5.82 min, 99.5% purity.

Example 38

(2R,15R)-2-[(1-Aminoisoquinolin-6-yl)amino]-8-fluoro-4,15,20-trimethyl-7-[(3R)-oxolan-3-yloxy]-13-oxa-4,11-diazatricyclo[14.2.2.1$^{6,10}$]henicosa-1(18),6,8,10(21),16,19-hexaene-3,12-dione; trifluoroacetic acid

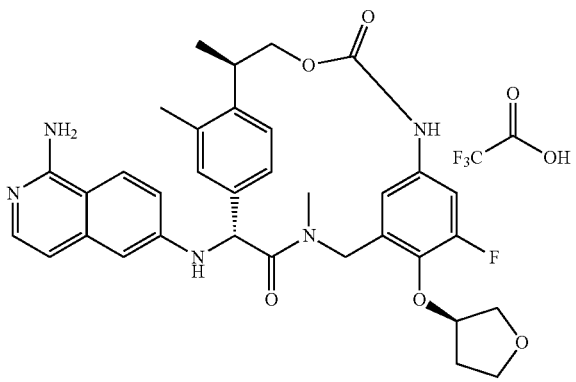

38A: (R)-tert-Butyl 3-fluoro-5-nitro-2-((tetrahydrofuran-3-yl)oxy)benzyl(methyl)carbamate

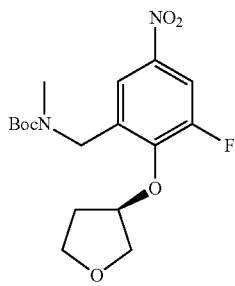 [SMILES: CN(Cc1cc([N+](=O)[O-])cc(F)c1O[C@@H]1CCOC1)C(=O)OC(C)(C)C]

To a solution of 17D (566 mg, 1.885 mmol), (S)-tetrahydrofuran-3-ol (365 mg, 4.15 mmol) and PPh$_3$ (1088 mg, 4.15 mmol) in THF (5 mL) was added DIAD (0.822 mL, 4.15 mmol) dropwise. The reaction was stirred at 0° C. for 0.5 h and then at rt for 16 h. The mixture was concentrated and purified by prep HPLC to give 38A (700 mg, 1.890 mmol, 100% yield). MS (ESI) m/z: 371.2 (M+H)$^+$.

38B: (R)-3-Fluoro-5-((methylamino)methyl)-4-((tetrahydrofuran-3-yl)oxy)aniline dihydrochloride

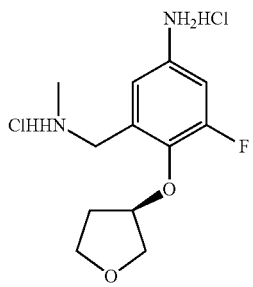

To 38A (680 mg, 1.836 mmol) in MeOH (10 mL) and THF (2.00 mL), was added zinc (1201 mg, 18.36 mmol) and NH$_4$Cl (2946 mg, 55.1 mmol). The mixture was stirred at rt for 3 h, then concentrated. The residue was stirred with sat. Na$_2$CO$_3$ for 30 min and then extracted with EtOAc (3×). The crude product was purified by flash chromatography to give the BOC-protected aniline intermediate. This intermediate was dissolved in EtOAc, HCl (4M in dioxane, 6 mL) was added. The reaction was stirred at rt for 2 h. The solvent was removed to give 38B (430 mg, 1.373 mmol, 74.8% yield) as a pink solid. MS (ESI) m/z: 241.3 (M+H)$^+$.

38C: (R)-Benzyl 5-amino-3-fluoro-2-((tetrahydrofuran-3-yl)oxy)benzyl(methyl)carbamate hydrochloride

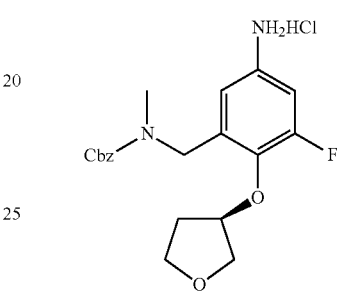

To 38B (200 mg, 0.639 mmol) and DIEA (0.445 ml, 2.55 mmol) in DMF (10 mL), was added N-(benzyloxycarbonyloxy) succinimide (167 mg, 0.671 mmol). The mixture was stirred at rt for 1 h, then quenched with H$_2$O. The mixture was extracted with EtOAc (3×) and the organic layer was washed with 1N HCl, sat. NaHCO$_3$, brine, and dried over Na$_2$SO$_4$. The crude was purified by flash column chromatography (0-60% EtOAc/hexanes) to give 38C (182 mg, 0.486 mmol, 76% yield). MS (ESI) m/z: 375.3 (M+H)$^+$.

38D: Benzyl 5-((((R)-2-(4-bromo-2-methylphenyl)propoxy)carbonyl)amino)-3-fluoro-2-(((R)-tetrahydrofuran-3-yl)oxy)benzyl(methyl)carbamate

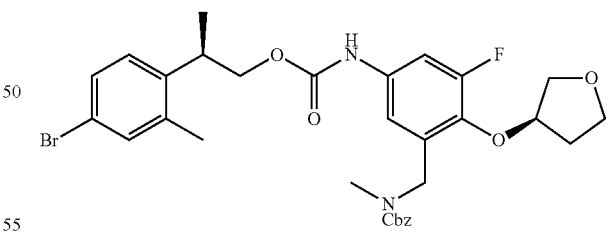

To 38C (182 mg, 0.486 mmol) and NaHCO$_3$ (408 mg, 4.86 mmol) in CH$_2$Cl$_2$ (10 ml) at 0° C. was added phosgene (0.481 ml, 0.972 mmol, 20% in toluene). The mixture was stirred at 0° C. for 30 min, then at rt for 1 h. The reaction was filtered and concentrated. To the resulting residue in CH$_2$Cl$_2$ (10 ml) at 0° C., was added TEA (0.133 ml, 0.972 mmol), followed by Intermediate 5A (111 mg, 0.486 mmol). The mixture was stirred rt overnight, quenched with H$_2$O, and extracted with EtOAc (2×). The combined organic layers were washed with 1N HCl, brine and dried (Na$_2$SO$_4$). The crude sample was purified by flash column chromatography (0-40% EtOAc/hexanes) to give 38D (258 mg, 0.410 mmol, 84% yield). MS (ESI) m/z: 629.3 (M+H)+.

38E: (4-((R)-1-(((3-((((Benzyloxy)carbonyl)(methyl)amino)methyl)-5-fluoro-4-(((R)-tetrahydrofuran-3-yl)oxy)phenyl)carbamoyl)oxy)propan-2-yl)-3-methylphenyl)boronic acid

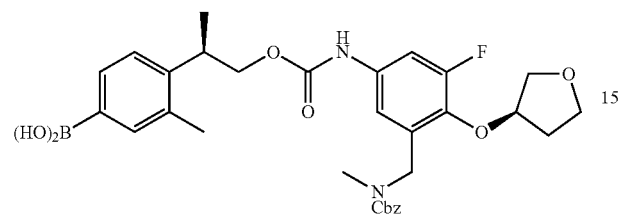

To a reaction tube was added 38D (258 mg, 0.410 mmol), 5,5,5',5'-tetramethyl-2,2'-bi(1,3,2-dioxaborinane) (111 mg, 0.492 mmol), KOAc (101 mg, 1.025 mmol) and Pd(dppf)Cl$_2$ (67.4 mg, 0.082 mmol) in DMSO (1.5 ml). The tube was filled with Ar, sealed and stirred at 85° C. for 2 h. The mixture was quenched with H$_2$O, and extracted with EtOAc (3×). The combined organic layers was filtered though silica gel and concentrated. The residue was purified by prep HPLC to give 38E (171 mg, 0.288 mmol, 70.2% yield) as a tan solid. MS (ESI) m/z: 595.4 (M+H)+.

38F: 2-((1-(Bis(tert-butoxycarbonyl)amino)isoquinolin-6-yl)amino)-2-(4-((R)-1-(((3-fluoro-5-((methylamino)methyl)-4-(((R)-tetrahydrofuran-3-yl)oxy)phenyl)carbamoyl)oxy)propan-2-yl)-3-methylphenyl)acetic acid

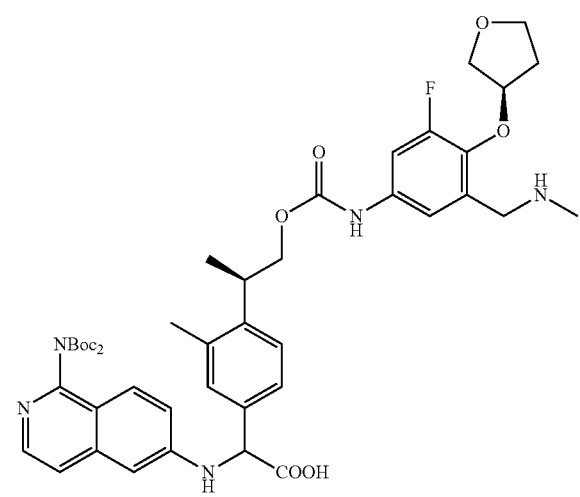

38E (171 mg, 0.288 mmol), Intermediate 1 (114 mg, 0.316 mmol) and glyoxylic acid monohydrate (26.5 mg, 0.288 mmol) were dissolved in acetonitrile (3 ml) and DMF (0.5 ml). The mixture was stirred at 85° C. for 2 h. The mixture was concentrated and purified by prep HPLC to give the acid intermediate (182 mg) as a yellow solid. The acid intermediate above in MeOH (8 mL) was hydrogenated (40 psi) over 10% Pd/C for 6 h. The mixture was filtered and concentrated to give 38F (158 mg, 0.190 mmol, 66.0% yield). MS (ESI) m/z: 830.5 (M−H)−.

38G: tert-Butyl N-[(tert-butoxy)carbonyl]-N-(6-{[(15R)-8-fluoro-4,15,20-trimethyl-3,12-dioxo-7-[(3R)-oxolan-3-yloxy]-13-oxa-4,11-diazatricyclo[14.2.2.1$^{6,10}$]henicosa-1(18),6,8,10 (21),16,19-hexaen-2-yl]amino}isoquinolin-1-yl)carbamate

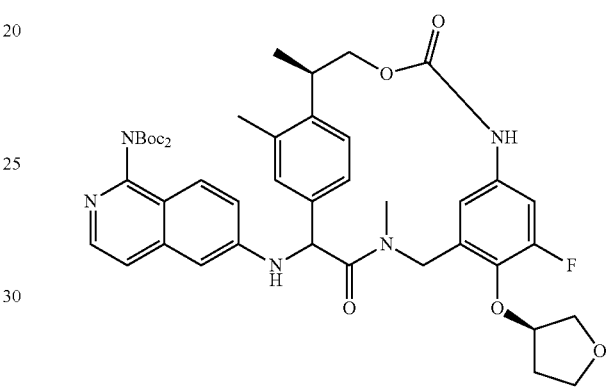

To BOP (167 mg, 0.377 mmol) and DMAP (115 mg, 0.944 mmol) in CH$_2$Cl$_2$ (40 mL) was added a solution of 38F (157 mg, 0.189 mmol) in DMF (10 mL) via a syringe pump over 6 h. The resulting mixture was stirred at rt for 16 h. The mixture was concentrated and purified by prep HPLC to give 38G (85 mg, 0.104 mmol, 55.3% yield) as a yellow solid. MS (ESI) m/z: 814.2 (M+H)+.

Example 38

To 38G (85 mg, 0.104 mmol) in EtOAc (3 mL) was added HCl (2 mL, 8.00 mmol). The mixture was stirred at rt for 2 h. The solvent was removed and concentrated to give a mixture of diastereoisomers. The diastereomers were separated by a prep chiral HPLC (R,R-Whelk-O column 21.1×250 mm) to yield Example 38 (15 mg, 0.018 mmol, 16.89% yield). MS (ESI) m/z: 614.1 (M+H)+. $^1$H NMR (400 MHz, CD$_3$CN) δ ppm 12.53 (s, 1H) 7.81 (d, J=8.79 Hz, 1H) 7.58-7.69 (m, 3H) 7.43 (d, J=7.91 Hz, 1H) 7.30 (s, 1H) 7.22-7.29 (m, 1H) 7.14 (dd, J=9.23, 2.20 Hz, 1H) 7.07 (s, 1H) 6.81 (d, J=7.03 Hz, 1H) 6.78 (d, J=2.20 Hz, 1H) 6.55 (dd, J=12.30, 2.20 Hz, 1H) 5.61-5.66 (m, 2H) 5.26 (d, J=17.14 Hz, 1H) 4.96 (s, 1H) 4.60 (t, J=10.99 Hz, 1H) 3.90-4.01 (m, 2H) 3.78-3.86 (m, 3H) 3.64-3.72 (m, 1H) 3.41 (ddd, J=11.10, 6.92, 4.39 Hz, 1H) 3.19 (s, 3H) 2.23 (s, 3H) 2.05-2.16 (m, 2H) 1.26 (d, J=7.03 Hz, 3H). Anal HPLC (low pH, 254 nM): Sunfire, RT=6.49 min, 100% purity; XBridge, RT=5.43 min, 99.8% purity.

Example 39

(15R)-2-[(1-Aminoisoquinolin-6-yl)amino]-8-fluoro-4,15,20-trimethyl-7-[(3S)-oxolan-3-yloxy]-13-oxa-4,11-diazatricyclo[14.2.2.1⁶,¹⁰]henicosa-1(18),6,8,10(21),16,19-hexaene-3,12-dione; trifluoroacetic acid

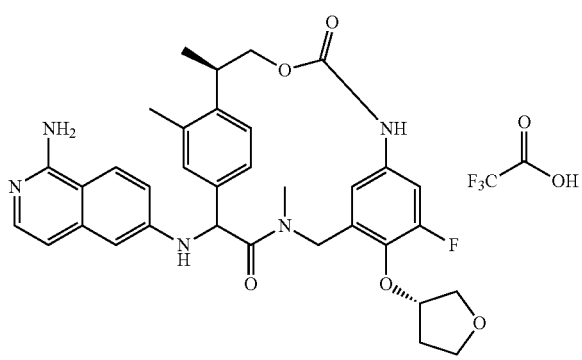 [SMILES: Cc1cc2ccc1[C@@H](C)COC(=O)Nc1cc(F)c(O[C@H]3CCOC3)c(c1)CN(C)C(=O)C2Nc1ccc2c(N)nccc2c1 ; O=C(O)C(F)(F)F]

39A: (S)-3-Fluoro-5-((methylamino)methyl)-4-((tetrahydrofuran-3-yl)oxy)aniline dihydrochloride

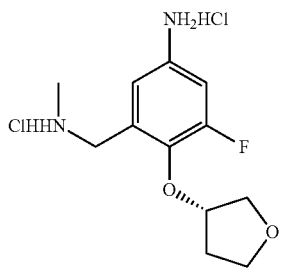

To a solution of 17D (640 mg, 2.131 mmol), (R)-tetrahydrofuran-3-ol (413 mg, 4.69 mmol) and triphenylphosphine in THF (5 mL) at 0° C., was added diisopropyl azodicarboxylate (0.930 mL, 4.69 mmol) dropwise. The reaction mixture was stirred 0° C. for 30 min, and at rt for 16 h. The mixture was concentrated and purified by flash chromatography (0-50% EtOAc in hexanes). The desired fractions were combined, concentrated. The residue was dissolved in MeOH (10 mL) and THF (2 mL). To this solution was added ammonium chloride (2.250 mL, 63.9 mmol) and zinc (0.195 mL, 21.31 mmol). The mixture was stirred at rt for 2 h, concentrated, stirred with sat. Na₂CO₃ (50 mL) for 20 min, extracted with EtOAc (3×20 mL). The residue was purified by flash chromatography. The desired fractions were concentrated, dissolved in EtOAc (5 mL), and treated with HCl (4N, 5 mL) for 3 h at rt. The mixture was concentrated to give 39A (630 mg, 2.012 mmol, 94% yield) as a yellow solid. MS (ESI) m/z: 242.2 (M+H)⁺.

39B: (S)-Benzyl 5-amino-3-fluoro-2-((tetrahydrofuran-3-yl)oxy)benzyl(methyl)carbamate

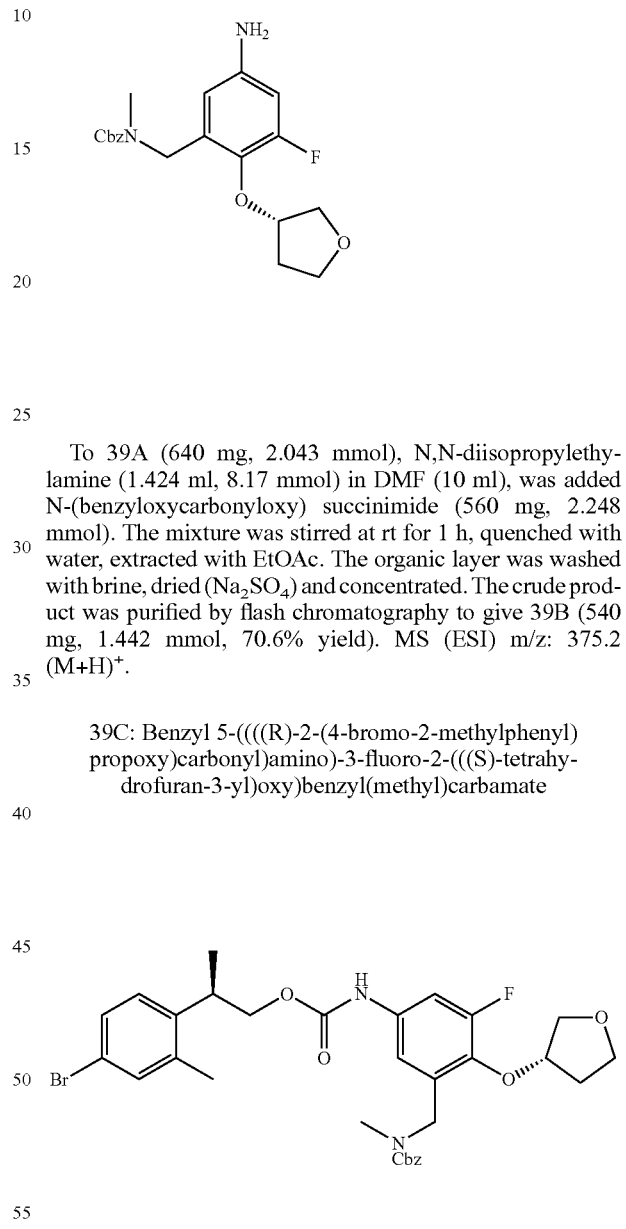

To 39A (640 mg, 2.043 mmol), N,N-diisopropylethylamine (1.424 ml, 8.17 mmol) in DMF (10 ml), was added N-(benzyloxycarbonyloxy) succinimide (560 mg, 2.248 mmol). The mixture was stirred at rt for 1 h, quenched with water, extracted with EtOAc. The organic layer was washed with brine, dried (Na₂SO₄) and concentrated. The crude product was purified by flash chromatography to give 39B (540 mg, 1.442 mmol, 70.6% yield). MS (ESI) m/z: 375.2 (M+H)⁺.

39C: Benzyl 5-((((R)-2-(4-bromo-2-methylphenyl)propoxy)carbonyl)amino)-3-fluoro-2-(((S)-tetrahydrofuran-3-yl)oxy)benzyl(methyl)carbamate To 39B (540 mg, 1.442 mmol) and NaHCO₃ (606 mg, 7.21 mmol) in CH₂Cl₂ (10 ml) at 0° C., was added phosgene (20% in toluene, 1.518 ml, 2.88 mmol). The mixture was stirred at 0° C. for 30 min, rt for 1 h, filtered, and concentrated. The residue in CH₂Cl₂ (10 ml) was added to a solution of Intermediate 5A (330 mg, 1.442 mmol) and TEA (0.393 ml, 2.88 mmol) in CH₂Cl₂ (10 ml) at 0° C. The mixture was stirred at rt for 3 h, quenched with water, and extracted with EtOAc. The combined organic layer was washed with 1N HCl, brine, dried (Na₂SO₄). The crude product was purified by flash chromatography to yield 39C (777 mg, 1.234 mmol, 86% yield). MS (ESI) m/z: 629.1 (M+H)+.

39D: (4-((R)-1-(((3-((((Benzyloxy)carbonyl)(methyl) amino)methyl)-5-fluoro-4-(((S)-tetrahydrofuran-3-yl)oxy)phenyl)carbamoyl)oxy)propan-2-yl)-3-methylphenyl)boronic acid

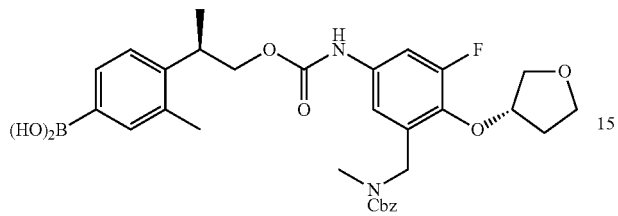

To a reaction tube was added 39C (770 mg, 1.223 mmol), 5,5,5',5'-tetramethyl-2,2'-bi(1,3,2-dioxaborinane) (332 mg, 1.468 mmol), KOAc (300 mg, 3.06 mmol), and Pd(dppf)Cl$_2$ (201 mg, 0.245 mmol) in DMSO (10 ml). The tube was filled with Ar, sealed and stirred at 85° C. for 2 h. The mixture was quenched with H$_2$O, and extracted with EtOAc (3×). The combined organic layers was filtered though silica gel and concentrated. The residue was purified by prep HPLC to give 39D (405 mg, 0.681 mmol, 55.7% yield) as a tan solid. MS (ESI) m/z: 595.4 (M+H)+.

39E: 2-((1-(Bis(tert-butoxycarbonyl)amino)isoquinolin-6-yl)amino)-2-(4-((R)-1-(((3-fluoro-5-((methylamino)methyl)-4-(((S)-tetrahydrofuran-3-yl)oxy) phenyl)carbamoyl)oxy)propan-2-yl)-3-methylphenyl)acetic acid

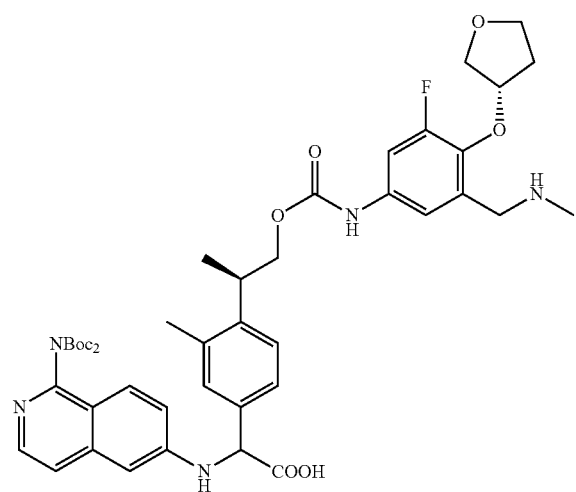

39D (405 mg, 0.681 mmol), Intermediate 1 (245 mg, 0.681 mmol) and glyoxylic acid monohydrate (50.4 mg, 0.681 mmol) were dissolved in CH$_3$CN (3 ml) and DMF (0.5 ml). The mixture was stirred at 85° C. for 20 h, quenched with water, and extracted with EtOAc (3×20 ml). The combined organic layer was washed with 1N HCl, brine, dried (Na$_2$SO$_4$) and concentrated. The crude was purified by flash chromatography (0-10% MeOH in CH$_2$Cl$_2$). The desired fractions were combined and concentrated. The residue was dissolved in MeOH (8 mL). Pd/C was added and the mixture was hydrogenated at 40 psi for 6 h. The mixture was filtered and concentrated gives 39E (298 mg, 0.358 mmol, 52.6% yield). MS (ESI) m/z: 832.2 (M+H)+.

39F: tert-Butyl N-[(tert-butoxy)carbonyl]-N-(6-{[(15R)-8-fluoro-4,15,20-trimethyl-3,12-dioxo-7-[(3S)-oxolan-3-yloxy]-13-oxa-4,11-diazatricyclo [14.2.2.1$^{6,10}$]henicosa-1(18),6,8,10 (21),16,19-hexaen-2-yl]amino}isoquinolin-1-yl)carbamate

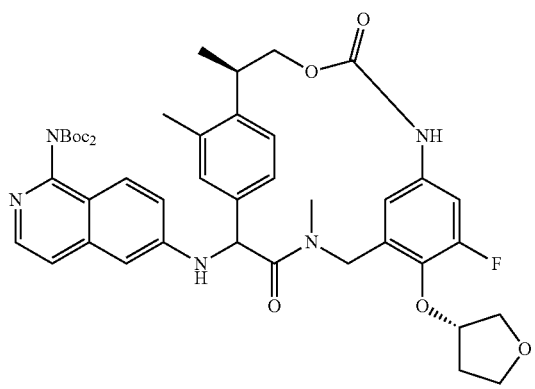

To BOP (317 mg, 0.716 mmol), 4-dimethylaminopyridine (219 mg, 1.791 mmol) in CH$_2$Cl$_2$ (40 mL), was added a solution of 39E (298 mg, 0.358 mmol) in DMF (10 mL) via a syringe pump over 6 h. The mixture was stirred rt for 16 h, then concentrated and purified by prep HPLC to give 39F (180 mg, 61.7% yield). MS (ESI) m/z: 814.3 (M+H)+.

Example 39

39F (152 mg, 0.187 mmol) in EtOAc (5 mL) was treated with 4.0 M HCl in dioxane (8 mL, 32.0 mmol) at rt for 2 h. The mixture was concentrated to give a mixture of diastereoisomers. The diastereomers were separated by a prep chiral HPLC equipped with an OD column to yield Example 39 (50 mg, 0.059 mmol, 31.6% yield). MS (ESI) m/z: 614.1 (M+H)+. $^1$H NMR (400 MHz, acetonitrile-d$_3$) d ppm 7.73-7.83 (m, 3H) 7.60 (s, 1H) 7.30 (s, 1H) 7.21-7.27 (m, 2H) 7.12 (dd, J=9.01, 2.42 Hz, 1H) 7.04 (d, J=8.35 Hz, 1H) 6.83 (d, J=7.03 Hz, 1H) 6.79 (d, J=2.20 Hz, 1H) 6.57 (dd, J=12.30, 2.20 Hz, 1H) 5.74 (s, 1H) 5.59 (s, 1H) 5.25 (d, J=17.14 Hz, 1H) 4.95 (s, 1H) 4.85 (dd, J=10.99, 2.64 Hz, 1H) 3.94-4.01 (m, 1H) 3.77-3.87 (m, 4H) 3.69 (dd, J=10.55, 3.95 Hz, 1H) 3.34-3.41 (m, 1H) 3.16 (s, 3H) 2.46 (s, 3H) 2.04-2.15 (m, 2H) 1.34 (d, J=7.03 Hz, 3H). Analytical HPLC (low pH, 254 nM): Sunfire, RT=6.60 min, 99.5% purity; XBridge, RT=5.51 min, 100% purity.

What is claimed is:

1. A compound of Formula (I):

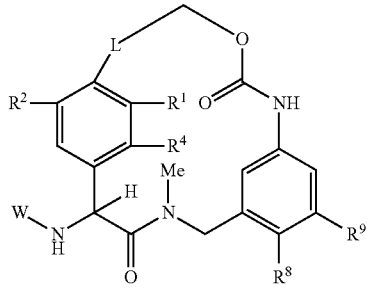
(I)

or a stereoisomer, a tautomer, or a pharmaceutically acceptable salt thereof, wherein:

W is

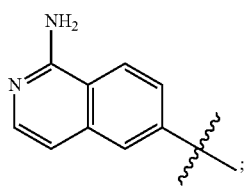 [SMILES: *c1ccc2c(N)nccc2c1]

wherein the ring moiety is substituted with 0-2 F atoms;

L is independently selected from: $CH(C_{1-2}$ alkyl), $CF_2$, $CH(CH_2F)$, $CH(CHF_2)$, and $CH_2CH(OH)$;

$R^1$ and $R^2$ are independently selected from: H, $C_{1-2}$ alkyl and $C_{1-2}$ alkoxy;

$R^4$ and $R^9$ are independently selected from: H, F and Cl; and $R^8$ is independently selected from: $-O(CH_2)_{1-4}O(C_{1-4}$ alkyl), $-CON(C_{1-4}$ alkyl)$_2$, $-SO_2(C_{1-6}$ alkyl), $-SO_2$ (cyclopropyl), $-P(=O)(OC_{1-4}$ alkyl)$_2$,

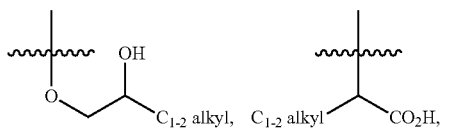

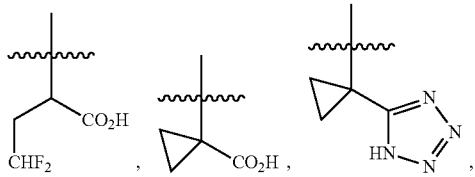

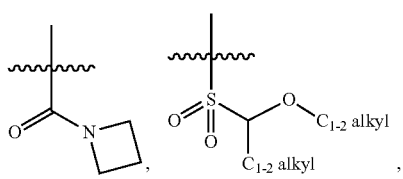

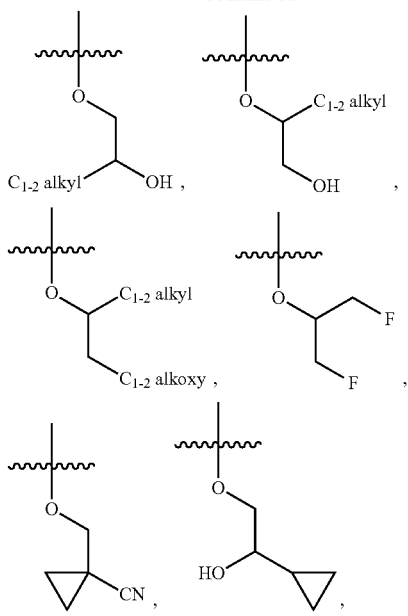

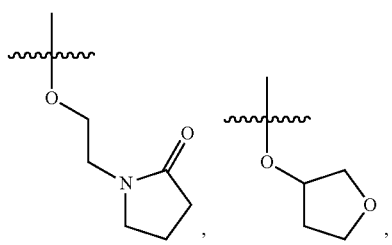

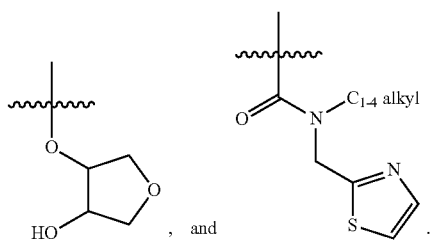

, and

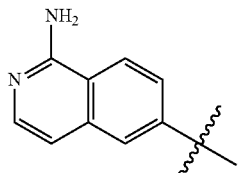

2. A compound according to claim 1, wherein:

W is independently selected from:

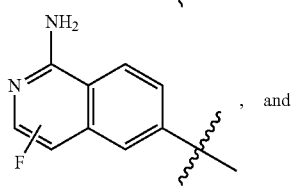

, and

-continued

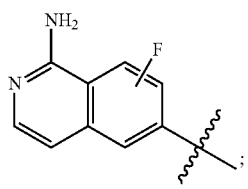

L is independently selected from: CH(Me), CF$_2$, CH(CH$_2$F), CH(CHF$_2$), and CH$_2$CH(OH);

R$^1$ and R$^2$ are independently selected from: H, Me and OMe; and

R$^4$ and R$^9$ are independently selected from: H and F.

3. A compound according to claim 1, wherein:

W is independently selected from:

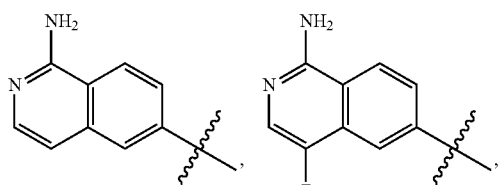

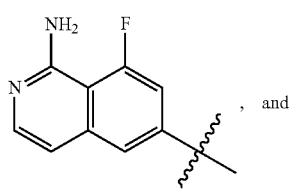, and

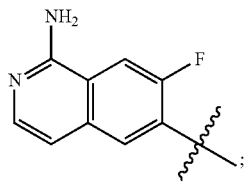;

and

R$^8$ is independently selected from: —O(CH$_2$)$_3$OMe, —CON(Me)$_2$, —CON(Et)$_2$, —SO$_2$Et, —SO$_2$(i-Pr), —SO$_2$(t-Bu), —SO$_2$(cyclopropyl), —P(=O)(OC$_{1-4}$ alkyl)$_2$,

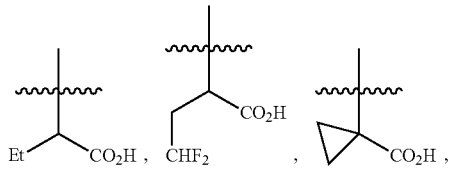

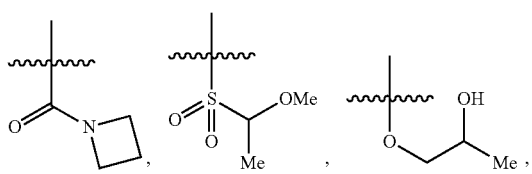

-continued

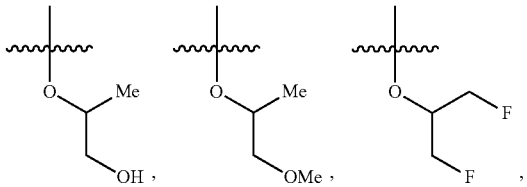

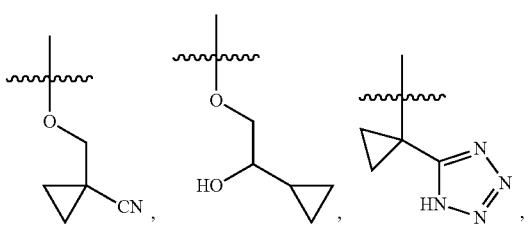

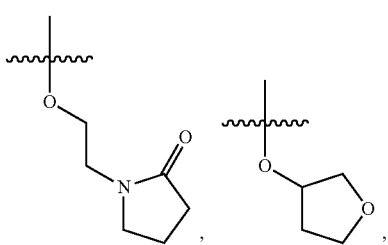

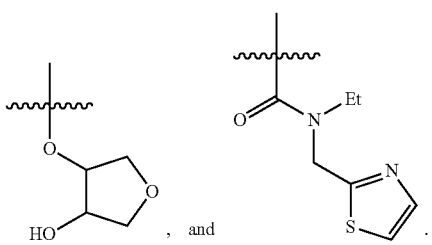, and

4. A compound according to claim 1, wherein the compound is selected from the list consisting of:

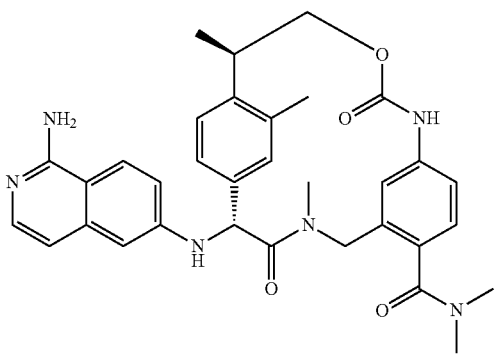

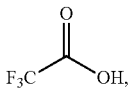

191
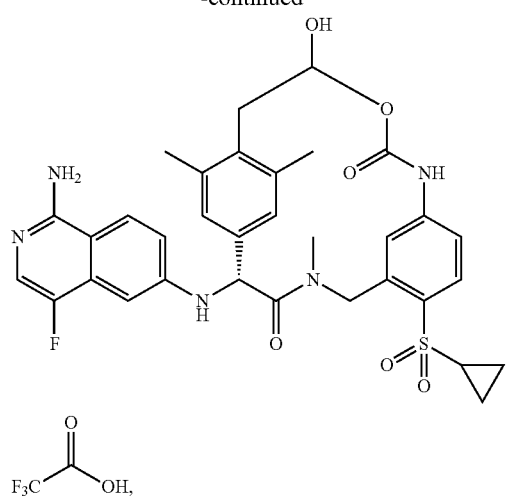
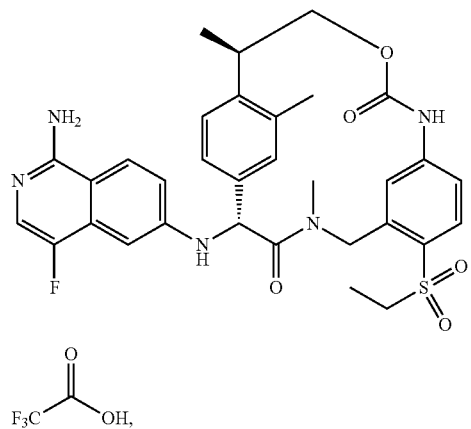
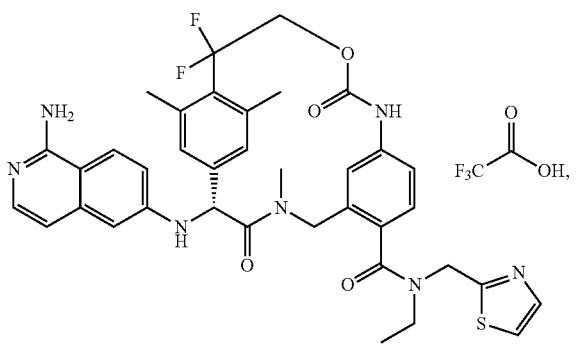
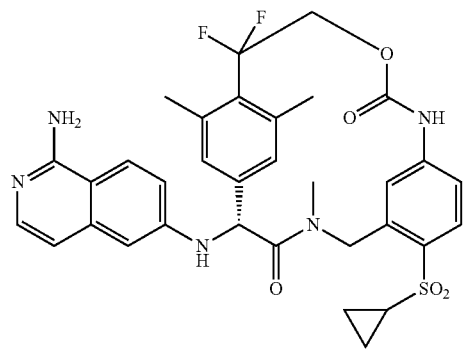
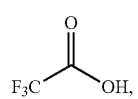
192
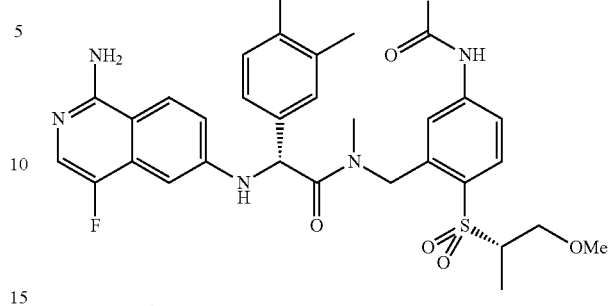
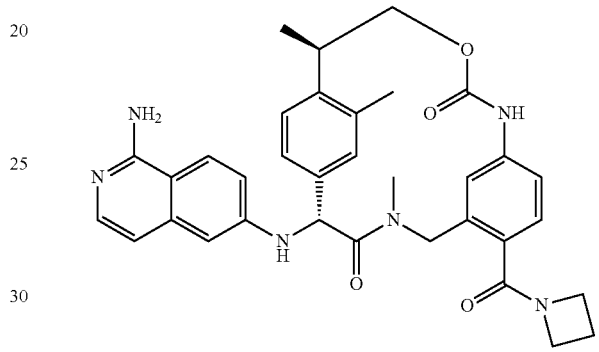
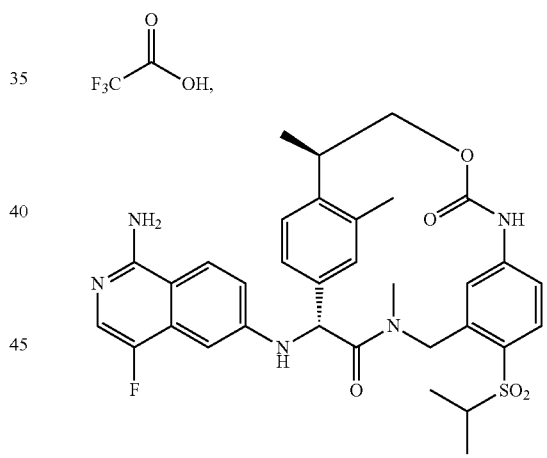
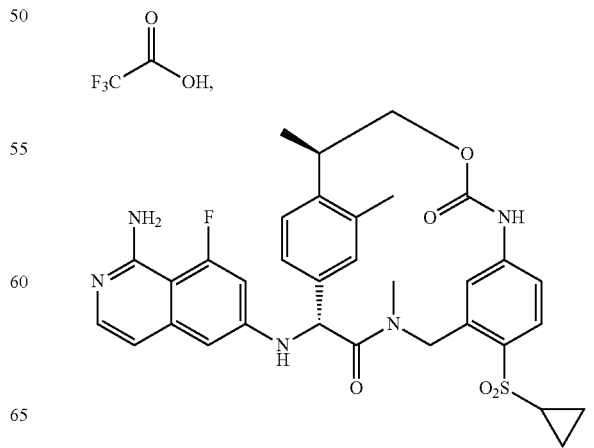

193
-continued
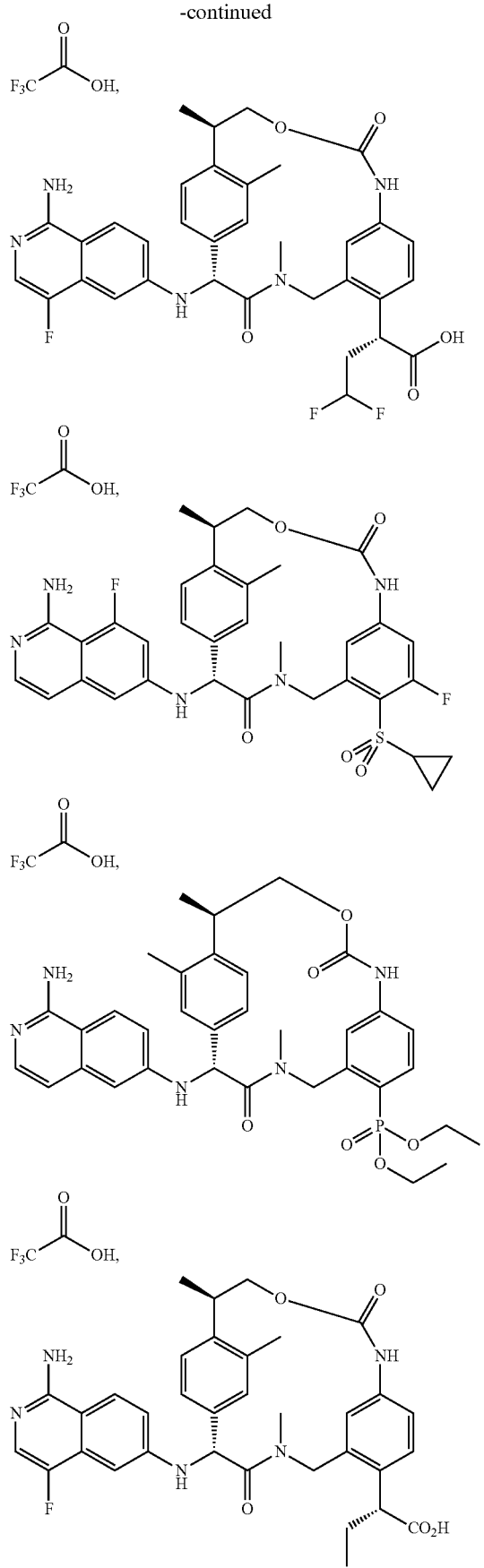
194
-continued
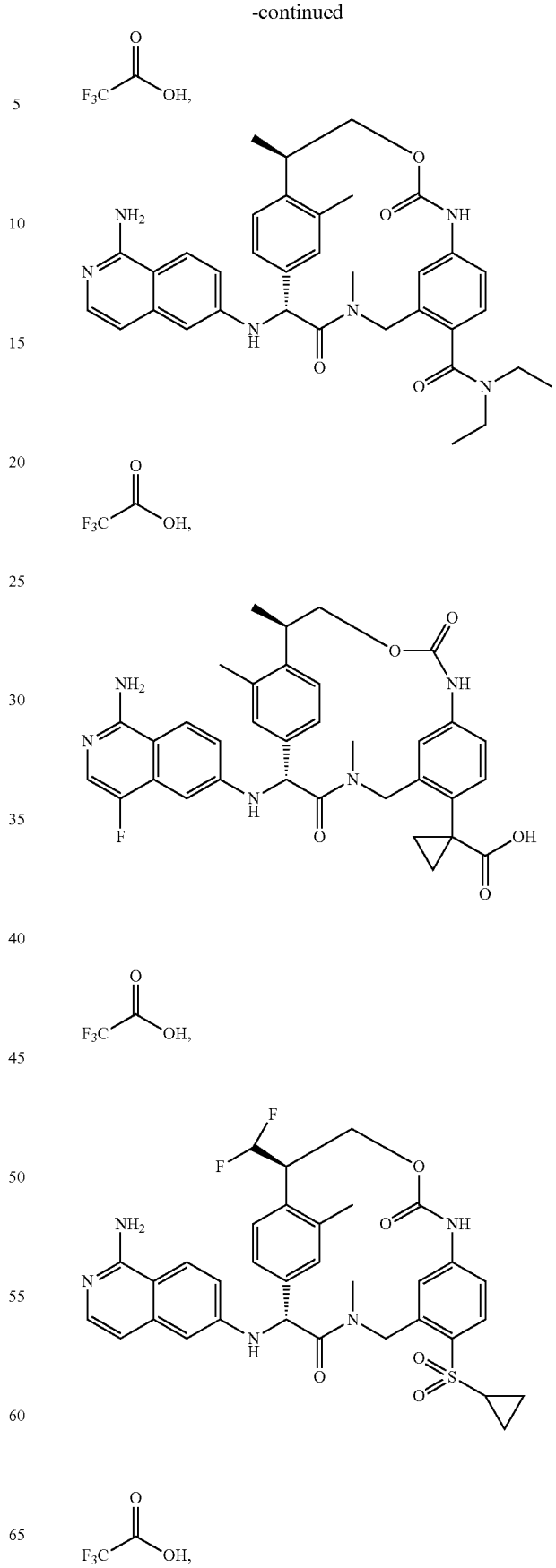

195
-continued
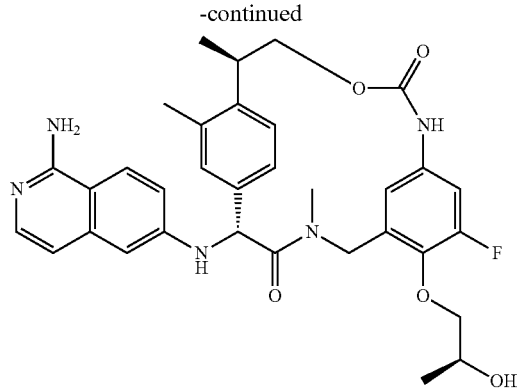
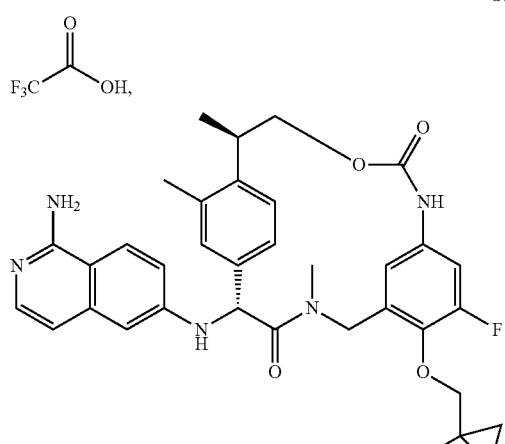
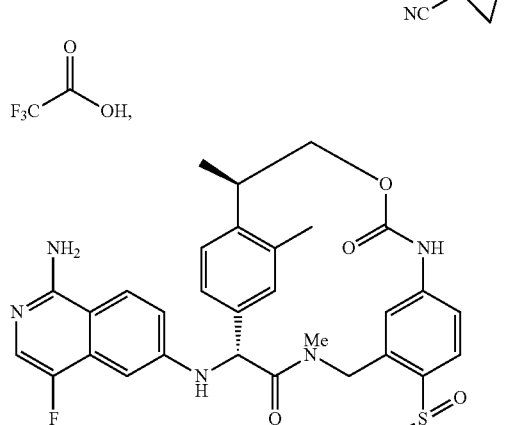
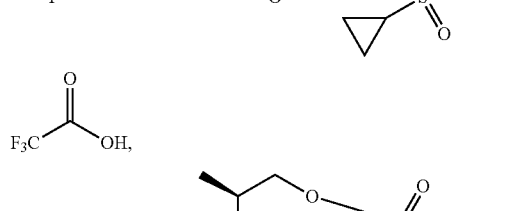
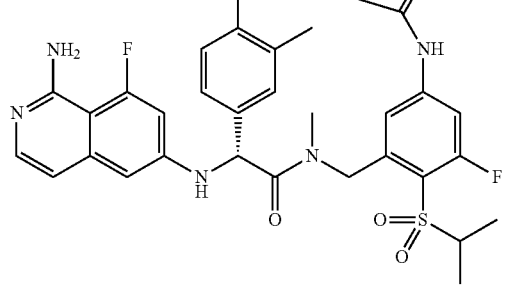
196
-continued
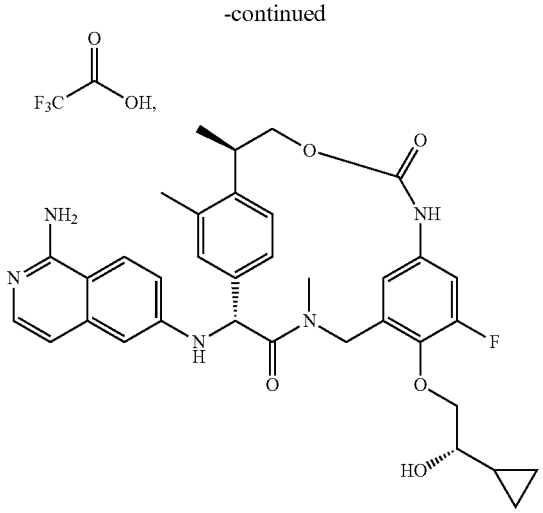
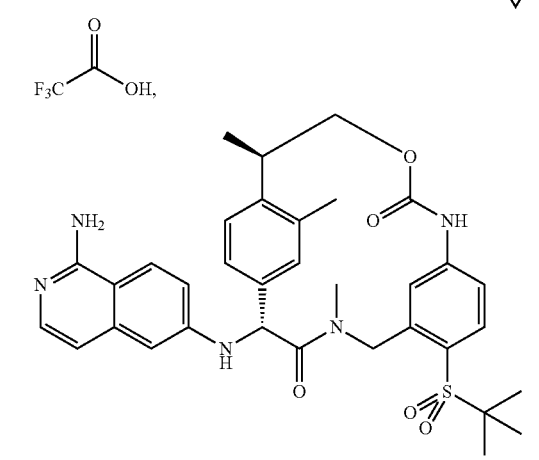
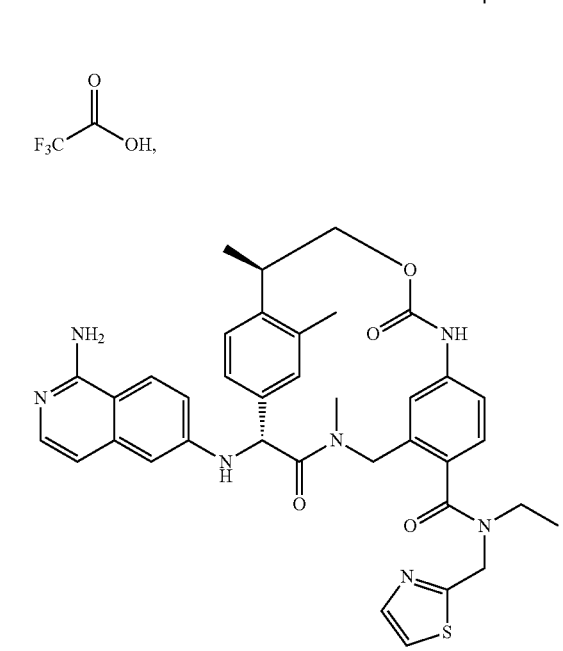

197
-continued
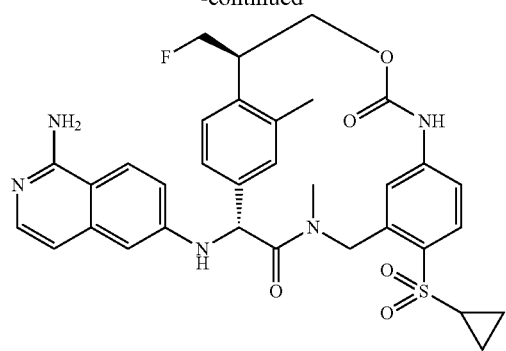
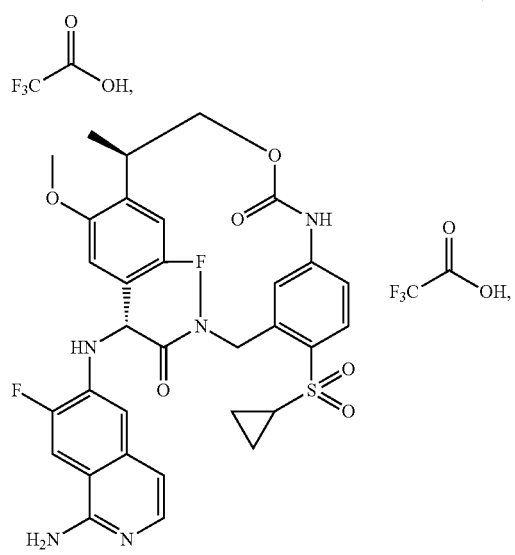
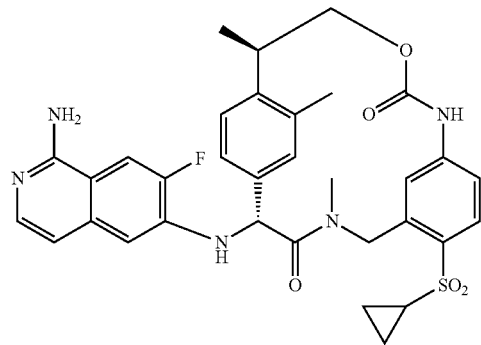
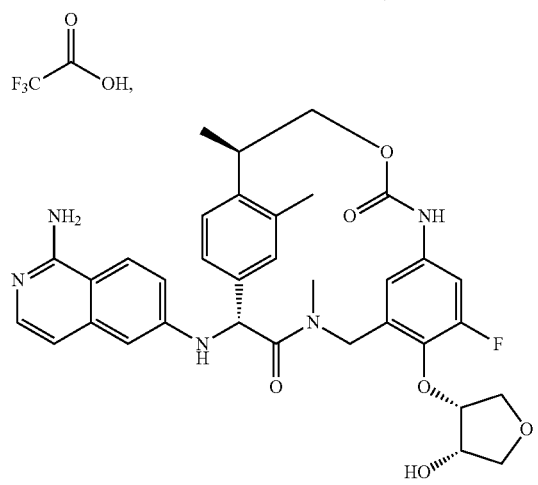
198
-continued
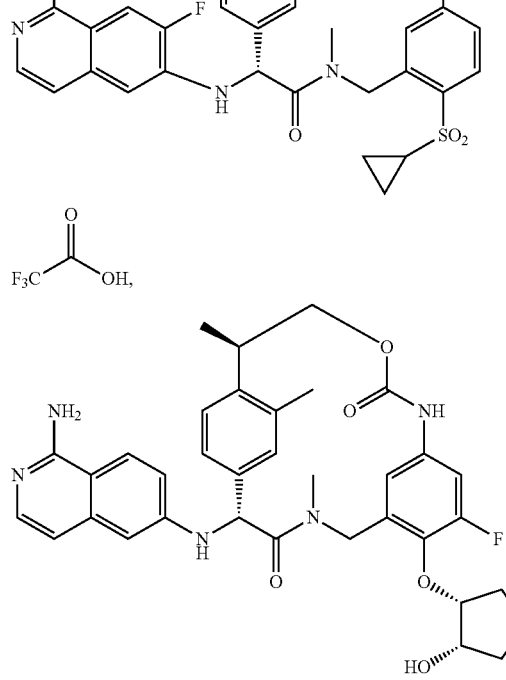

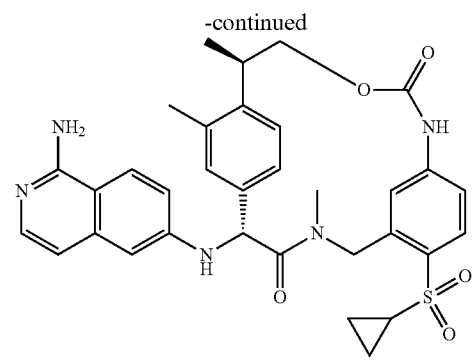
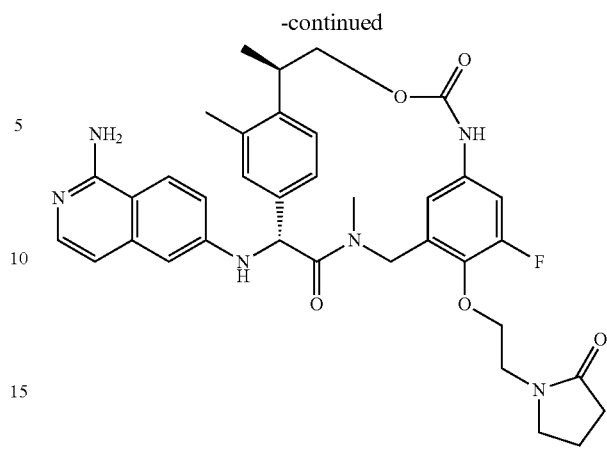
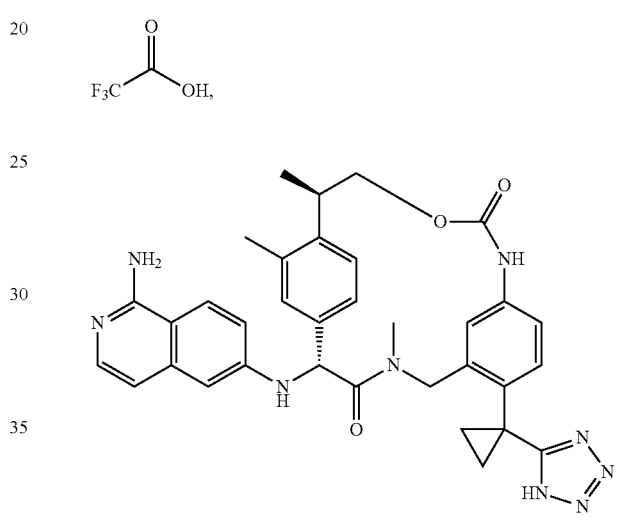
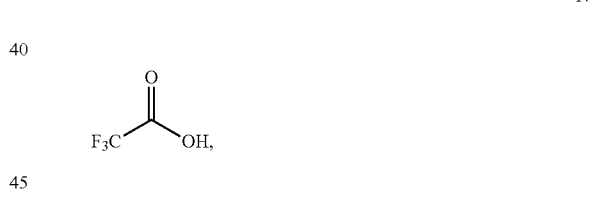
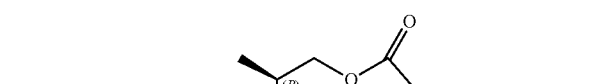
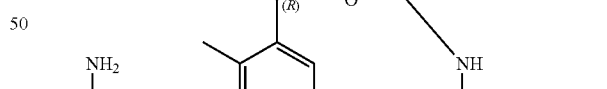
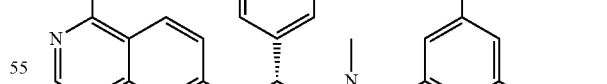
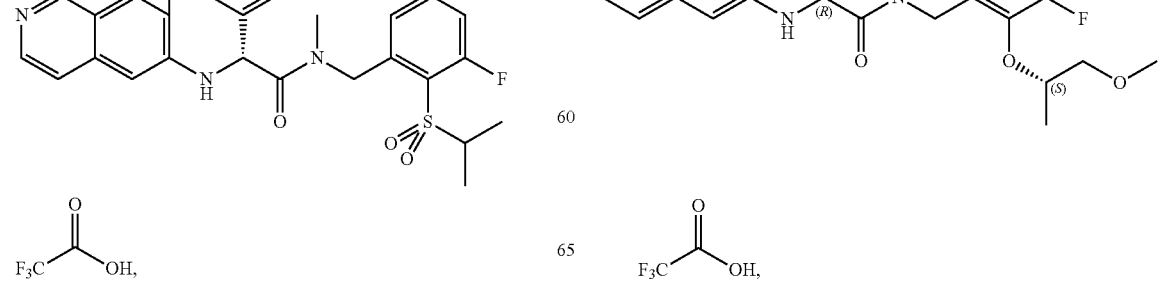

201

-continued

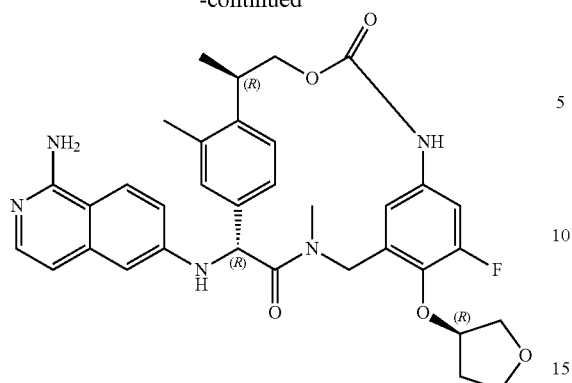

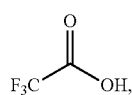

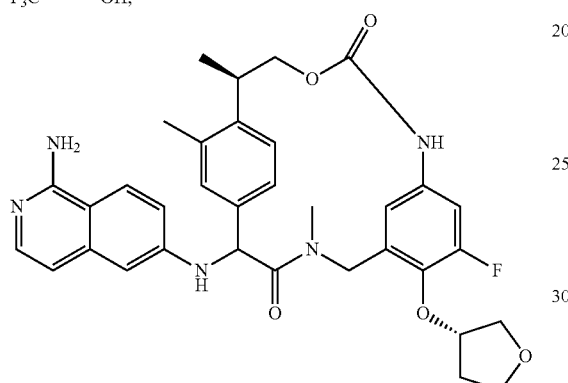

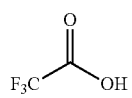

or a stereoisomer, or a pharmaceutically acceptable salt thereof.

5. A pharmaceutical composition, comprising: a pharmaceutically acceptable carrier and a compound of claim 1.

6. A method for the treatment of thromboembolic disorders comprising administering to a patient in need of such treatment at least one of the compounds of claim 1.

7. A method for the treatment of thromboembolic disorders comprising administering to a patient in need of such treatment at least one of the compounds of claim 4.

8. A compound according to claim 1, wherein the compound is selected from the list consisting of:

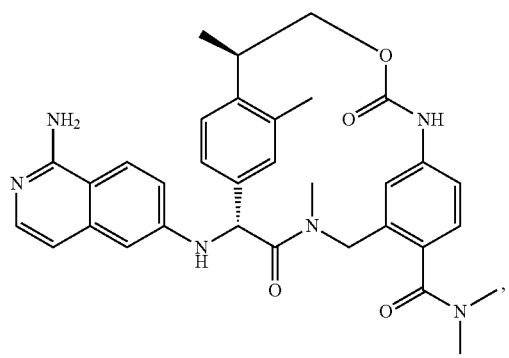

202

-continued

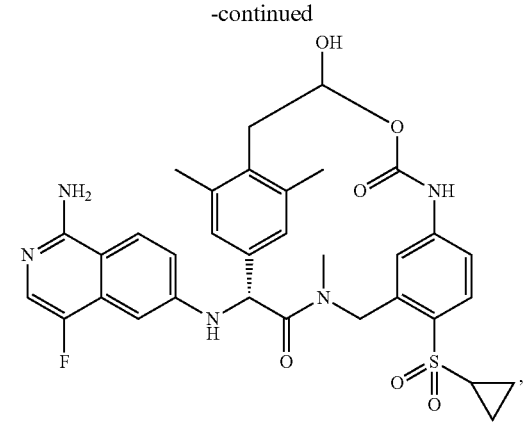

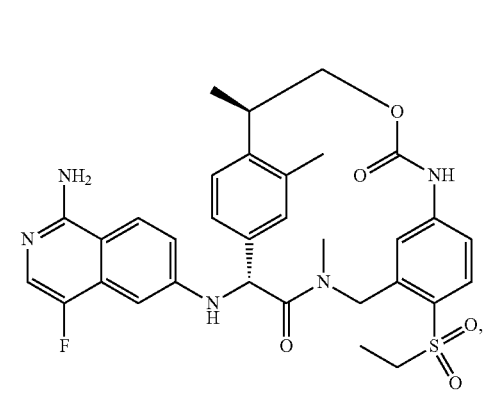

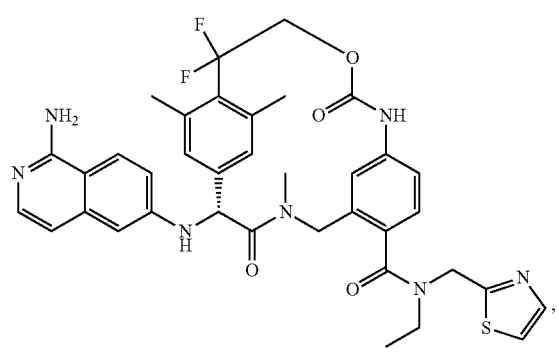

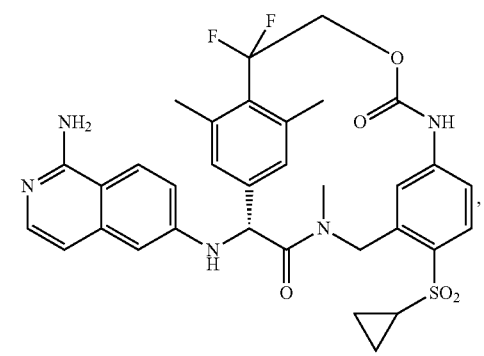

203
-continued
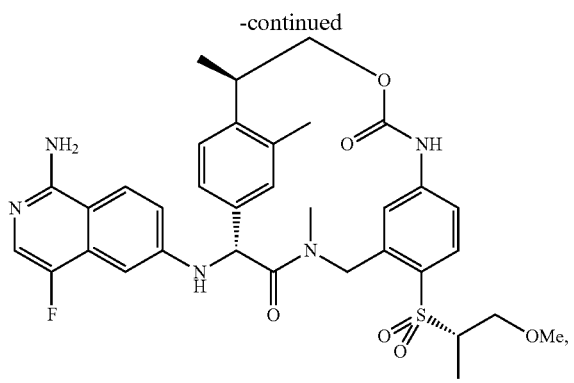
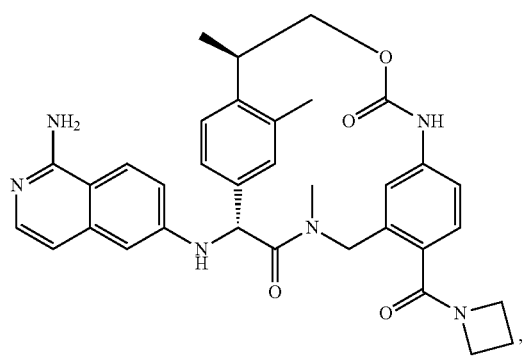
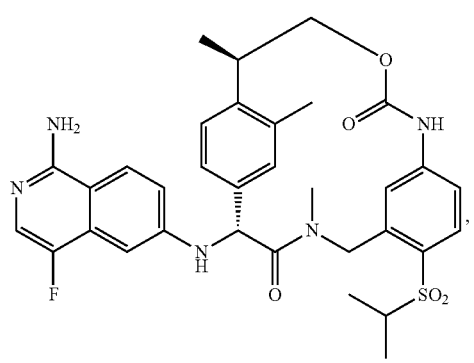
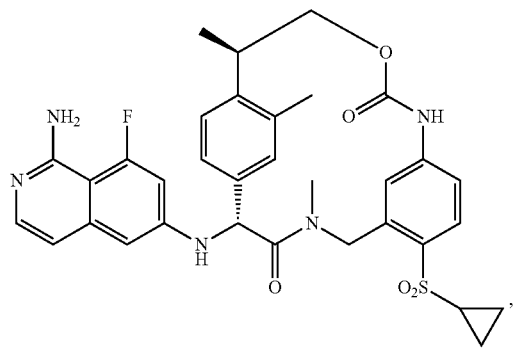
204
-continued
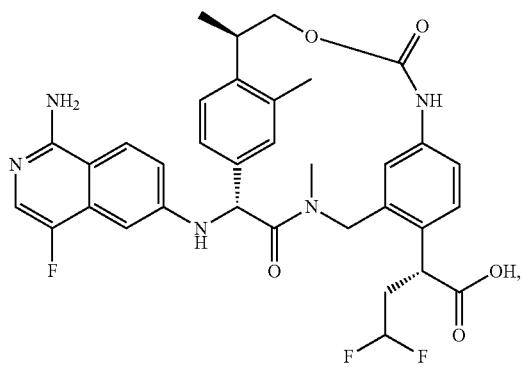
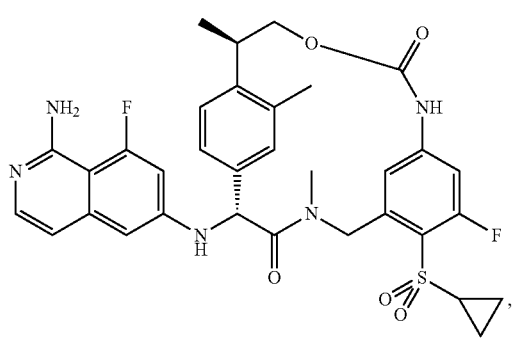
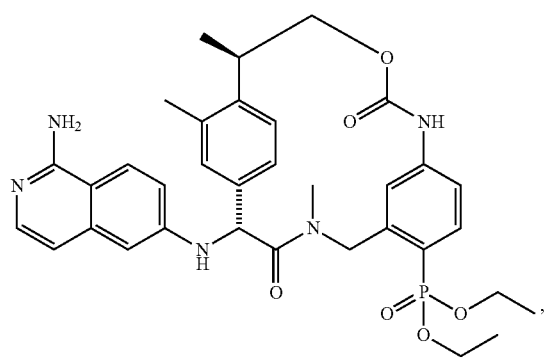
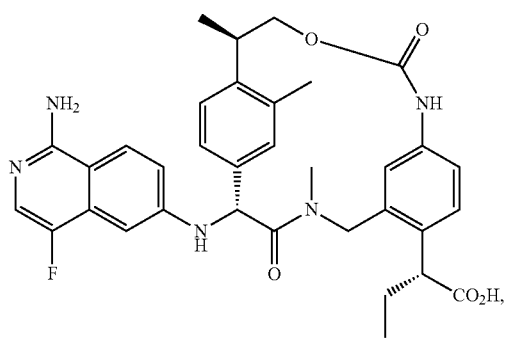

205
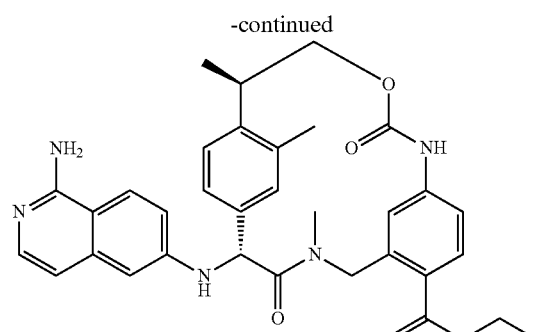
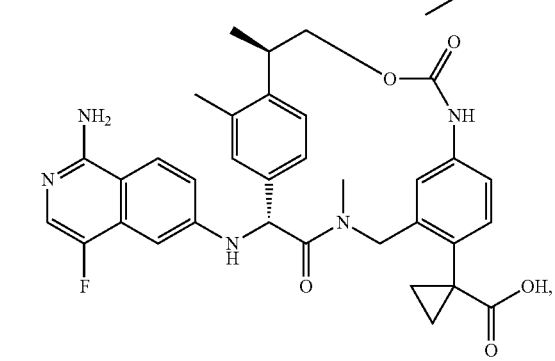
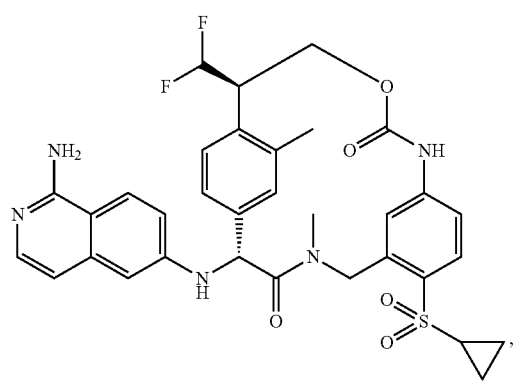
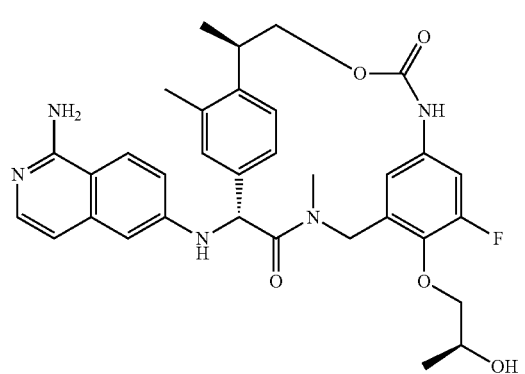
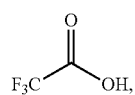
206
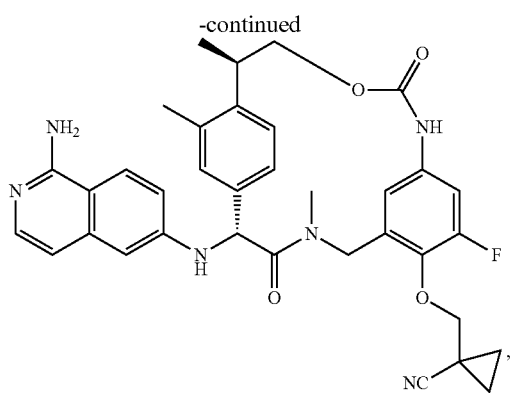
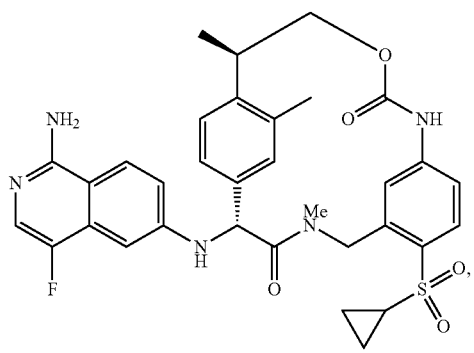
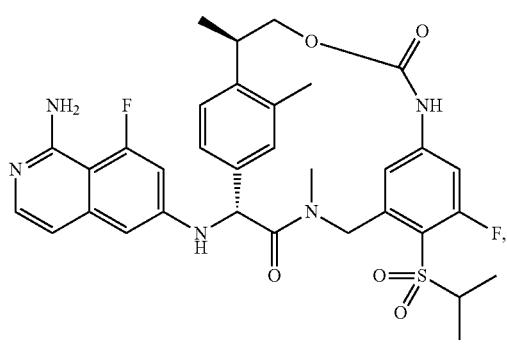
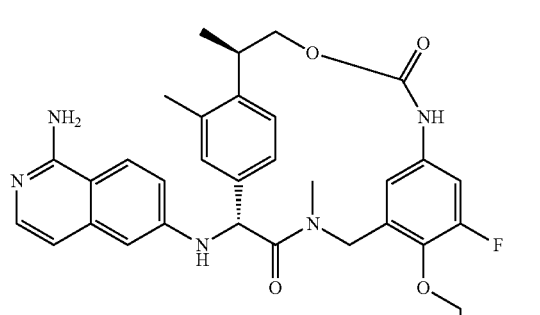
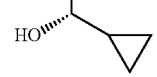

207
-continued
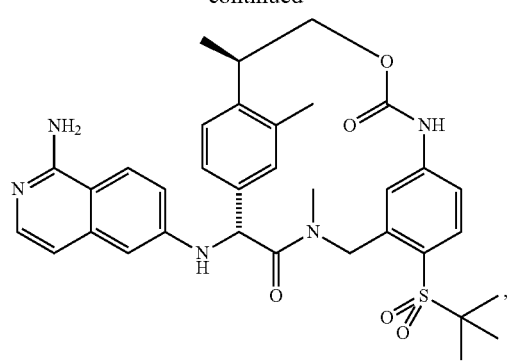
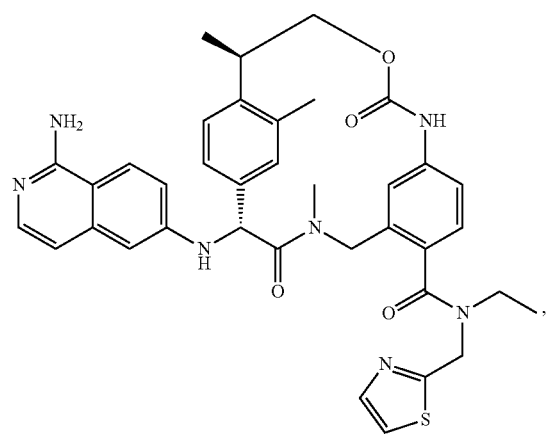
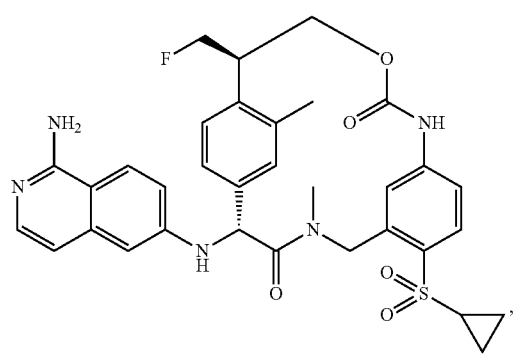
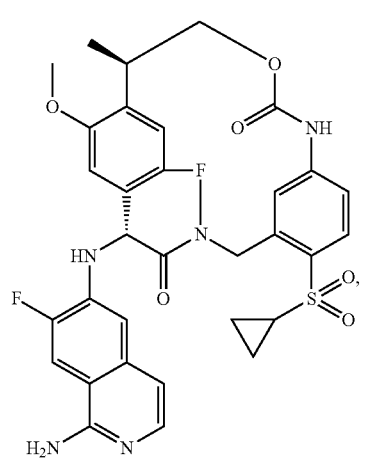
208
-continued
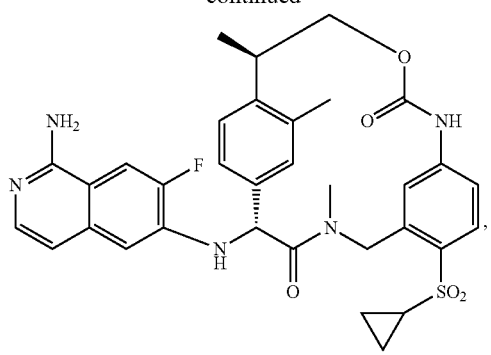
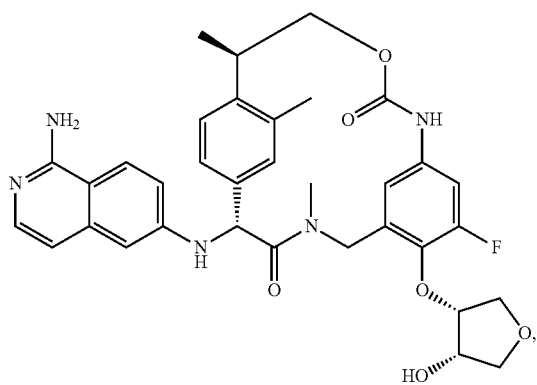
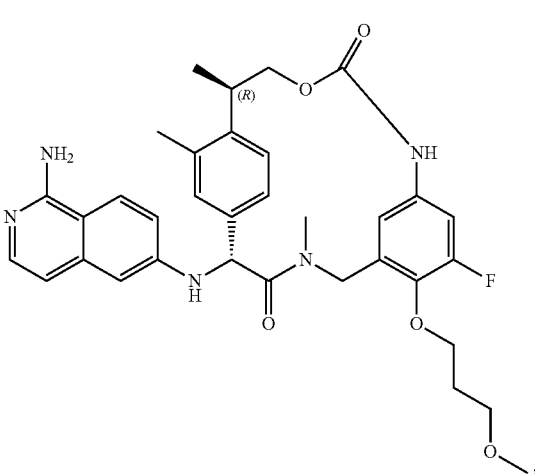
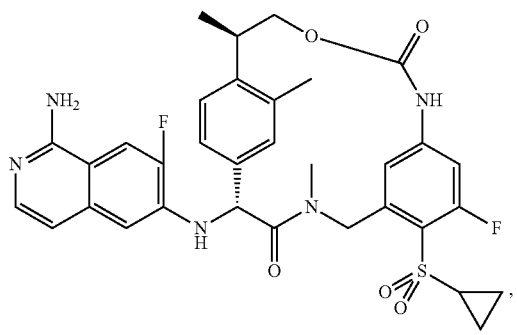

209
-continued
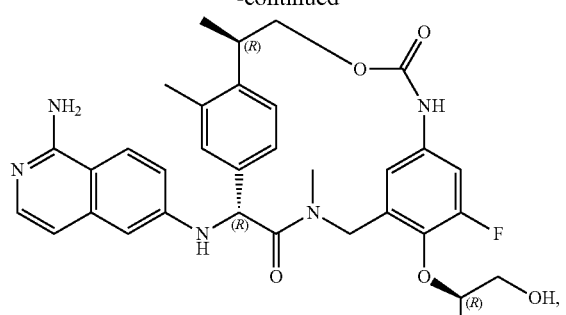
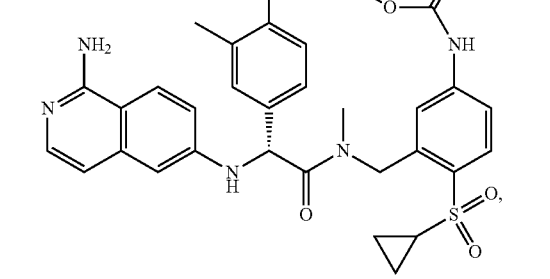
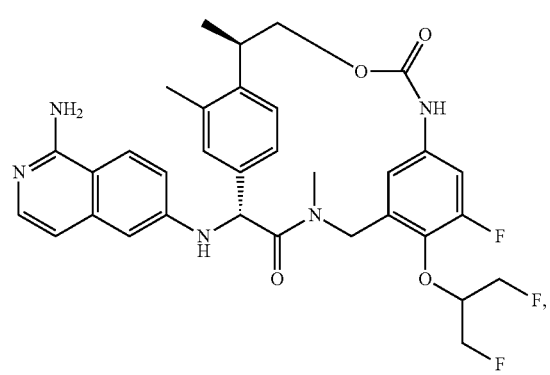
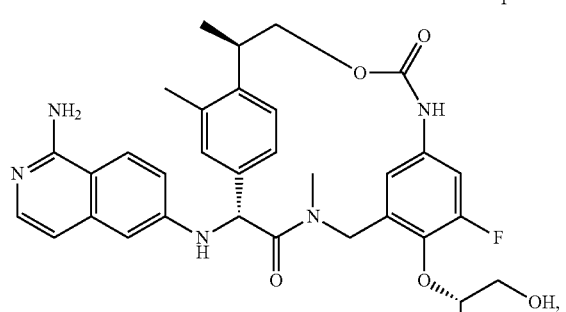
210
-continued
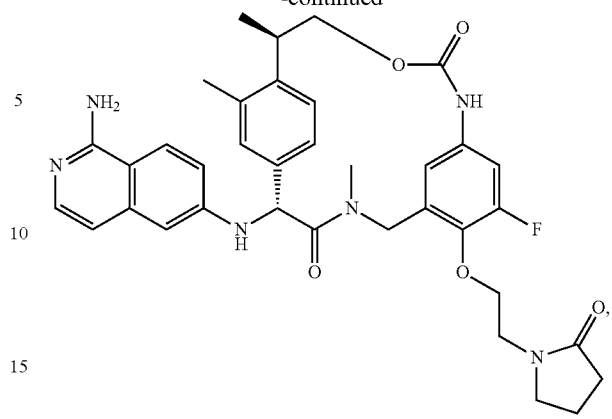
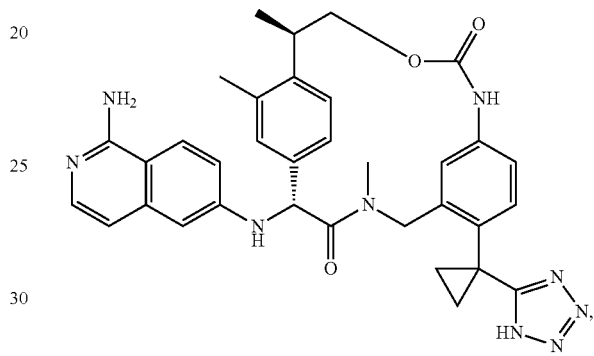
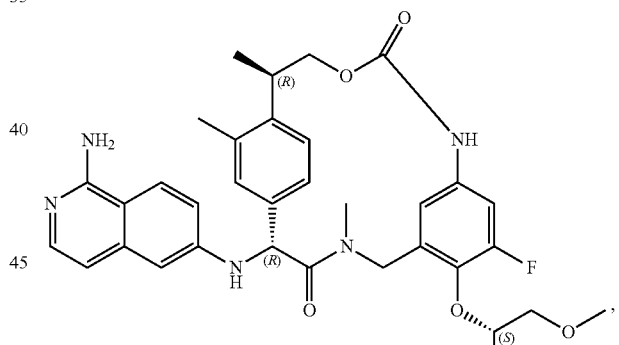
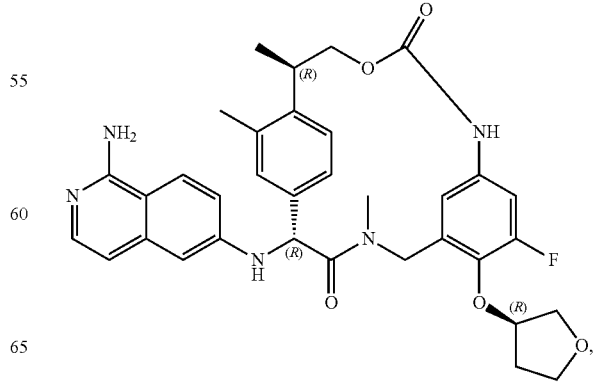

-continued
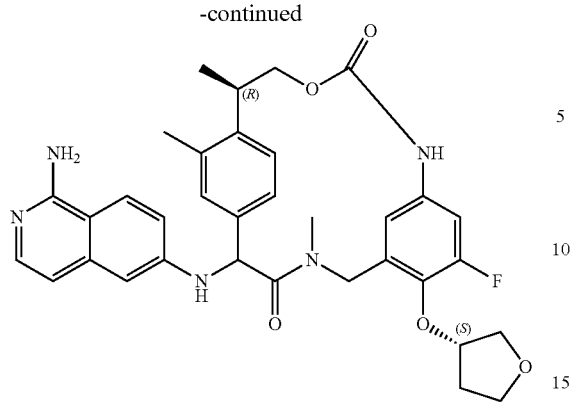
or a stereoisomer, or a pharmaceutically acceptable salt thereof.
9. A method for the treatment of thromboembolic disorders comprising administering to a patient in need of such treatment at least one of the compounds of claim 8.
* * * * *